United States Patent
Wikholm et al.

(10) Patent No.: US 12,117,459 B2
(45) Date of Patent: Oct. 15, 2024

(54) ROVER-BASED INTEGRATED LABORATORY SYSTEM INCLUDING AUTONOMOUS MOBILE ROBOTS

(71) Applicant: FORMULATRIX, INC., Bedford, MA (US)

(72) Inventors: David Wikholm, Bedford, MA (US); Rasmus Lindblom, Bedford, MA (US)

(73) Assignee: Formulatrix International Holding Ltd., Dubai (AE)

( * ) Notice: Subject to any disclaimer, the term of this patent is extended or adjusted under 35 U.S.C. 154(b) by 960 days.

(21) Appl. No.: 16/960,998

(22) PCT Filed: Jan. 9, 2019

(86) PCT No.: PCT/US2019/012814
§ 371 (c)(1),
(2) Date: Jul. 9, 2020

(87) PCT Pub. No.: WO2019/139930
PCT Pub. Date: Jul. 18, 2019

(65) Prior Publication Data
US 2020/0348324 A1    Nov. 5, 2020

Related U.S. Application Data

(60) Provisional application No. 62/615,127, filed on Jan. 9, 2018.

(51) Int. Cl.
*G01N 35/00* (2006.01)
*B01L 3/00* (2006.01)
(Continued)

(52) U.S. Cl.
CPC ........ *G01N 35/0099* (2013.01); *B01L 3/5085* (2013.01); *B01L 9/06* (2013.01);
(Continued)

(58) Field of Classification Search
CPC ............ G01N 35/0099; G01C 21/3804; B01L 2200/18
See application file for complete search history.

(56) References Cited

U.S. PATENT DOCUMENTS

| | | | |
|---|---|---|---|
| 9,381,524 B2 * | 7/2016 | Bailey | G01N 35/026 |
| 2002/0146347 A1 * | 10/2002 | McNeil | G05D 1/0291 |
| | | | 422/65 |

(Continued)

FOREIGN PATENT DOCUMENTS

| | | |
|---|---|---|
| CN | 203493082 U | 3/2014 |
| JP | H06094728 A | 4/1994 |

(Continued)

OTHER PUBLICATIONS

International Search Report and Written Opinion issued in counterpart PCT Application No. PCT/US2019/012814 dated Apr. 15, 2019 (nineteen (19) pages).

(Continued)

*Primary Examiner* — Kyle O Logan
(74) *Attorney, Agent, or Firm* — E. Eric Mills; Bryan L. Baysinger; Maynard Nexsen PC

(57) ABSTRACT

A rover-based integrated laboratory system including autonomous mobile robots is disclosed. Namely, a rover-based integrated laboratory system is disclosed comprising a workspace; a laboratory component within the workspace, the laboratory component being adapted to perform a laboratory technique; a labware component within the workspace that is adapted to be used in the laboratory technique; and a rover component within the workspace that is operatively connected to the laboratory and the labware components, the rover component being an autonomous mobile robot.

30 Claims, 113 Drawing Sheets

(51) Int. Cl.
*B01L 9/06* (2006.01)
*B25J 5/00* (2006.01)
*B65G 1/04* (2006.01)
*C12M 1/00* (2006.01)
*C12M 1/32* (2006.01)
*C12M 1/36* (2006.01)
*C12M 3/00* (2006.01)
*G01C 21/00* (2006.01)
*G01N 35/04* (2006.01)
*G01N 35/10* (2006.01)
*G05B 19/042* (2006.01)
*G05D 1/00* (2006.01)
*B25J 13/08* (2006.01)

(52) U.S. Cl.
CPC ............ *B25J 5/007* (2013.01); *B65G 1/0471* (2013.01); *C12M 23/12* (2013.01); *C12M 23/44* (2013.01); *C12M 23/50* (2013.01); *C12M 23/52* (2013.01); *C12M 41/48* (2013.01); *G01C 21/3804* (2020.08); *G01N 35/00732* (2013.01); *G01N 35/00871* (2013.01); *G01N 35/04* (2013.01); *G01N 35/1072* (2013.01); *G01N 35/1081* (2013.01); *G05B 19/0426* (2013.01); *G05D 1/0088* (2013.01); *G05D 1/0234* (2013.01); *G05D 1/0246* (2013.01); *G05D 1/0274* (2013.01); *B01L 2200/18* (2013.01); *B25J 13/086* (2013.01); *G01N 2035/00742* (2013.01); *G01N 2035/042* (2013.01); *G01N 2035/0425* (2013.01); *G01N 2035/0489* (2013.01); *G05B 2219/2641* (2013.01)

(56) References Cited

U.S. PATENT DOCUMENTS

| | | | |
|---|---|---|---|
| 2005/0058573 A1* | 3/2005 | Frost, III | G01N 35/0099 422/62 |
| 2005/0265896 A1* | 12/2005 | Itoh | G01N 35/04 422/65 |
| 2013/0116102 A1 | 5/2013 | Hansen | |
| 2014/0039825 A1 | 2/2014 | Antonini | |
| 2017/0217027 A1* | 8/2017 | Boucard | B25J 19/023 |
| 2017/0364074 A1* | 12/2017 | Lau | G06Q 10/08355 |
| 2020/0348324 A1* | 11/2020 | Wikholm | G05D 1/0246 |

FOREIGN PATENT DOCUMENTS

| | | |
|---|---|---|
| JP | 2007532867 A | 11/2007 |
| JP | 2013537487 A | 10/2013 |
| JP | 2014520018 A | 8/2014 |
| JP | 2017109256 A | 6/2017 |
| WO | 2009147252 A1 | 12/2009 |
| WO | 2016061471 A1 | 4/2016 |

OTHER PUBLICATIONS

Li, et al. 2010. "Optimizing S-curve Velocity for Motion Control" [Retrived from the internet] <URL: https://wwwresearchgate.net/publication/257576837 Optimize_ SCurve_Velocity for Motion_ Control>.

Schneider et al. 2002. "Autonomous Navigation and Control of a Mobile Robot in a Cell Culture Laboratory" [Retrived from the internet] <URL: file:///Z:/Schneider%20et%20al..pdf>.

Lee et al. 2013. "A Vision-Based Automated Guided Vehicle System with Marker Recognition for Indoor Use" [Retrived from the internet] <URL: file:///Z:/lee%20et%20al..pdf>.

* cited by examiner

ROVER-BASED INTEGRATED LABORATORY SYSTEM INCLUDING AUTONOMOUS MOBILE ROBOTS

CROSS REFERENCE TO RELATED APPLICATIONS

This application is a 35 U.S.C. § 371 U.S. national phase entry of International Application No. PCT/US2019/012814 filed Jan. 9, 2019, which is related to and claims priority under 35 U.S.C. § 119(e) to U.S. Provisional Patent App. No. 62/615,127, entitled "Rover-Based Integrated Laboratory System Including Autonomous Mobile Robots," filed on Jan. 9, 2018; the entire disclosures of which are incorporated herein by reference.

TECHNICAL FIELD

The subject matter relates generally to integrated laboratory systems, and, more particularly, to a rover-based integrated laboratory system including autonomous mobile robots.

BACKGROUND

In the field of laboratory automation, it is common to integrate individual automated instruments in order to fully automate a workflow, especially in the life science and pharmaceutical industries. Generally, each automated instrument performs a specialized function within that work flow. Integration is achieved by automating the transport of materials between the instruments. Integrated laboratory systems are often applicable for high throughput workflows, which benefit from processing materials in high volume. Automation of such processes can often improve the efficiency of the process, ensure consistency, and reduce human errors.

The instruments used in an integrated laboratory system are specific to the requirements of a particular workflow. Particular laboratory instruments can need to be integrated with material storage systems to increase the amount of work that can be completed without human interaction. As an example, a typical liquid handling device can have a fixed capacity to hold labware on its deck. The capacity of such a liquid handling device can be expanded by integrating the device with storage modules for labware, consumables, experiment samples, and waste. Robotic transfer of materials between the fixed deck space and the storage modules is one approach to creating an integrated system.

As another example, a typical cell culture workflow in which some aspects of the workflow have been automated can require the following components: environmentally-controlled storage for cell samples and reagents, an automated liquid handler for transferring reagents between labware containers, and robotic microscopes for imaging and analyzing cell culture samples. In such an example, although automated solutions can exist for each individual task in the workflow, humans are required to manually schedule operations and transfer materials. To automate the entire workflow, an automated system of transferring materials between each instrument and scheduling operations is needed. Thus a fully automated workflow can greatly reduce the requirement for human participation, as well as increase the throughput of the workflow if materials can be transferred between each instrument.

A fully automated workflow can be expanded by integrating new instruments to enable additional functionalities. To accomplish this, each instrument added to an automated workflow must be able to interface with the integration system. However, this interfacing capability can impact which modules can be included in an integrated workflow, and which particular products can be integrated with the overall system. For example, one automation company can produce a suite of automated products, each addressing an individual step of a greater workflow, as well as an integration system that can interface each of the automated products in order to automate the full workflow. However, to integrate a group of instruments not specifically designed to integrate in the same manner, often can pose a significant challenge that requires a very specialized and expensive automation solution.

Typical approaches of integrating automated instruments can include a linear conveyor and a robotic arm carrying a gripper tool. A robotic arm can move a gripper tool through complex motion paths in order to access labware in an instrument the same way a human might access the labware. Thus robotic arms can be a nearly universal tool for transferring materials from one location to another. However robotic arms capable of such universal movement are typically prohibitively expensive for automating anything but the largest scale and profitable work flows. Conveyors can transport labware, tools, and consumable materials along a fixed path between system components. Conveyors can also transport robotic arms to work at various stations. Continuing with the example of the automated liquid handling system, a liquid handling device with a fixed and limited deck space can be integrated with a robotic arm carrying a gripper tool to move labware between any position on the instrument deck and storage modules, conveyors, waste, or some combination thereof. For example, a gripper can move an empty box of pipette tips from a position on the instrument deck onto a conveyor platform, which then moves the empty box of tips to a waste bin, where the empty box is disposed of.

Typical approaches of integrating automated instruments, such as robotic arms and conveyors, are arranged and calibrated for a very specific layout of instruments and set of tasks. In the above example, where a robotic arm is implemented as way to integrate an automated liquid handler with a conveyor, the robotic arm is specifically calibrated for a certain physical arrangement between the liquid handler device and the conveyor device. Any expansion or adjustment of the layout of integrated components will require reprogramming of the entire workflow. These predetermined features of an automated workflow are therefore not easy to adapt, expand, or rearrange within the integrated system. Thus integrated systems are not typically applied to low-throughput, dynamic workflows that can change over a short period of time.

What is more, if a component within an integrated system malfunctions, the entire workflow can come to a halt until the malfunctioning component can be repaired or replaced. Servicing such complex systems requires a service representative to visit the system site prepared with any replacement parts required to repair the malfunctioning unit. This can be a costly and inefficient process for the service provider, and the downtime presents lost productivity for the operator of the integrated system. Additionally, due to the aforementioned sensitivity of an integrated system to changes in component layout, the robotic components generally need to be recalibrated if a malfunctioning component must be removed or replaced.

Thus there is a need for an automated laboratory integration system that can be readily adapted to suit dynamic workflows and rearrangement of components and which can be more efficiently repaired in the event of a malfunction.

Relevant patents in this field include the following:

U.S. Pat. No. 6,429,016, entitled "System and method for sample positioning in a robotic system," describes a system of self-propelled mobile robots moving along predefined tracks or pathways for macro positioning of labware between stations, and a micro positioning mechanism appearing to employ a kinematic mount activated between the mobile robot and the station to allow the station to interact with the labware.

U.S. Pat. No. 9,182,419, entitled "Conveying system for material samples, especially medical samples," describes a self-propelled sample conveyor that drives along predefined paths of slots in a work area. The conveyor has a pin that follows the slot paths.

U.S. Pat. No. 9,459,273, entitled "Laboratory product transport element and path arrangement," describes mobile robots to carry samples around predefined and specially constructed pathways.

U.S. Pat. No. 9,772,342, entitled "Dispatching device, sample distribution system and laboratory automation system" and U.S. Pat. No. 9,423,410, entitled "Transport device, sample distribution system, and laboratory automation system," relate to a specific lab automation platform employing mobile labware carriers that travel along fixed paths driven by magnetic forces. The labware carriers can track their positions in the fixed paths by measuring RFID codes in the current segment of the track.

U.S. Pat. No. 6,099,230, entitled "Automated labware storage system," describes a labware storage system paired with a 'labware shuttle' (conveyor) capable of moving labware between a first position in the labware storage system and a second position remote from the labware storage system. This is an example of a component of a "fixed" integrated system, where the labware is transported along fixed paths to fixed positions, and integration modules must be designed and assembled in a very particular way in order to transfer labware between the specific positions.

U.S. Pat. No. 7,746,229, entitled "Device and method for identifying, locating, and tracking objects on laboratory equipment," describes a laboratory instrument with a fixed deck work table that is divided into a grid of fixed positions to place labware, racks, or tools. Each position on the deck has RFID sensors to read RFID tags on labware, racks, or tools placed in each position, so that the system can automatically know the location of certain labware as it is placed in the deck.

U.S. Pat. No. 7,411,508, entitled "Methods and Systems for locating and identifying labware using radio-frequency identification tags," describes a lab instrument with a deck of fixed positions, each position having some locating mechanism to register labware carriers to that specific position, and each position having an RFID reader to read RFID tags on the carriers or labware to identify what items are positioned on the deck and their locations on the deck.

SUMMARY

In an aspect, a laboratory integrated system is described herein comprising a workspace; a laboratory component within the workspace, the laboratory component being adapted to perform a laboratory technique; a labware component within the workspace that is adapted to be used in the laboratory technique; and a rover component within the workspace that is operatively connected to the laboratory and the labware components, the rover component being an autonomous mobile robot.

A laboratory component described herein can comprise a liquid handler device in some embodiments. The liquid handler device can be a multi-channel liquid handler with independent spanning and independent Z-actuation on each of the channels. In some cases, the liquid handler device is an 8-channel liquid handler with independent spanning and independent Z-actuation on each of the 8 channels. In some embodiments, a laboratory technique described herein comprises a pipetting operation or cell culturing.

In some embodiments, a rover component described herein comprises up to five rover devices that are operatively connected with the liquid handler device. Each autonomous mobile robot can be holonomic in some cases, where the autonomous mobile robot comprises an omni-wheel based drivetrain and capable of moving in any direction without turning around. In some embodiments, each autonomous mobile robot comprises one or more navigational cameras. In some cases, the rover component is adapted to transport and position the labware component or materials contained by the labware component. In some embodiments, the rover component comprises a rover device having a labware component carrier platform with a weigh scale. A rover device described herein can comprise a gripper tool. Furthermore, in some embodiments, the rover component can comprise an omni-wheel based drive train with or without a gripping tool.

In some embodiments, a workspace described herein comprises a plurality of fiducial markers forming a 2D coordinate system. Navigational cameras on each autonomous mobile robot can be adapted to identify a location of the autonomous mobile robot within the workspace through recognition of one or more of the fiducial markers.

In some instances, an autonomous mobile robot described herein comprises a labware component transfer mechanism. In some instances, the labware component transfer mechanism comprises a spatula mechanism that is adapted to transfer a labware component from the autonomous mobile robot to a location within the workspace. In some cases, the autonomous mobile robot can comprise a labware component carrier platform; and capacitive sensing regions that sense a presence or absence of a labware component positioned on the labware component carrier.

In further embodiments, the autonomous mobile robot is adapted to move within the workspace using an S-curve velocity motion profile. This S-curve velocity motion profile can reduce "jerk," which can minimize or eliminate sloshing or spilling of liquid being transported by the autonomous mobile robot.

A workspace, a laboratory component, a labware component, or any combination thereof described herein can in some cases comprise an RFID tag, and the autonomous mobile robot can comprise an RFID reader.

In some embodiments, a fleet controller is adapted to command a rover component described herein to engage the labware component for the laboratory technique. In cases where a workspace comprises two or more system modules and a fleet controller, a rover component described herein is adapted to generate a map of the workspace and the system modules, and the rover component can navigate freely within the workspace using the map. In some instances, the rover component is in wireless communication with the fleet controller, and the fleet controller commands the rover component to execute tasks of a workflow. In some embodiments, the rover component is in wireless communication with the system modules, and the system modules command the rover component to execute tasks of a workflow.

A workspace described herein can comprise in some a platform adapted to be expanded vertically with additional platforms in some cases. In some cases, the workspace can comprise a plurality of the platforms. Moreover, in some embodiments, a workspace described herein can comprise an elevator adapted to lift and lower the rover component within the workspace.

In another aspect, a method for integrating a laboratory system comprises the steps of providing a laboratory integrated system described herein; programming a protocol for the laboratory technique using a controller; and commanding the rover component with the controller to execute the protocol. In some embodiments, the protocol comprises transporting and positioning of the labware component or materials contained by the labware component in the workspace.

Further embodiments of a method described herein comprise the step of generating a map of the workspace using the rover component. Moreover, additional steps can comprises in some cases navigating the rover component freely within the workspace using the map. The rover component can navigate within the workspace using an S-curve velocity motion profile in some embodiments.

A method described herein can further comprise the step of communicating wirelessly between the rover component and the laboratory component during execution of the protocol by the rover component.

A commanding step of a method described herein can in some embodiments include commanding a pipetting technique. In other embodiments, the commanding step can include commanding a cell culture technique.

In some embodiments where a workspace disclosed herein comprises an autonomous mobile robot-navigable surface having an array of fiducial marks that define a coordinate system of the workspace, a method described can further comprise tracking a current position of the autonomous mobile robot within the workspace using a downward-facing camera positioned on the autonomous mobile robot, the current position of the autonomous mobile robot being determined by identifying one or more of the fiducial marks under the autonomous mobile robot using images captured by the downward-facing camera.

BRIEF DESCRIPTION OF DRAWINGS

Figure 1:
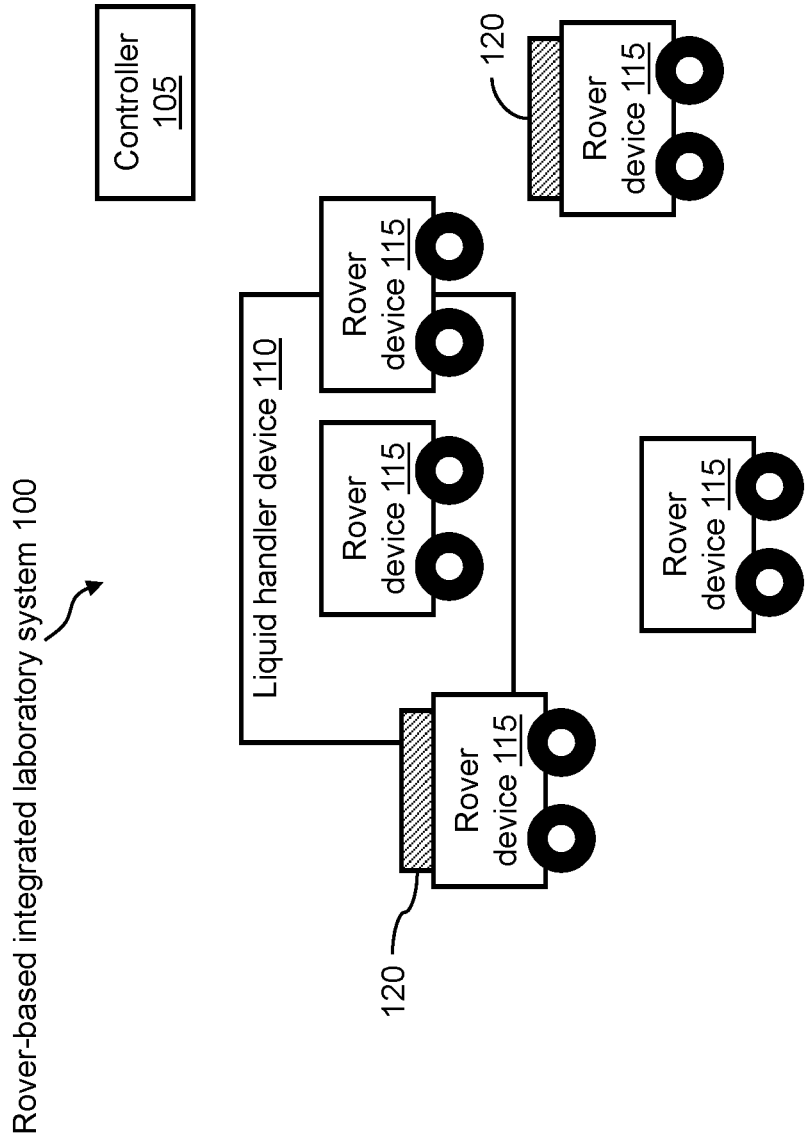
Figure 2:
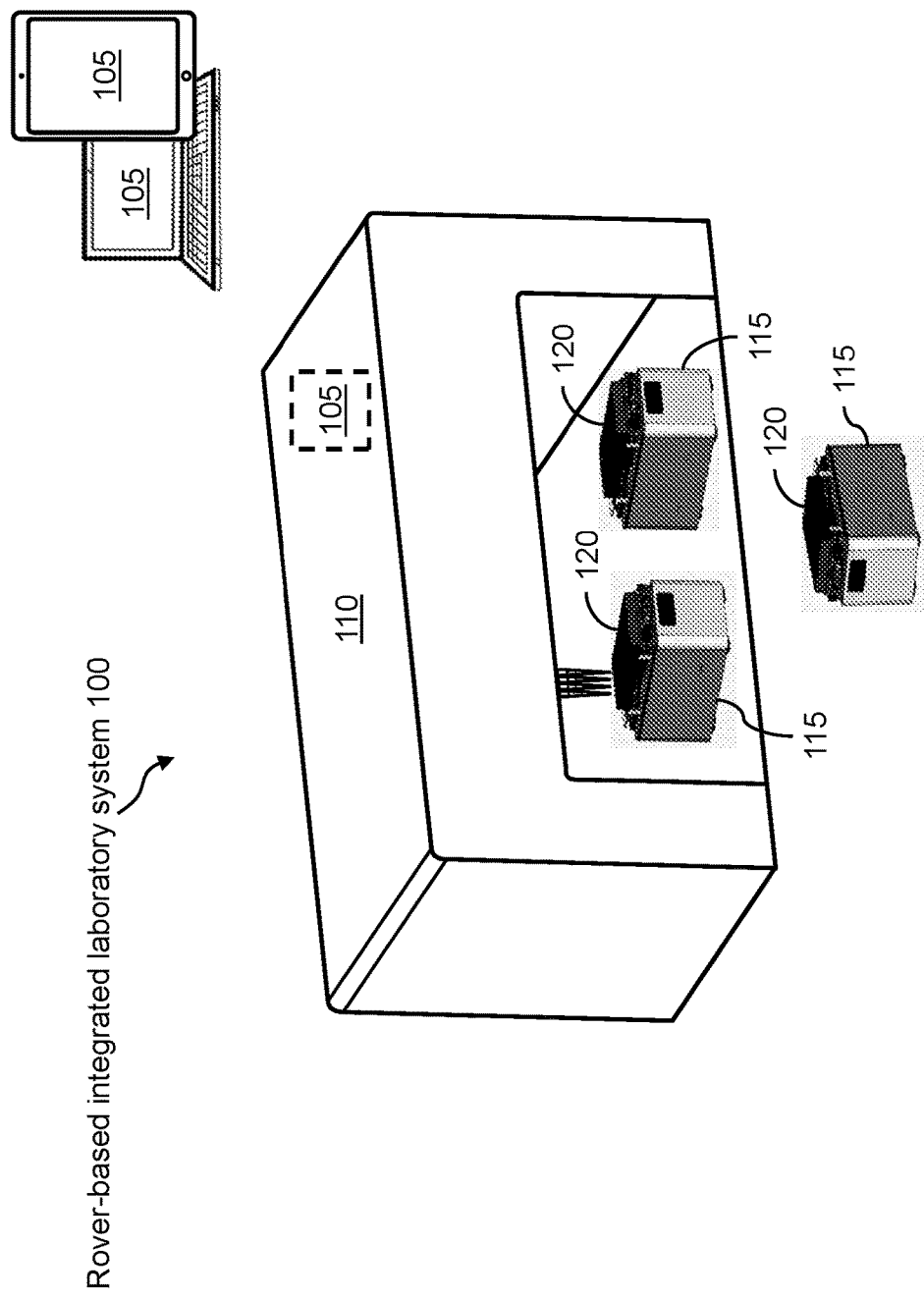
Figure 3:
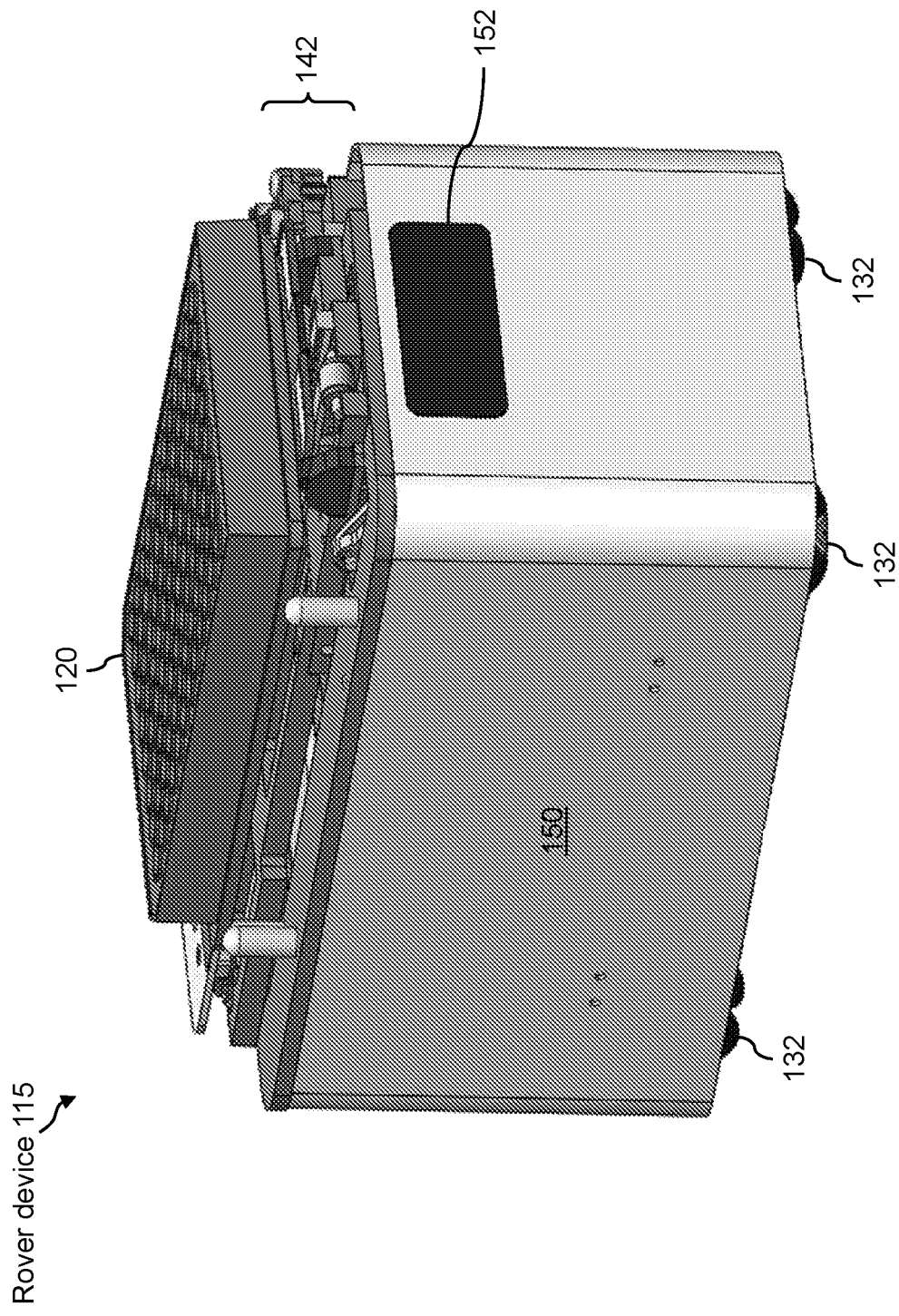
Figure 4:
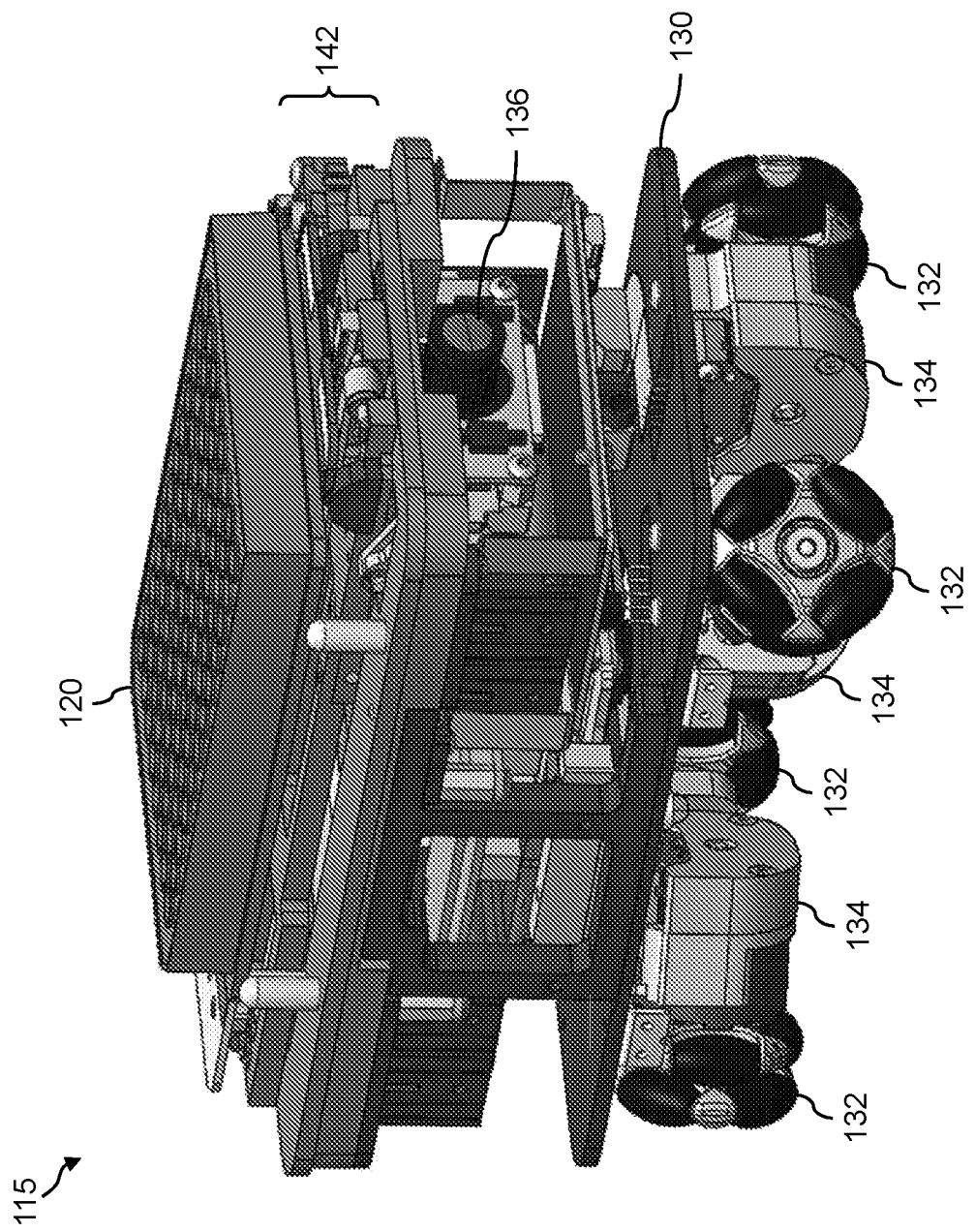
Figure 5:
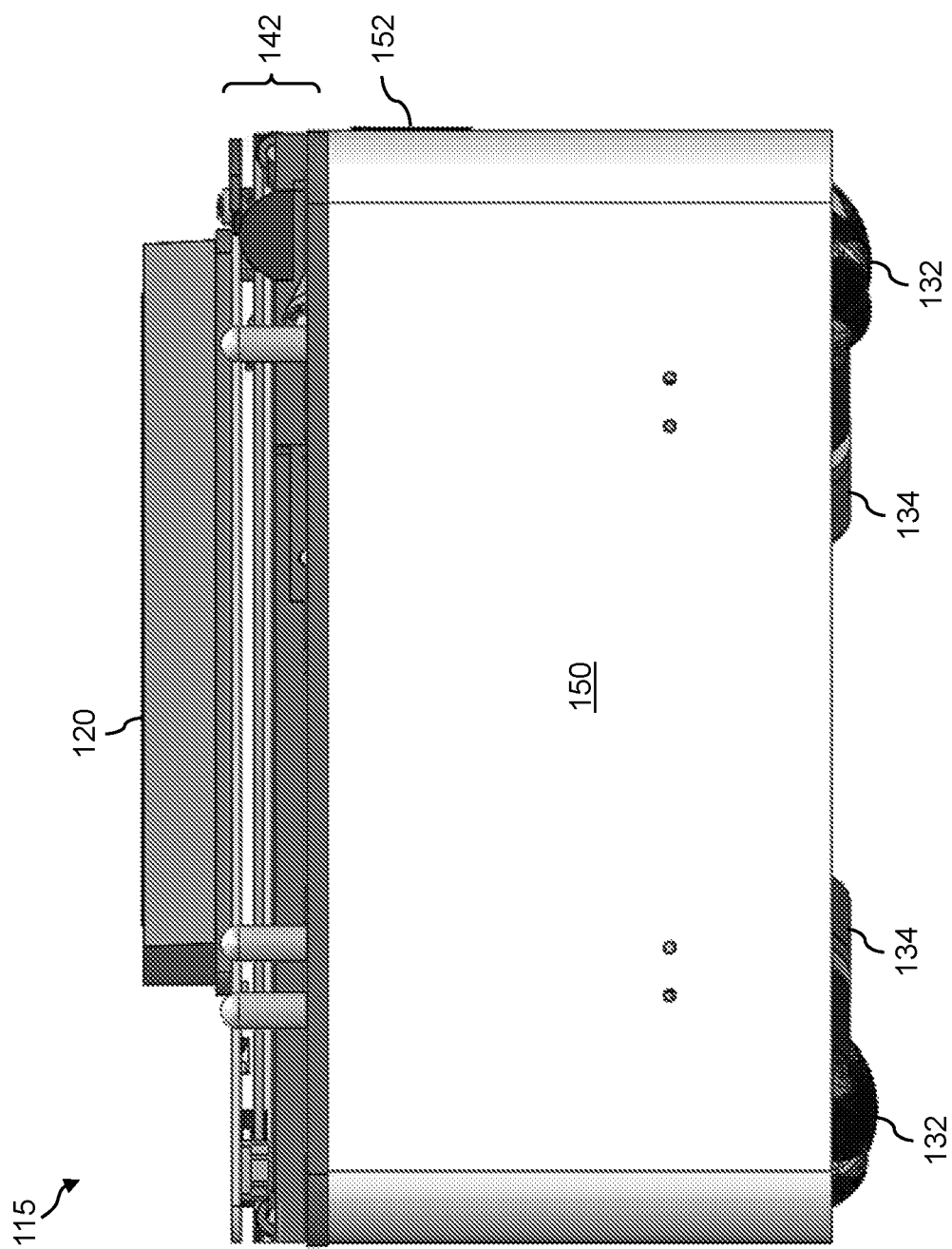
Figure 6:
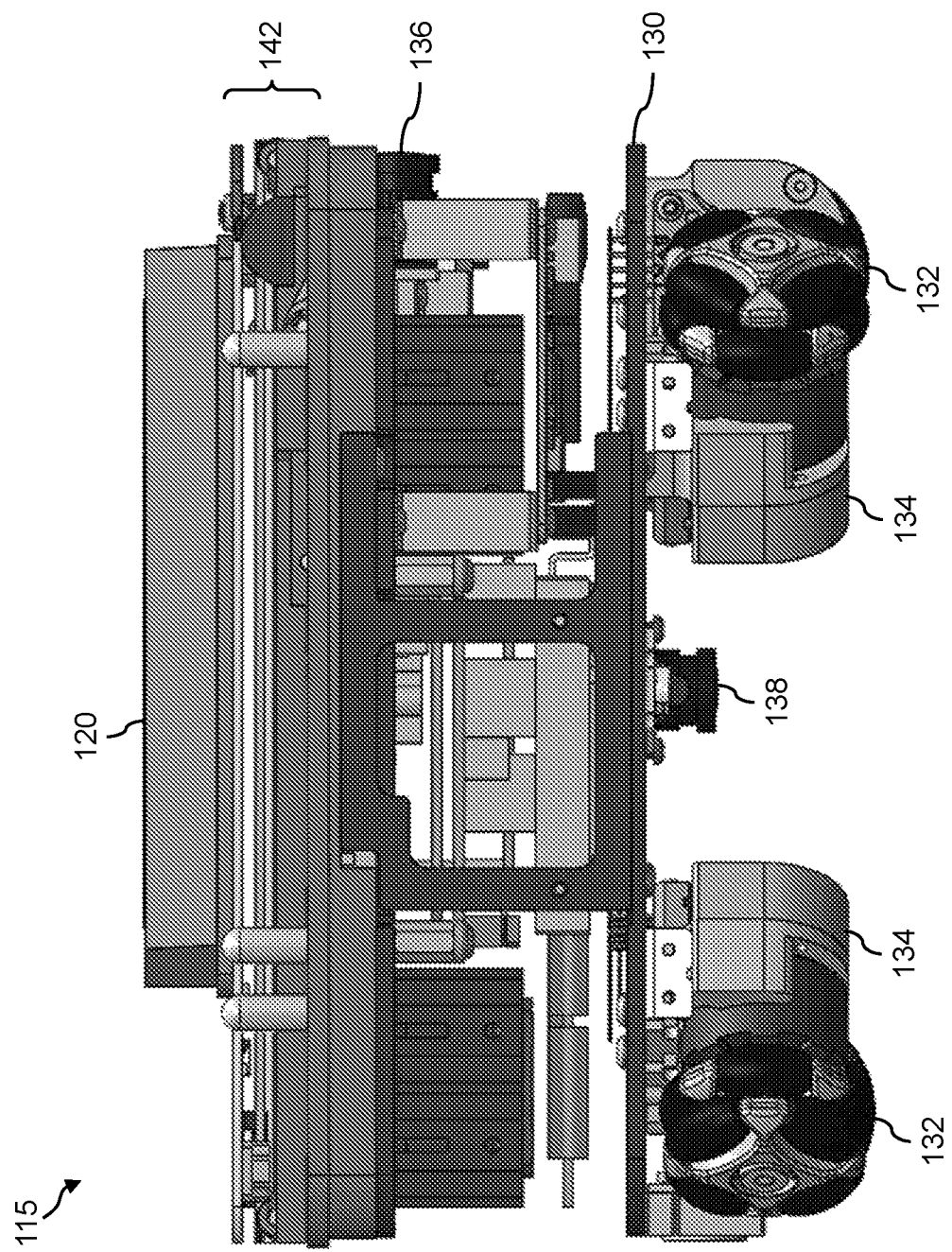
Figure 7:
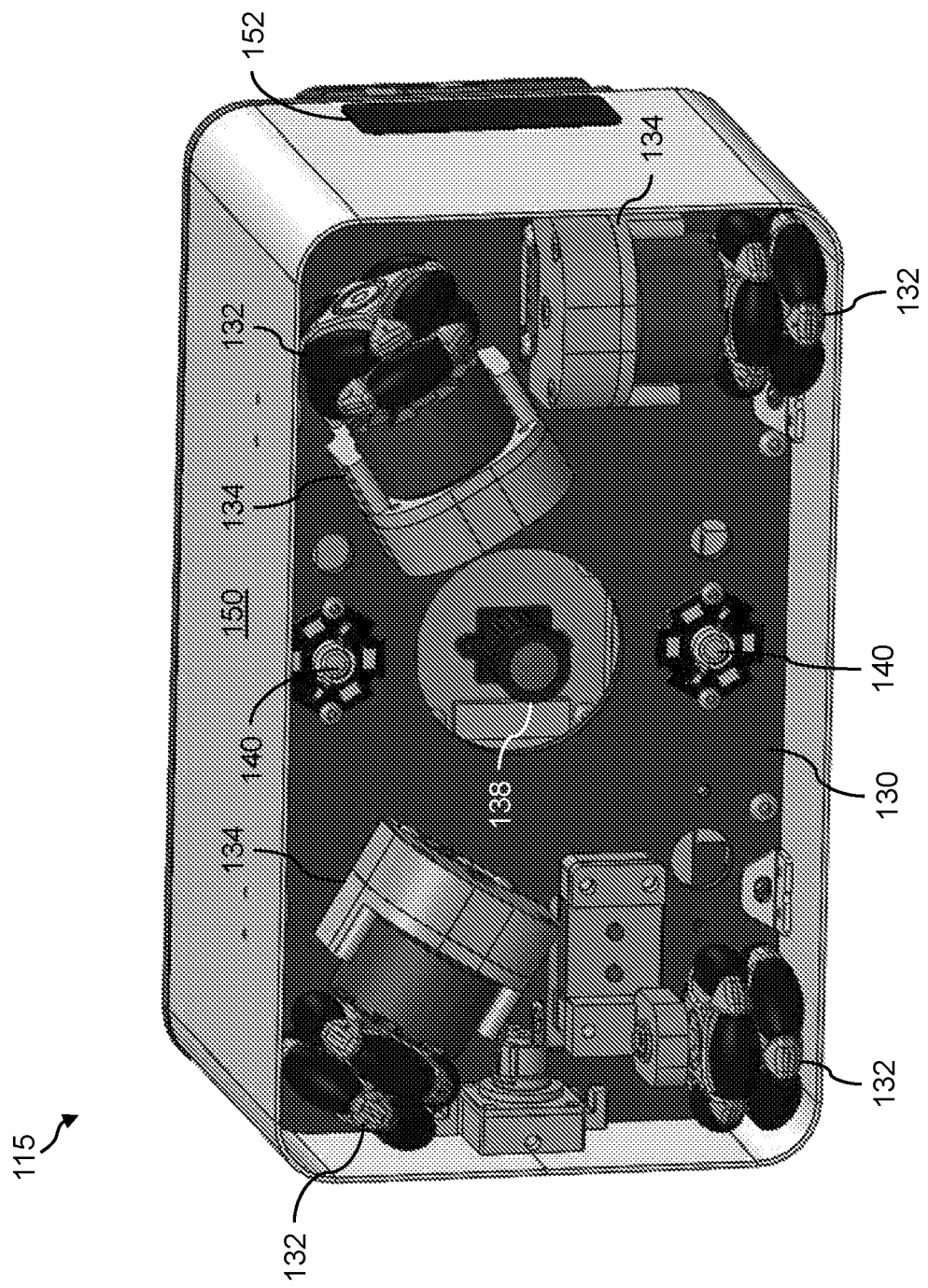
Figure 8:
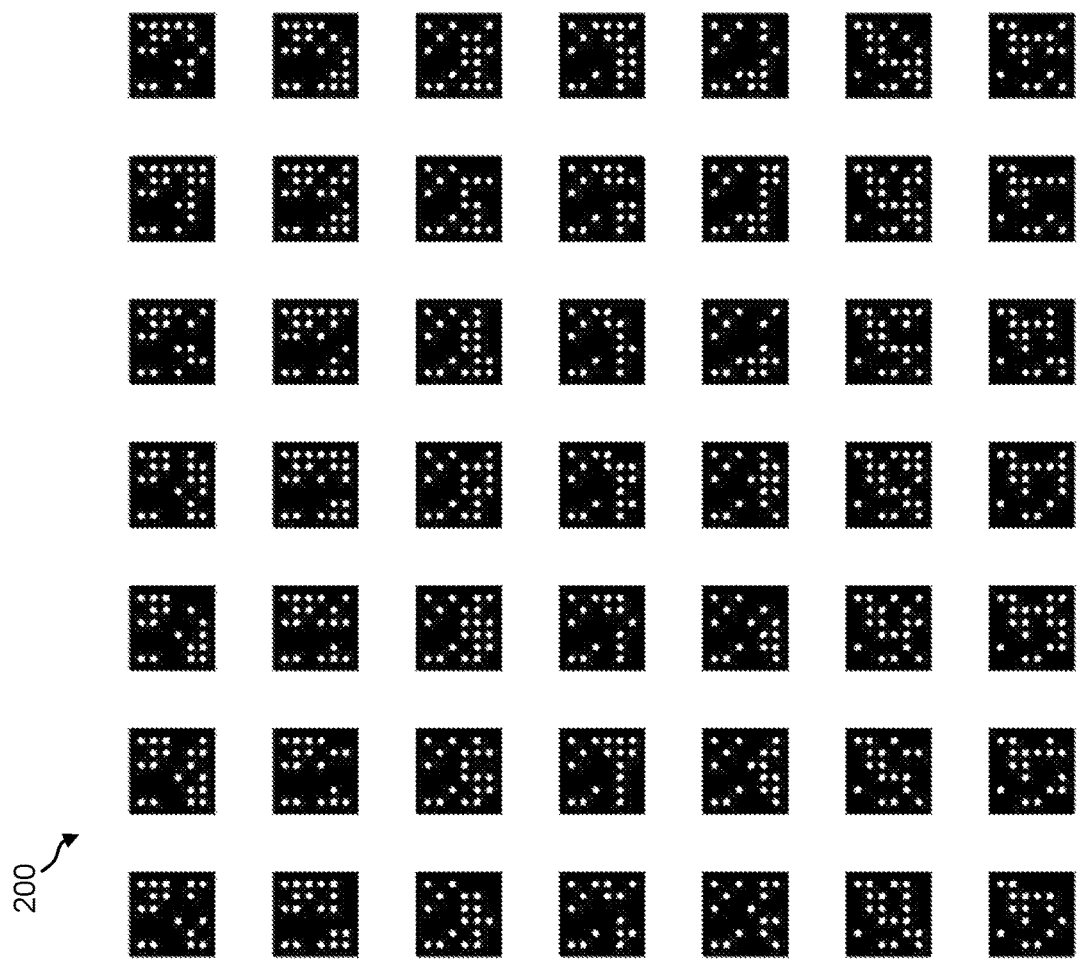
Figure 9:
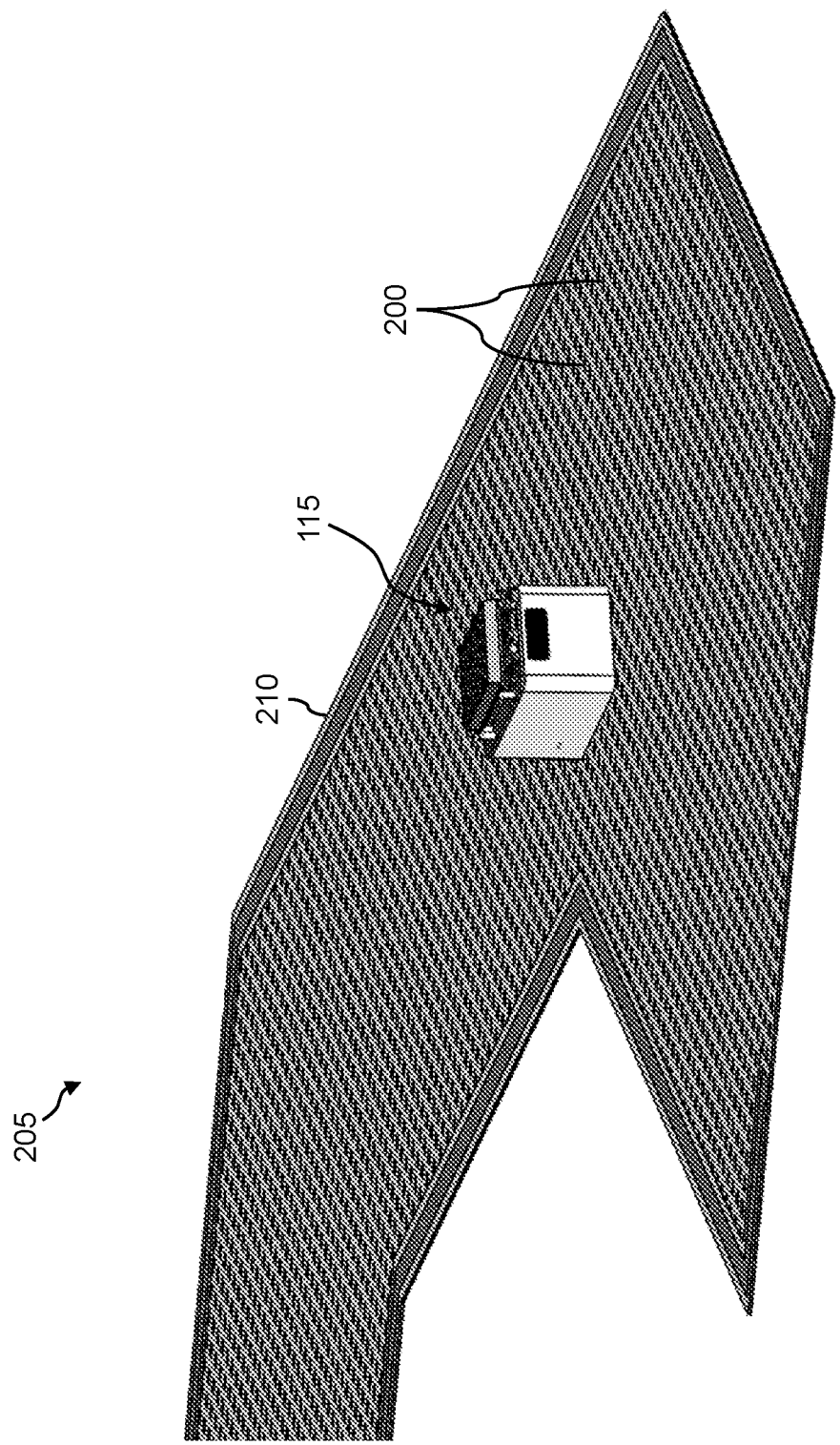
Figure 14:
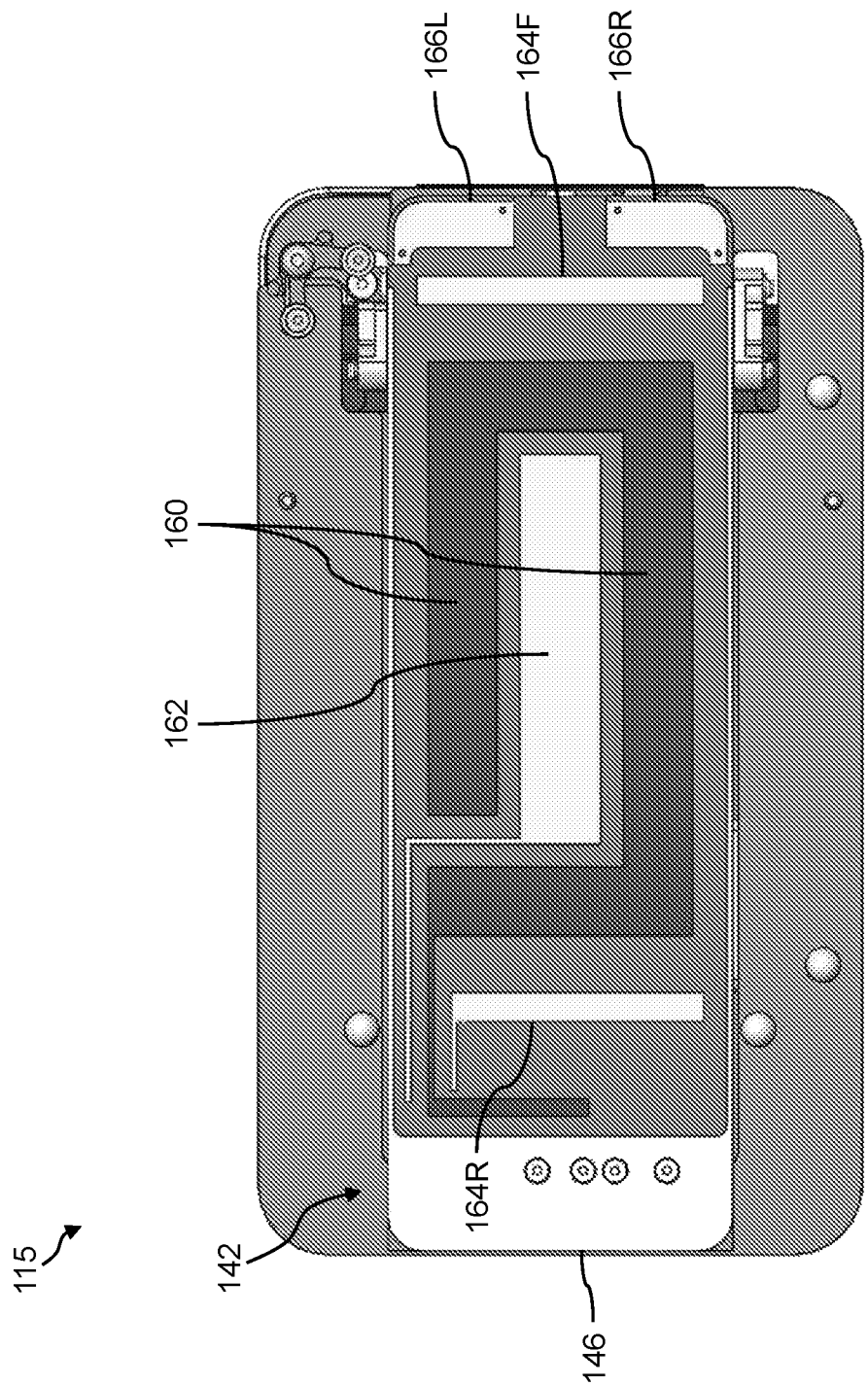
Figure 15:
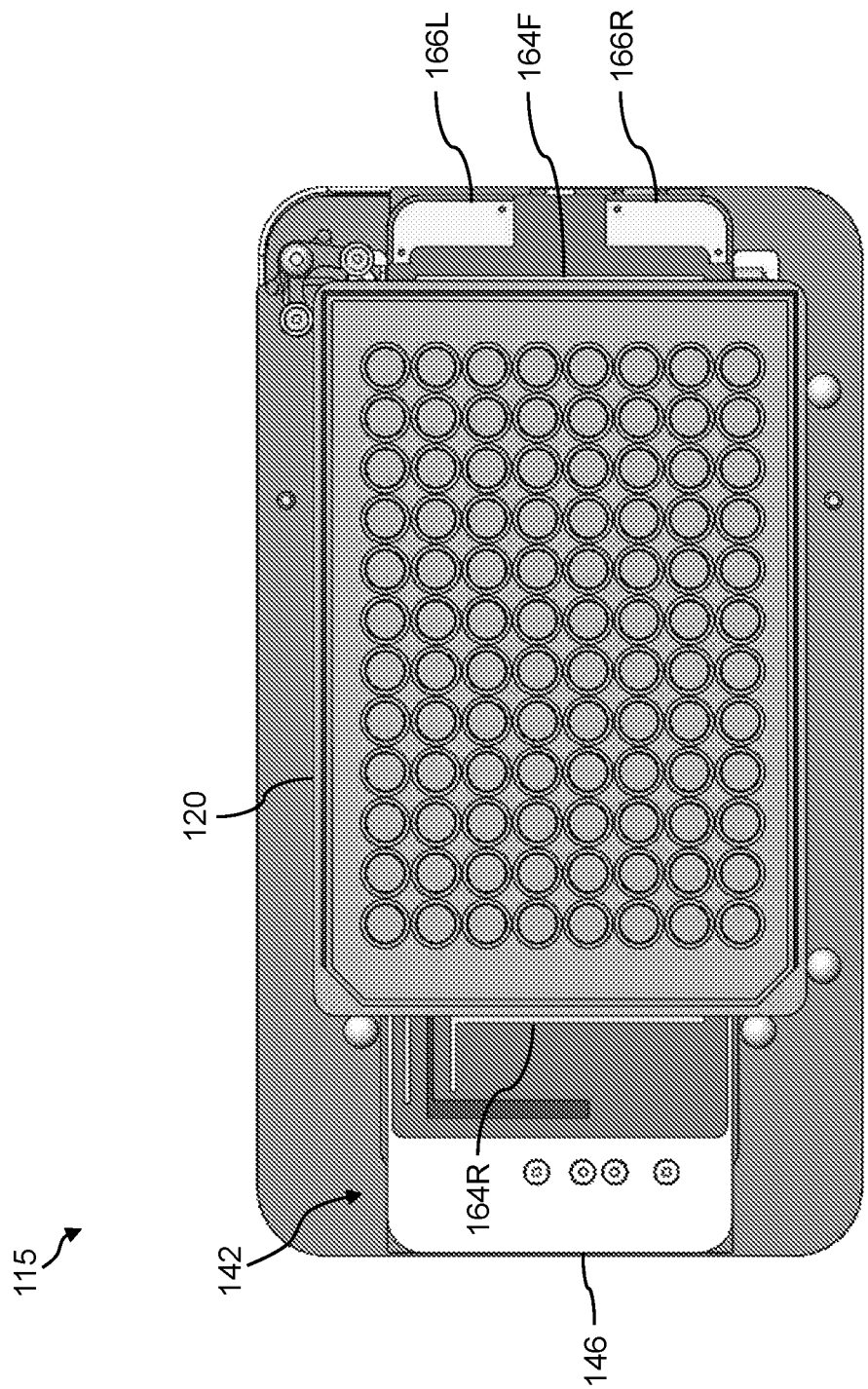
Figure 16:
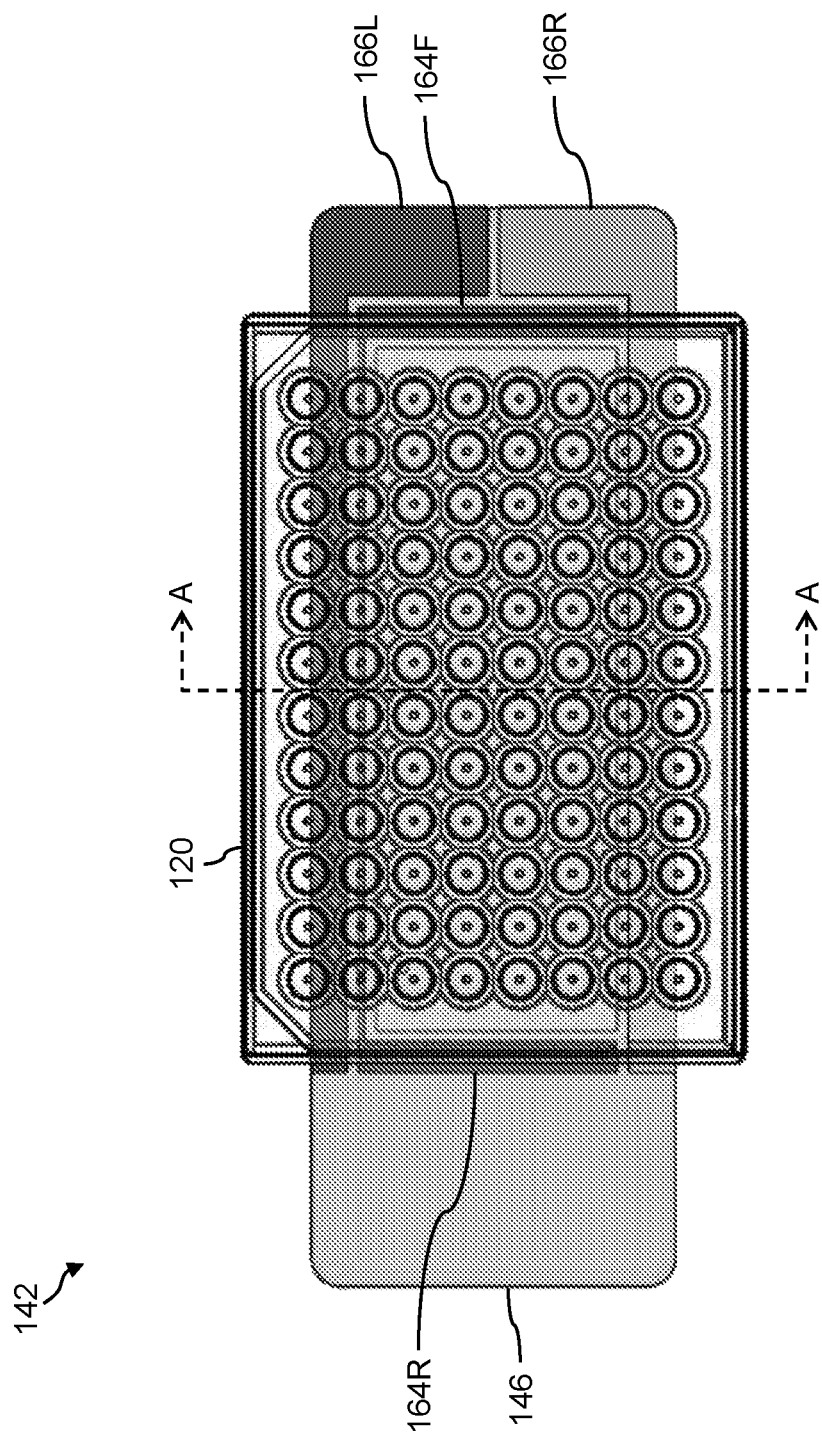
Figure 17:
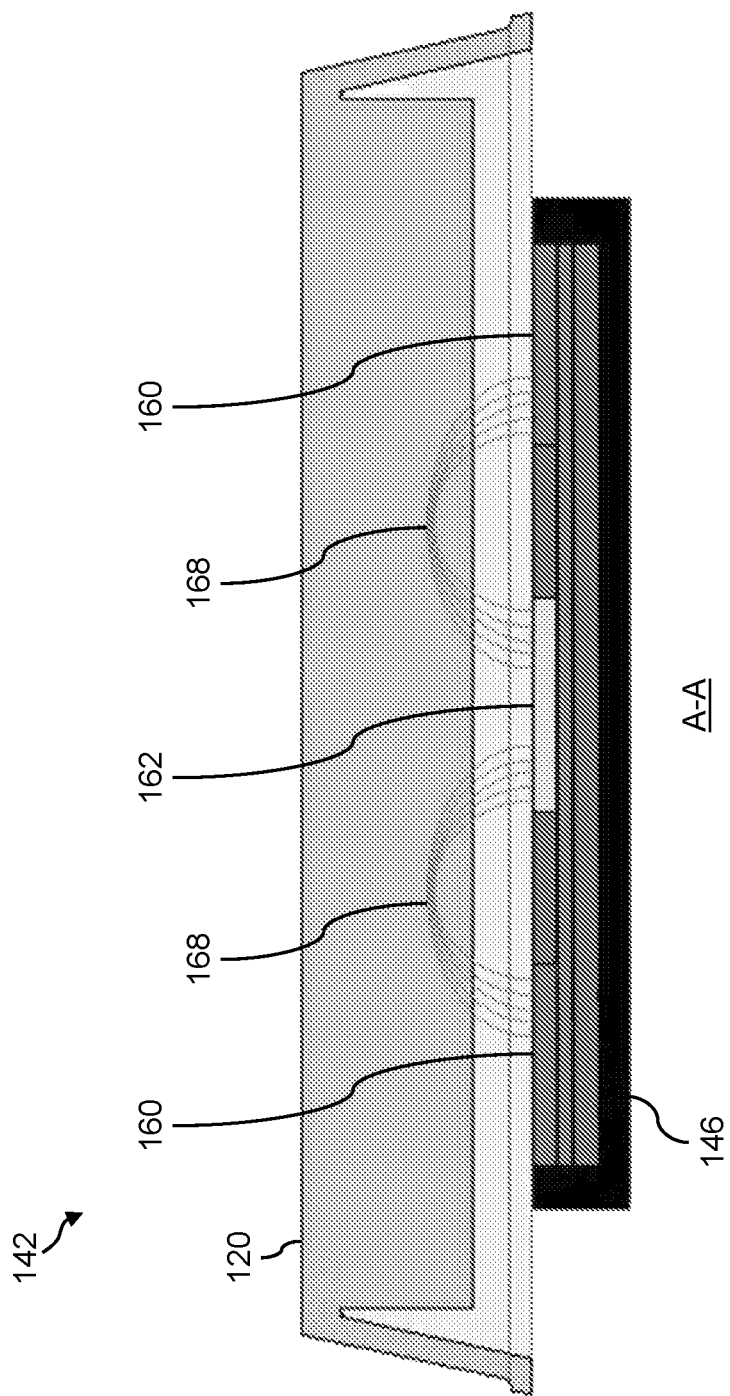
Figure 18B:
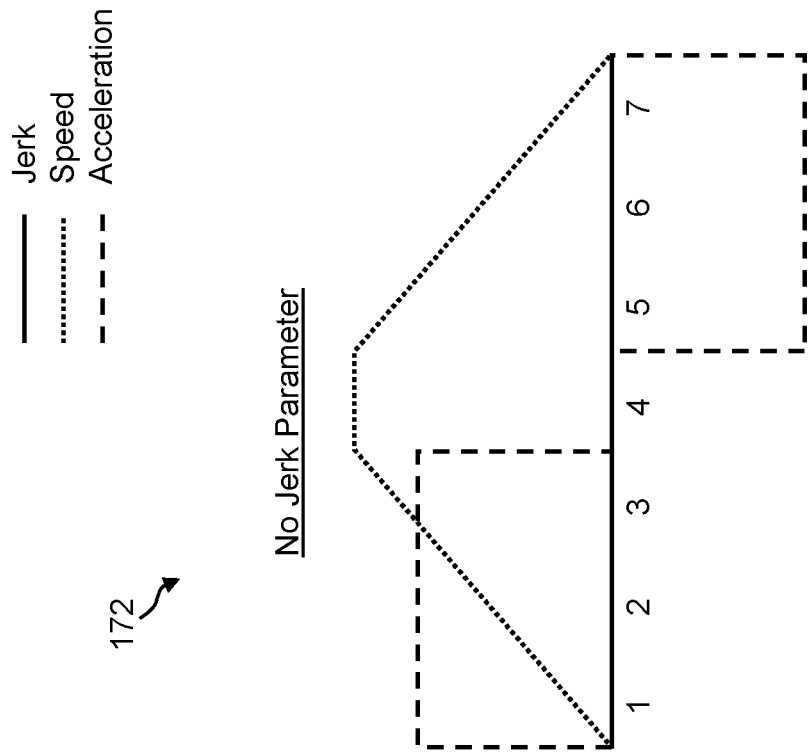
Figure 18A:
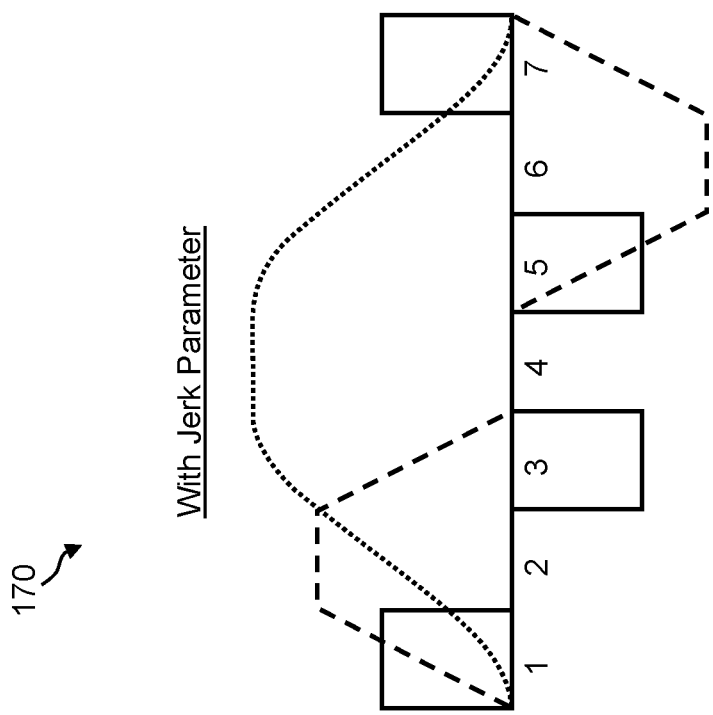
Figure 19:
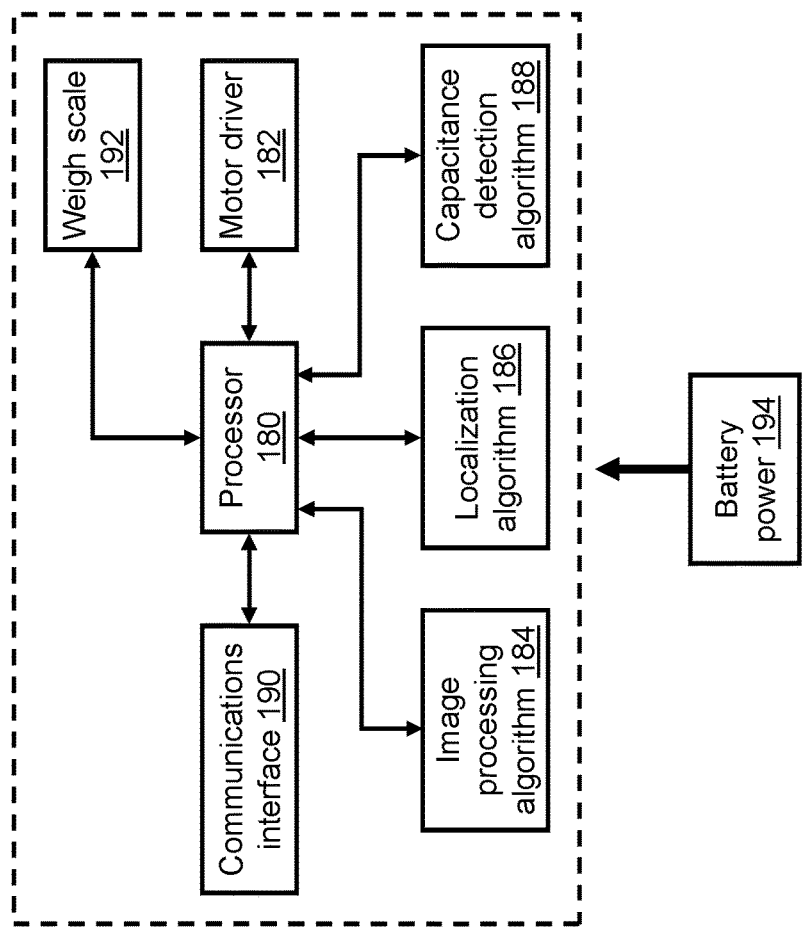
Figure 20:
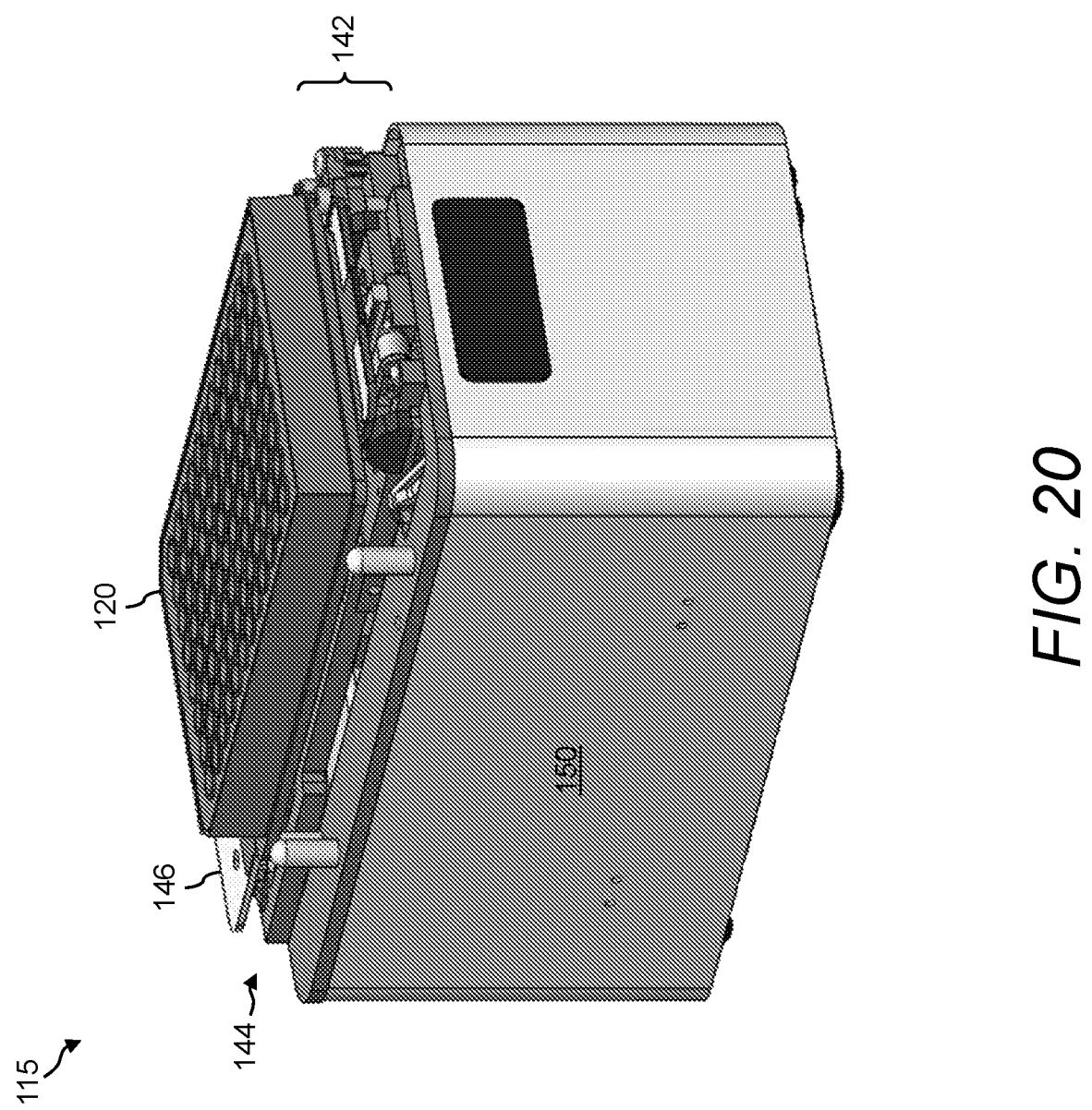
Figure 21:
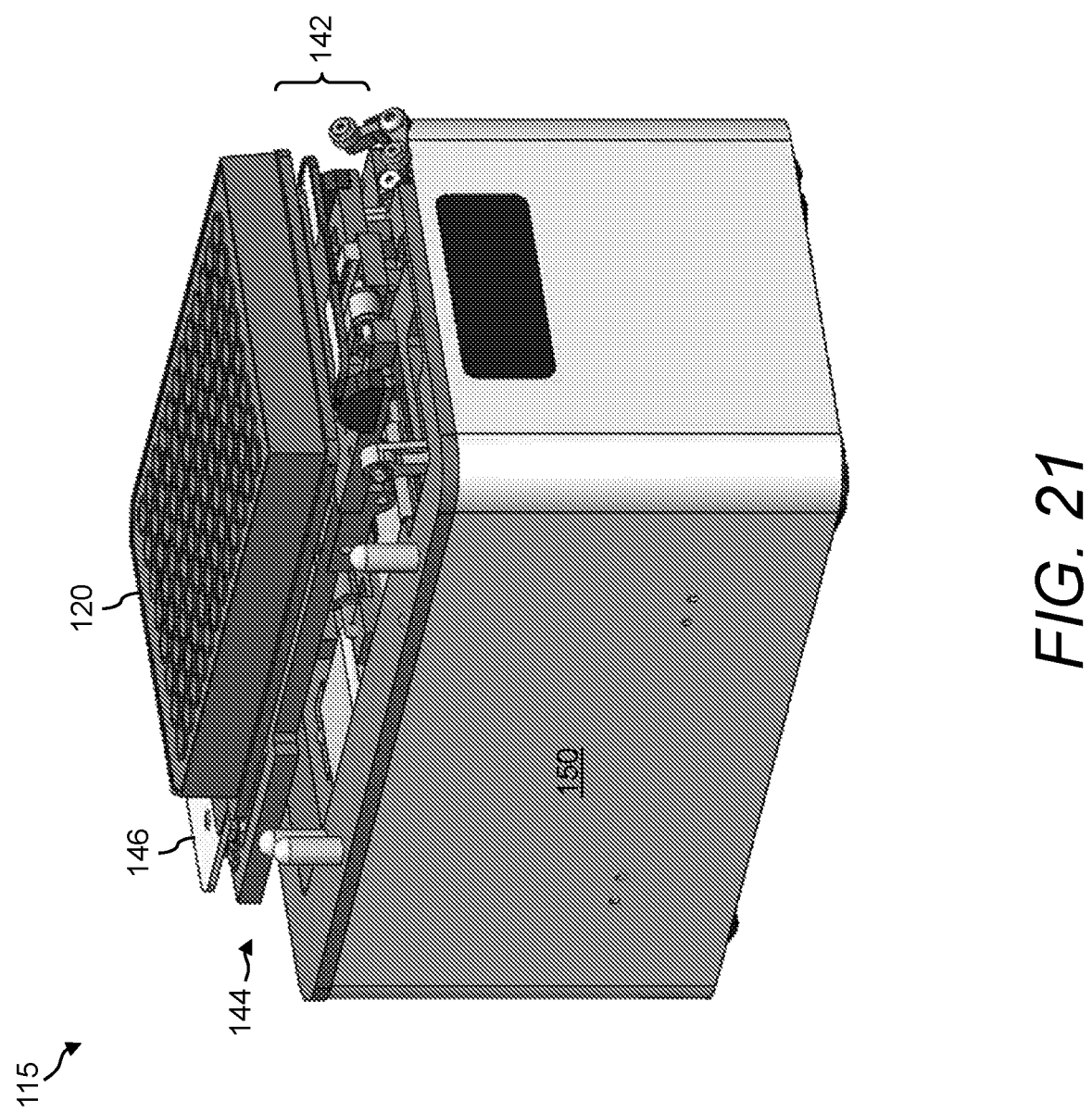
Figure 22:
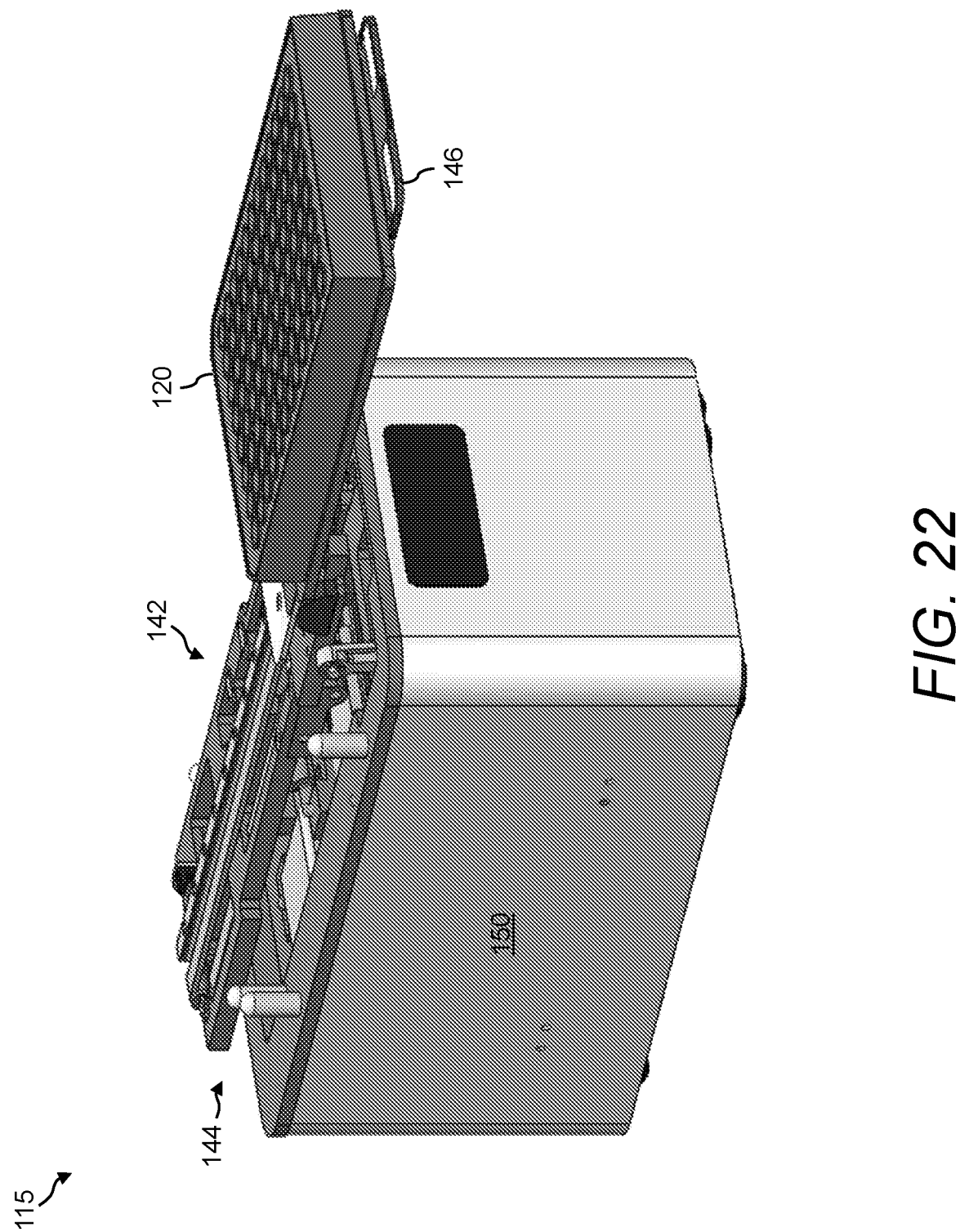
Figure 23:
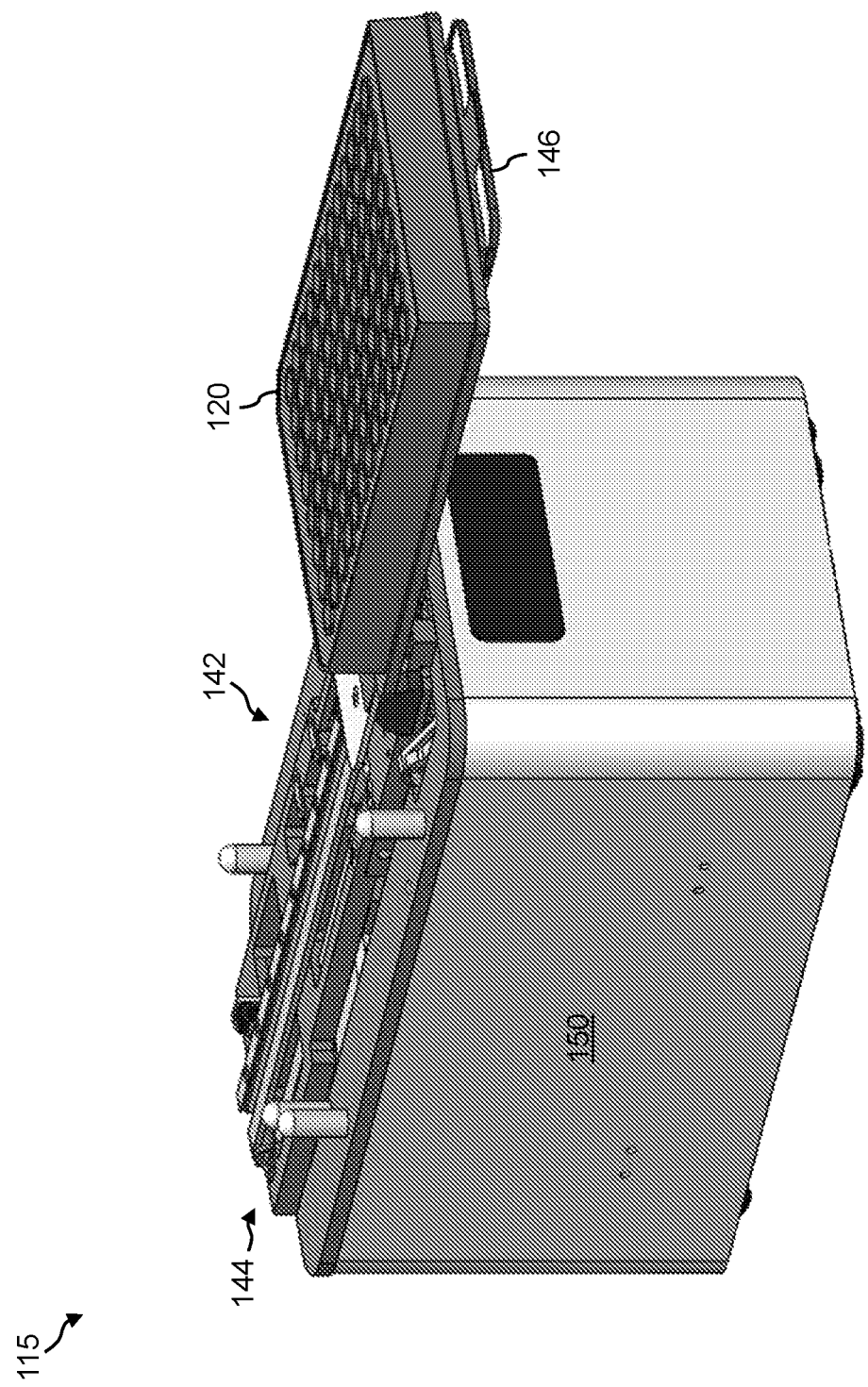
Figure 24:
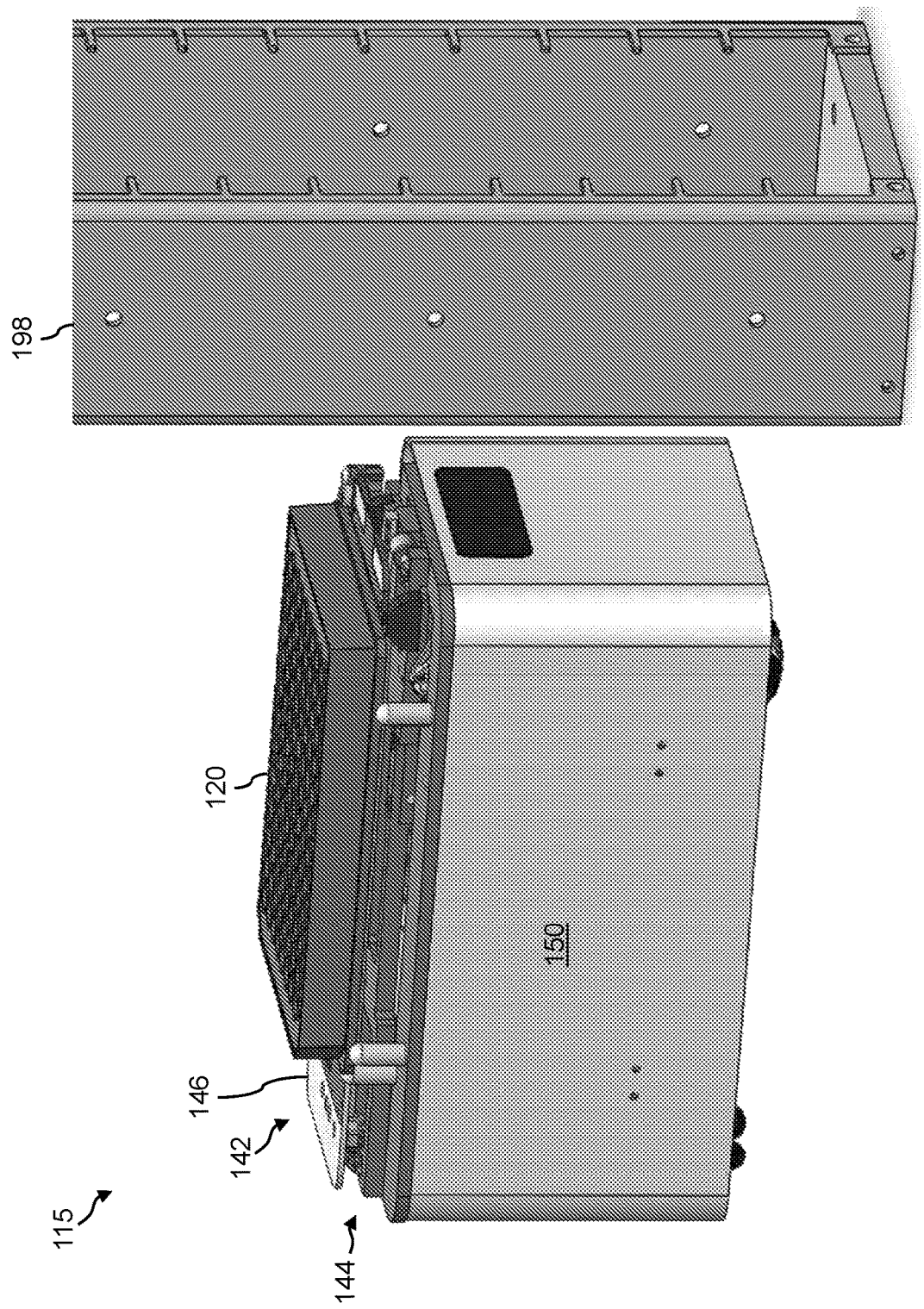
Figure 25:
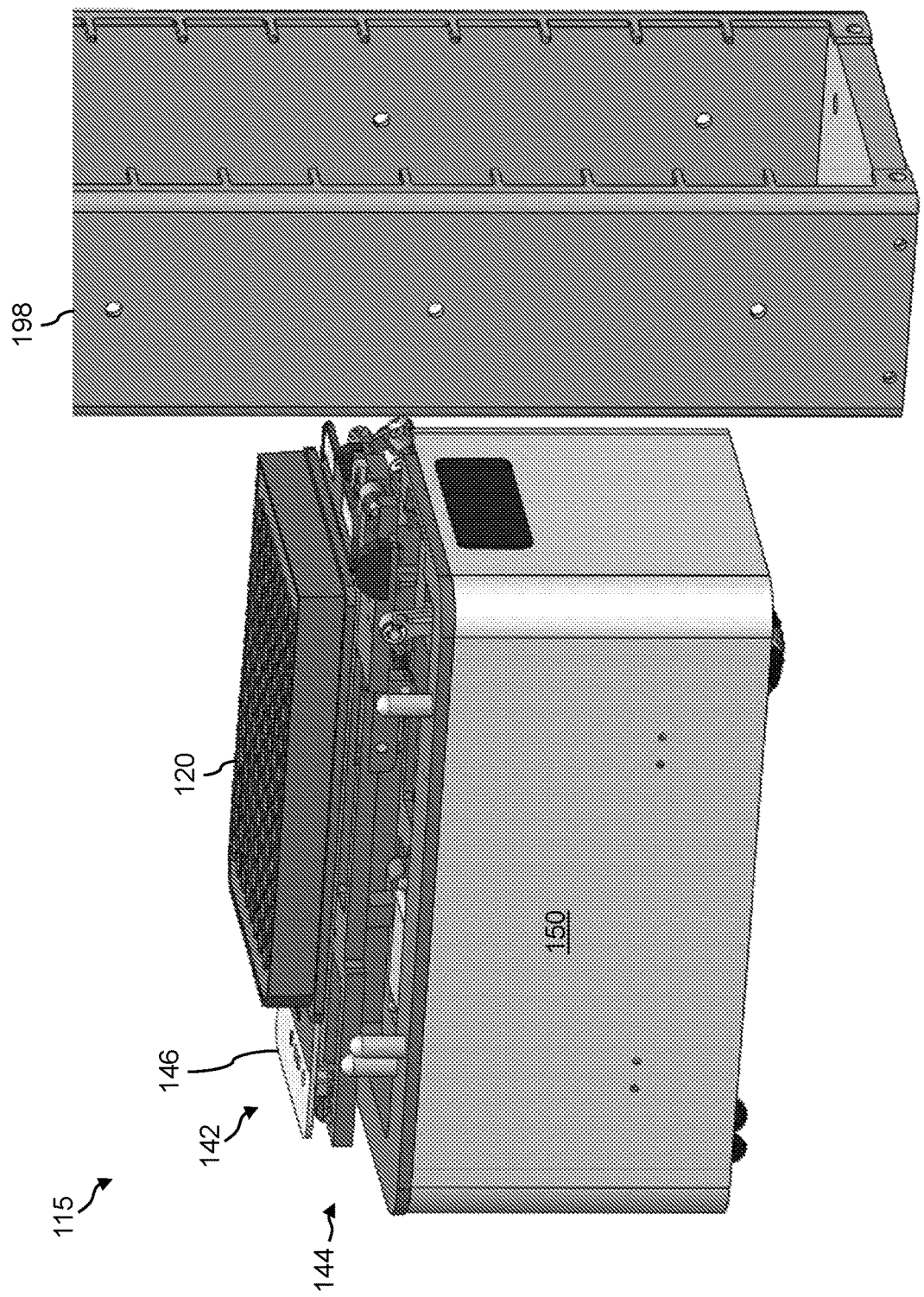
Figure 26:
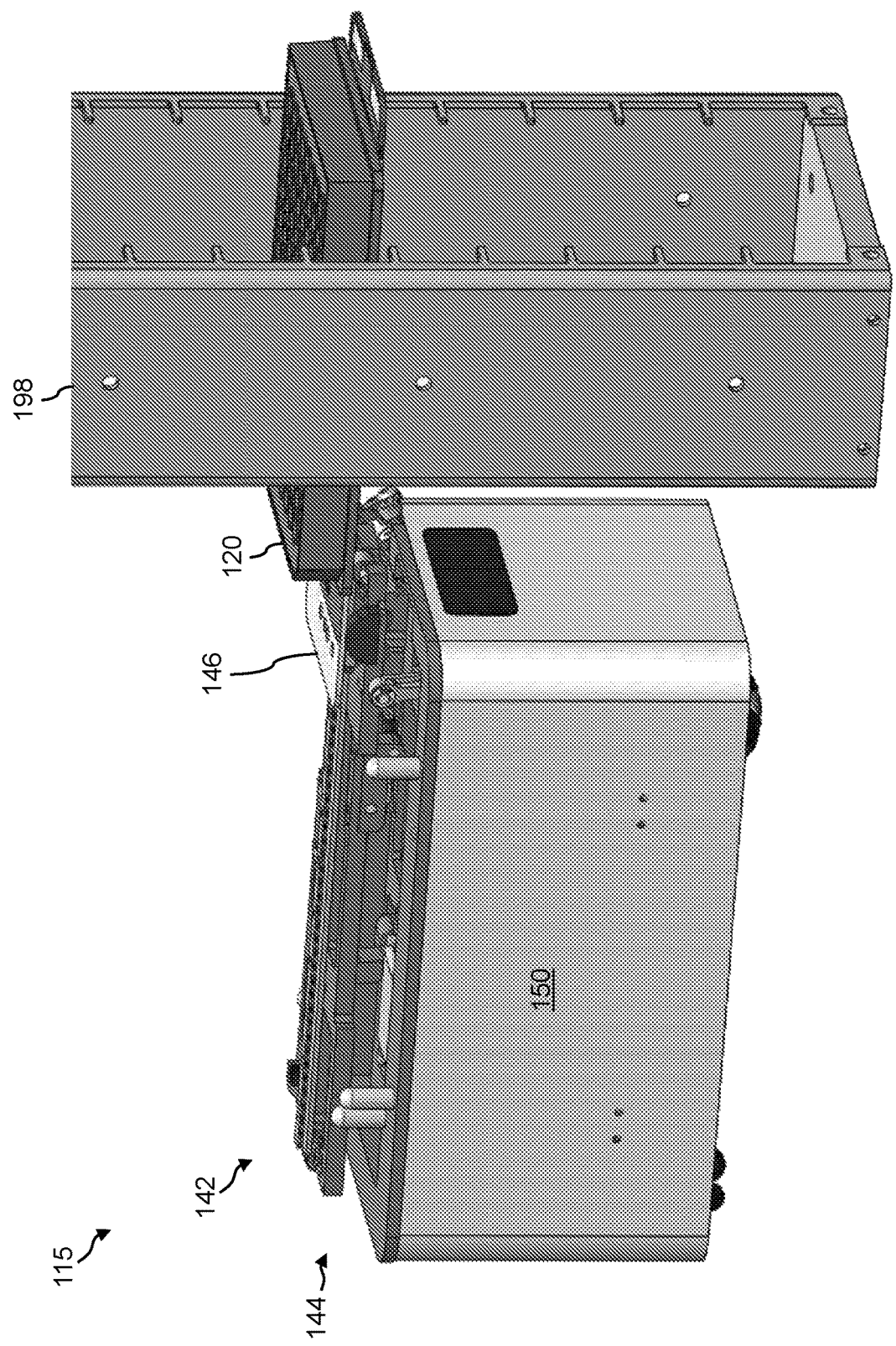
Figure 27:
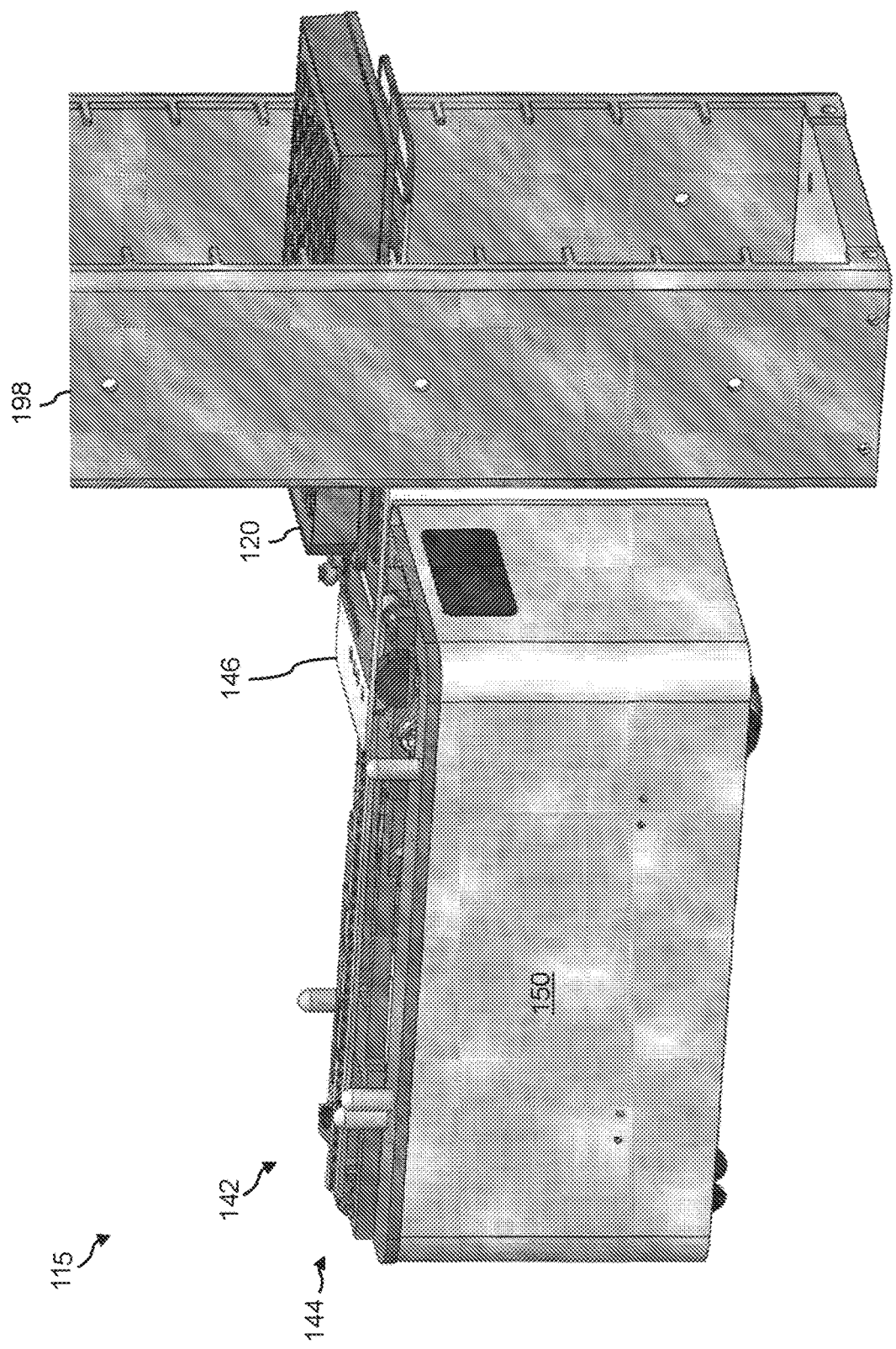
Figure 28:
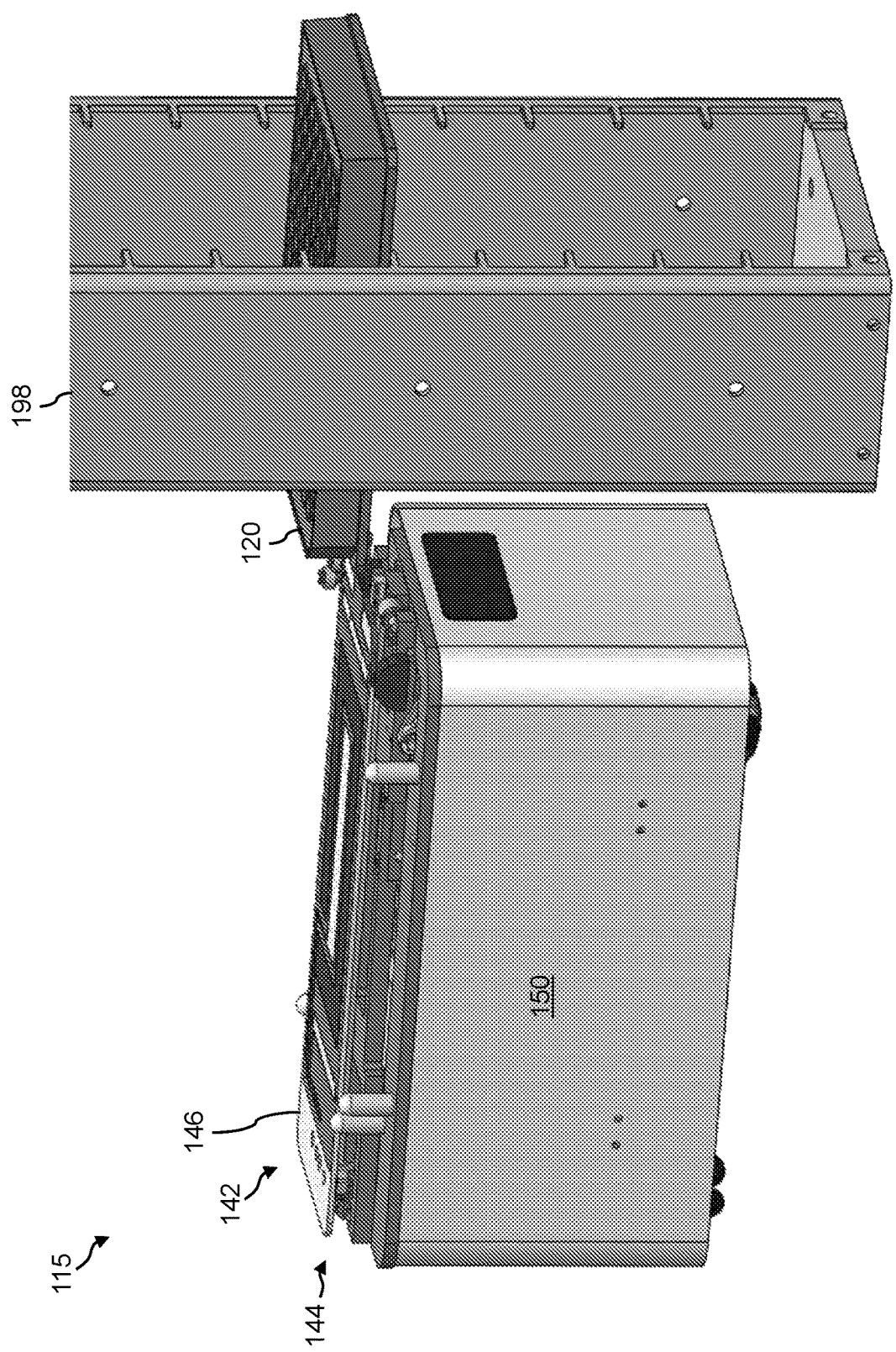
Figure 29:
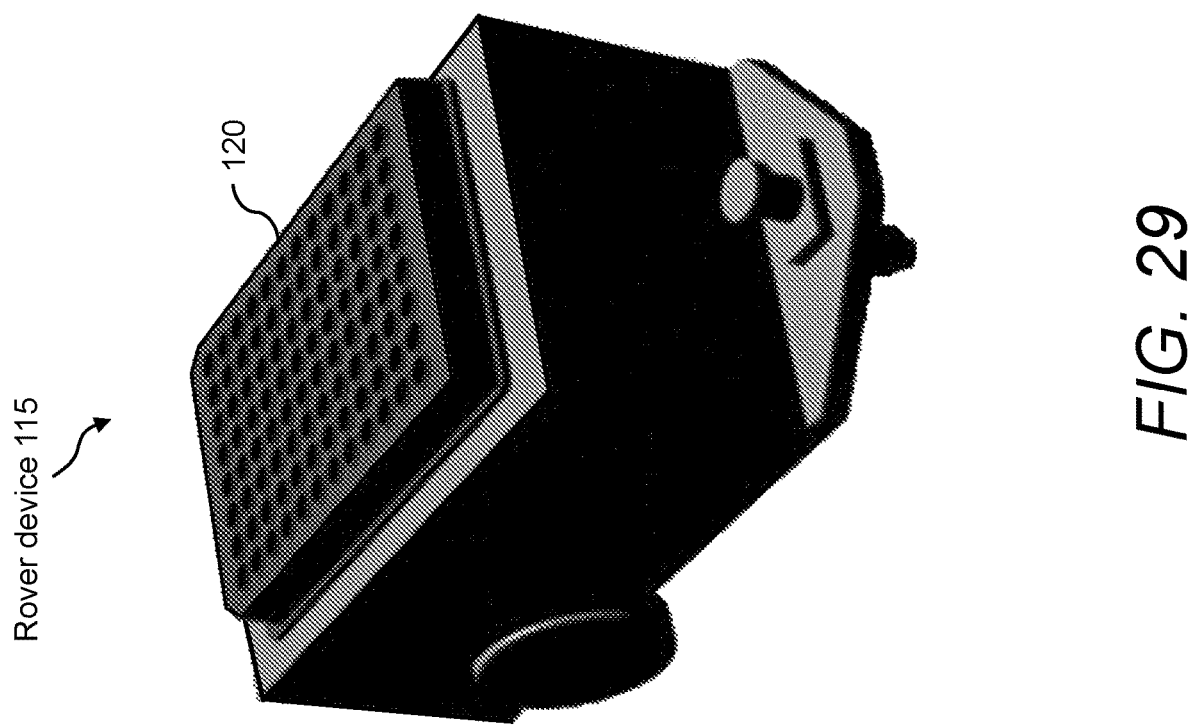
Figure 30:
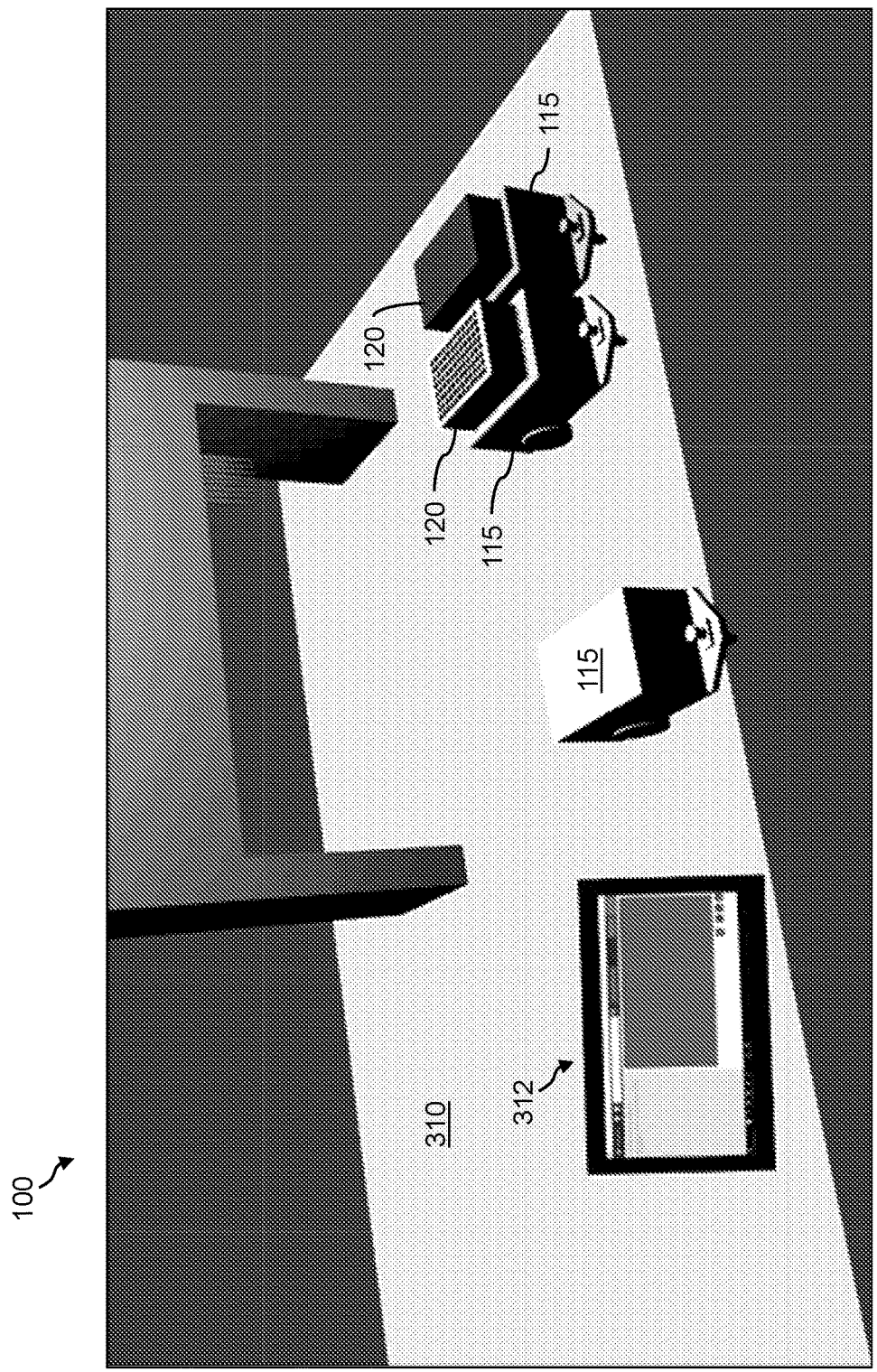
Figure 31:
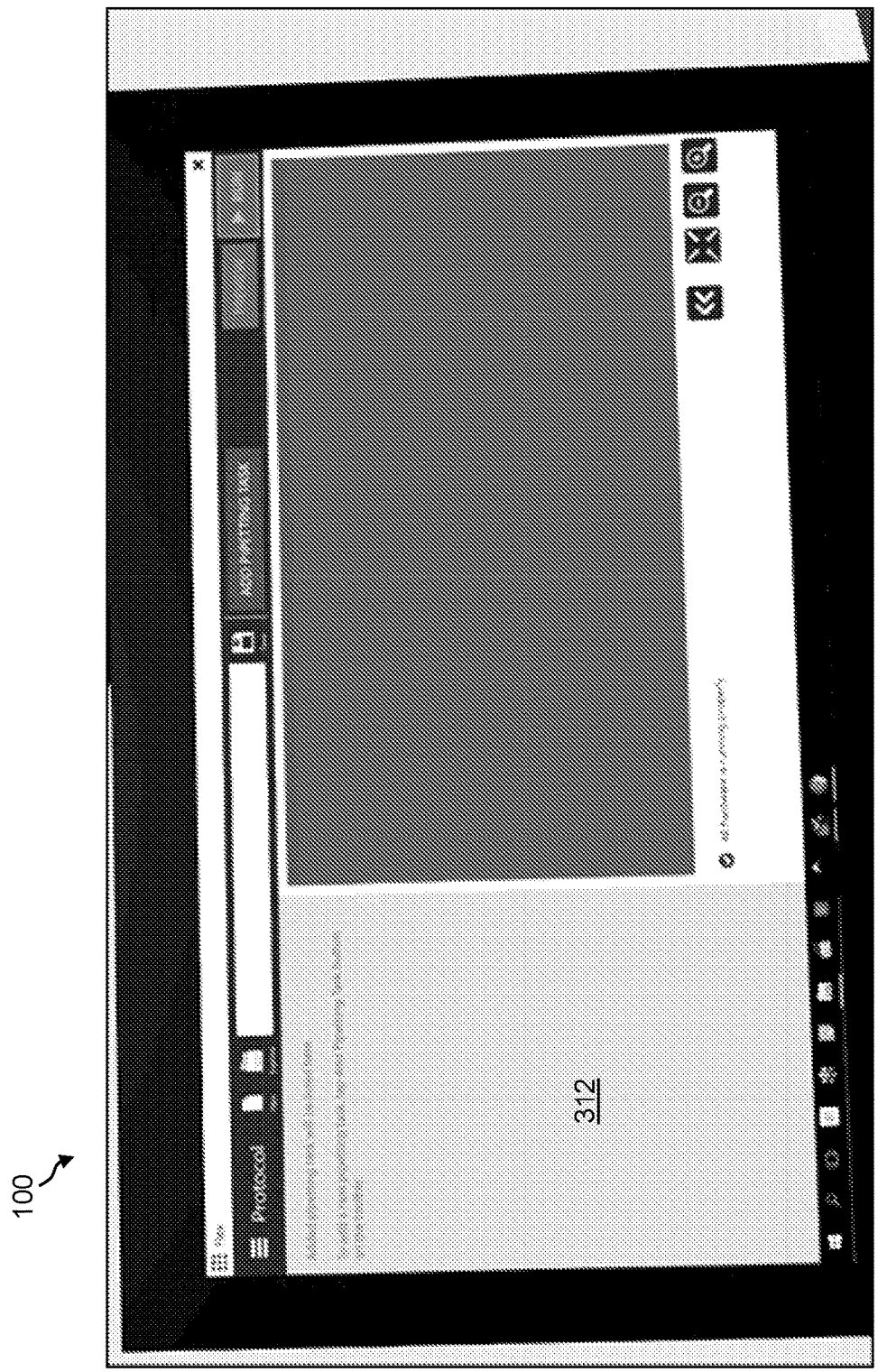
Figure 32:
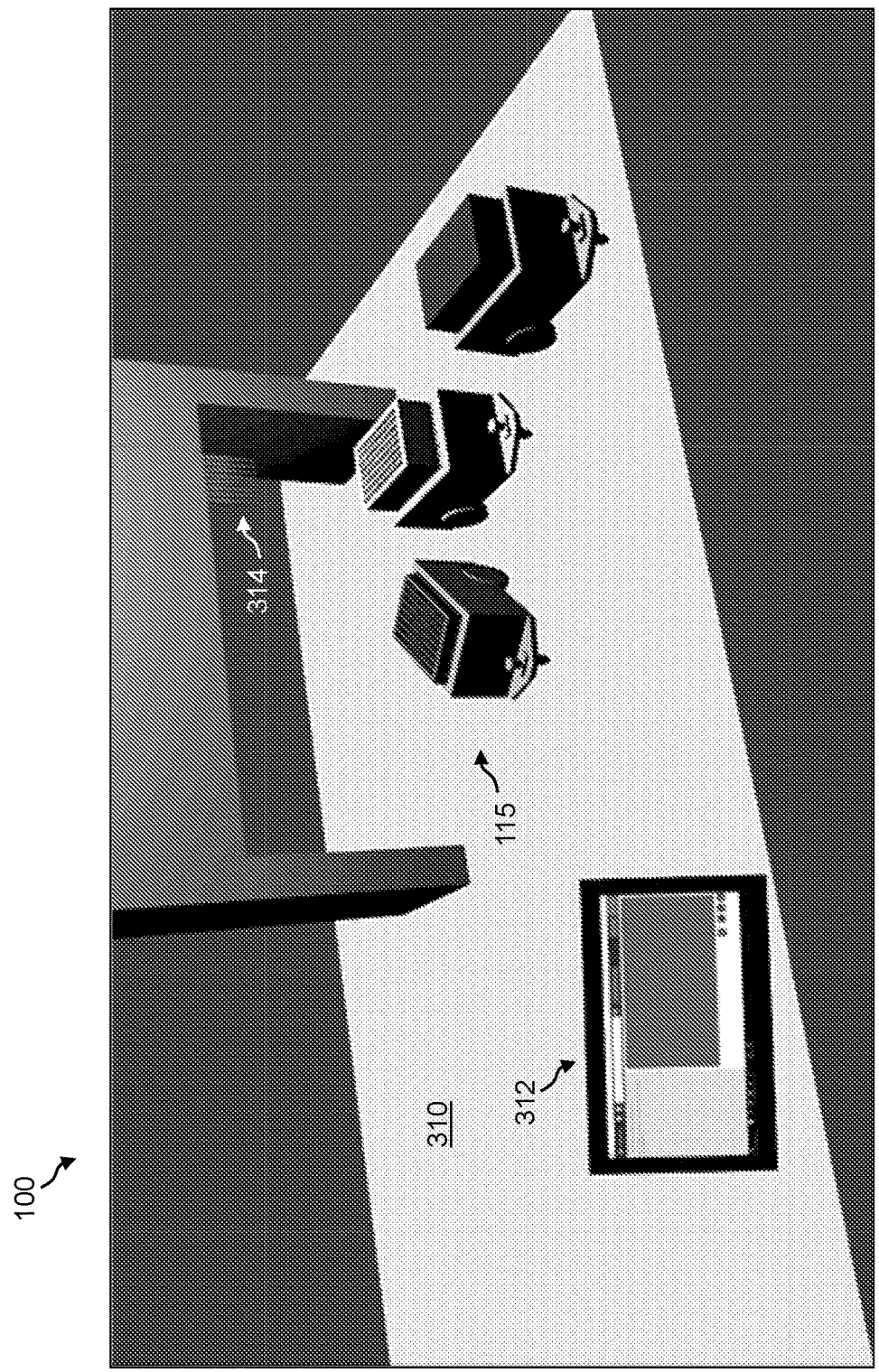
Figure 33:
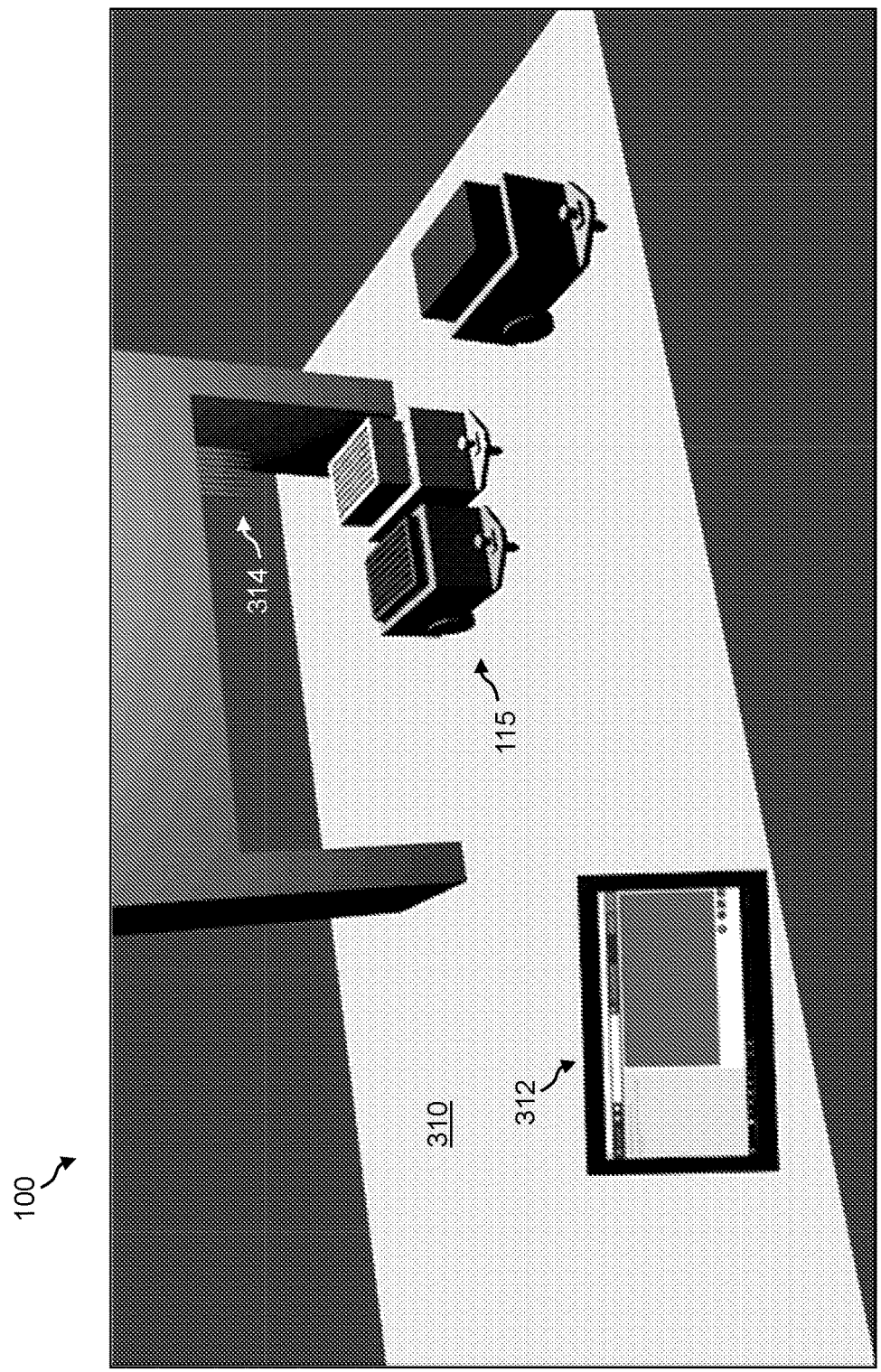
Figure 34:
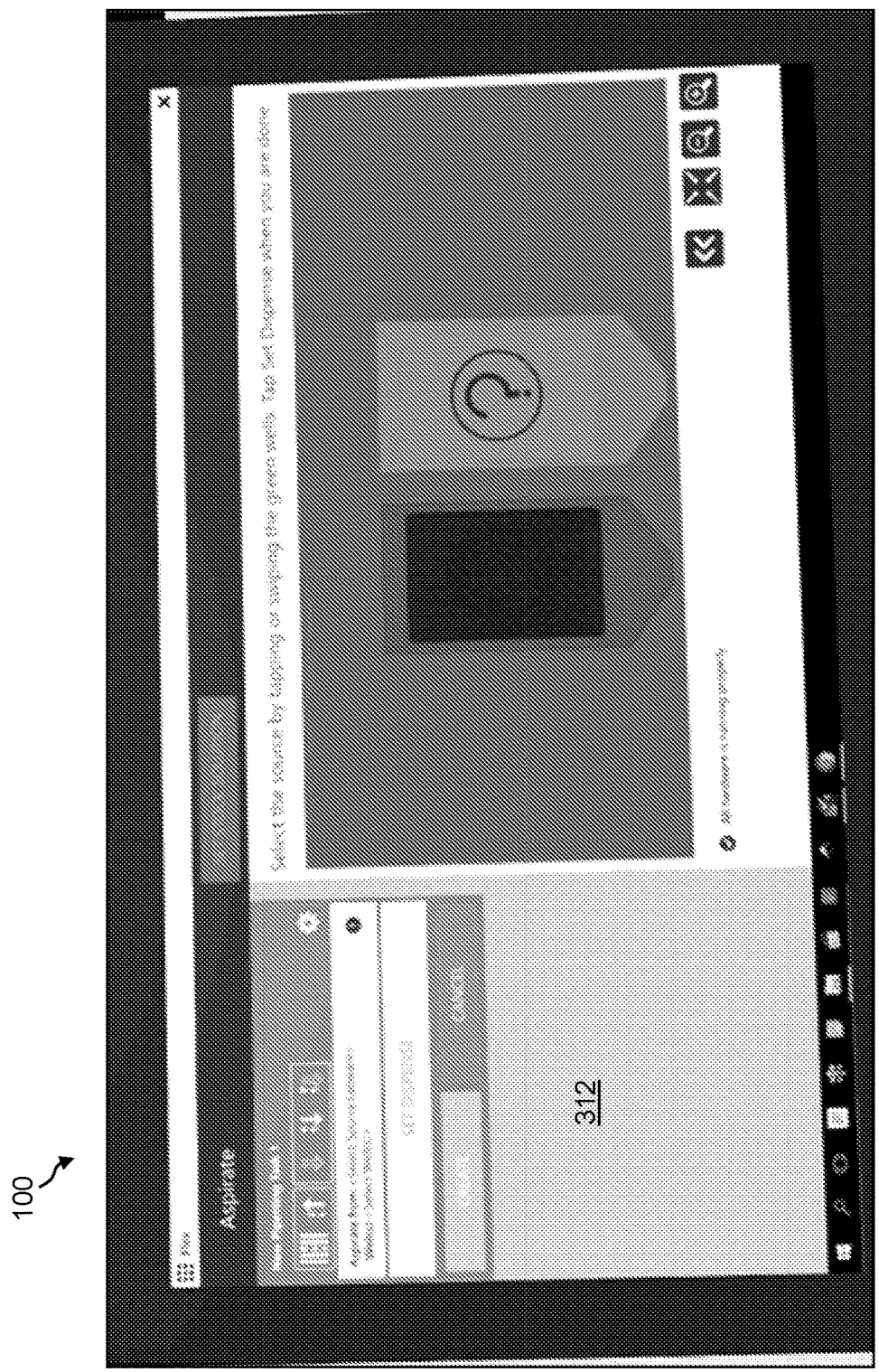
Figure 35:
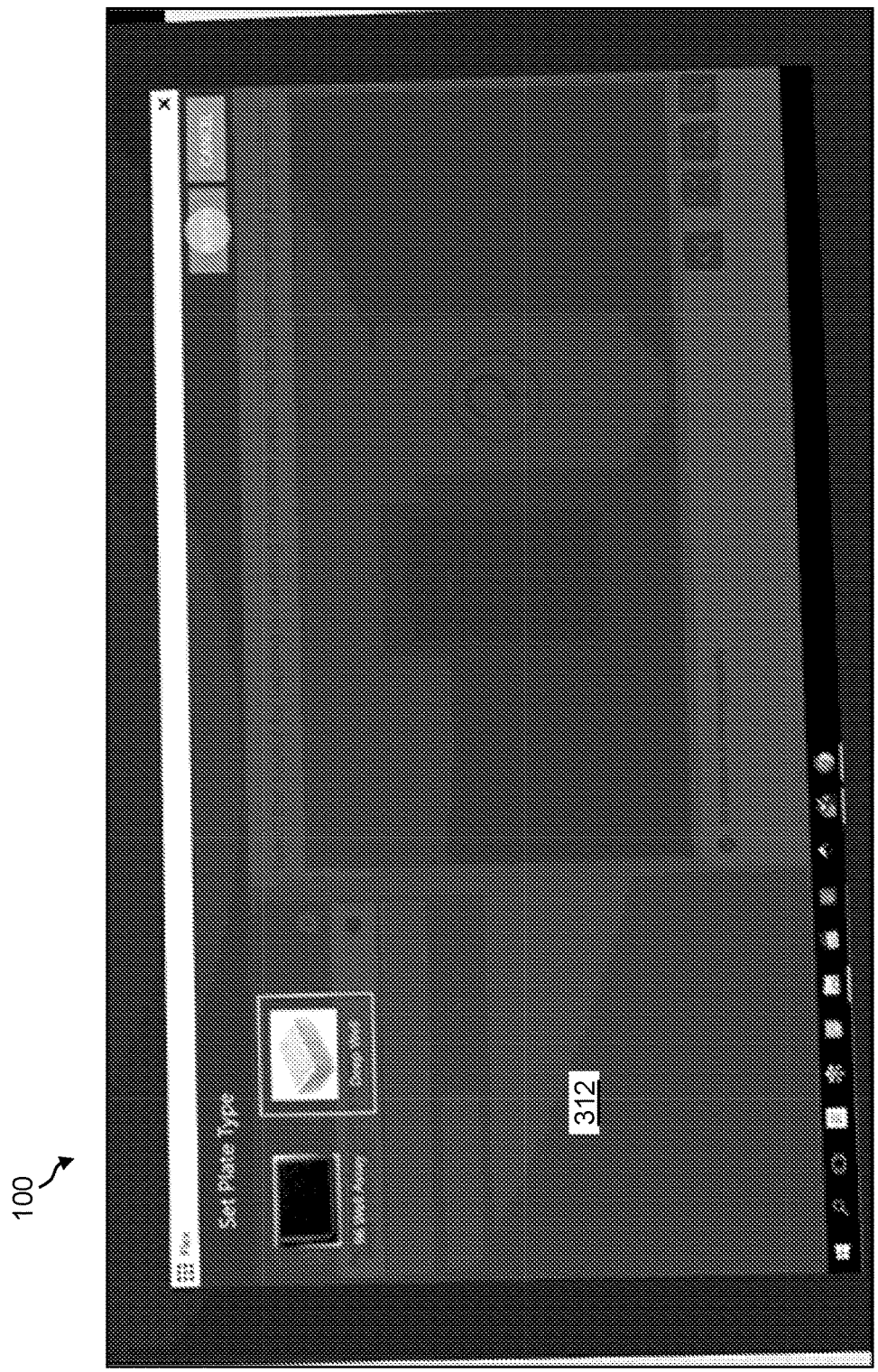
Figure 36:
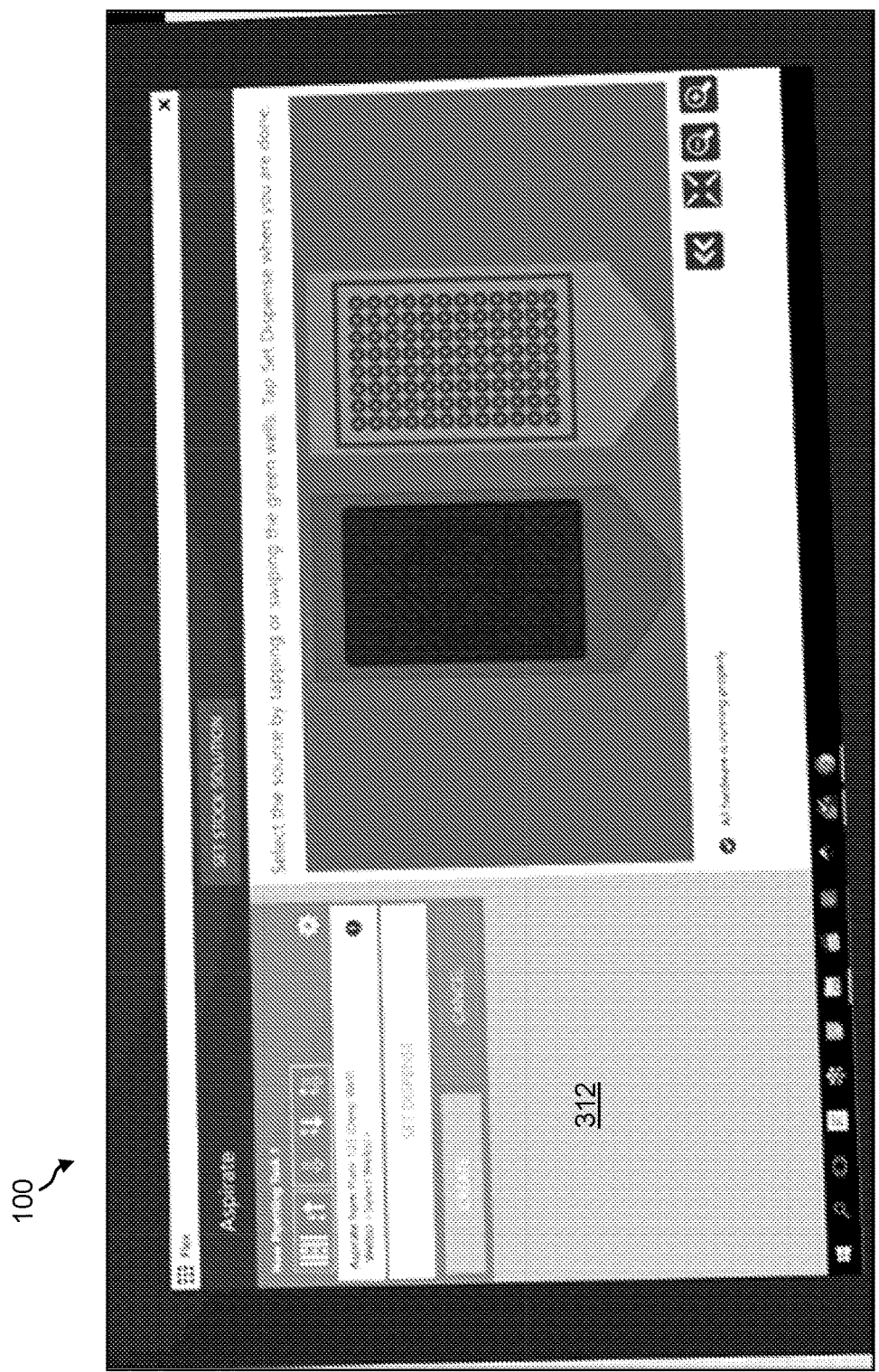
Figure 37:
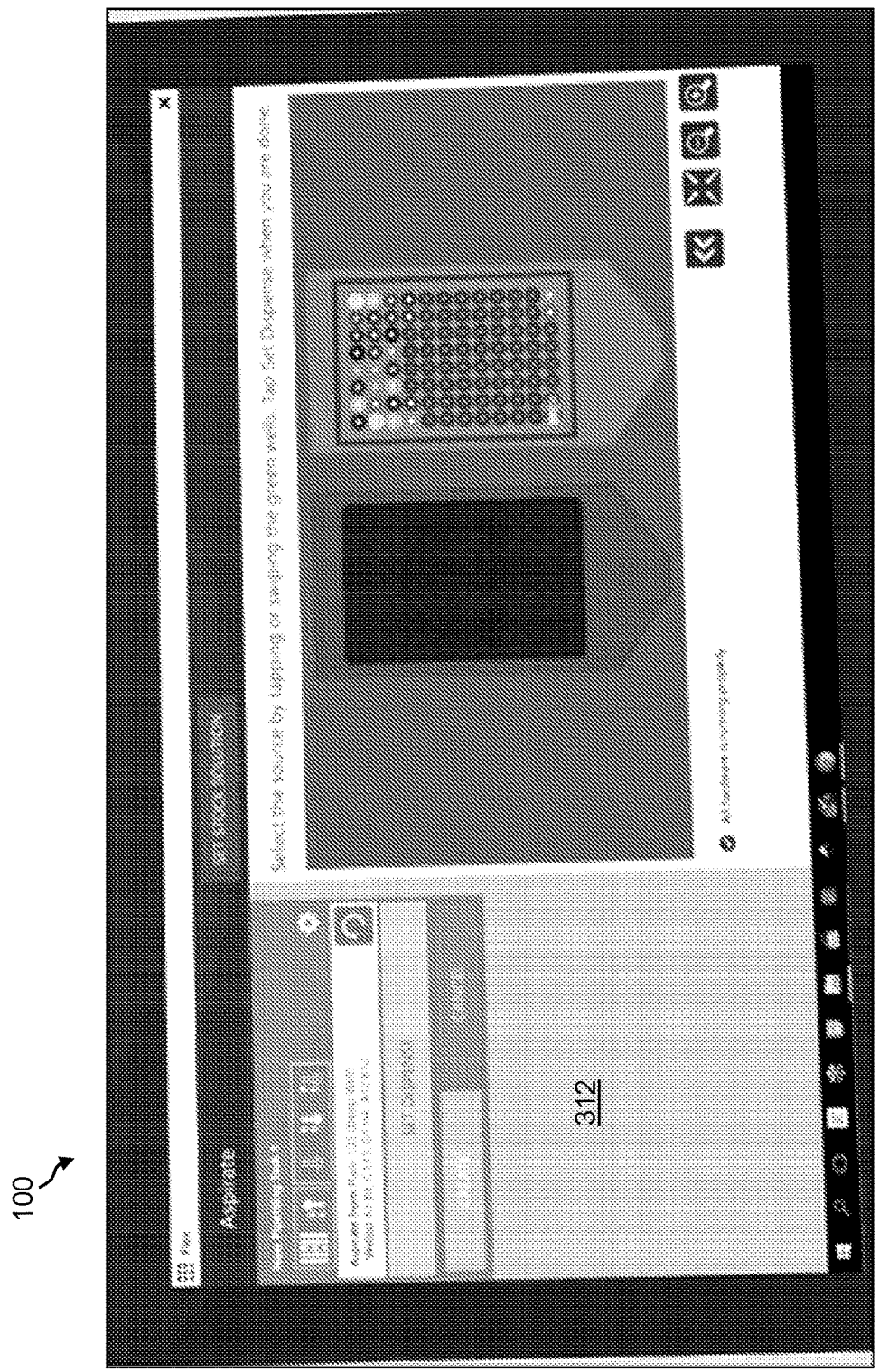
Figure 38:
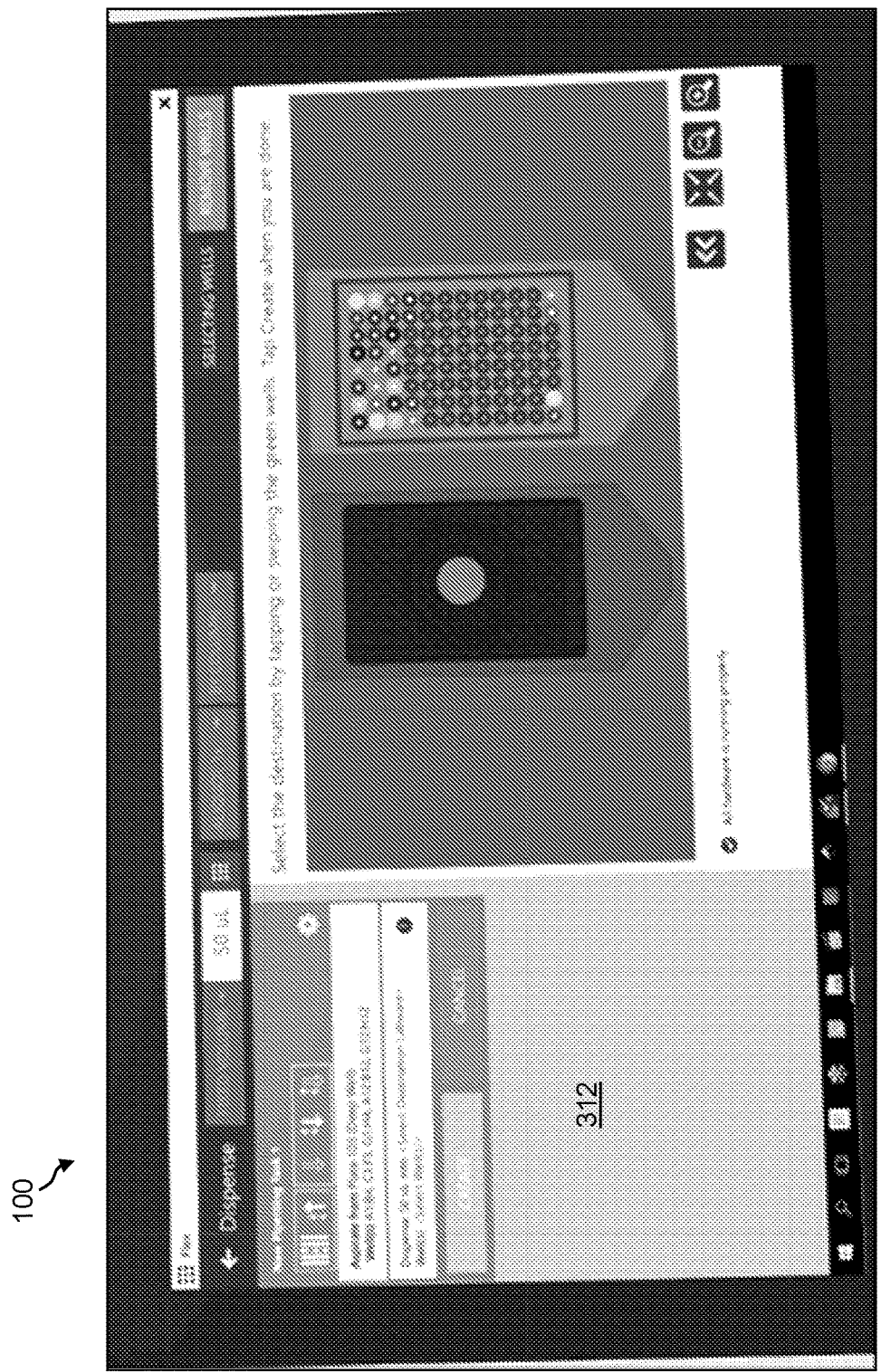
Figure 39:
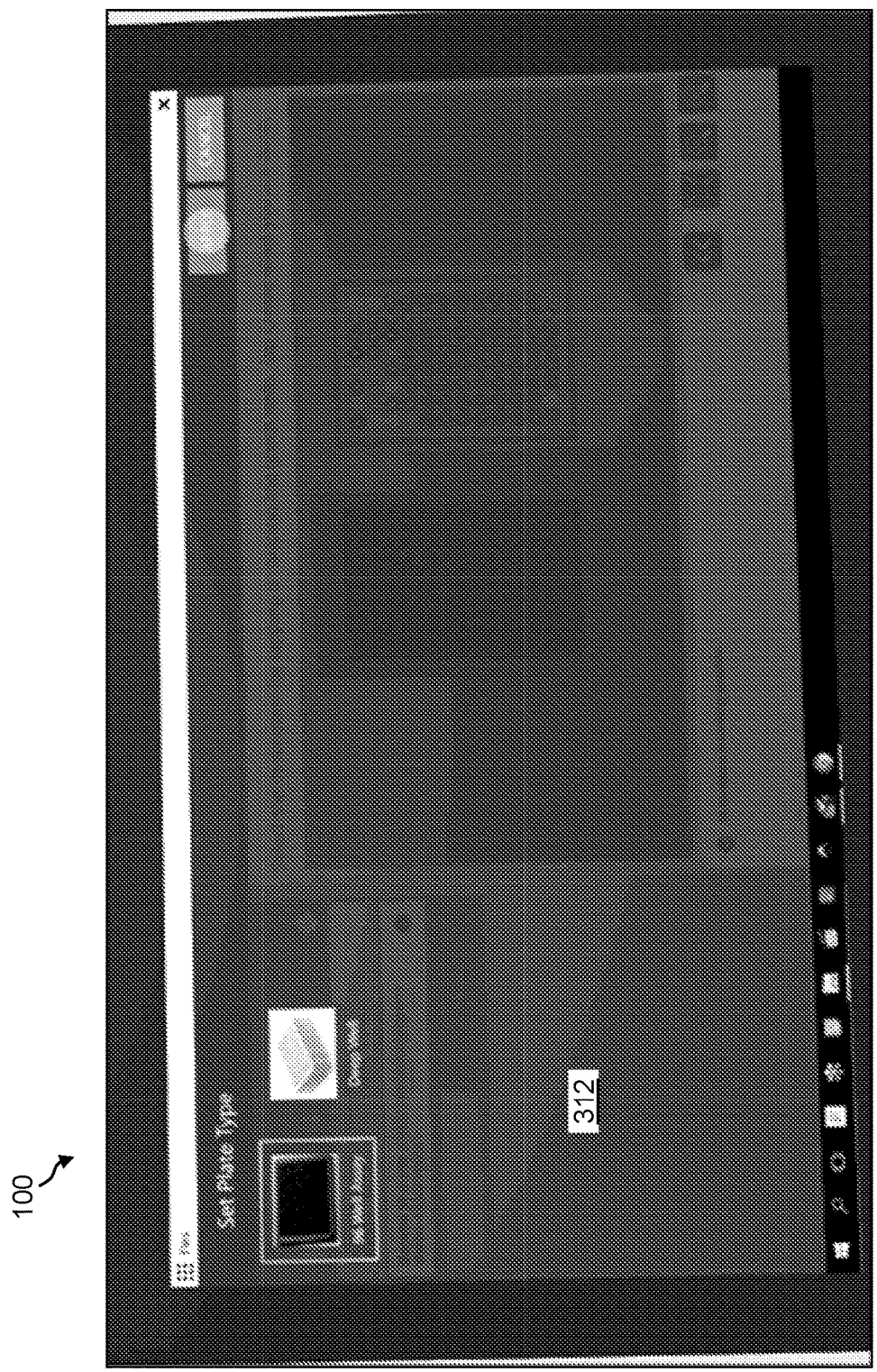
Figure 40:
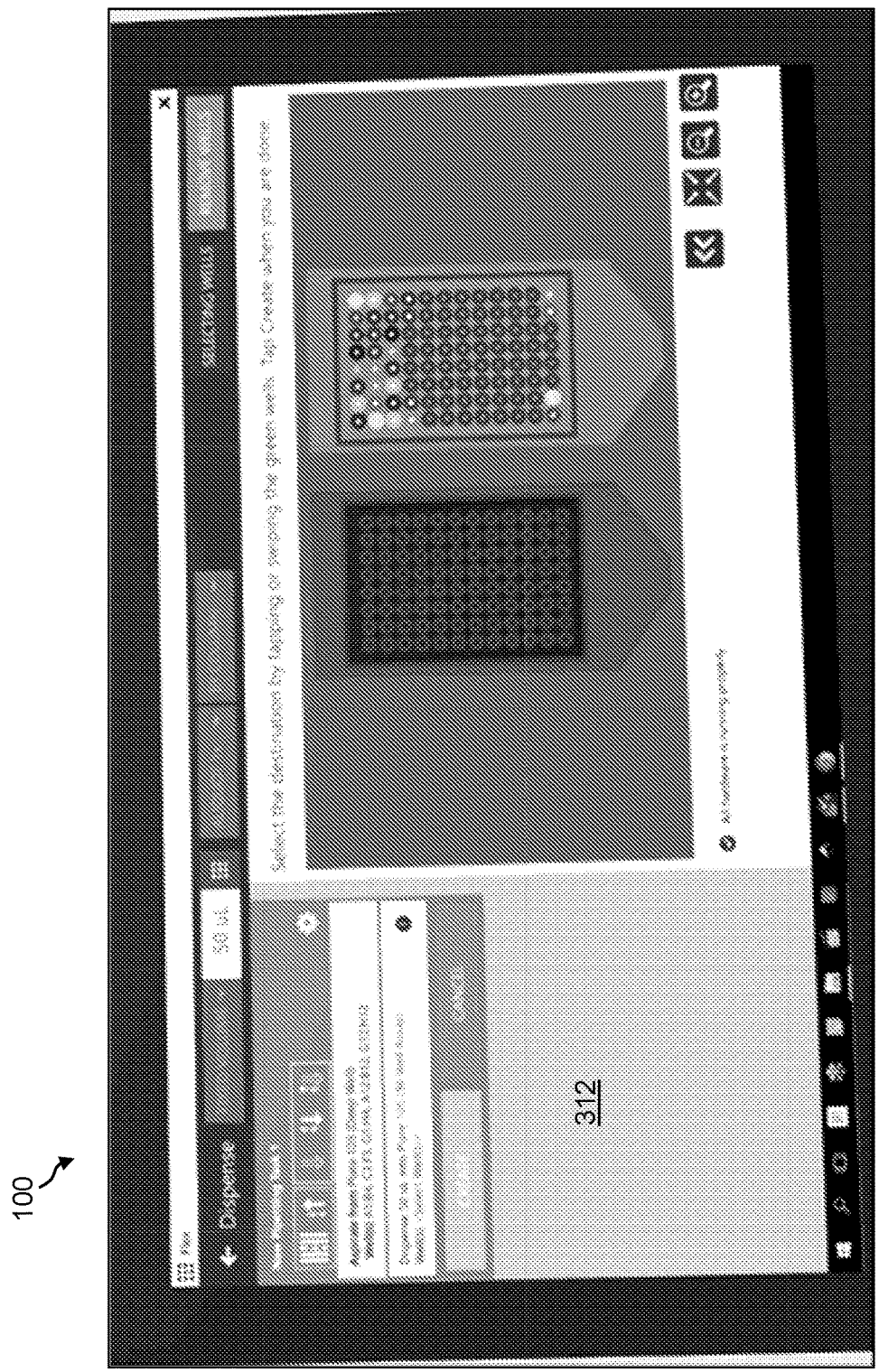
Figure 41:
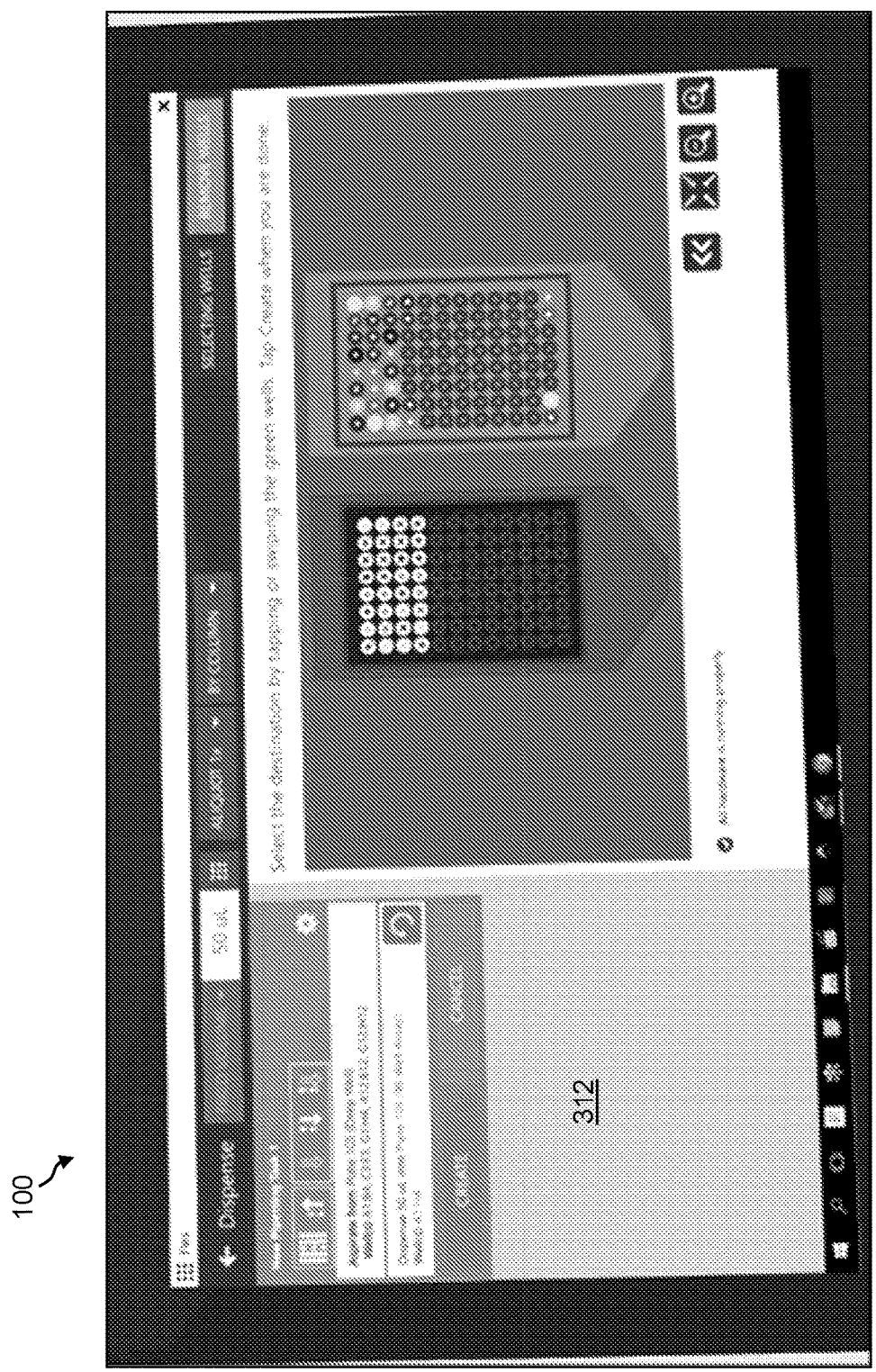
Figure 42:
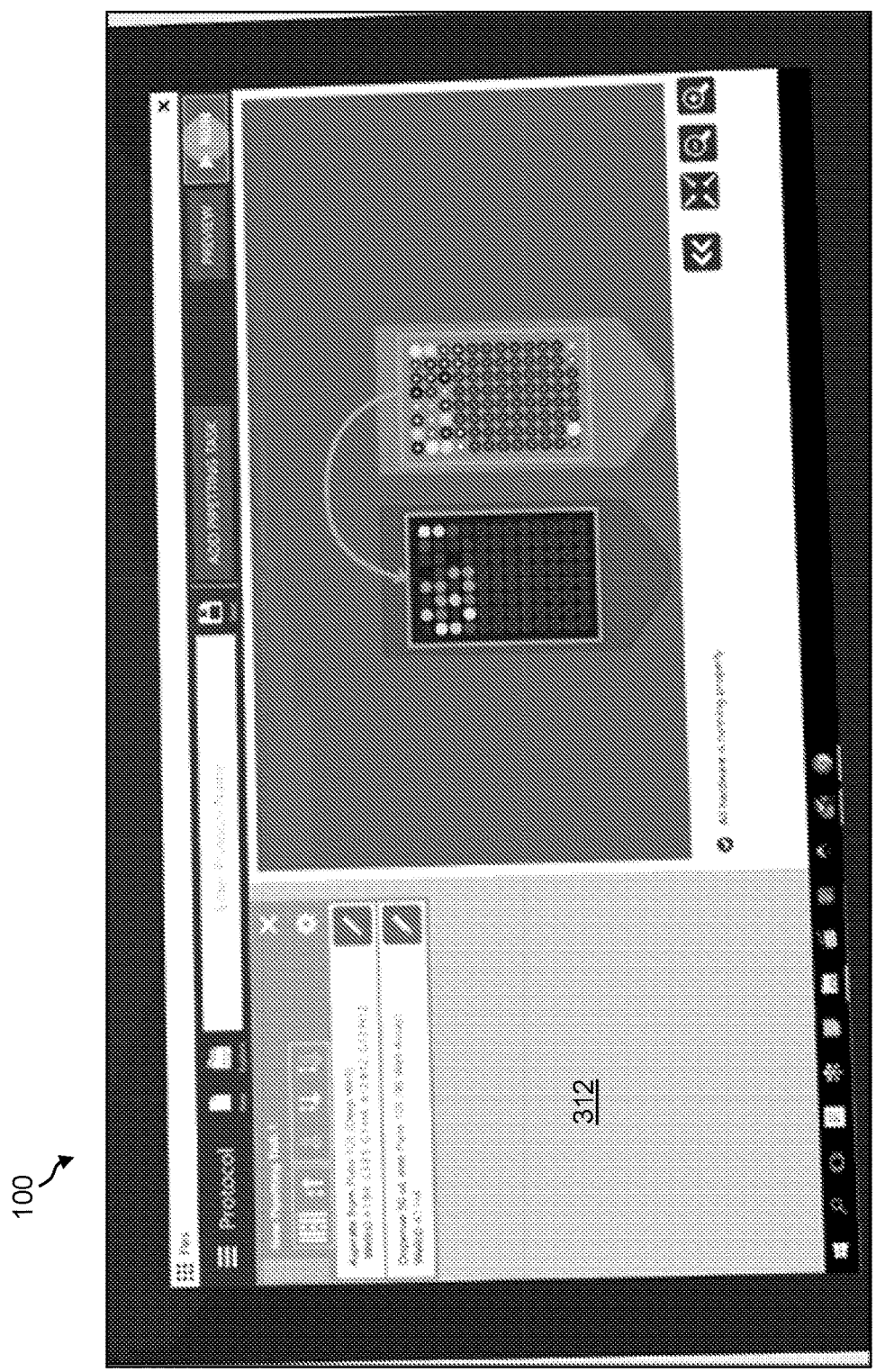
Figure 43:
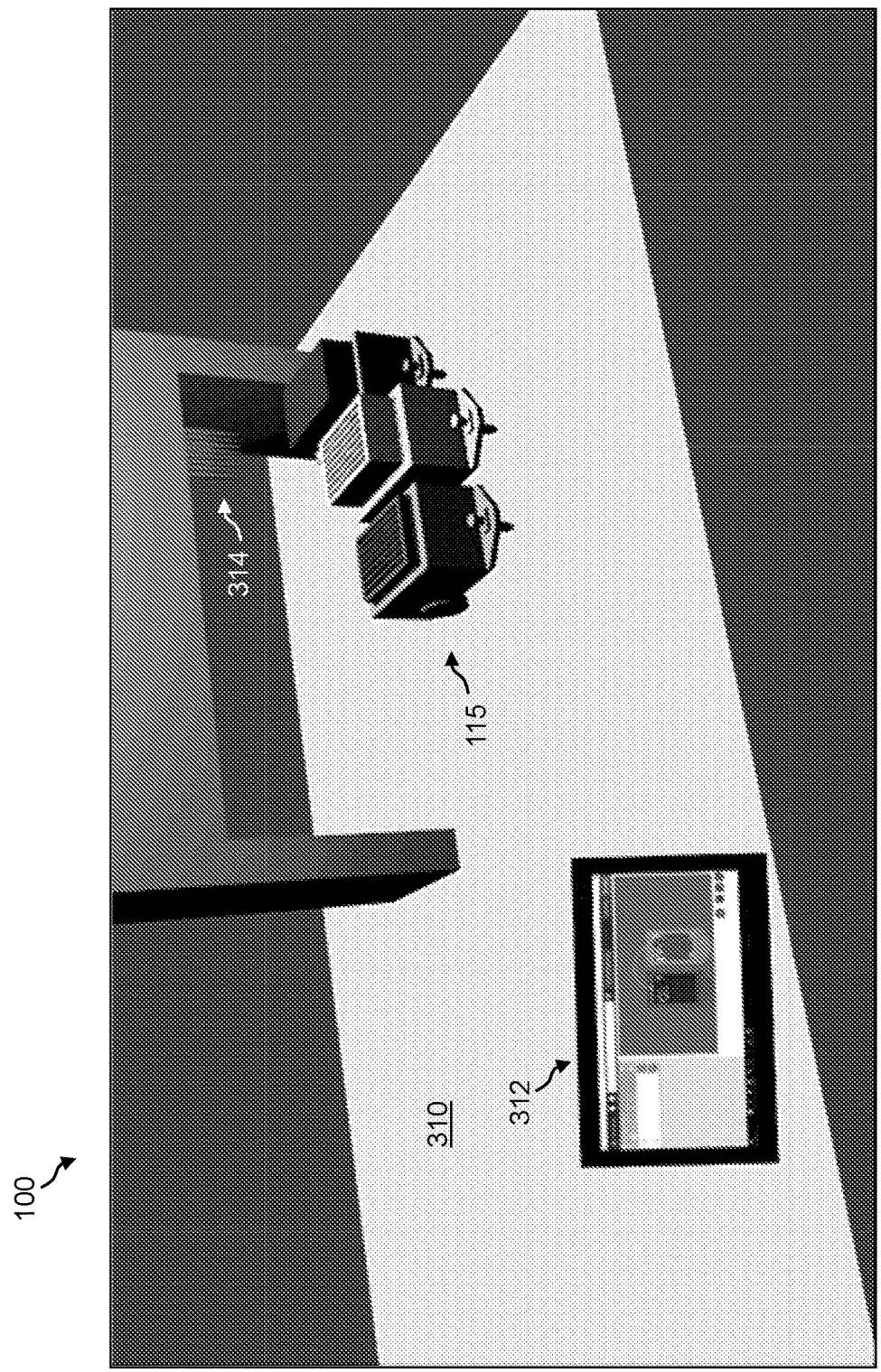
Figure 44:
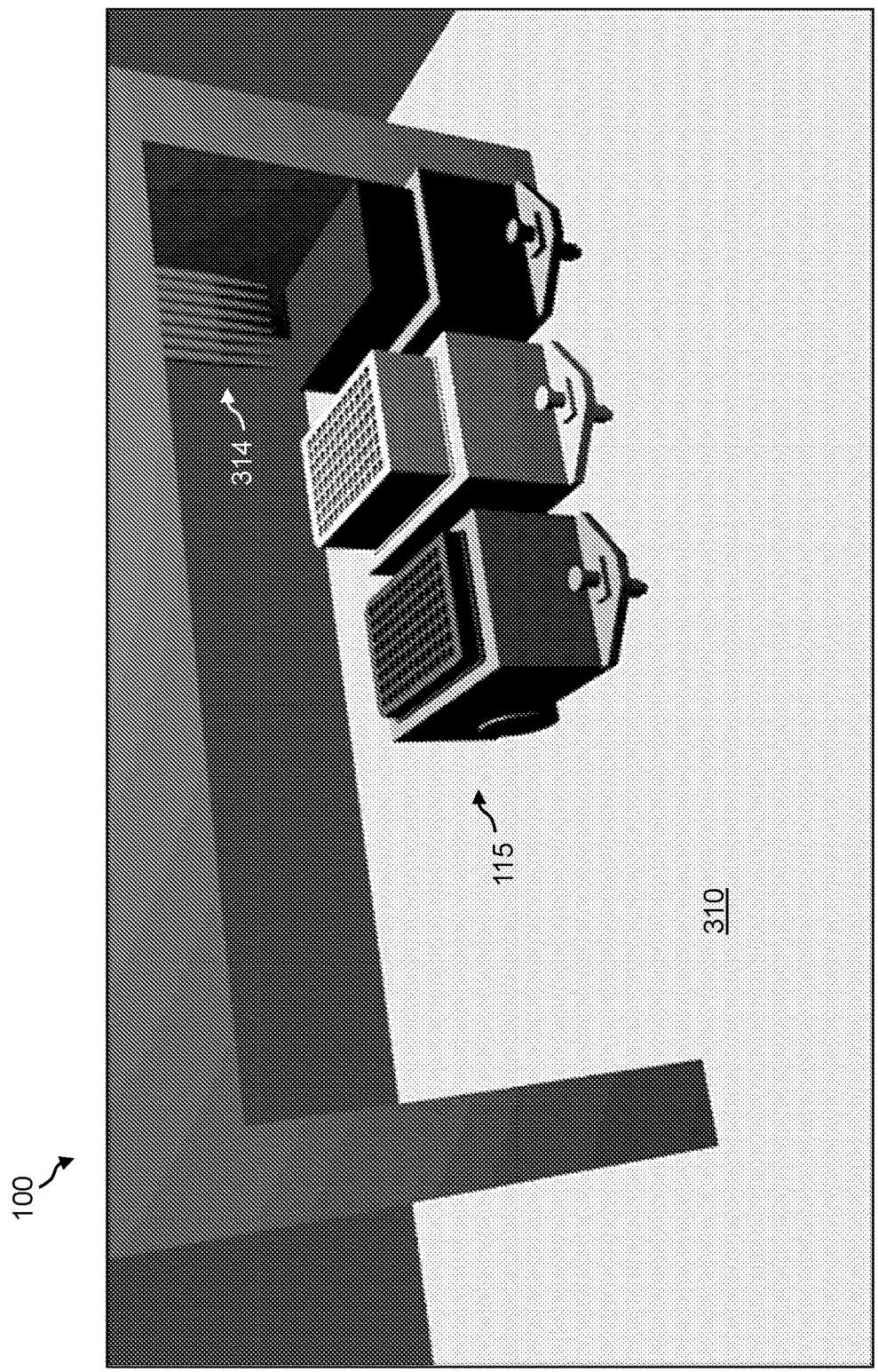
Figure 45:
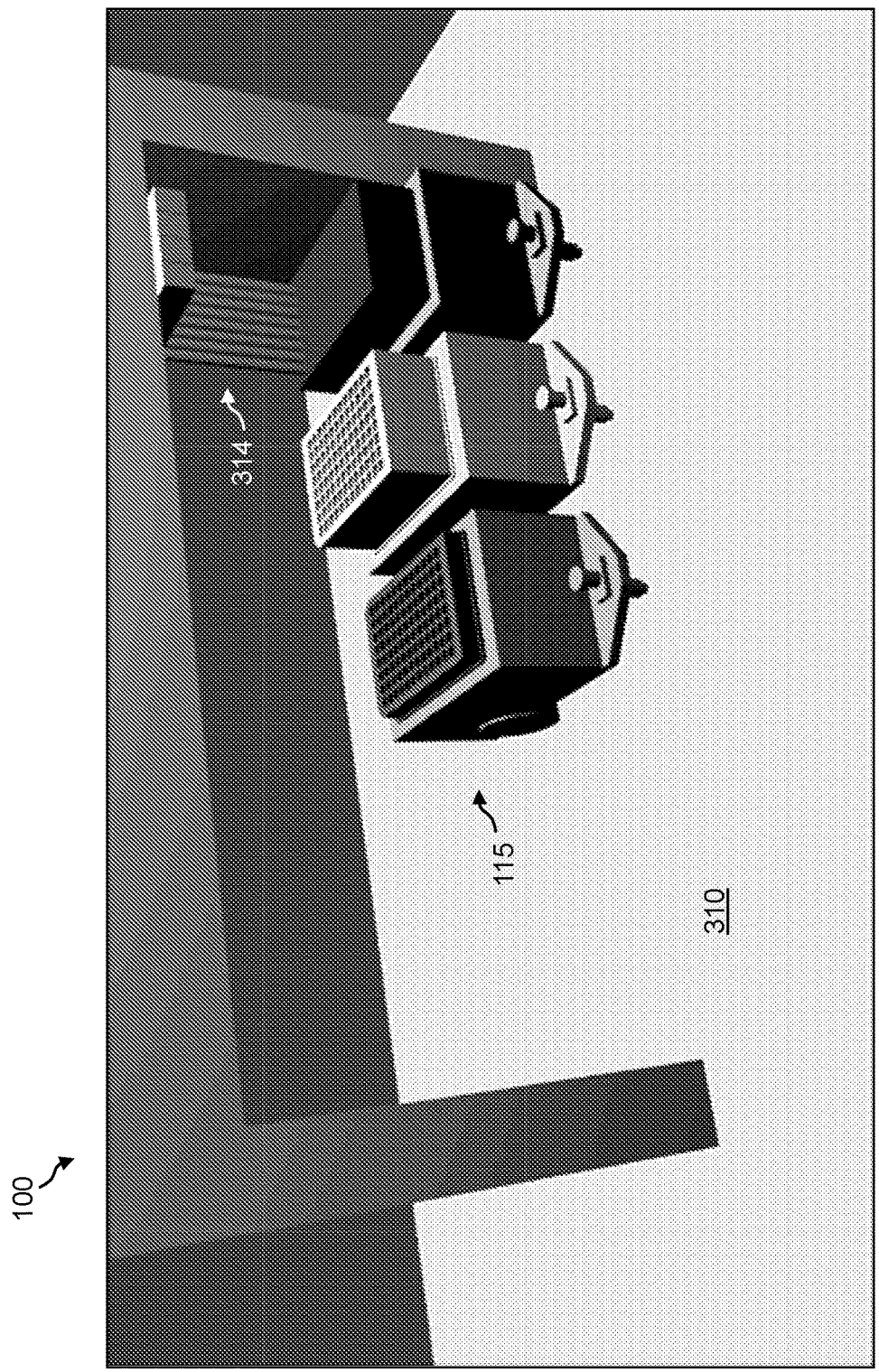
Figure 46:
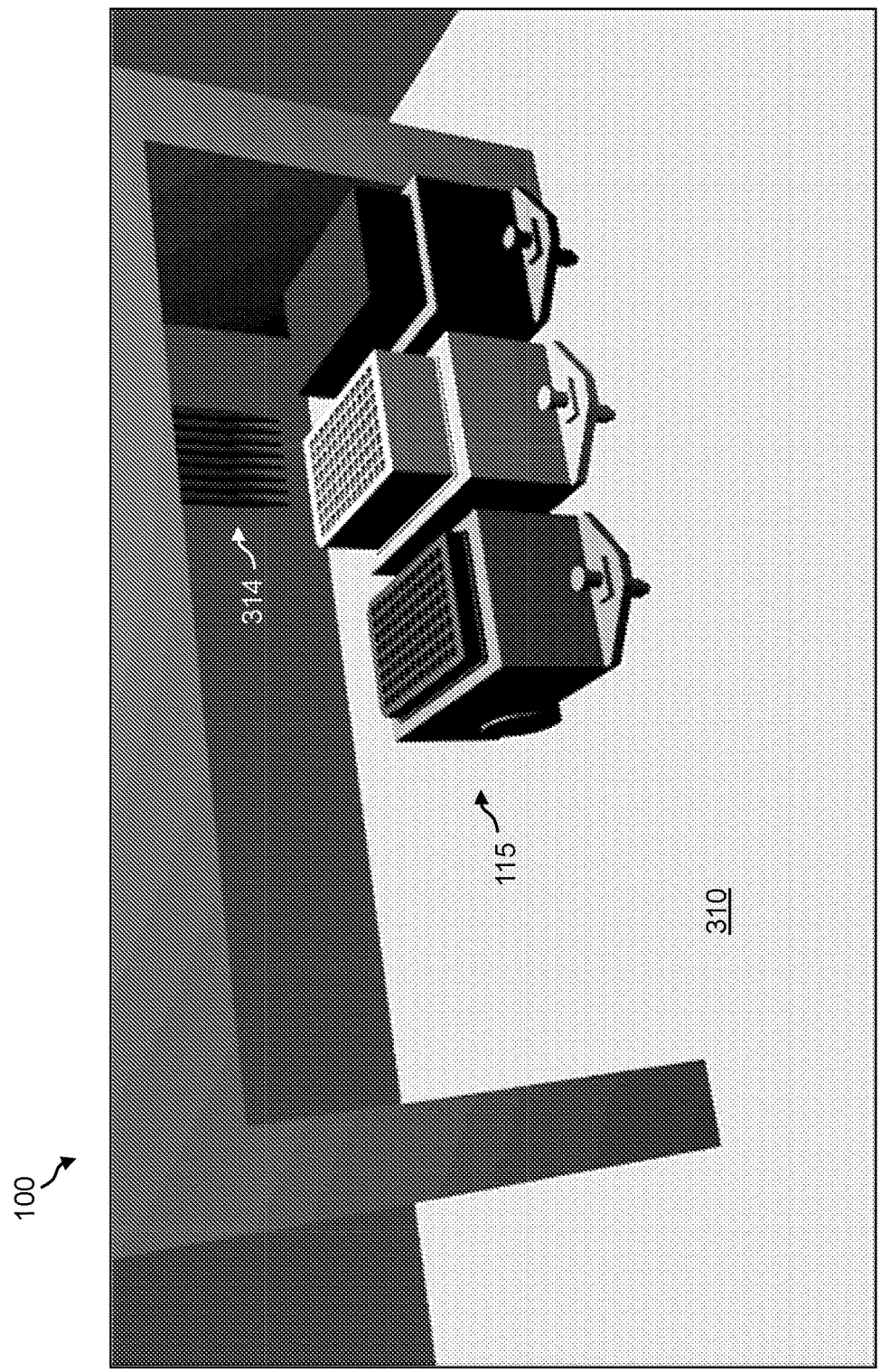
Figure 47:
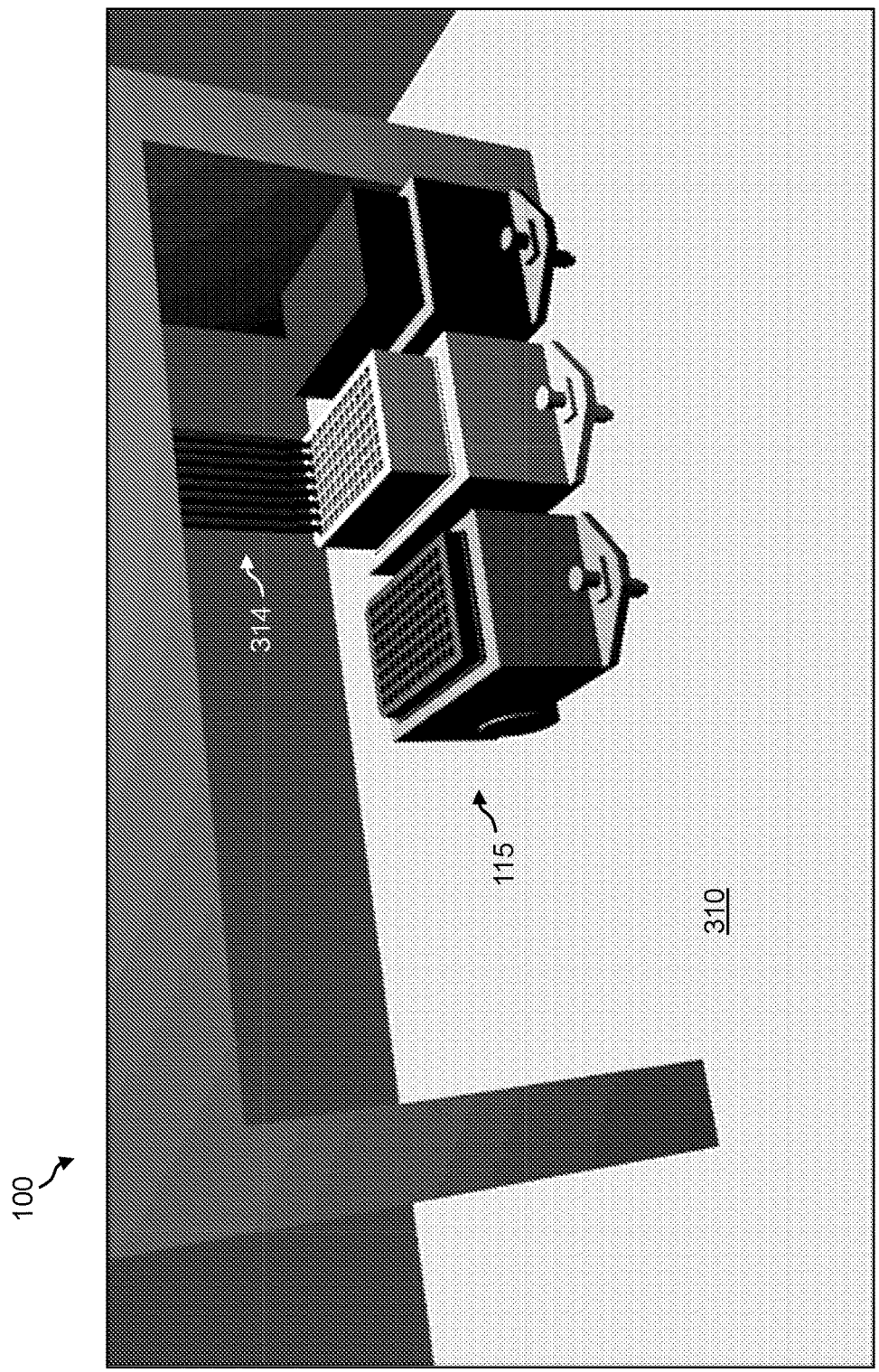
Figure 48:
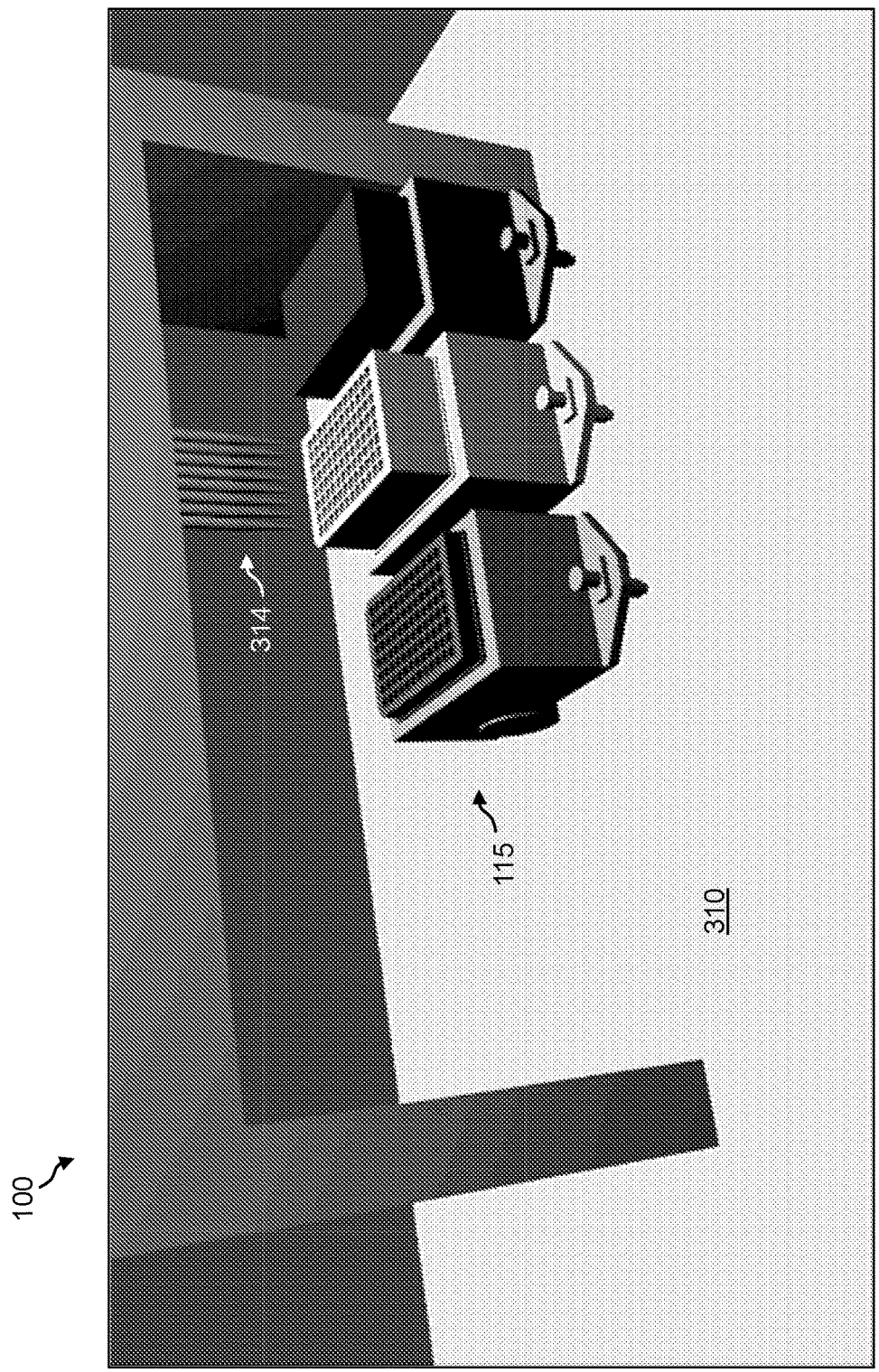
Figure 49:
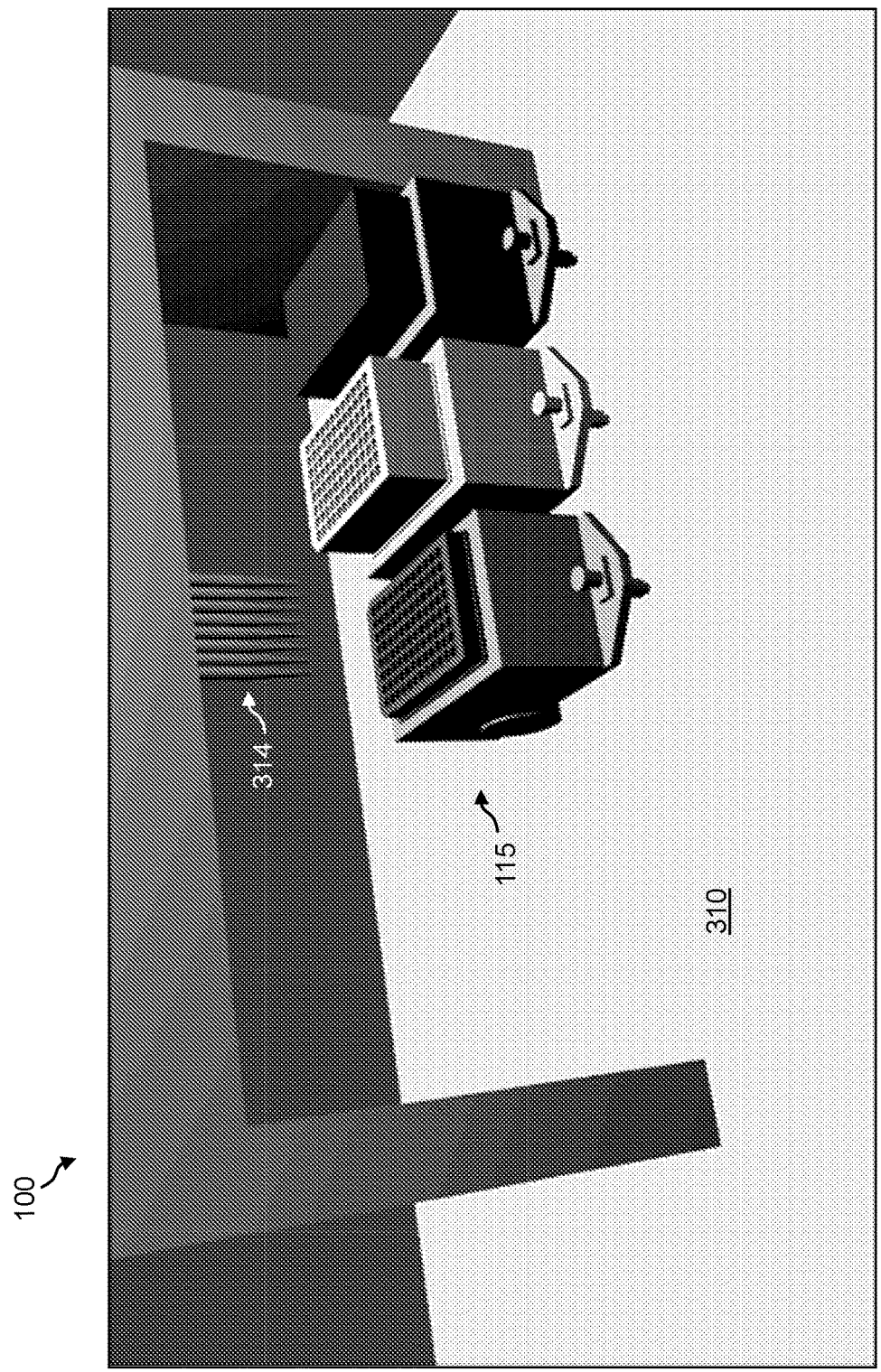
Figure 50:
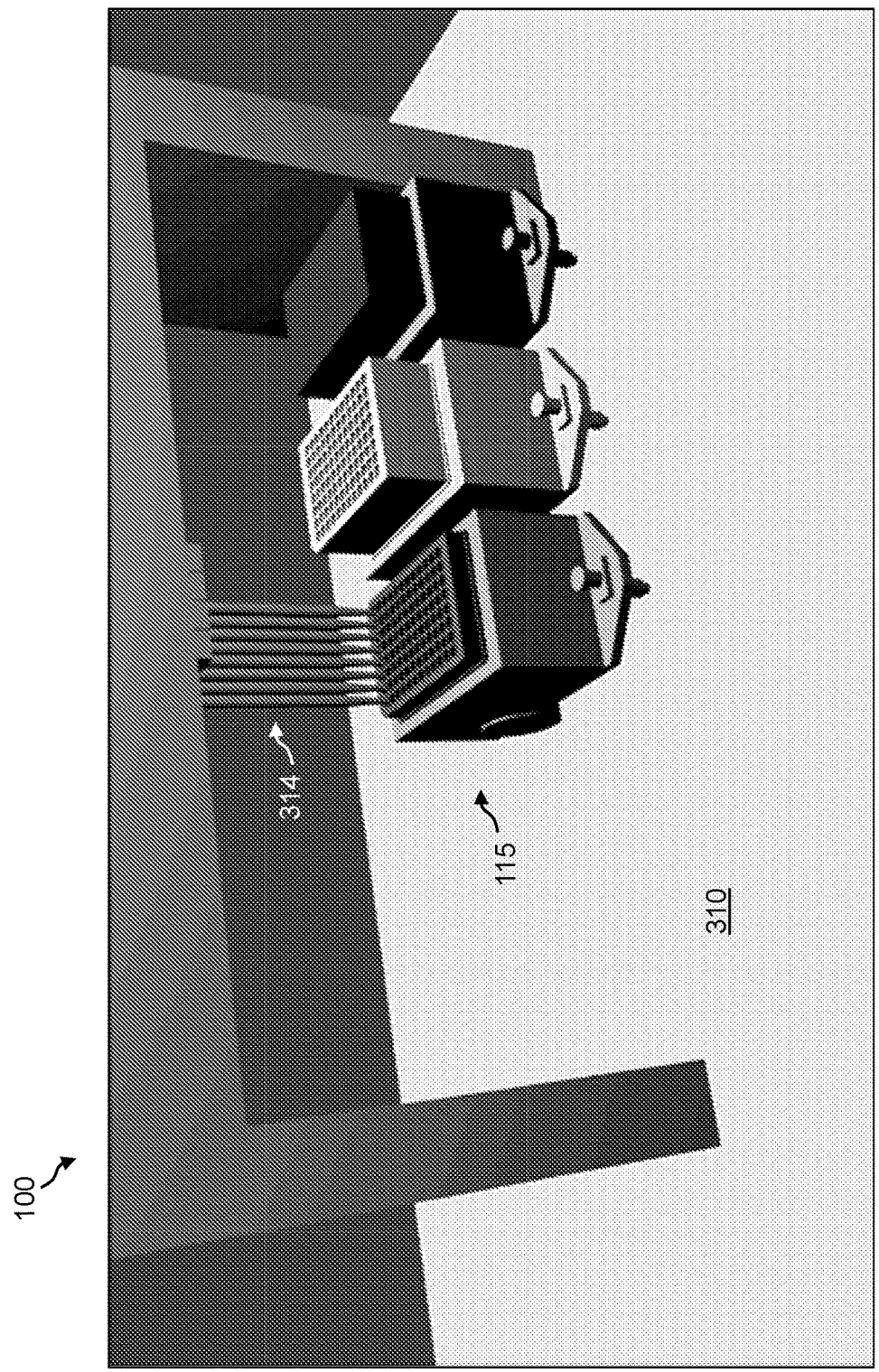
Figure 51:
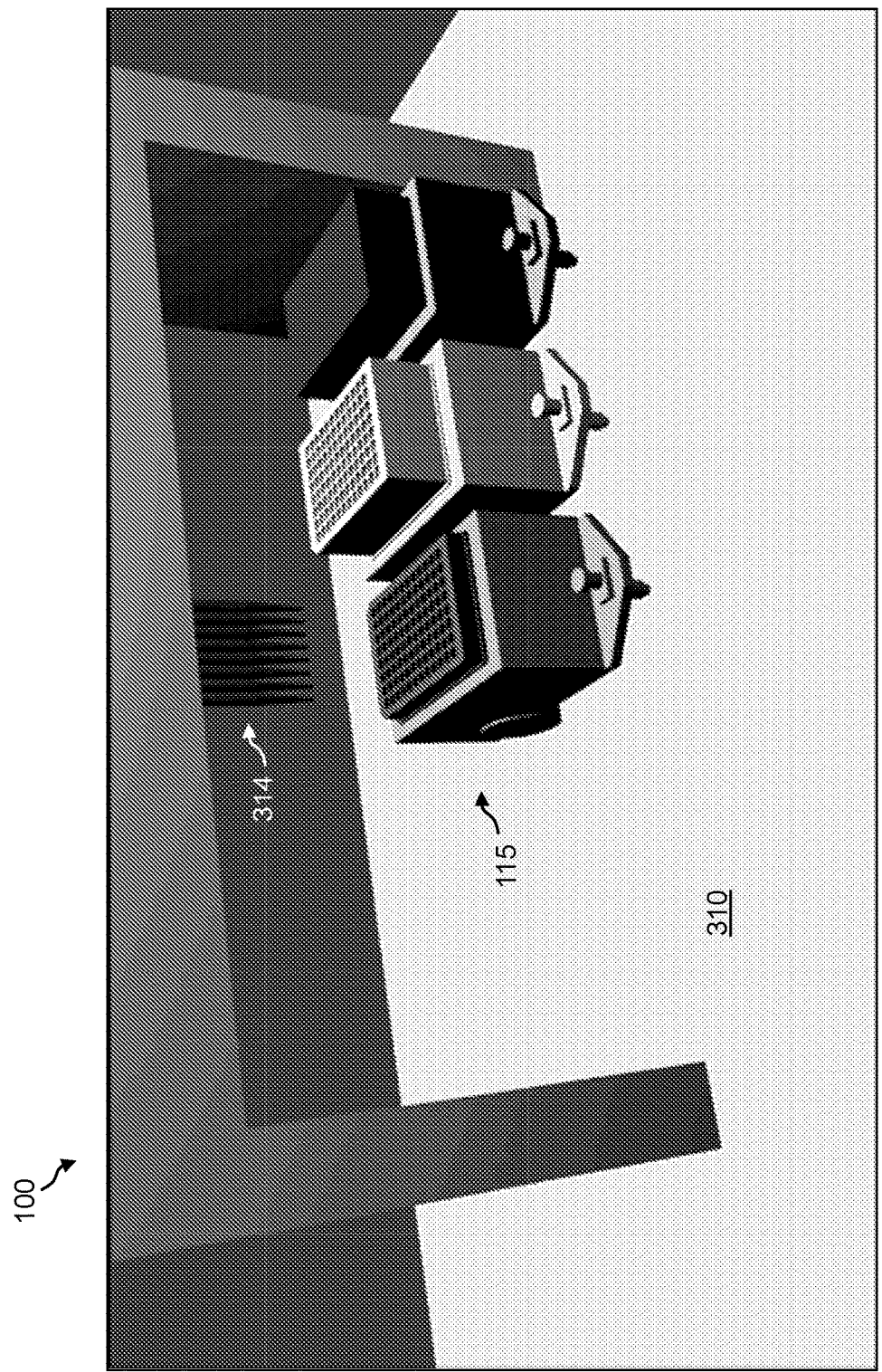
Figure 52:
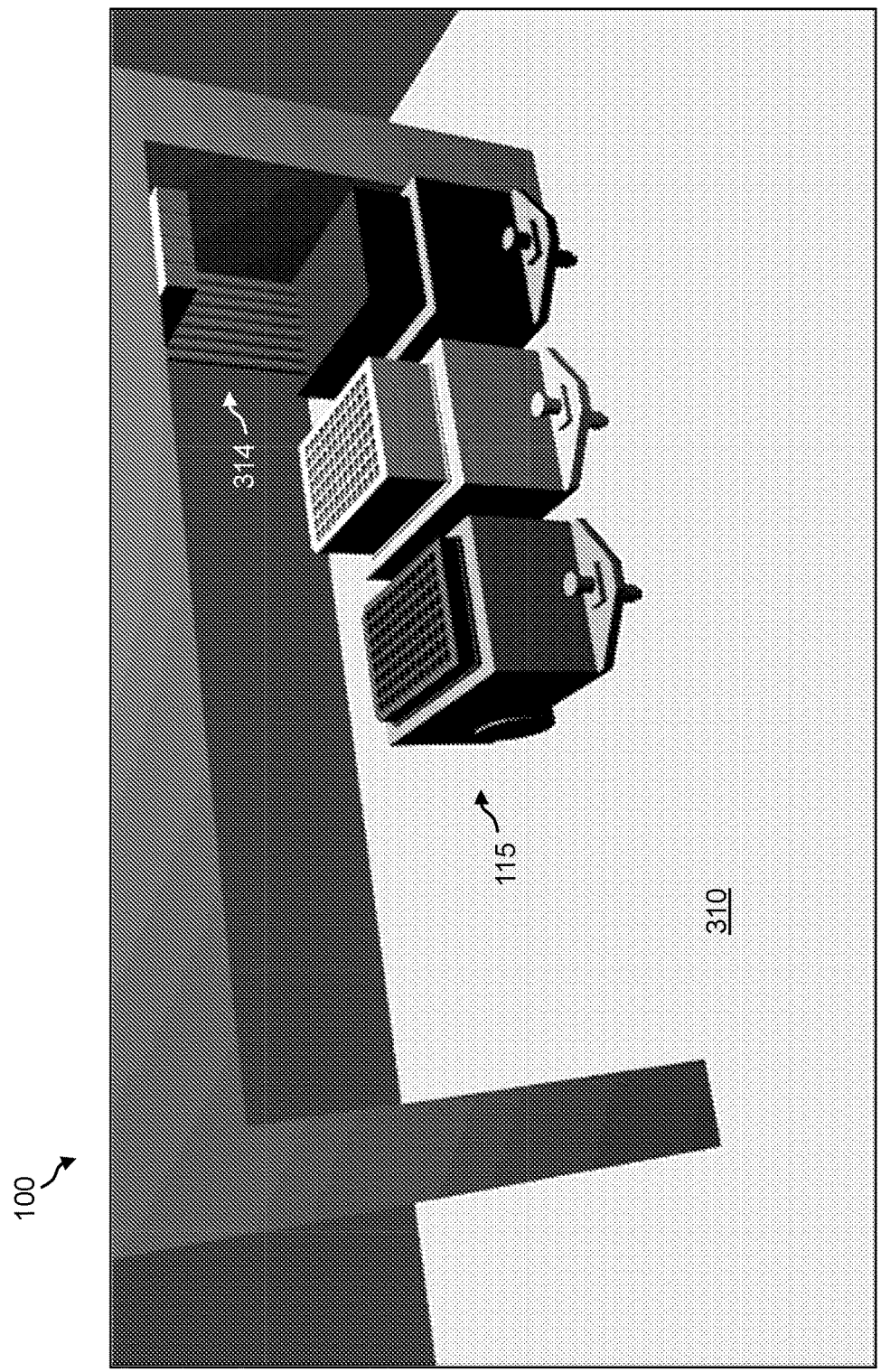
Figure 53:
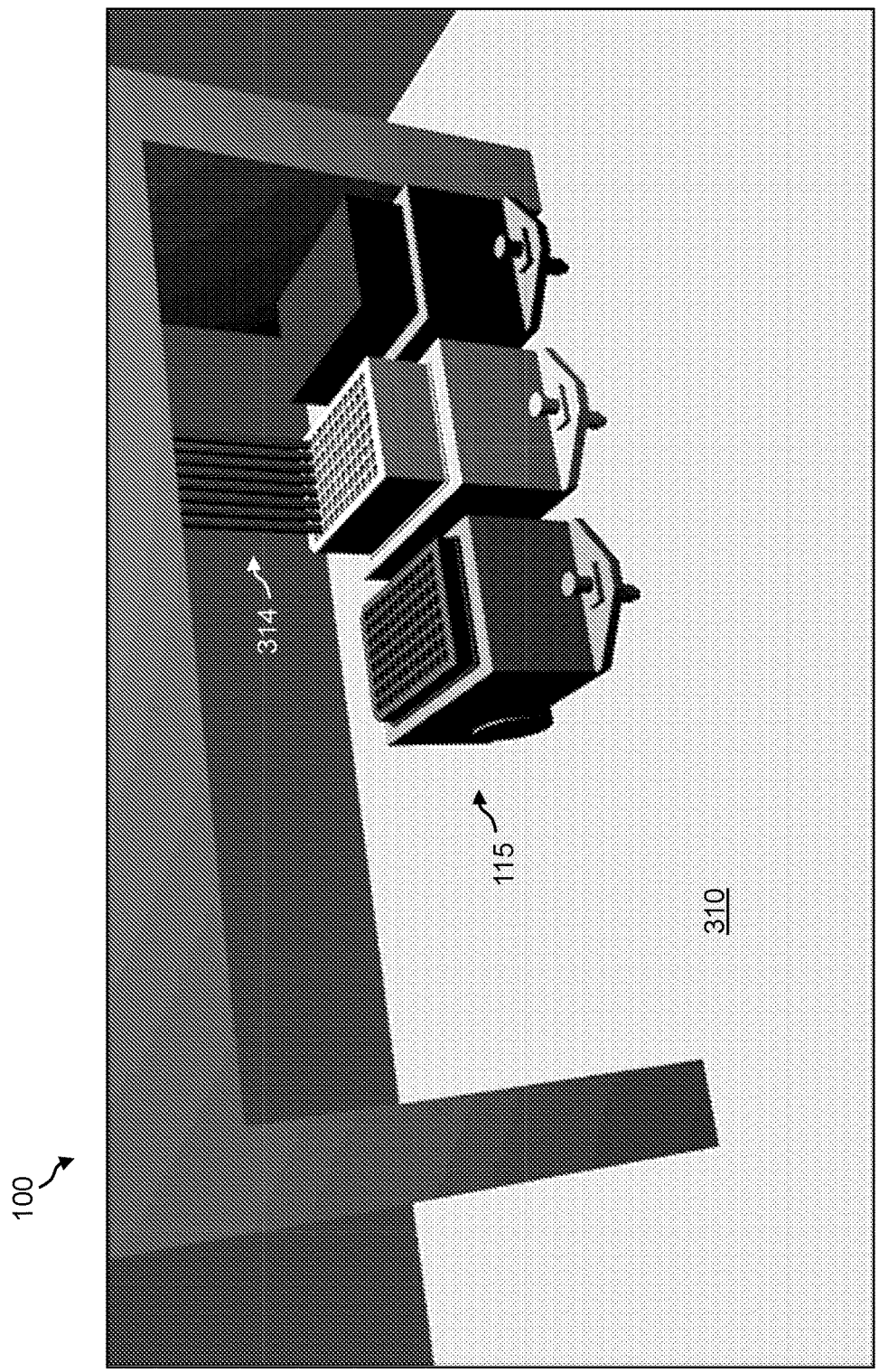
Figure 54:
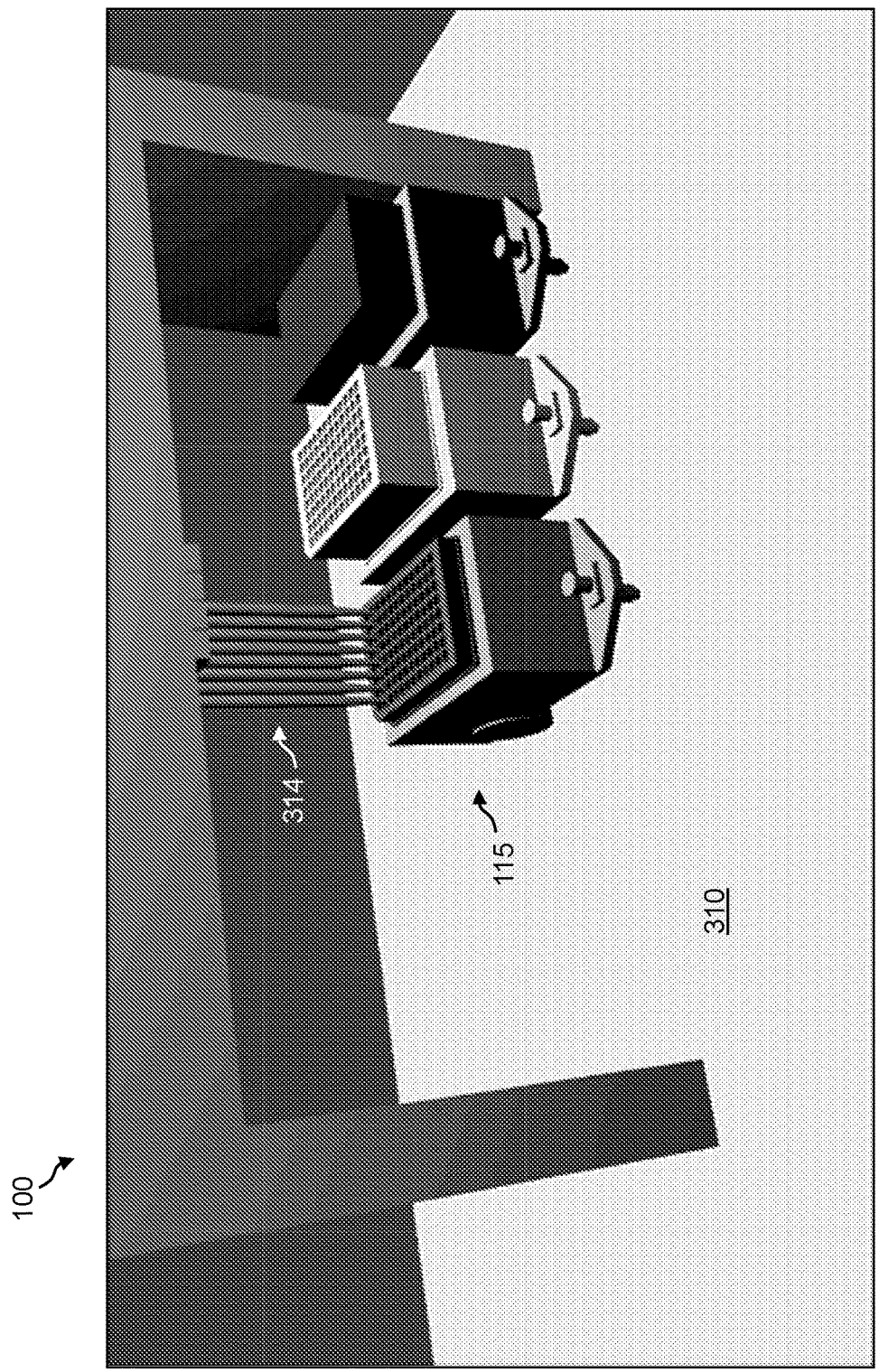
Figure 55:
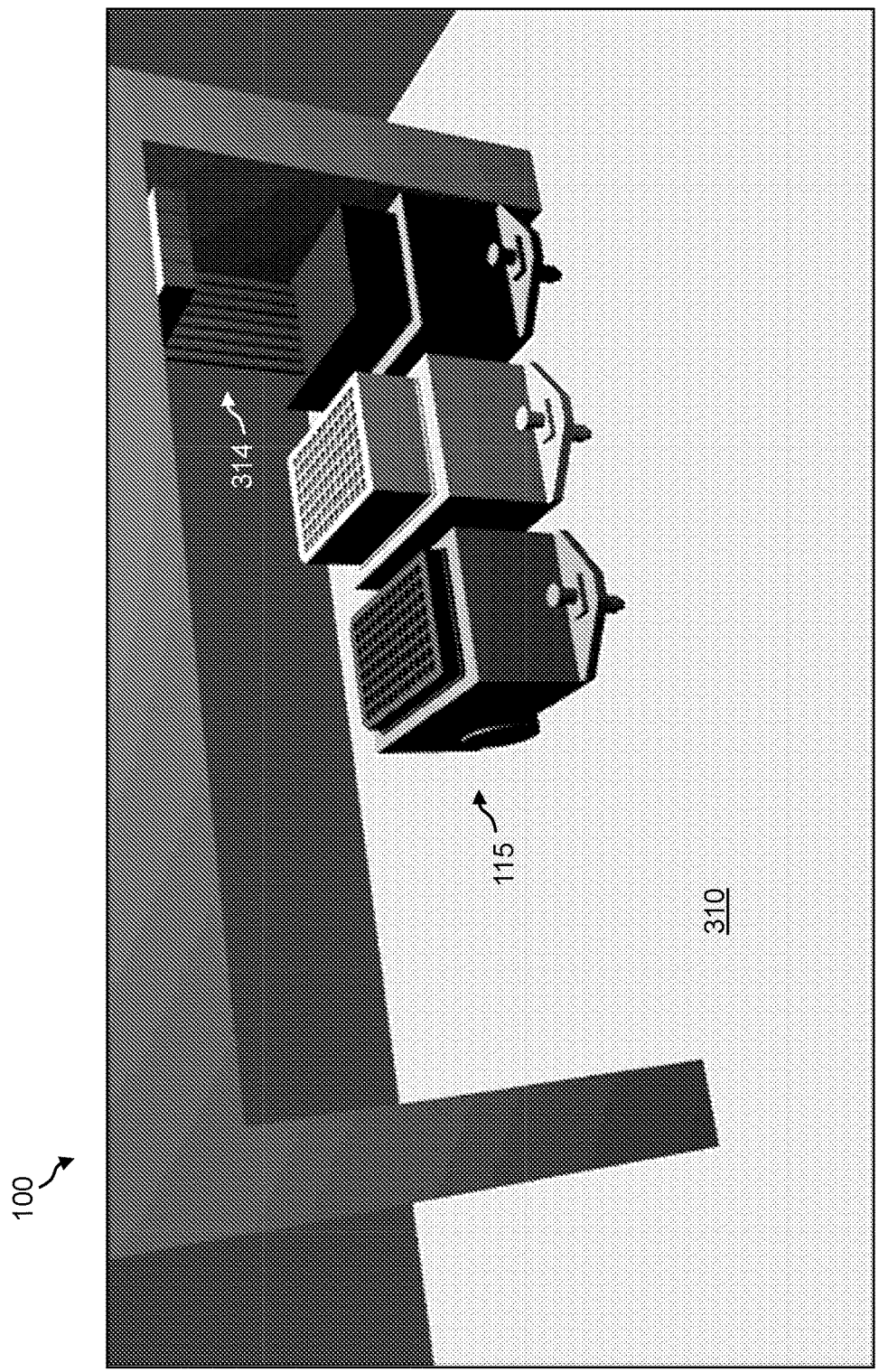
Figure 56:
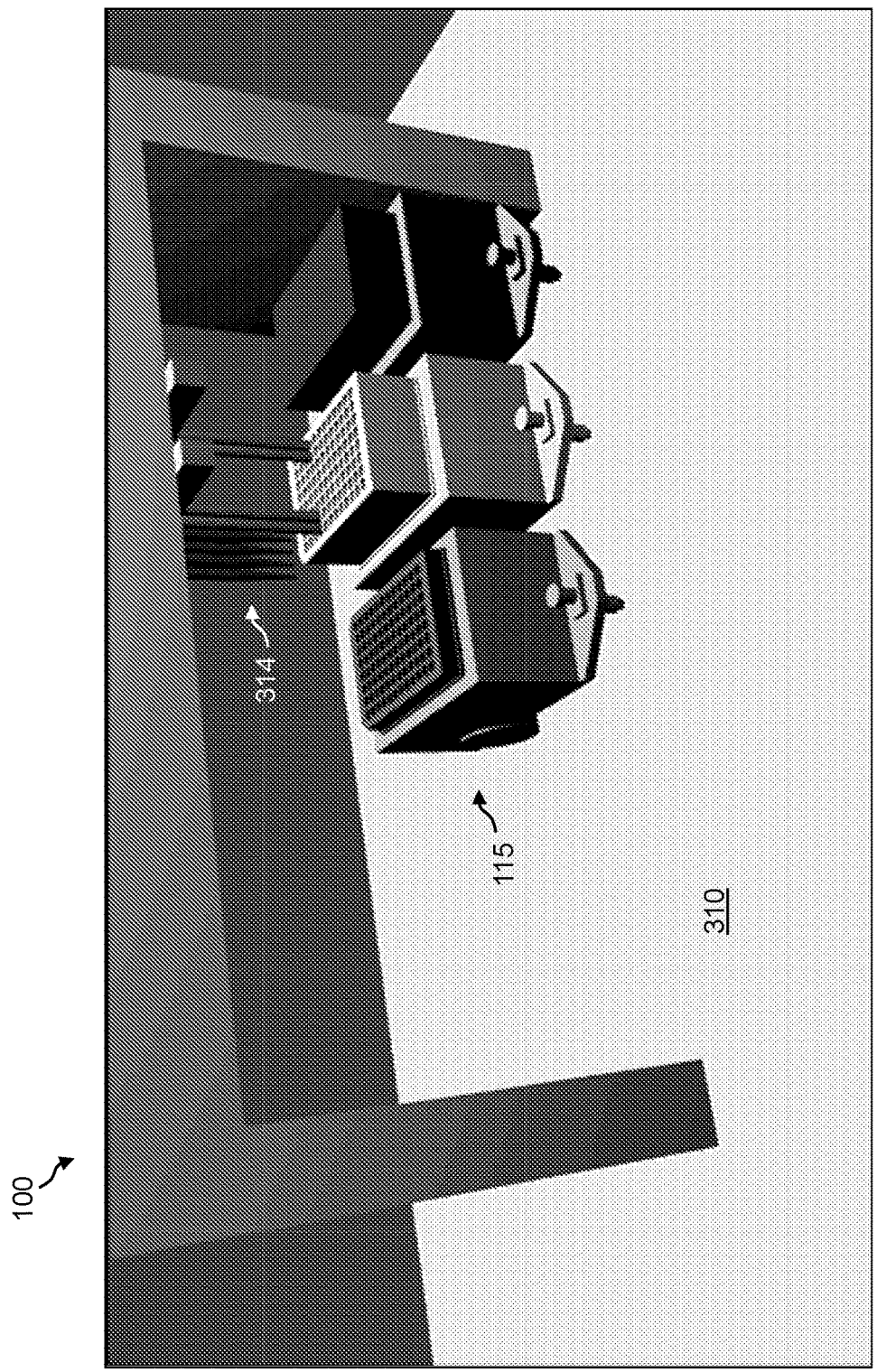
Figure 57:
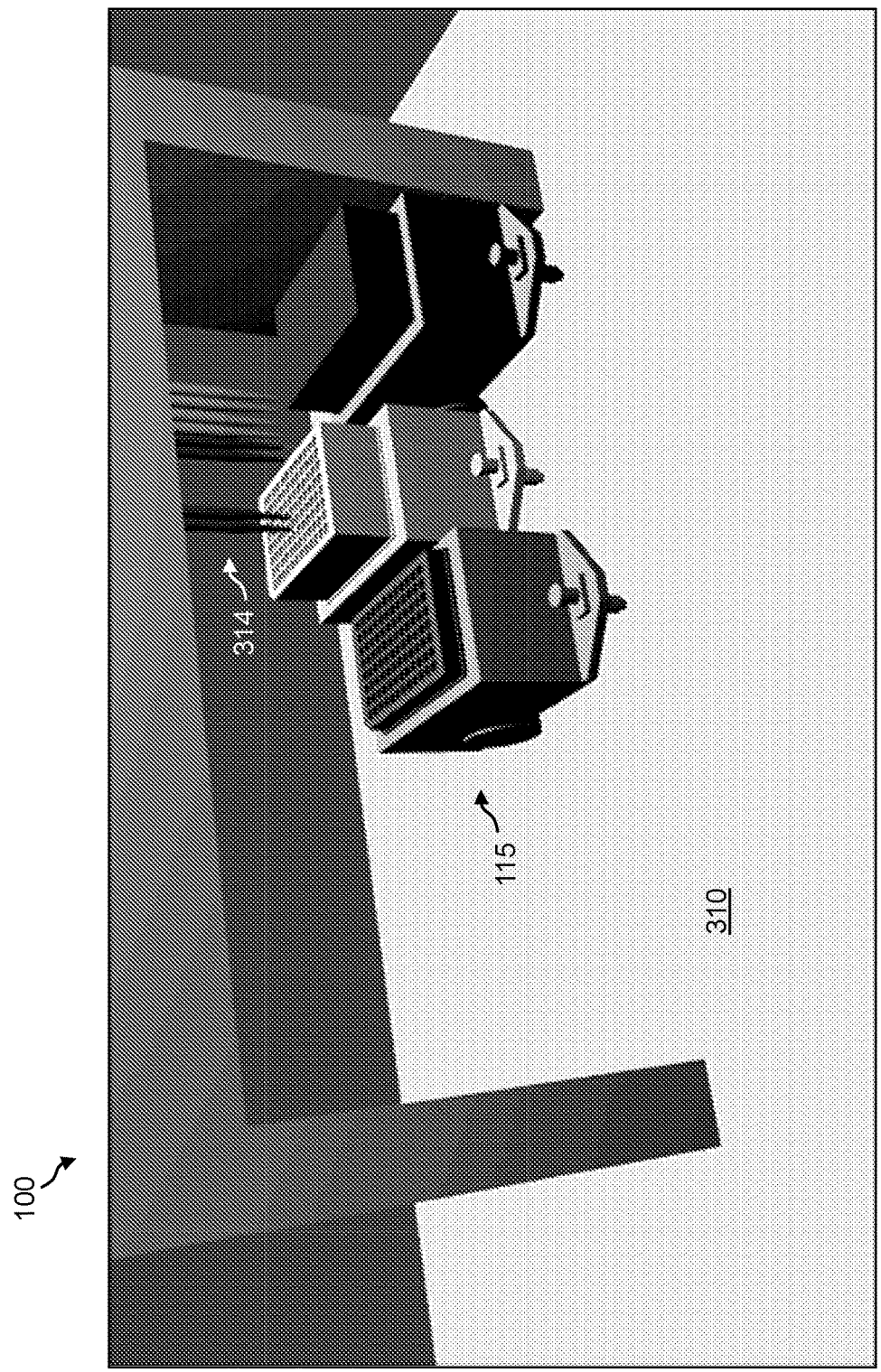
Figure 58:
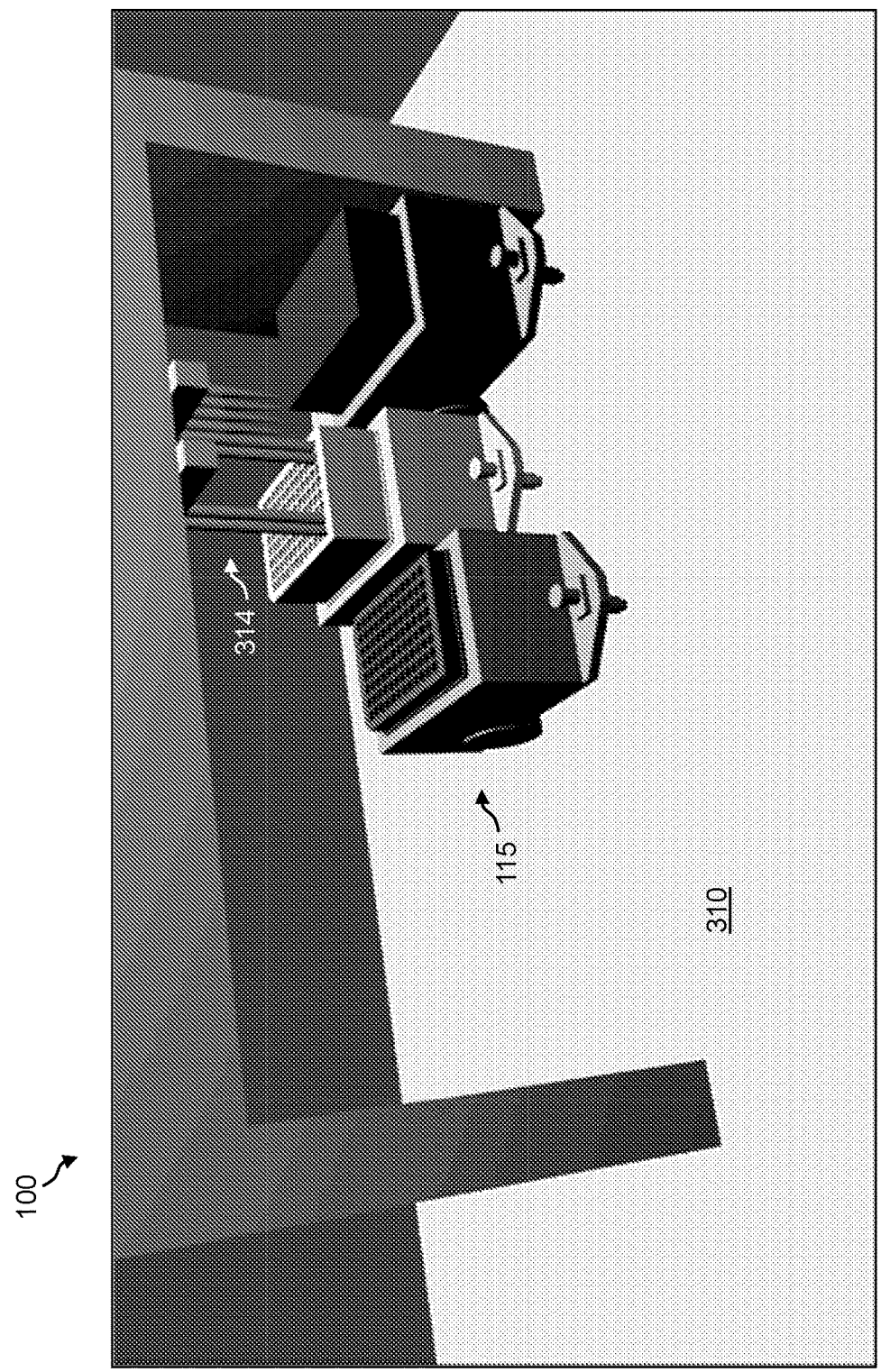
Figure 59:
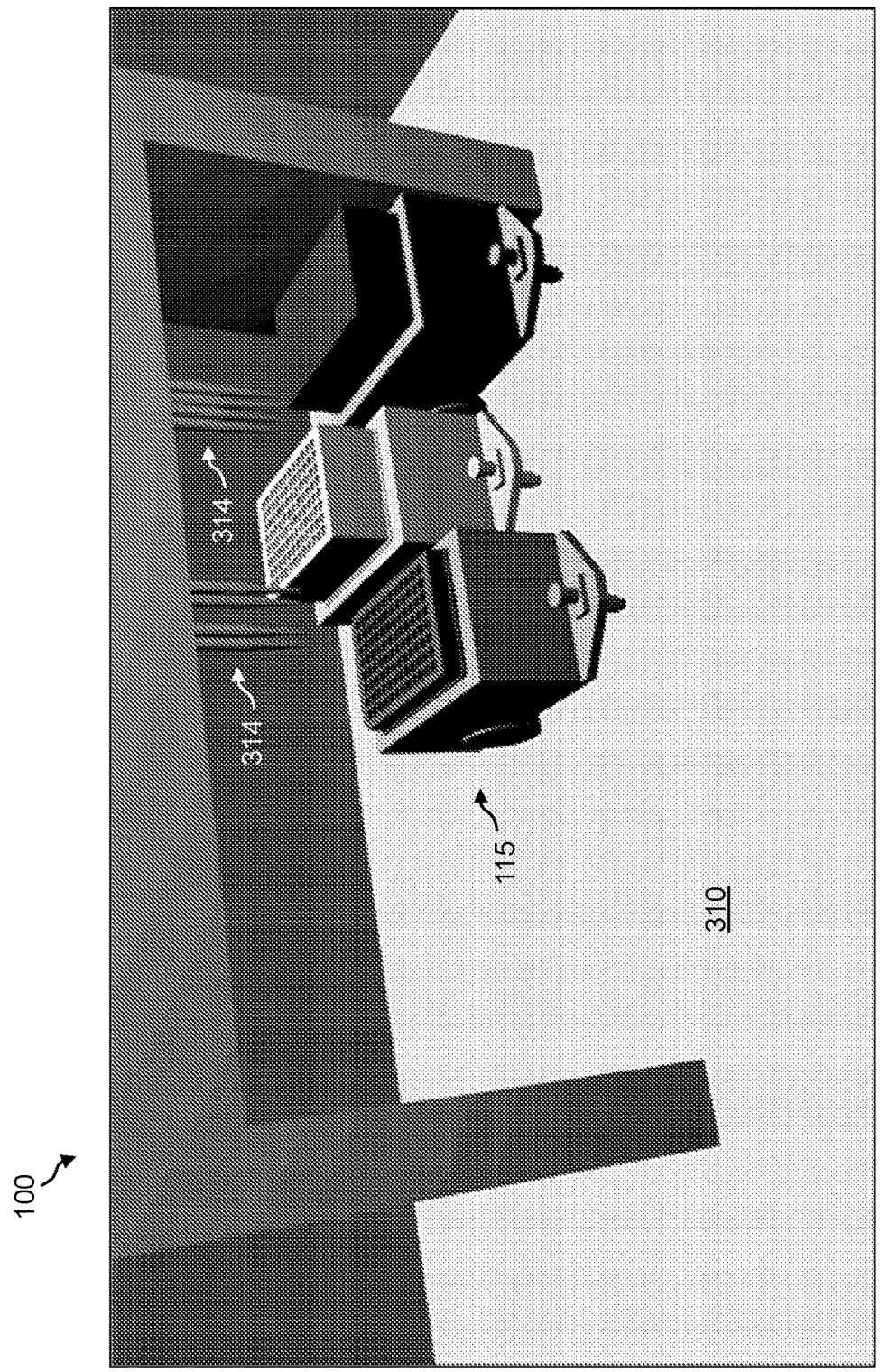
Figure 60:
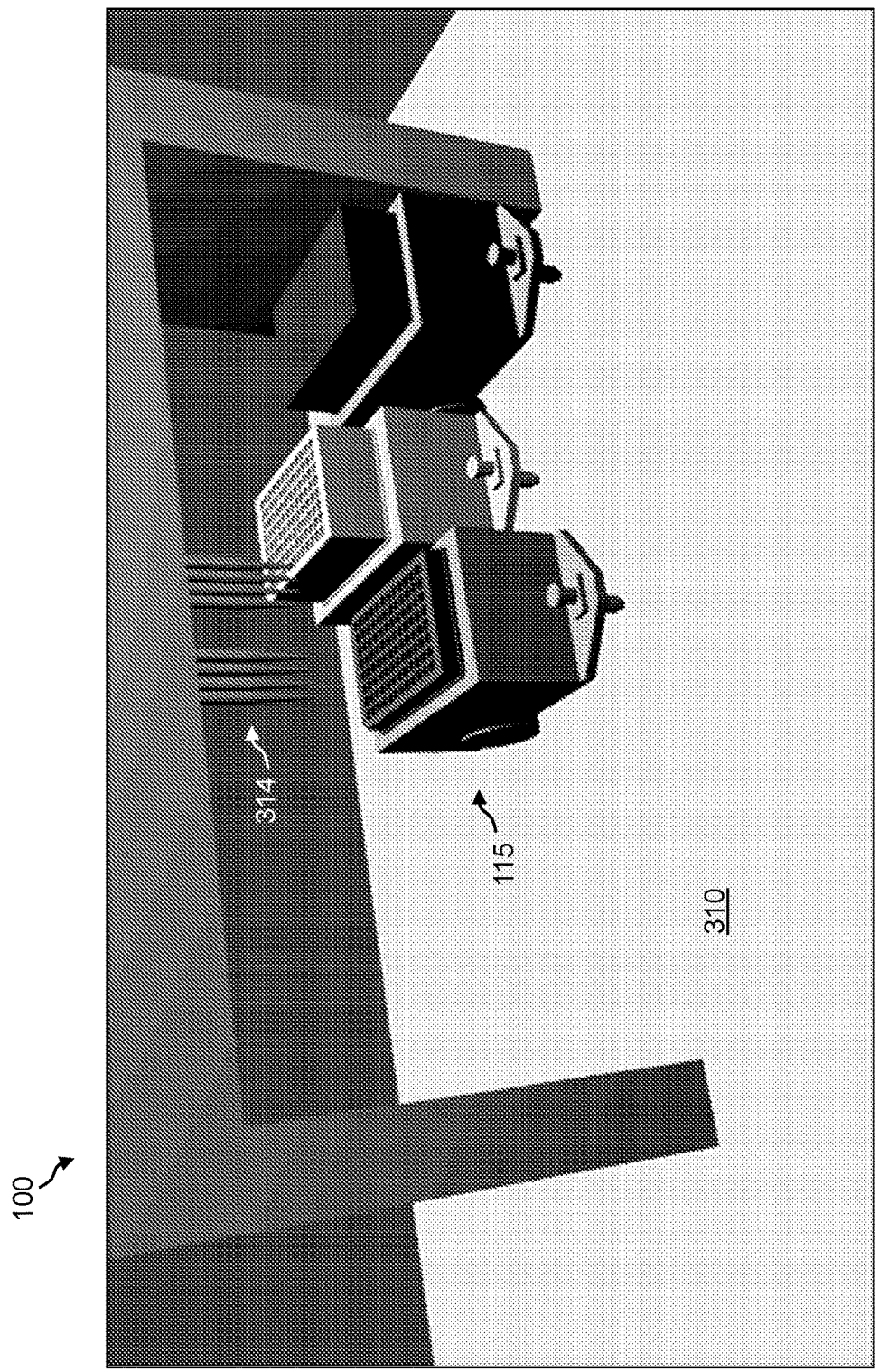
Figure 61:
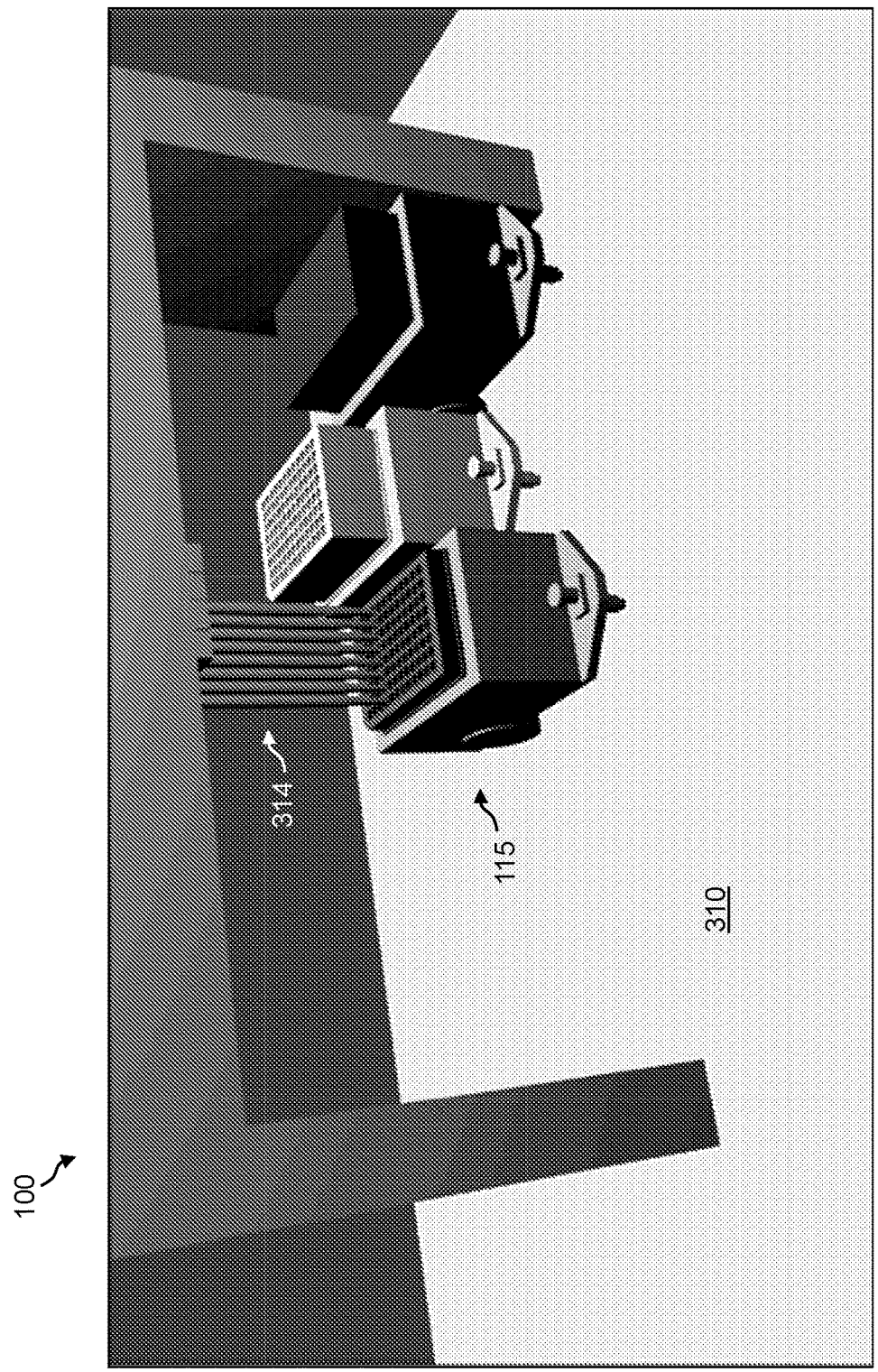
Figure 62:
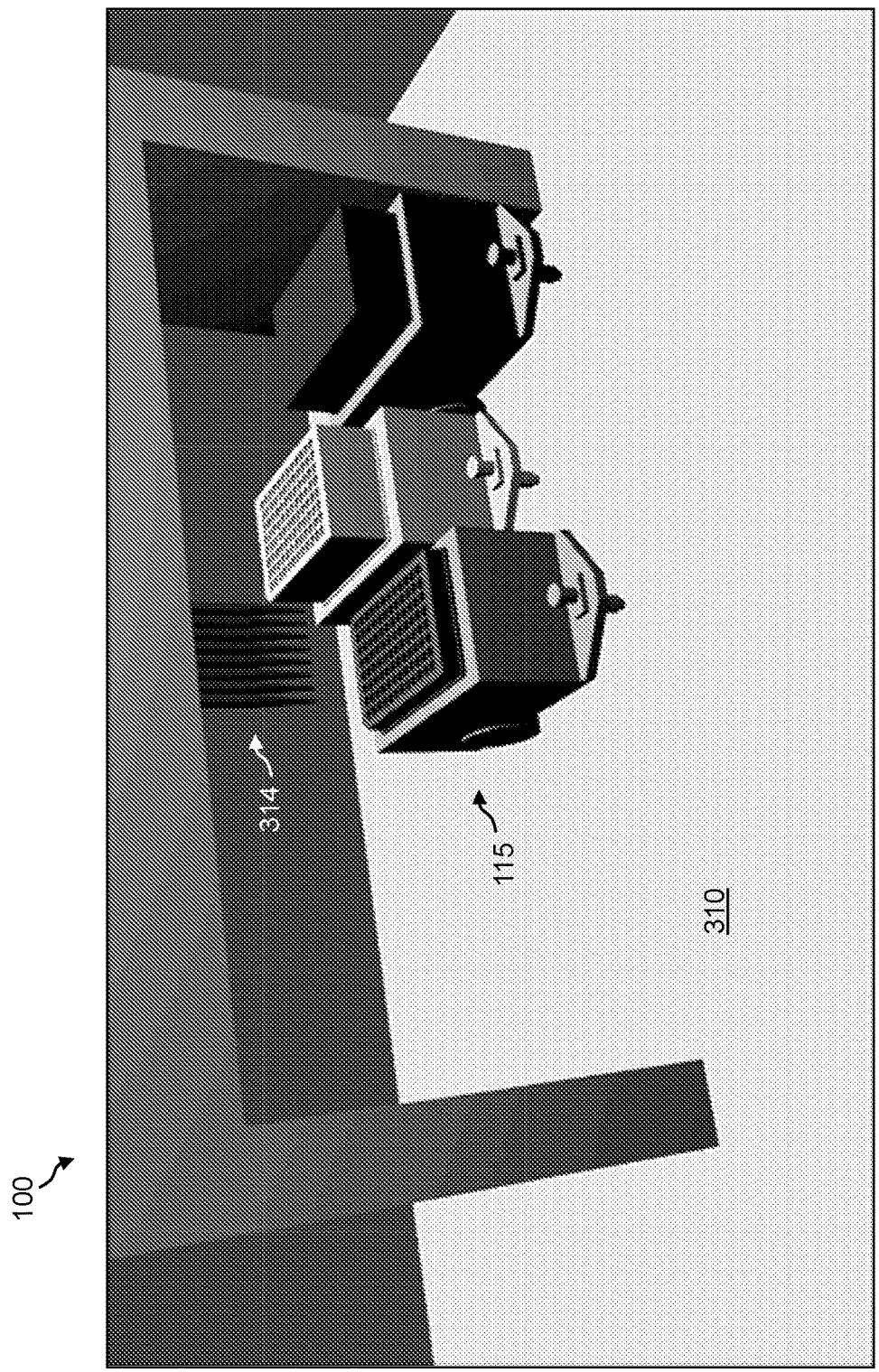
Figure 63:
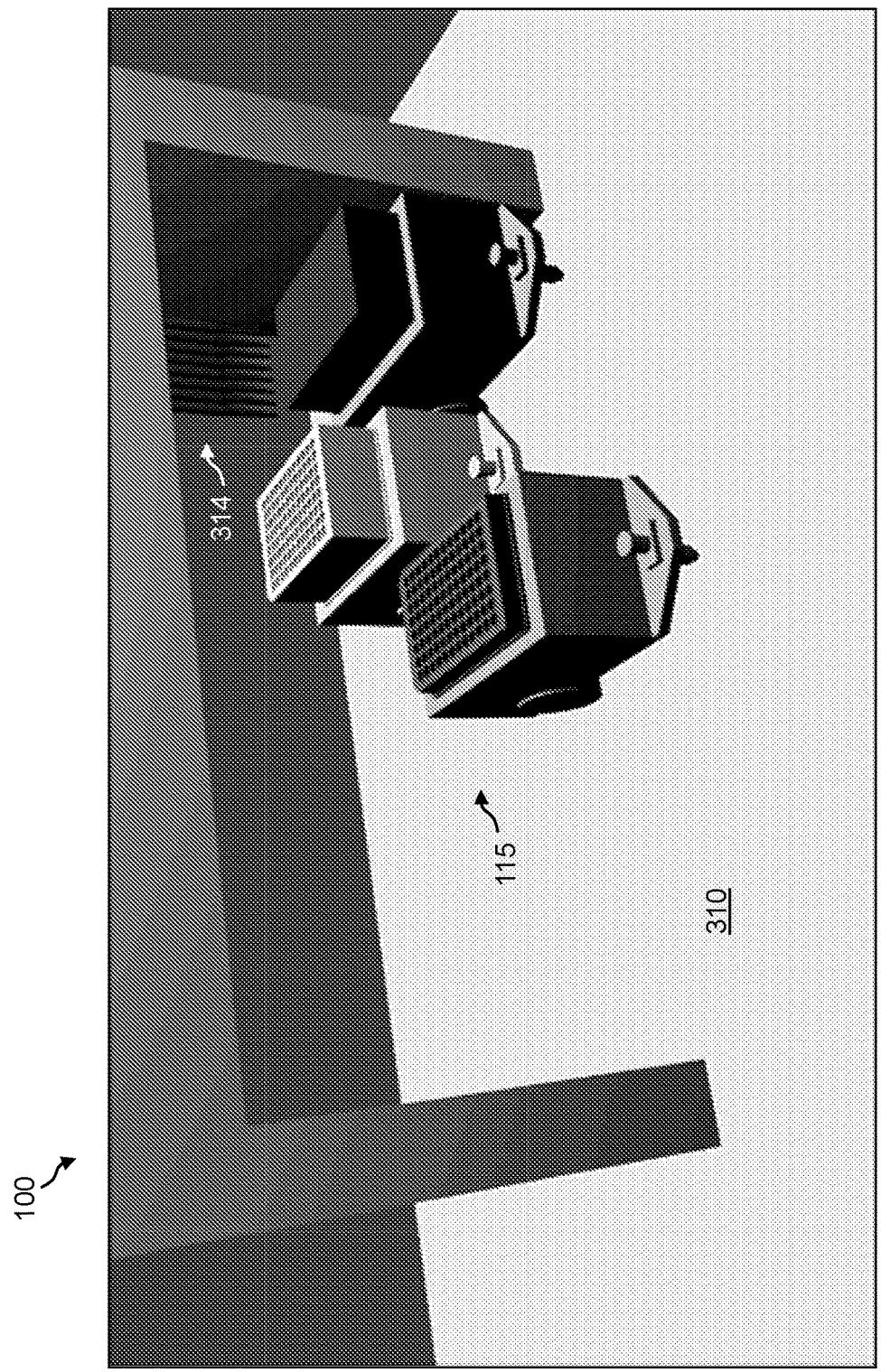
Figure 64:
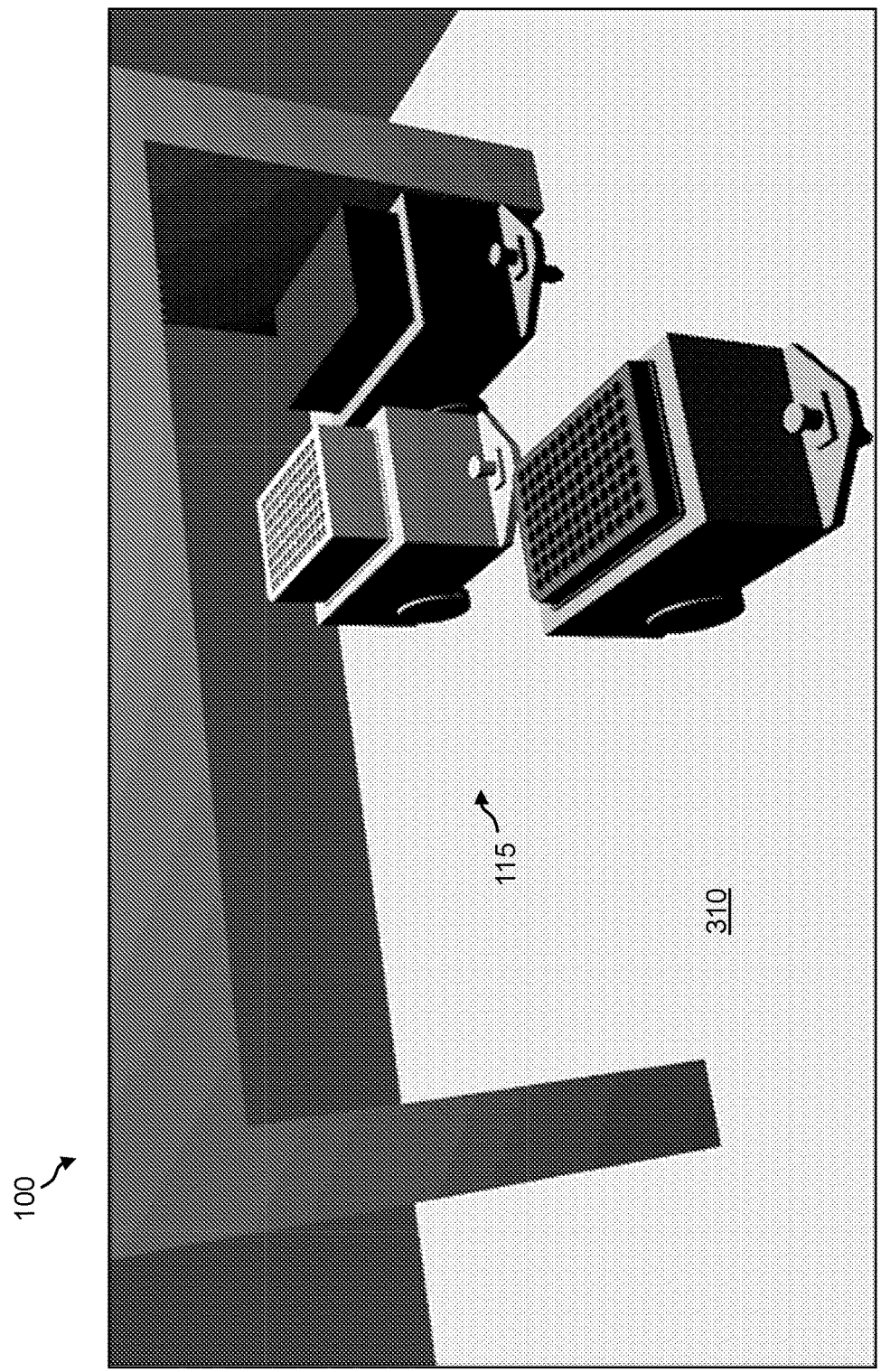
Figure 65:
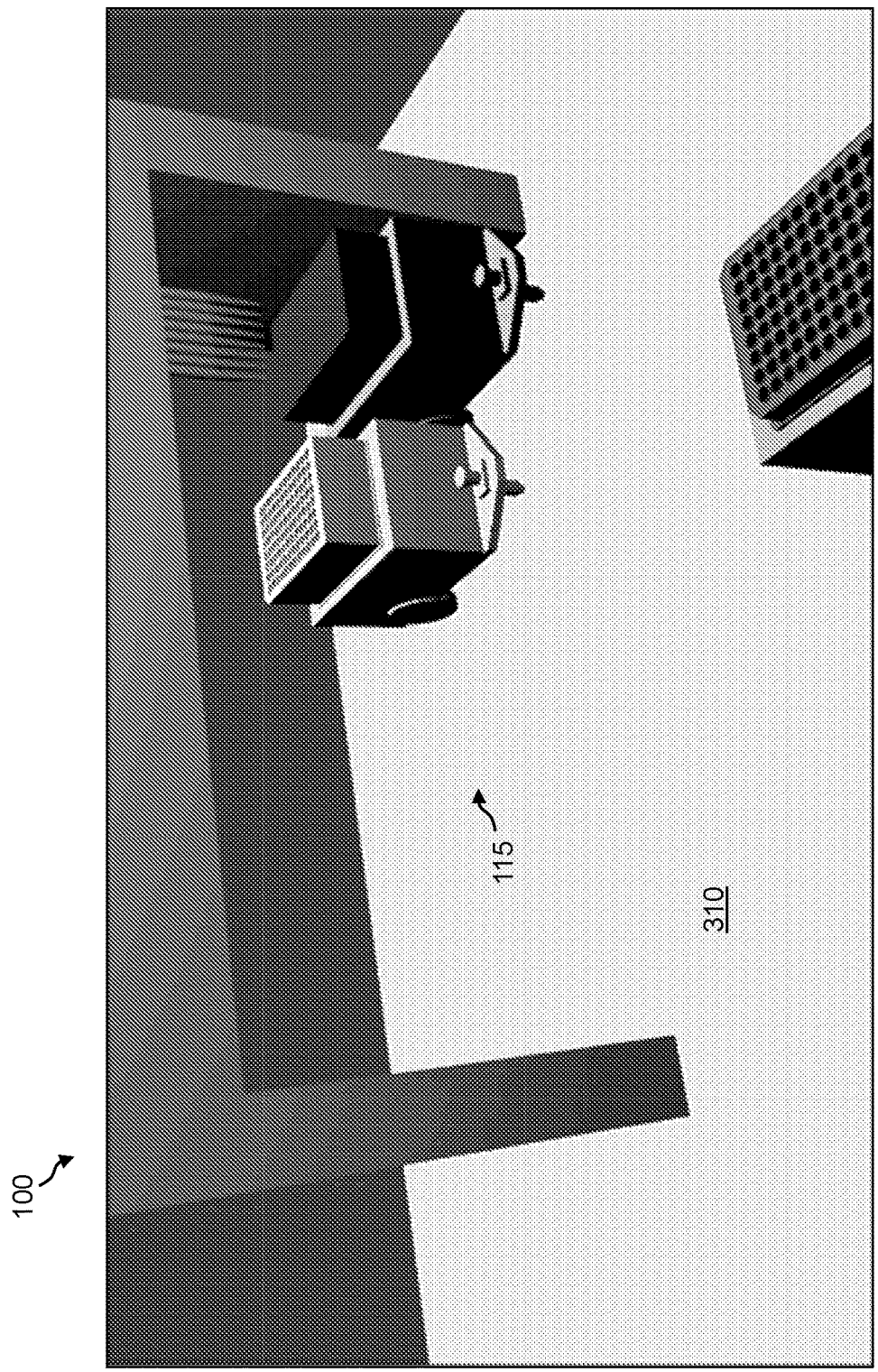
Figure 66:
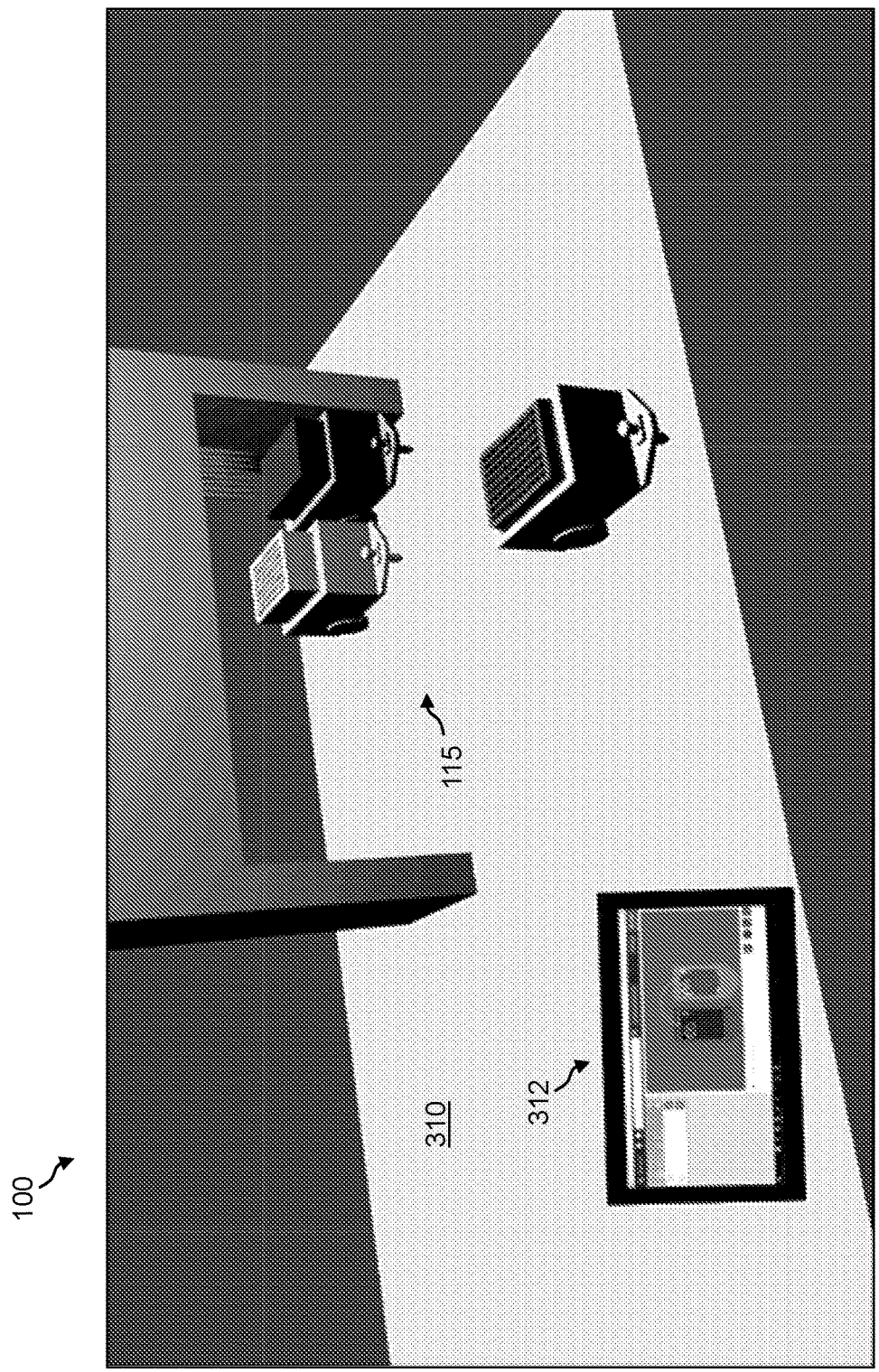
Figure 67:
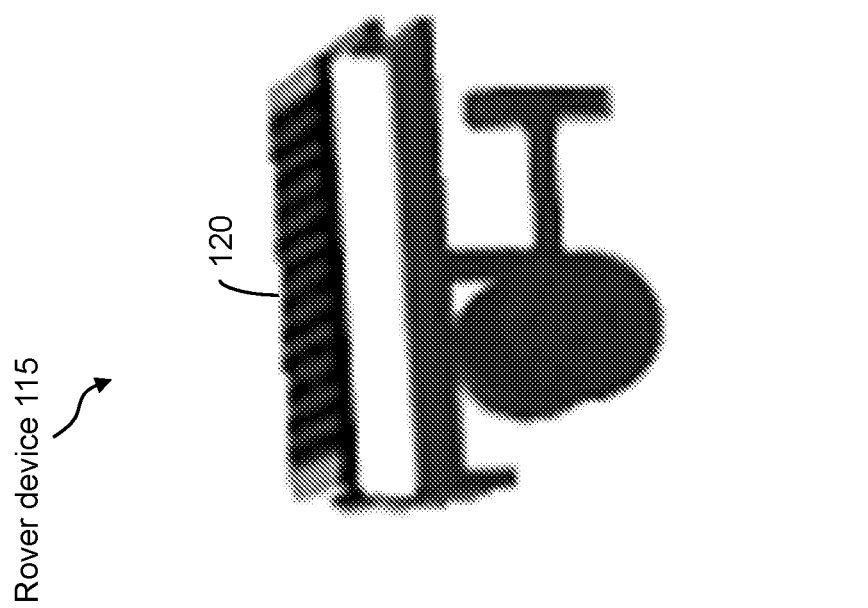
Figure 68:
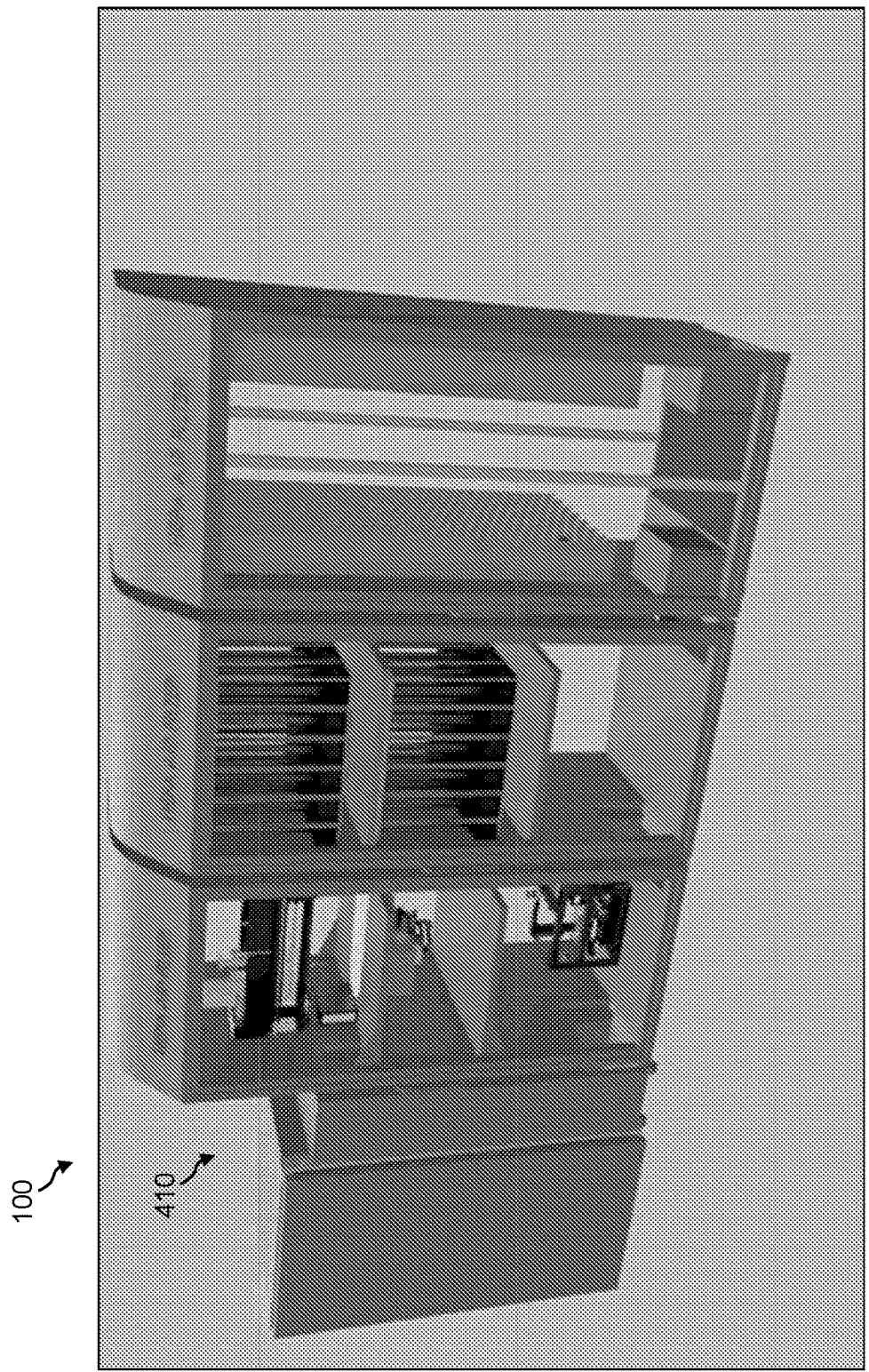
Figure 69:
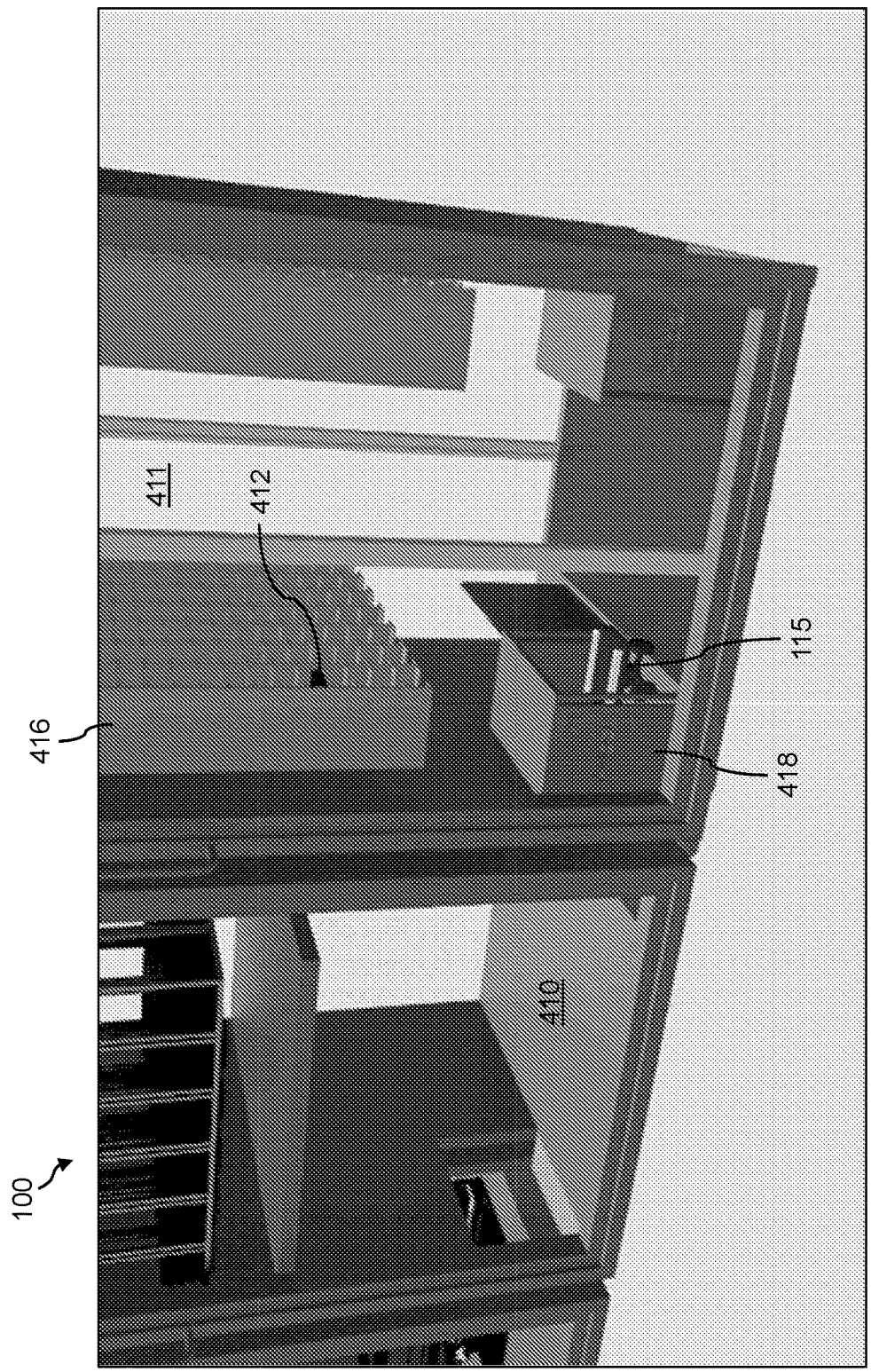
Figure 70:
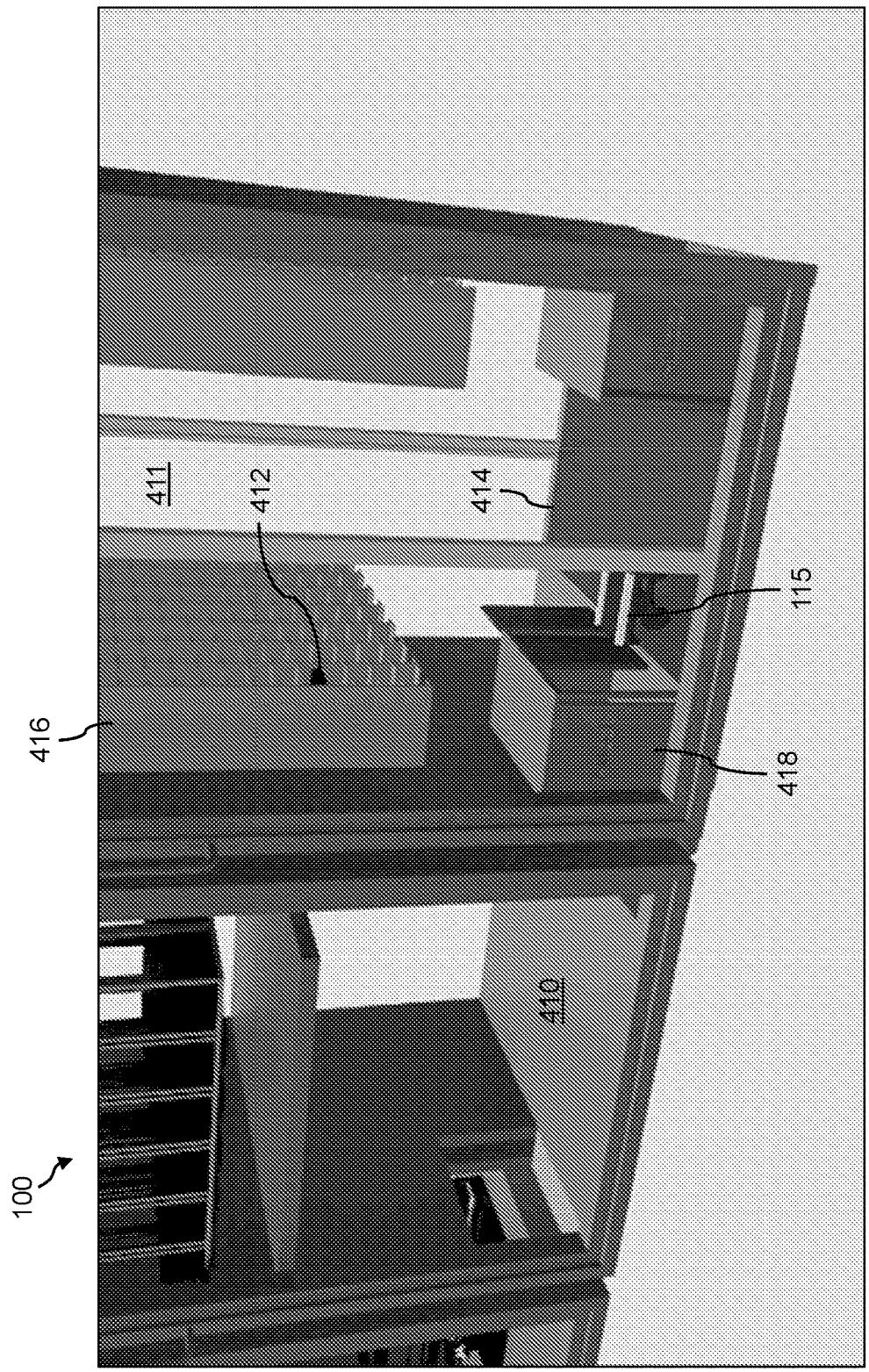
Figure 71:
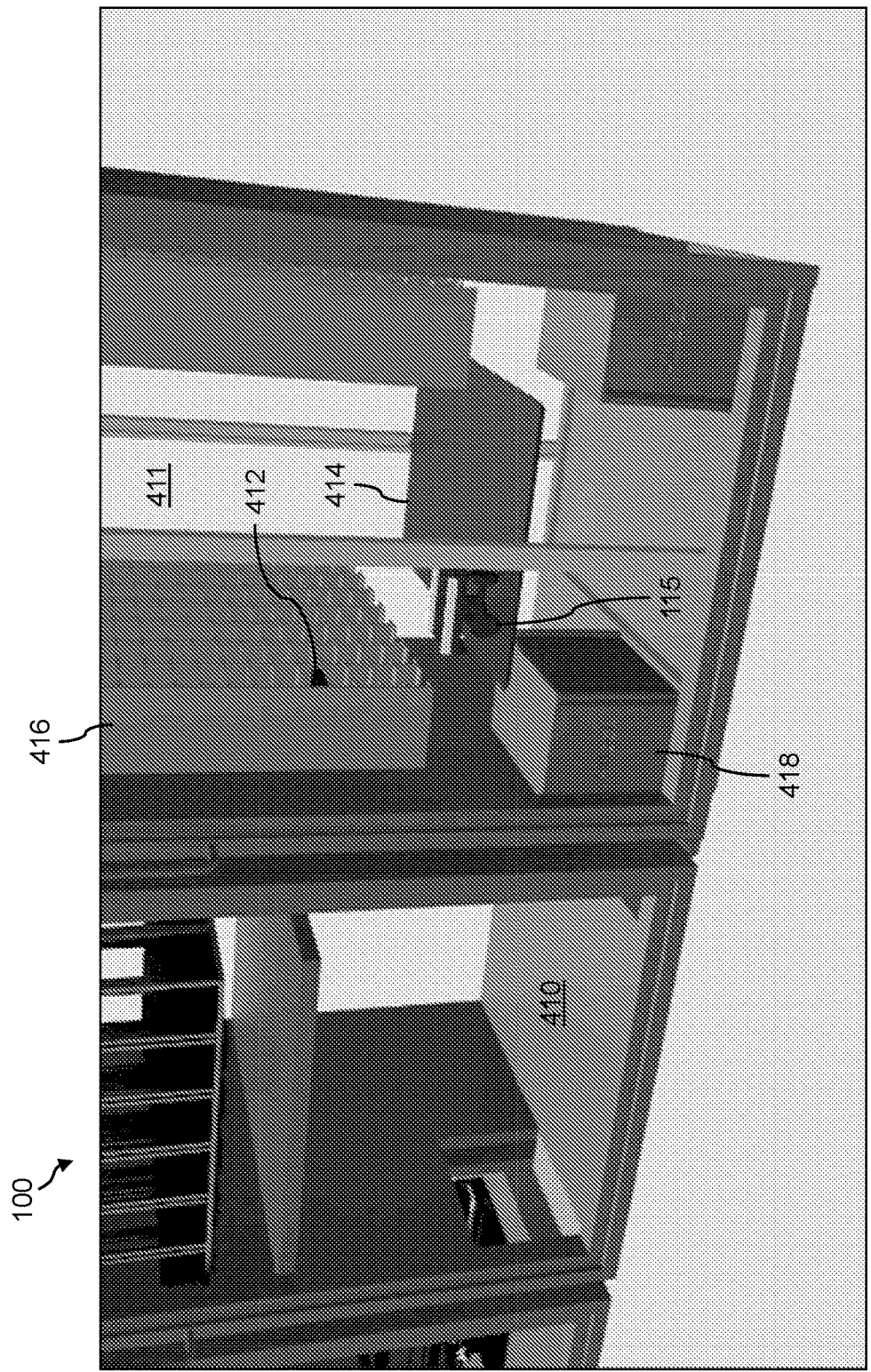
Figure 72:
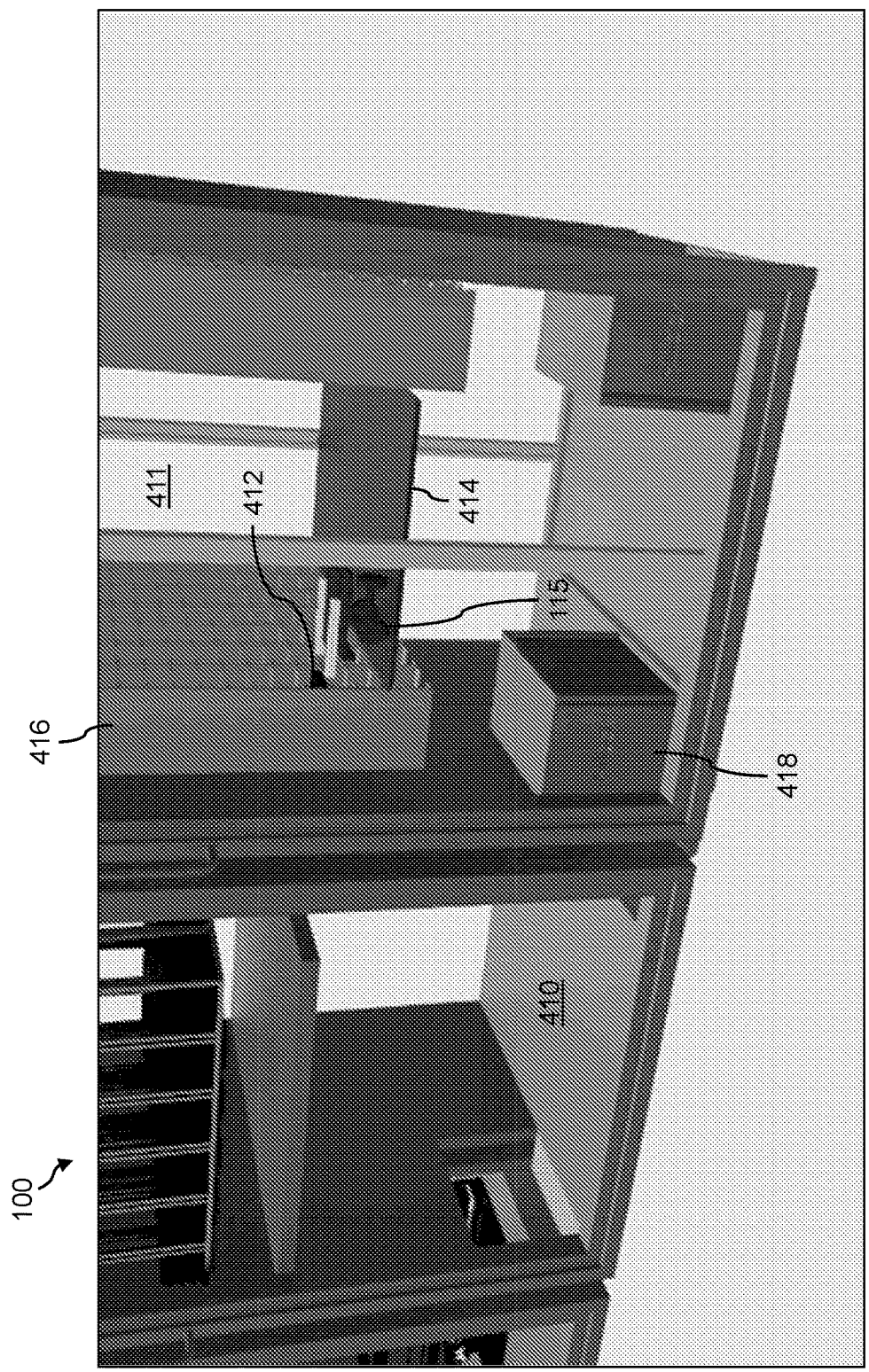
Figure 73:
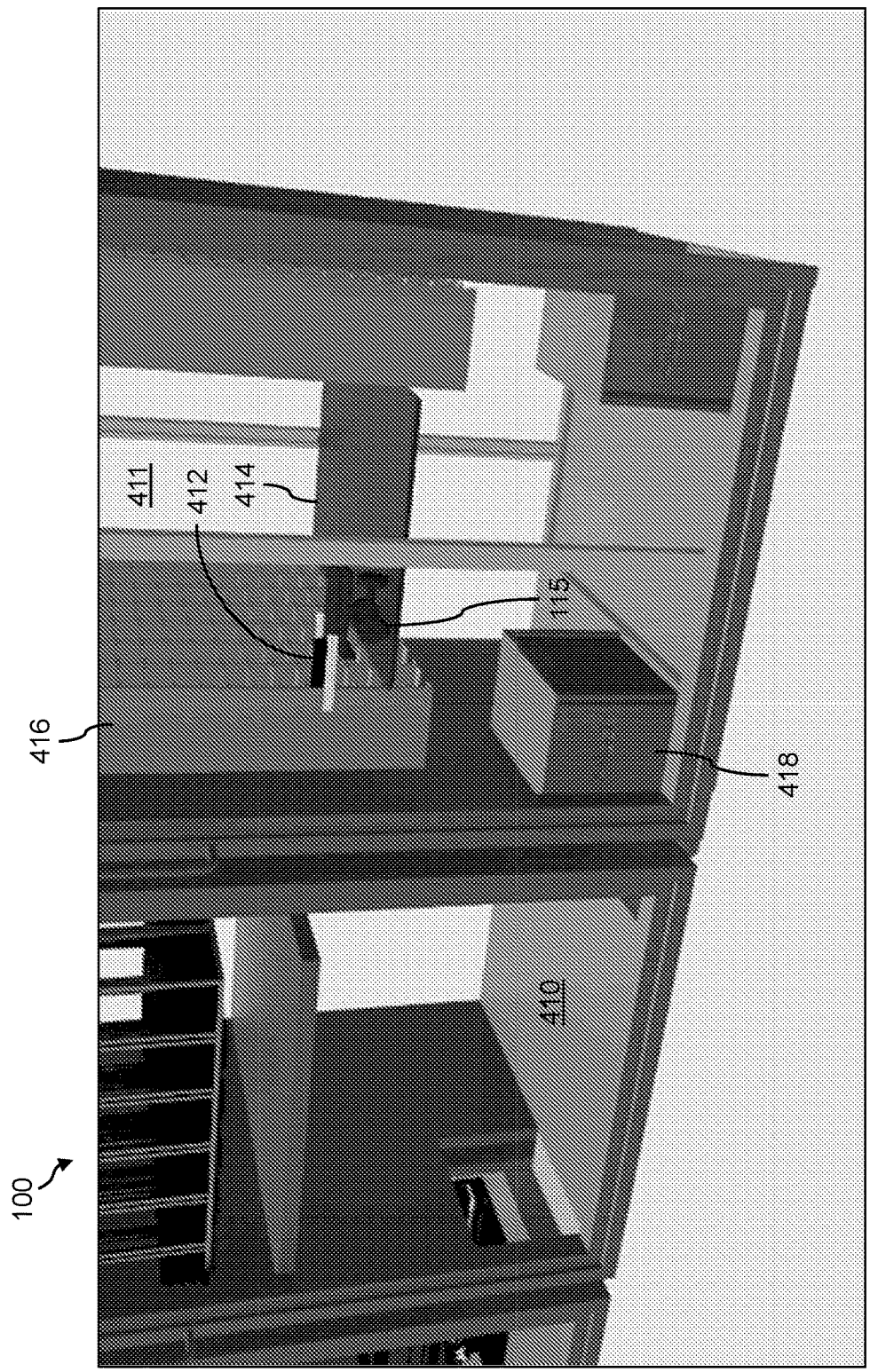
Figure 74:
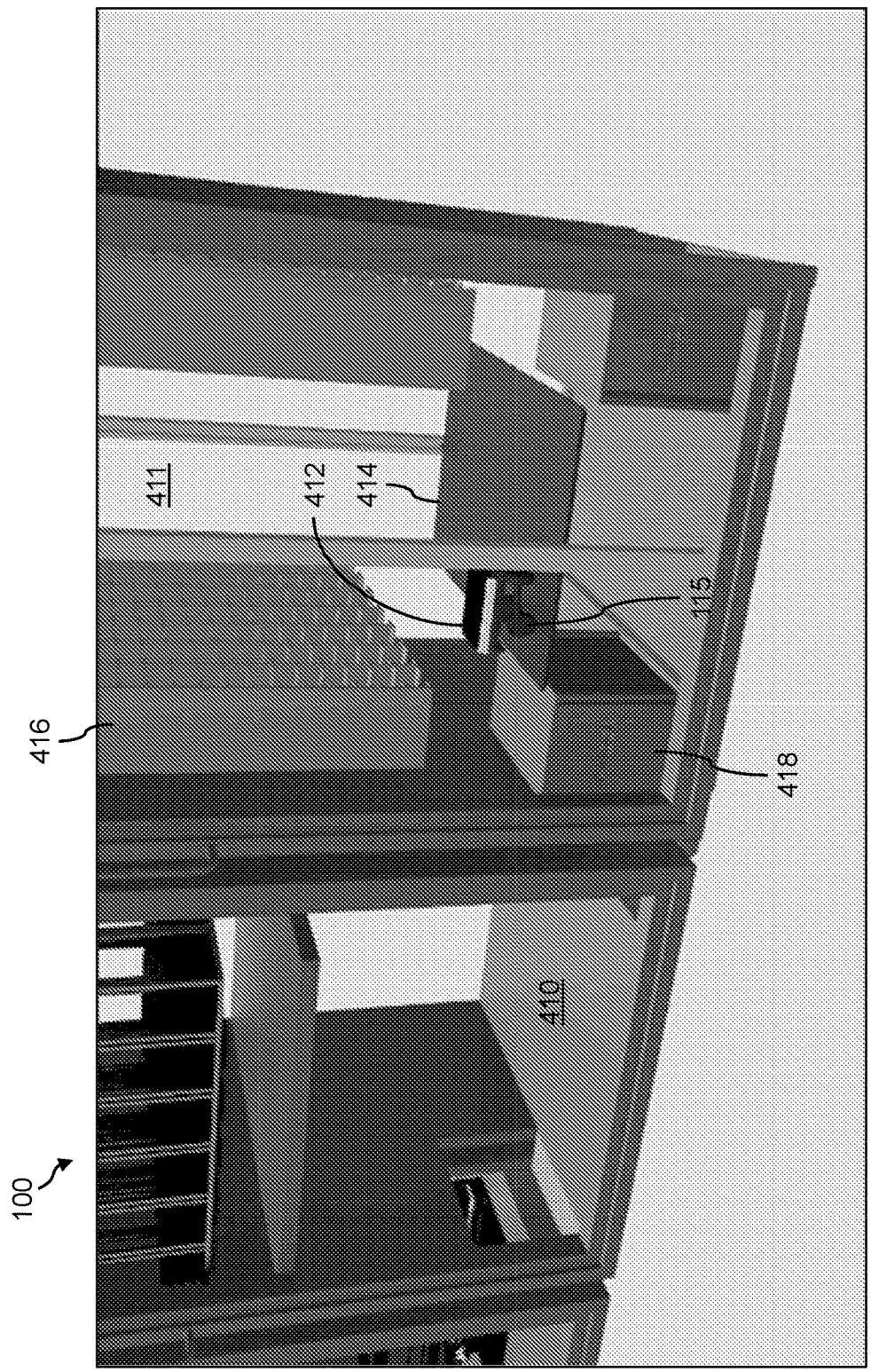
Figure 75:
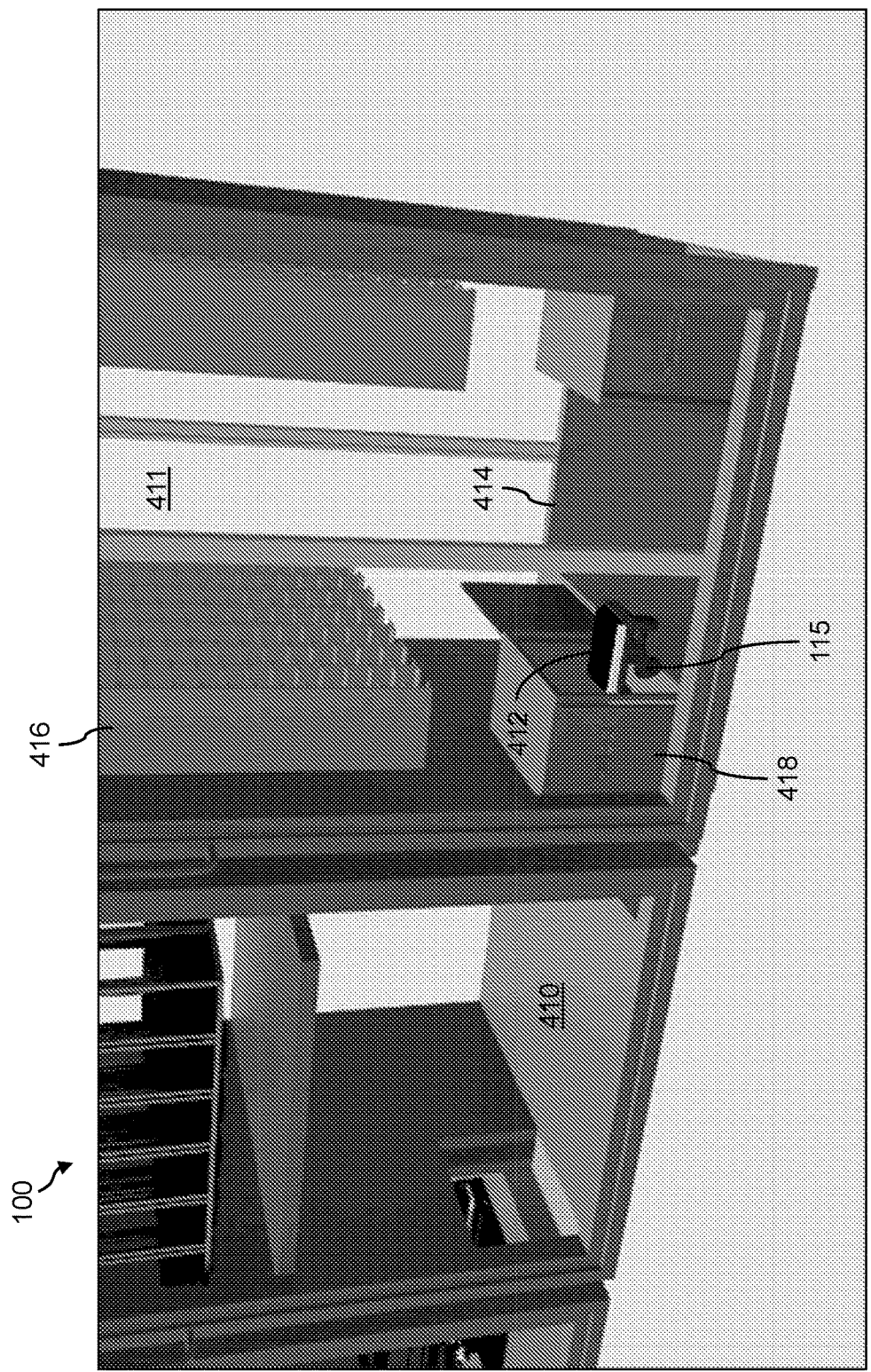
Figure 76:
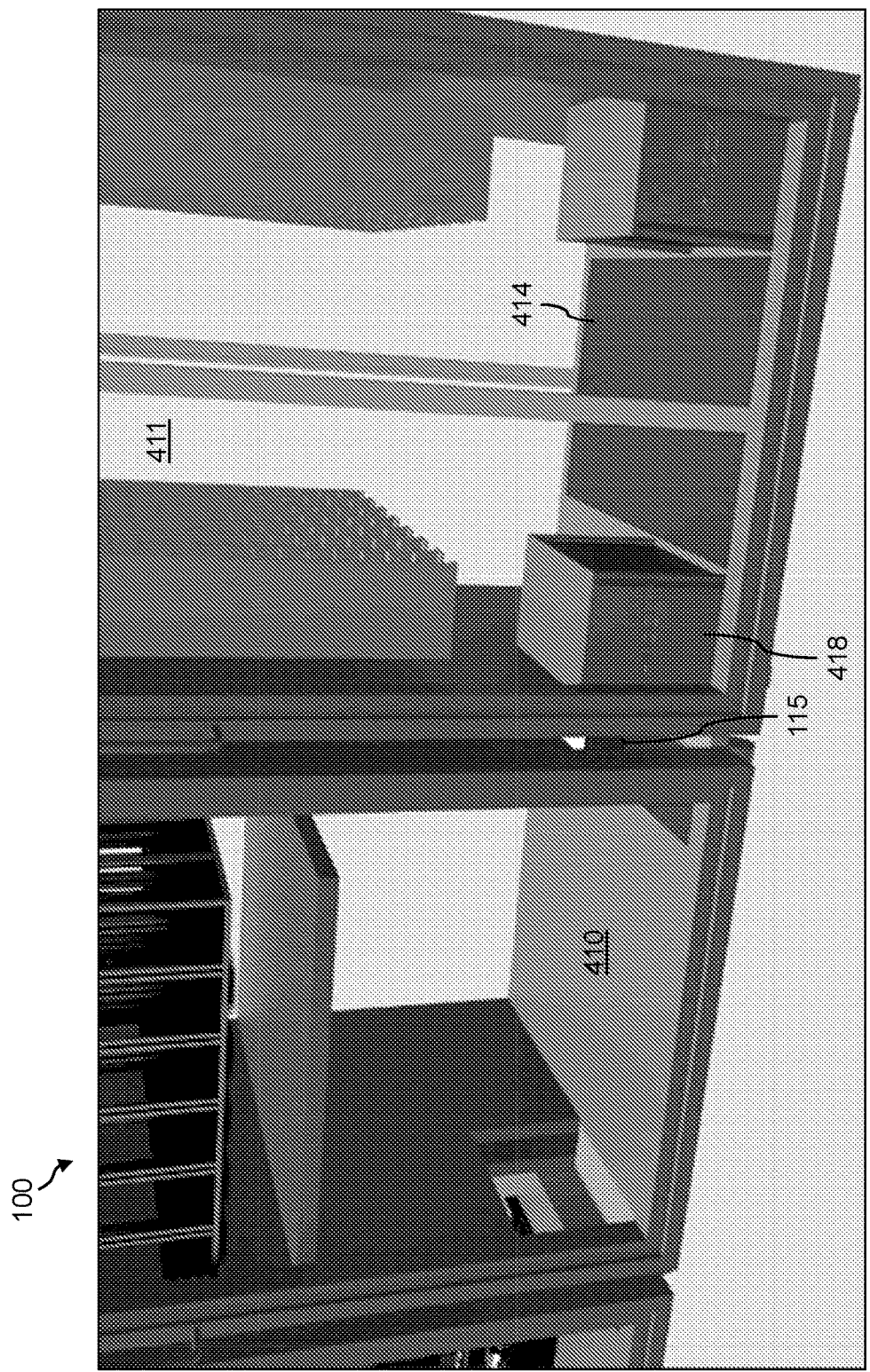
Figure 77:
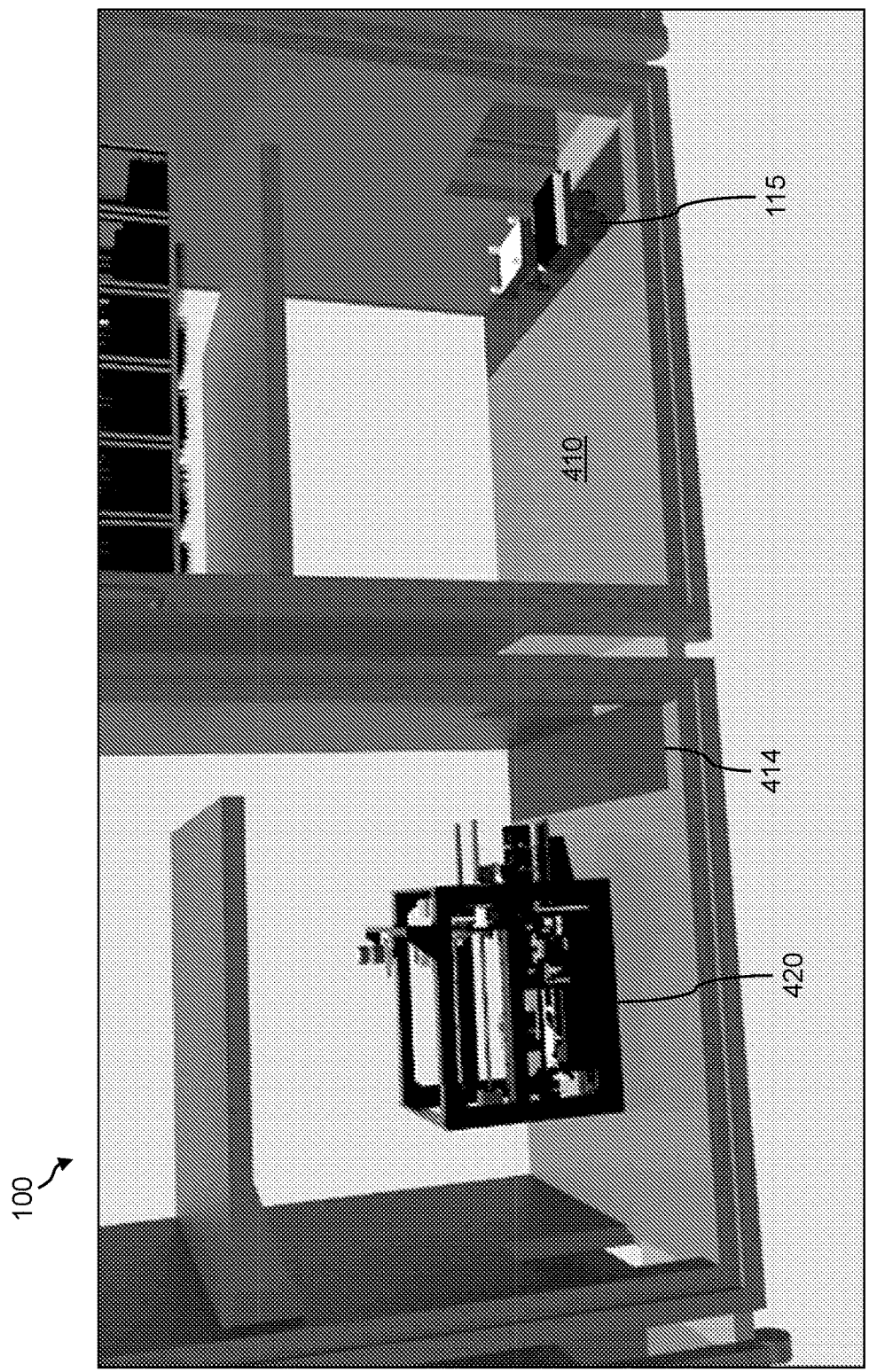
Figure 78:
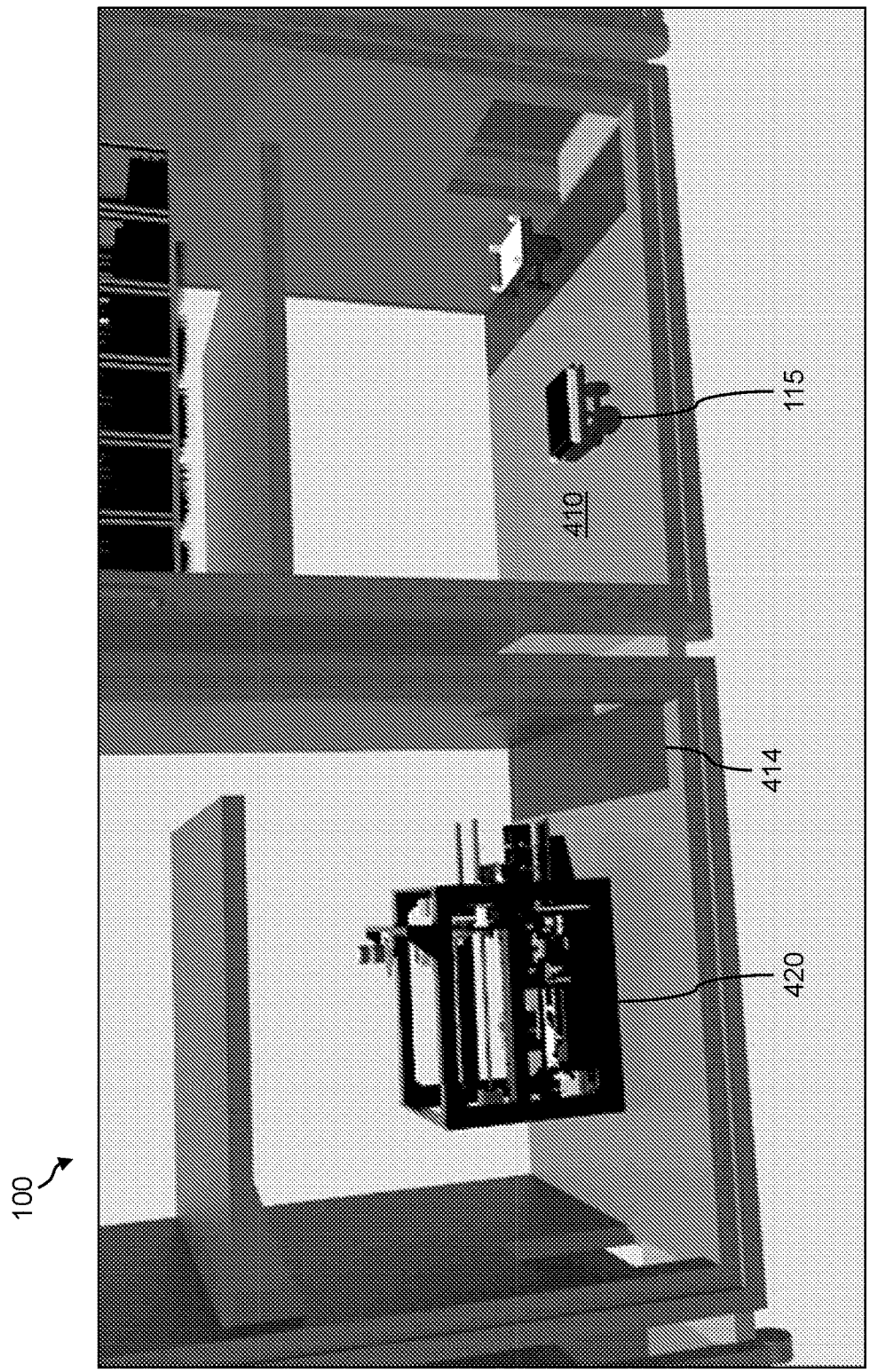
Figure 79:
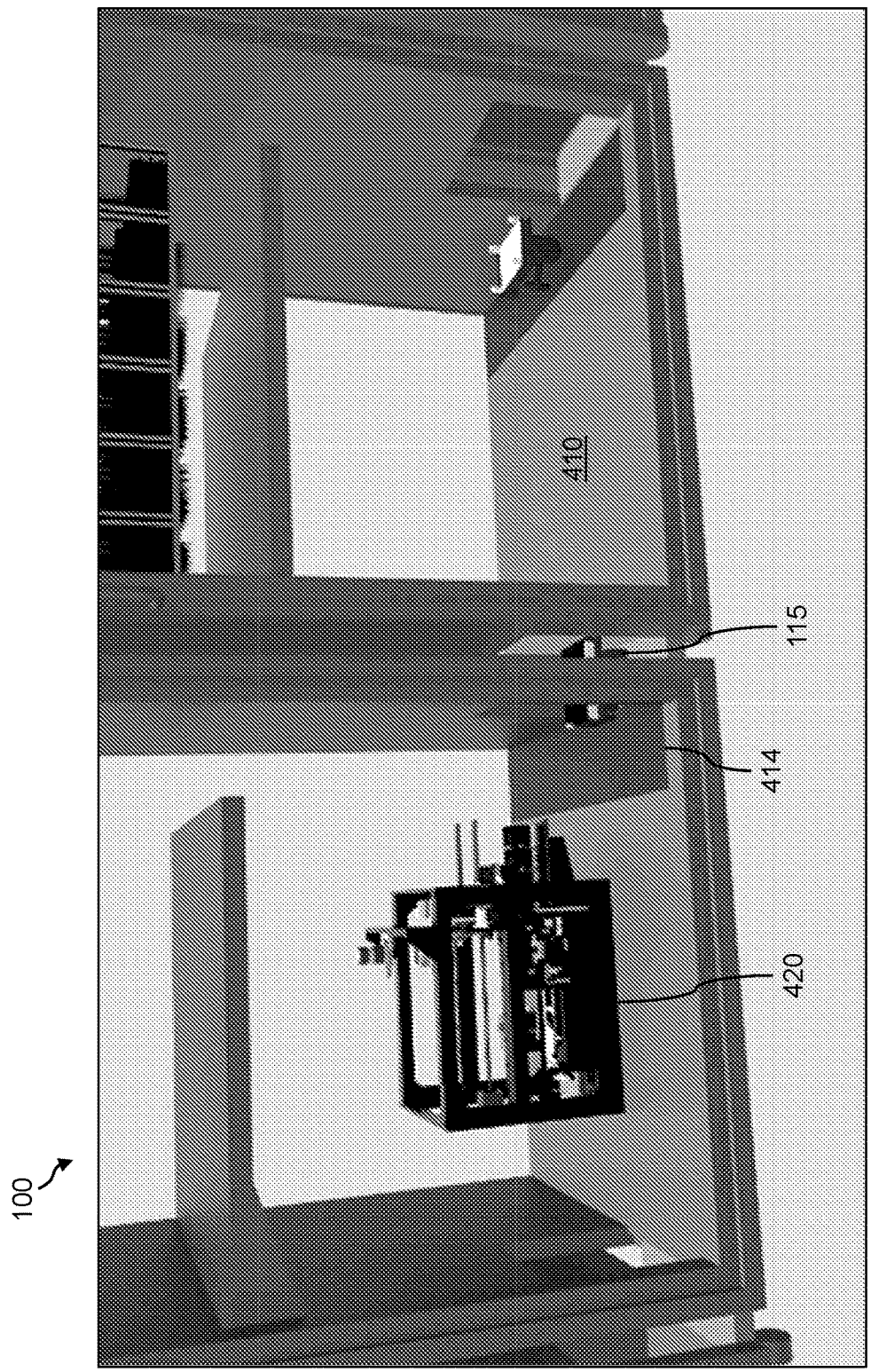
Figure 80:
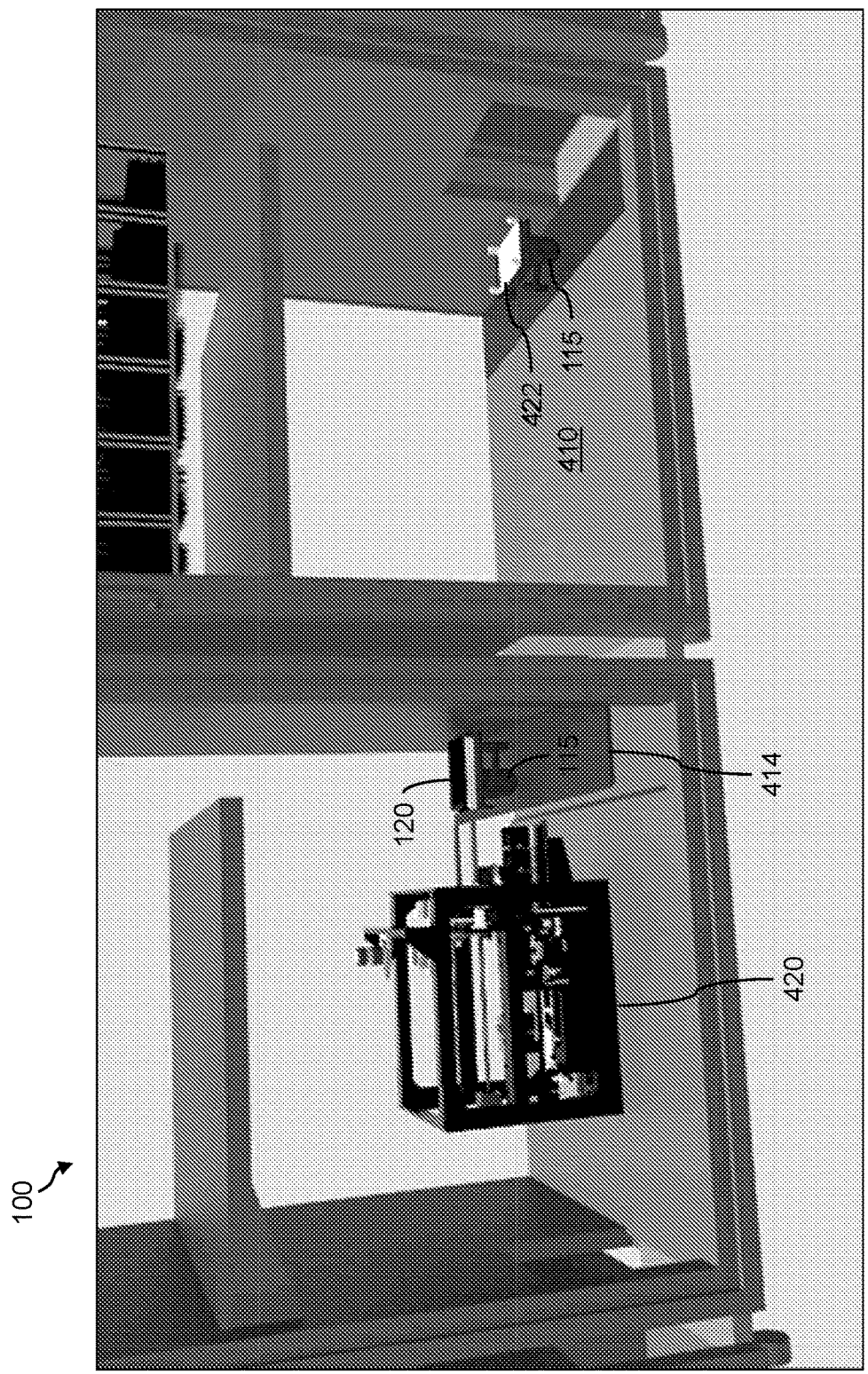
Figure 81:
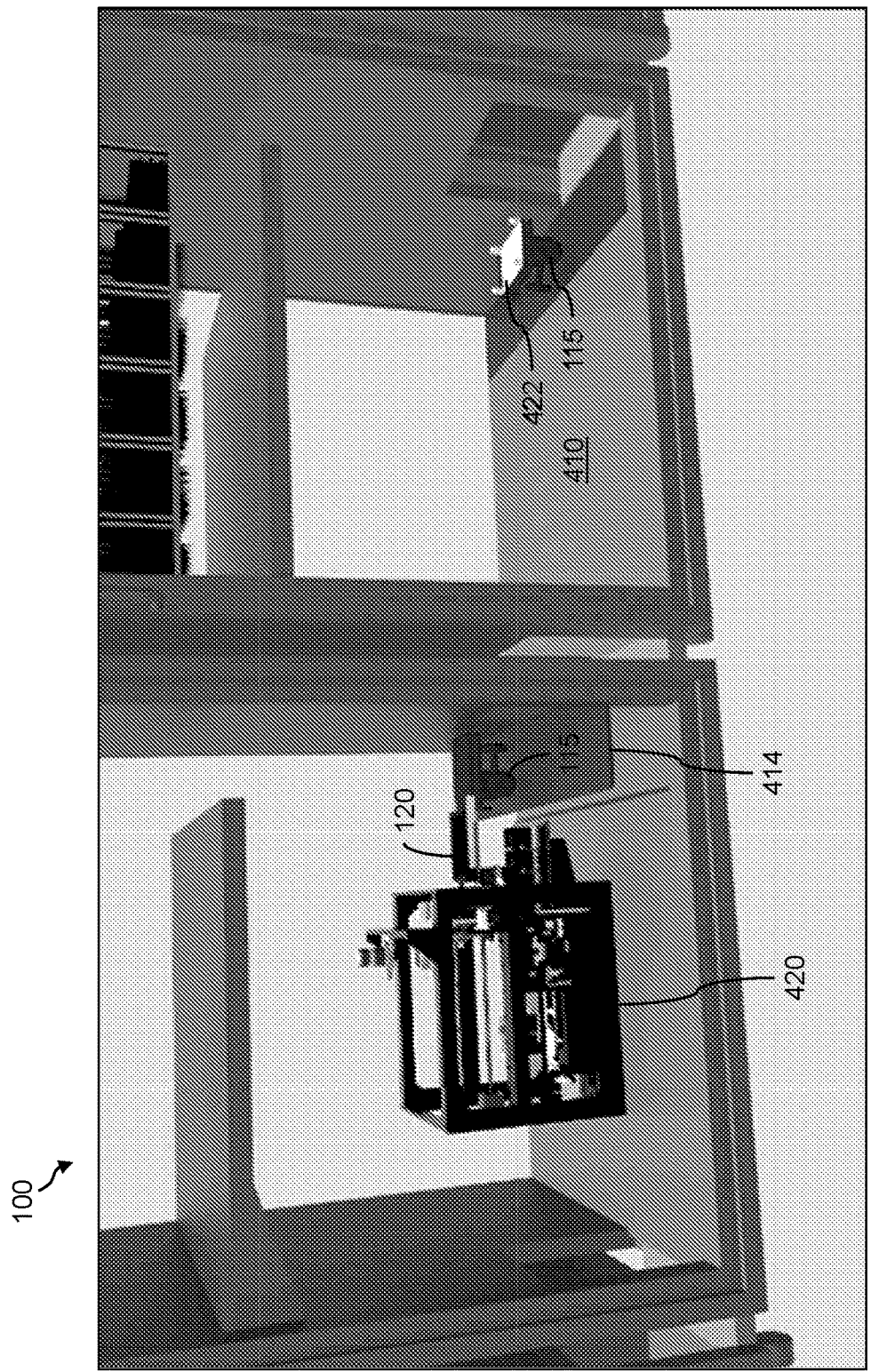
Figure 82:
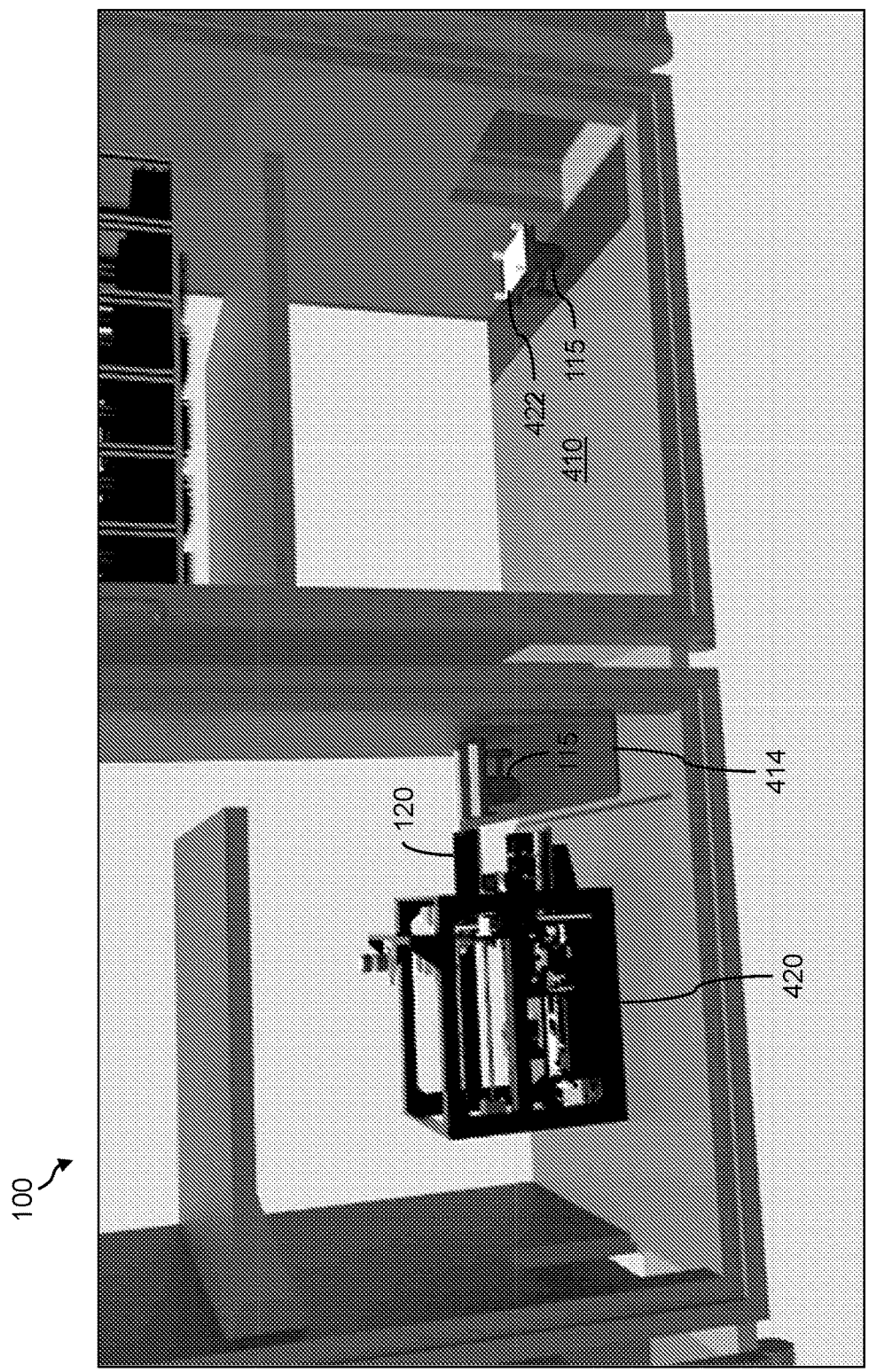
Figure 83:
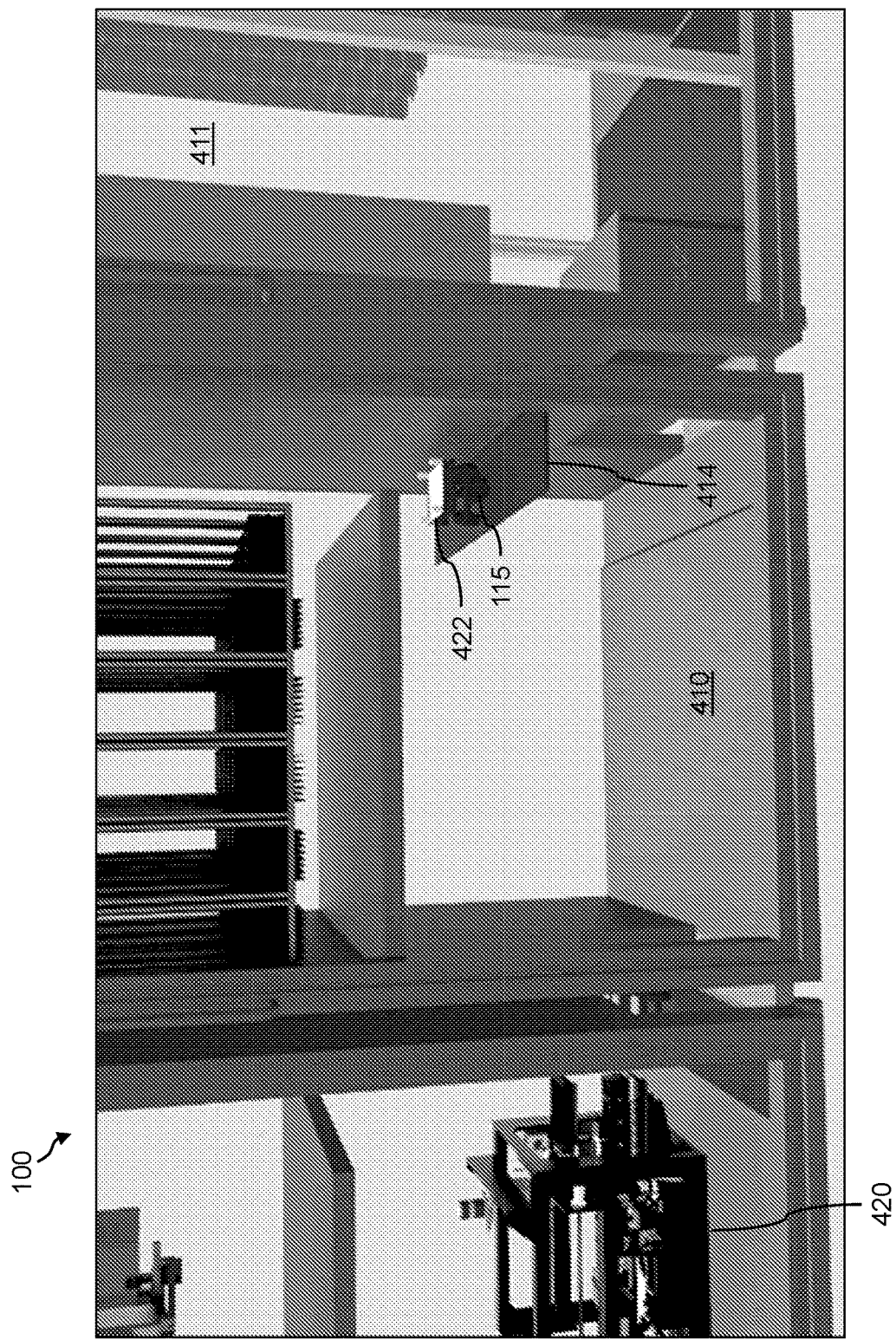
Figure 84:
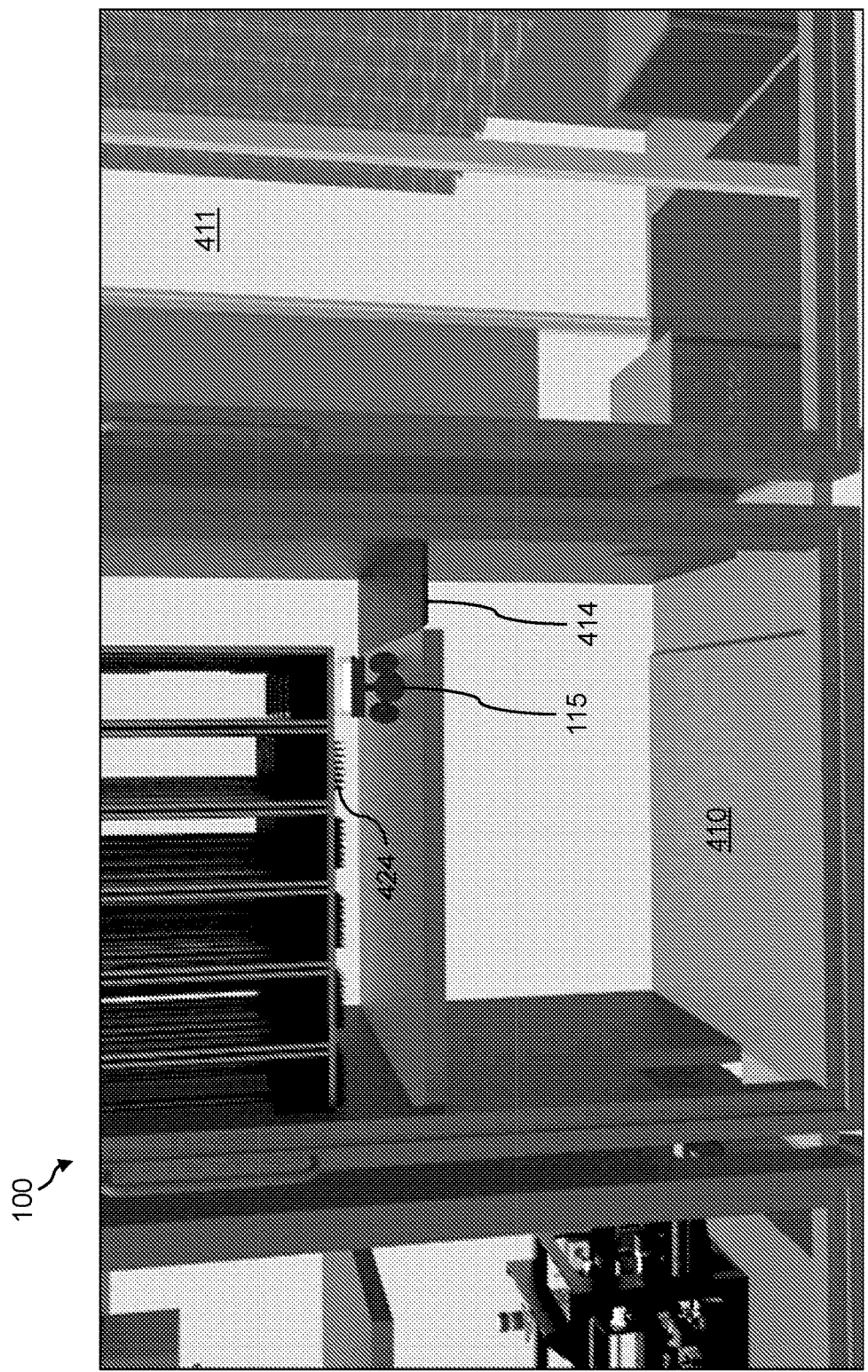
Figure 85:
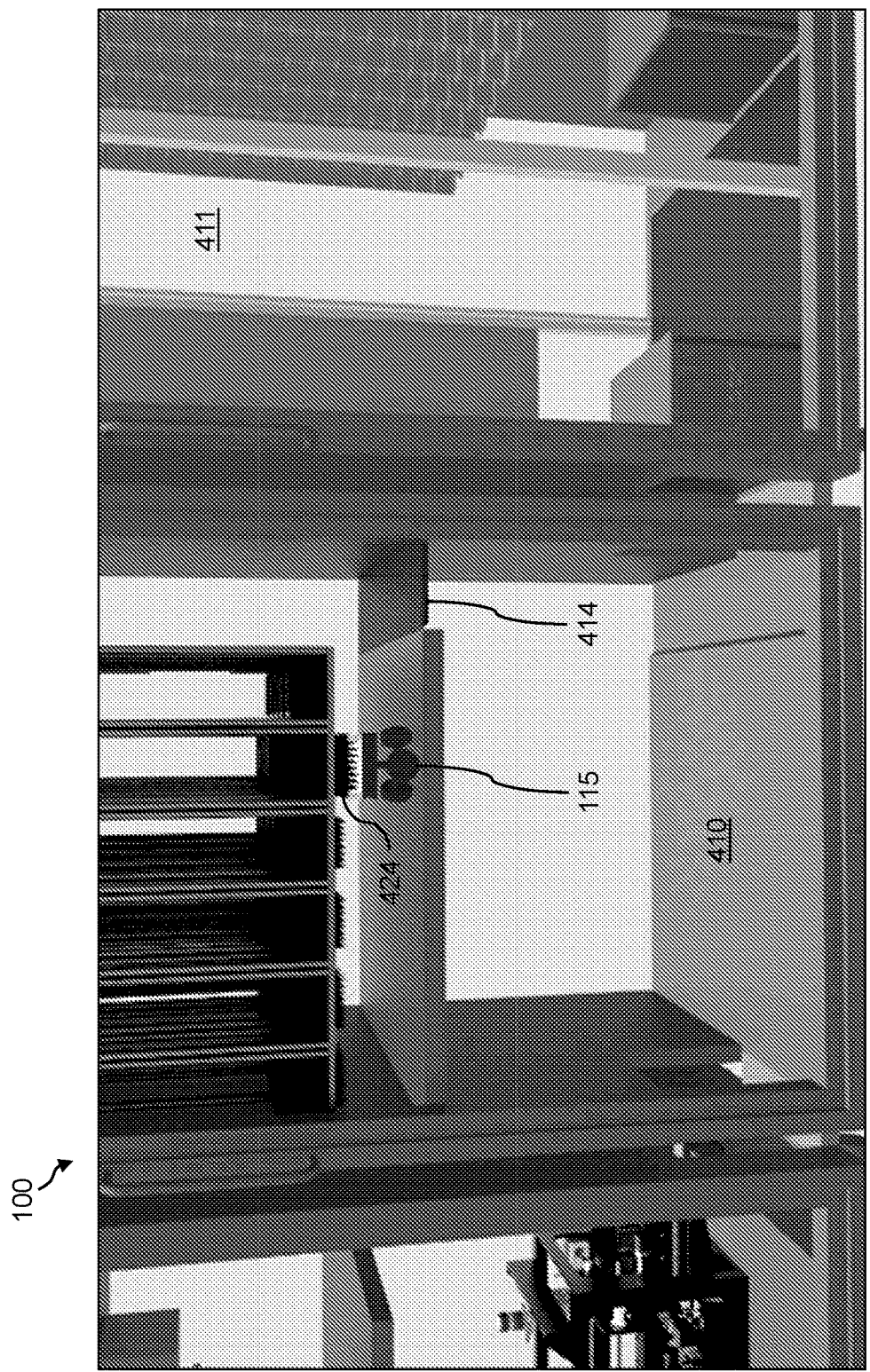
Figure 86:
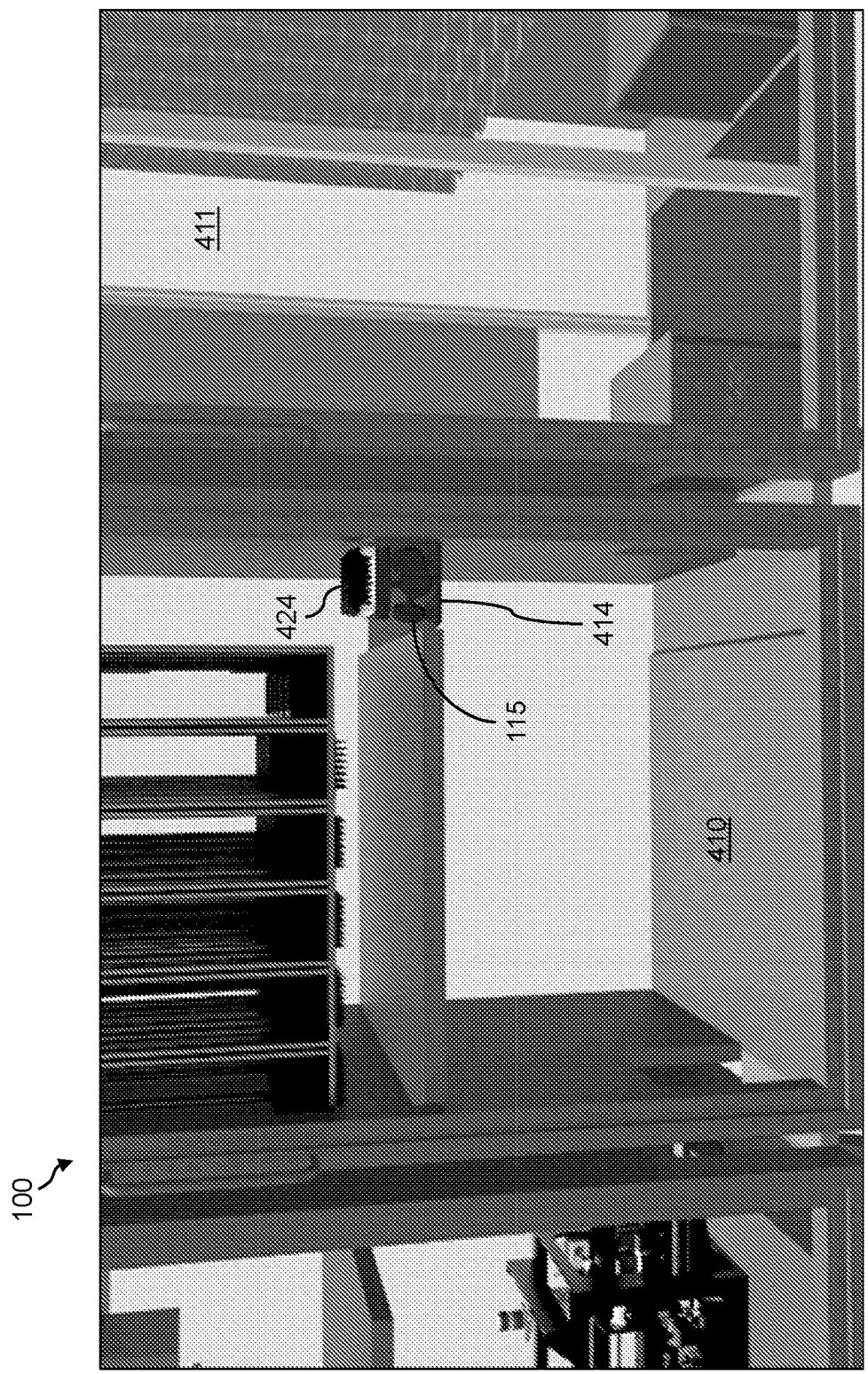
Figure 87:
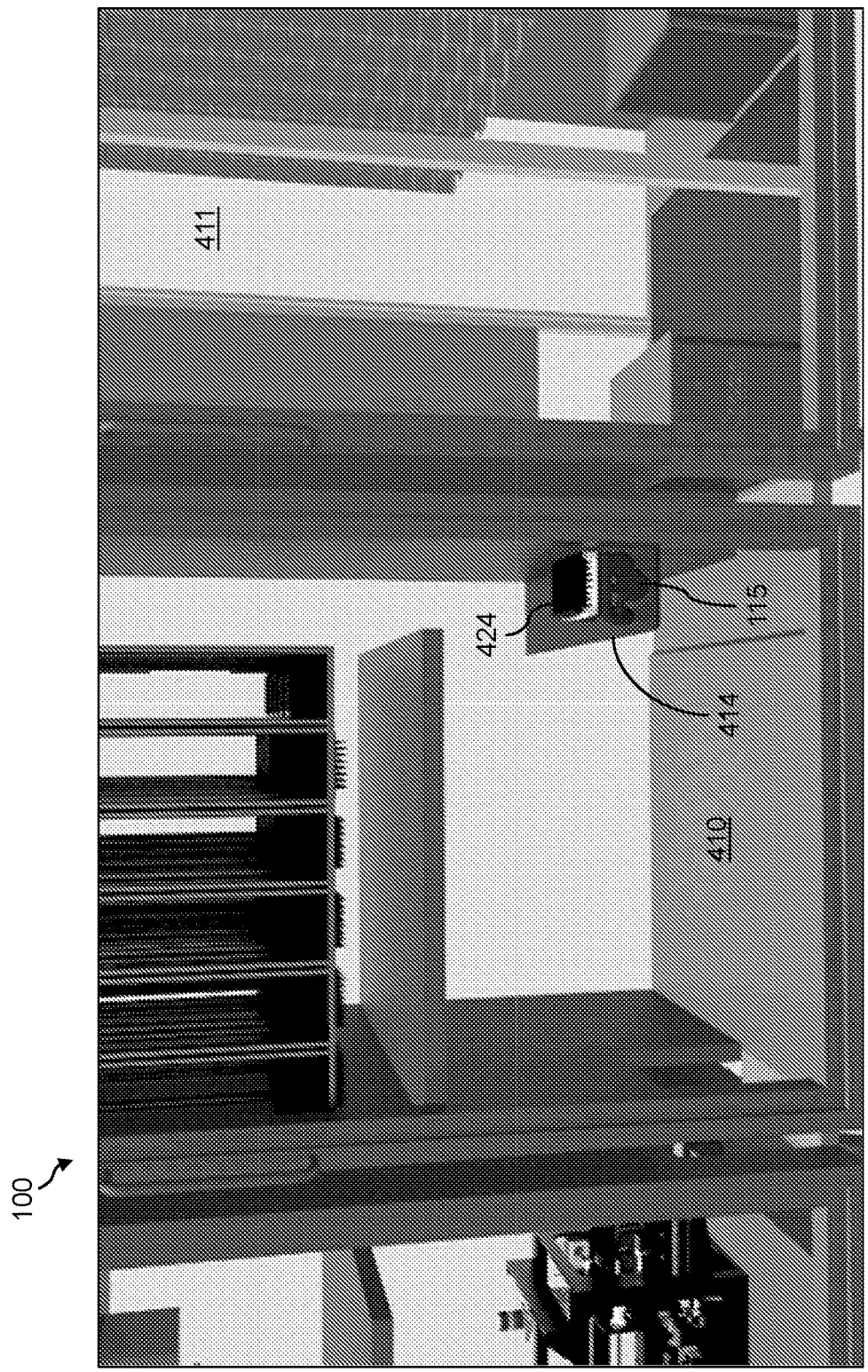
Figure 88:
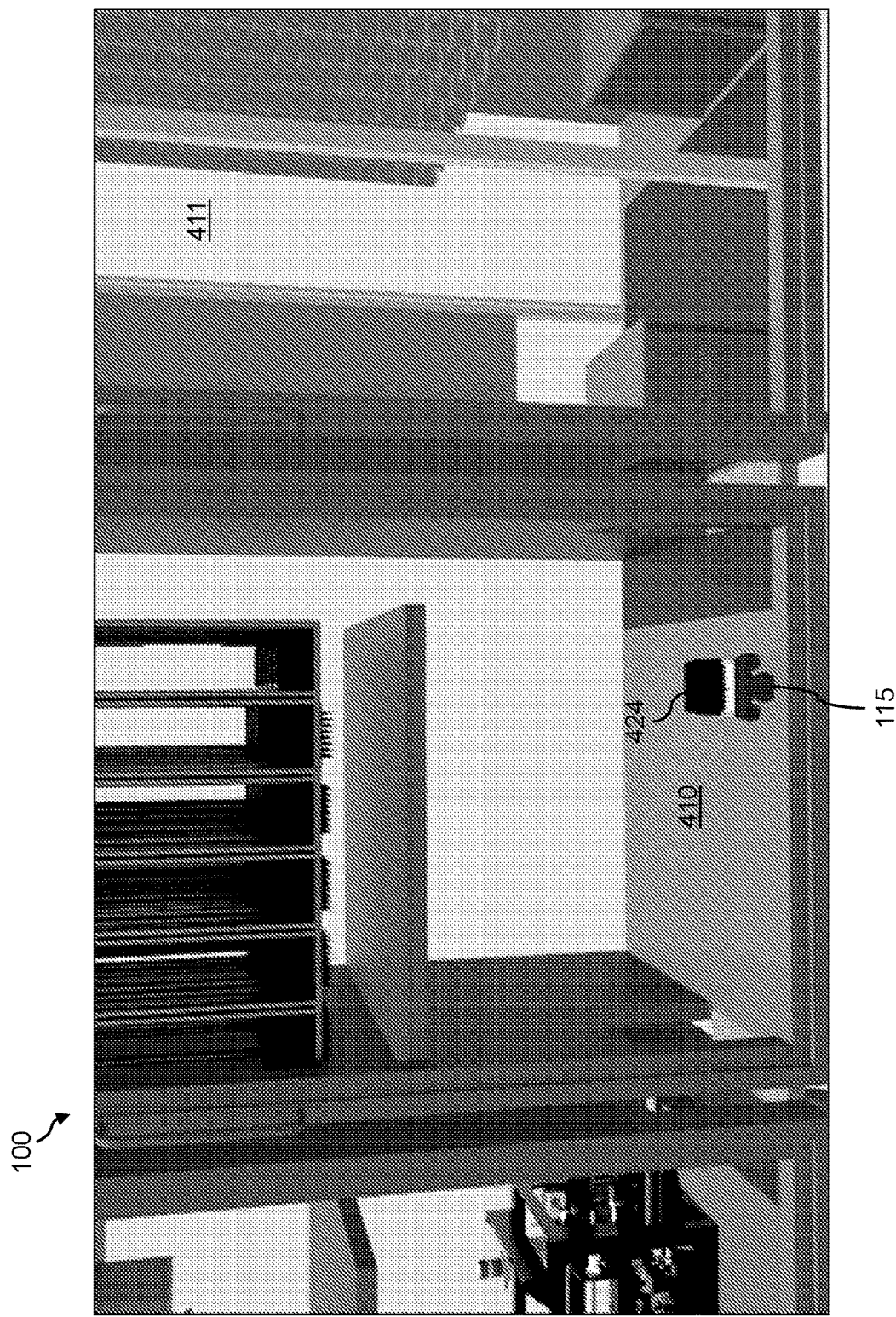
Figure 89:
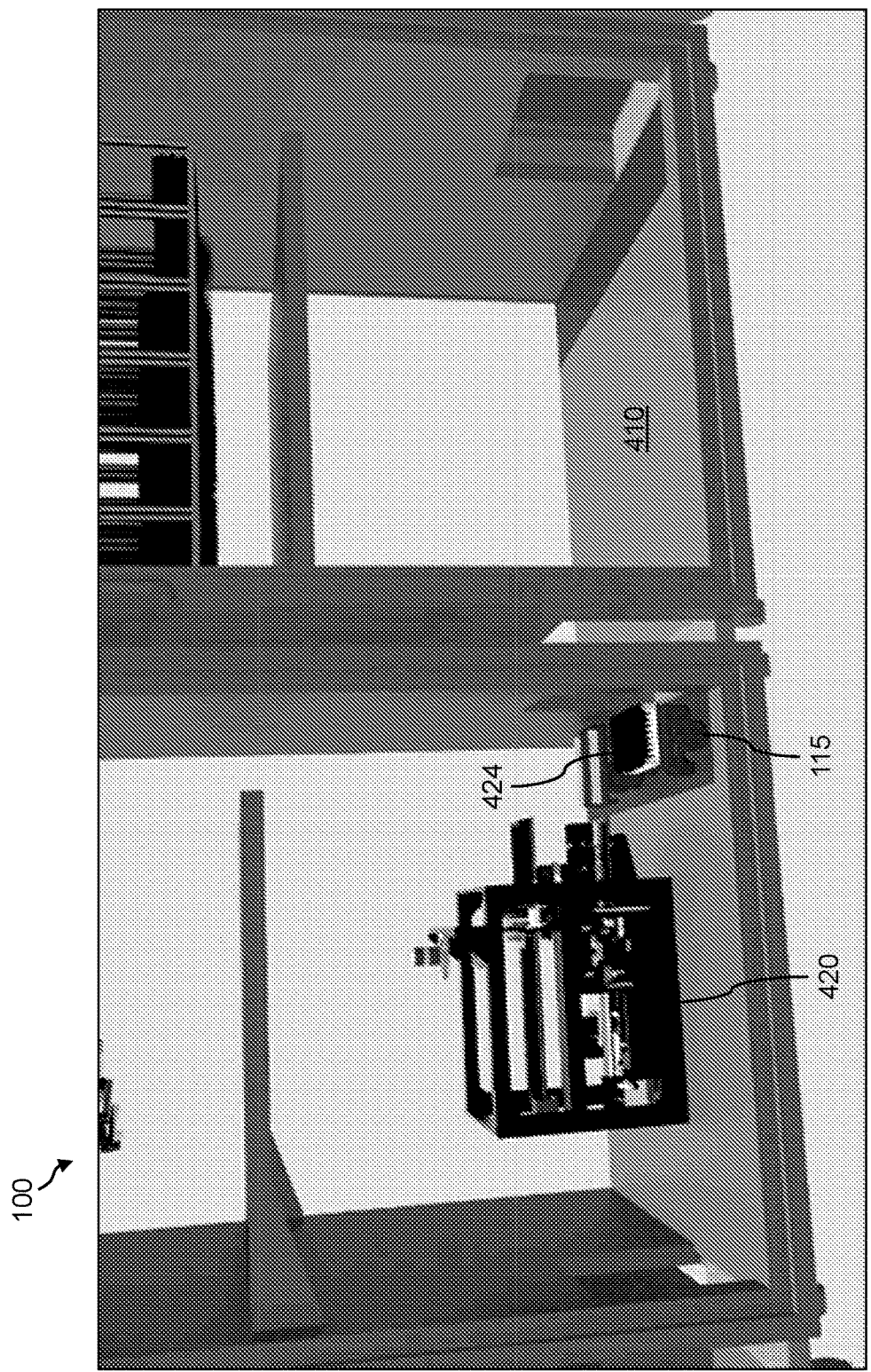
Figure 90:
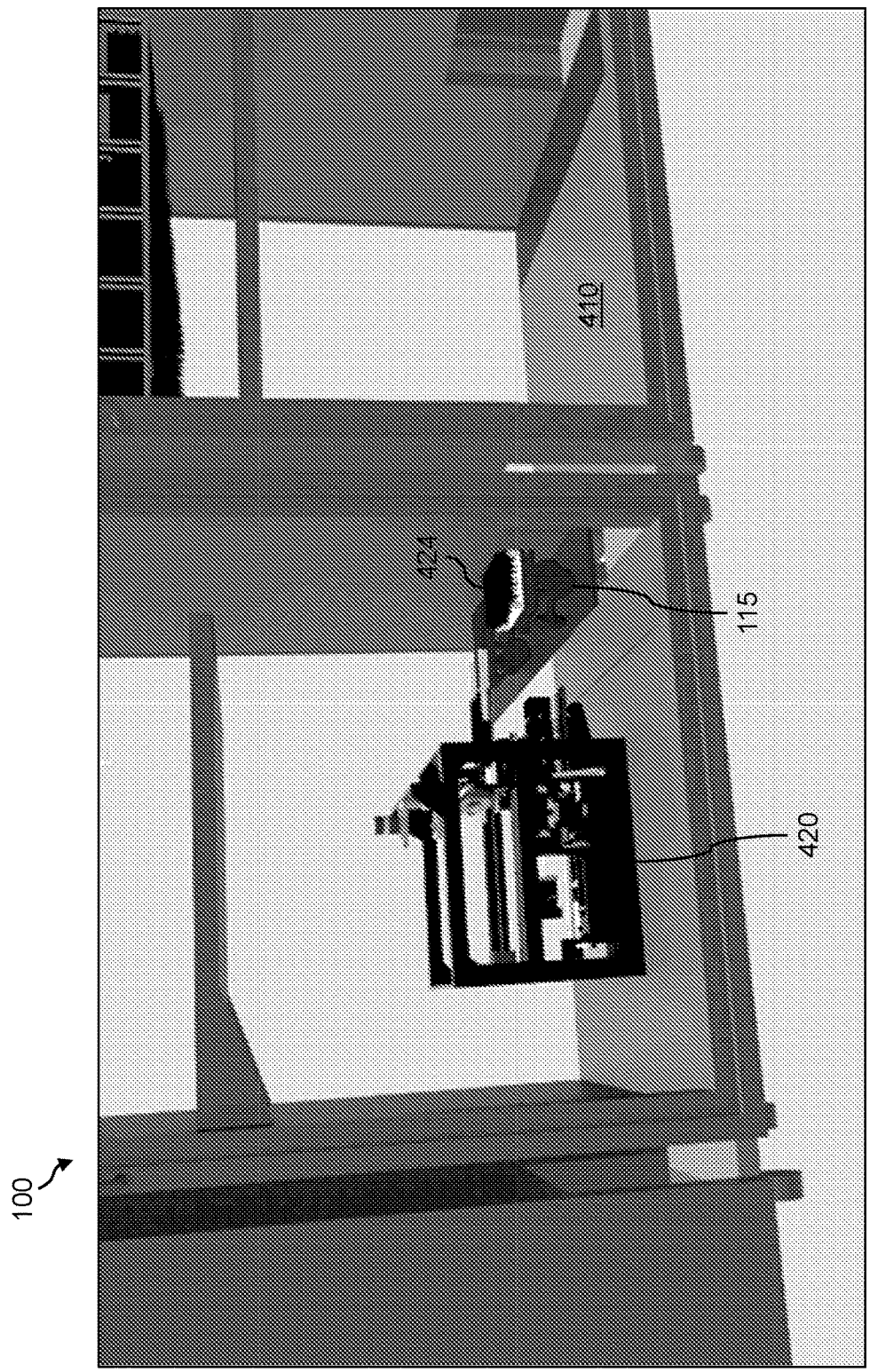
Figure 91:
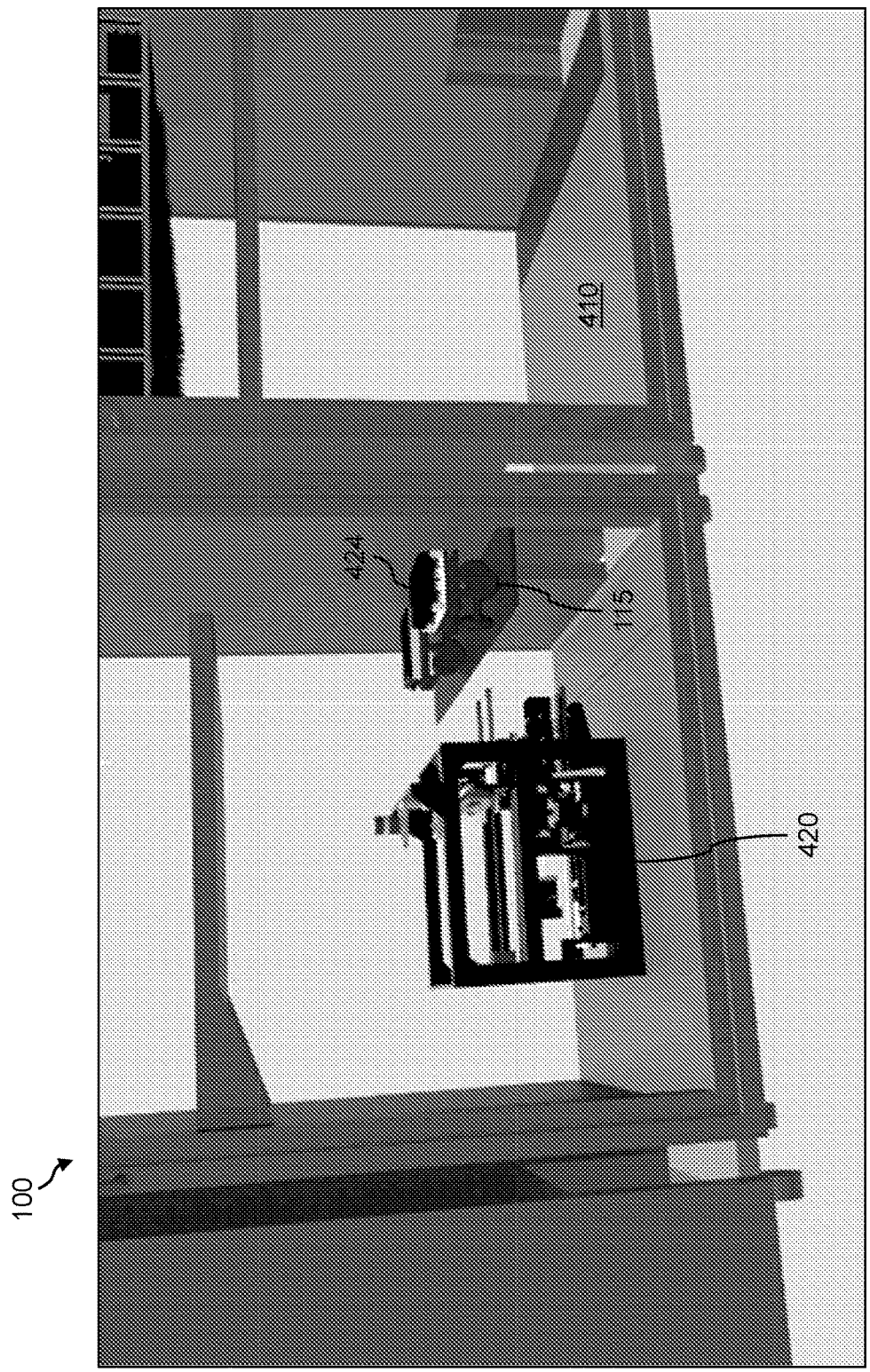
Figure 92:
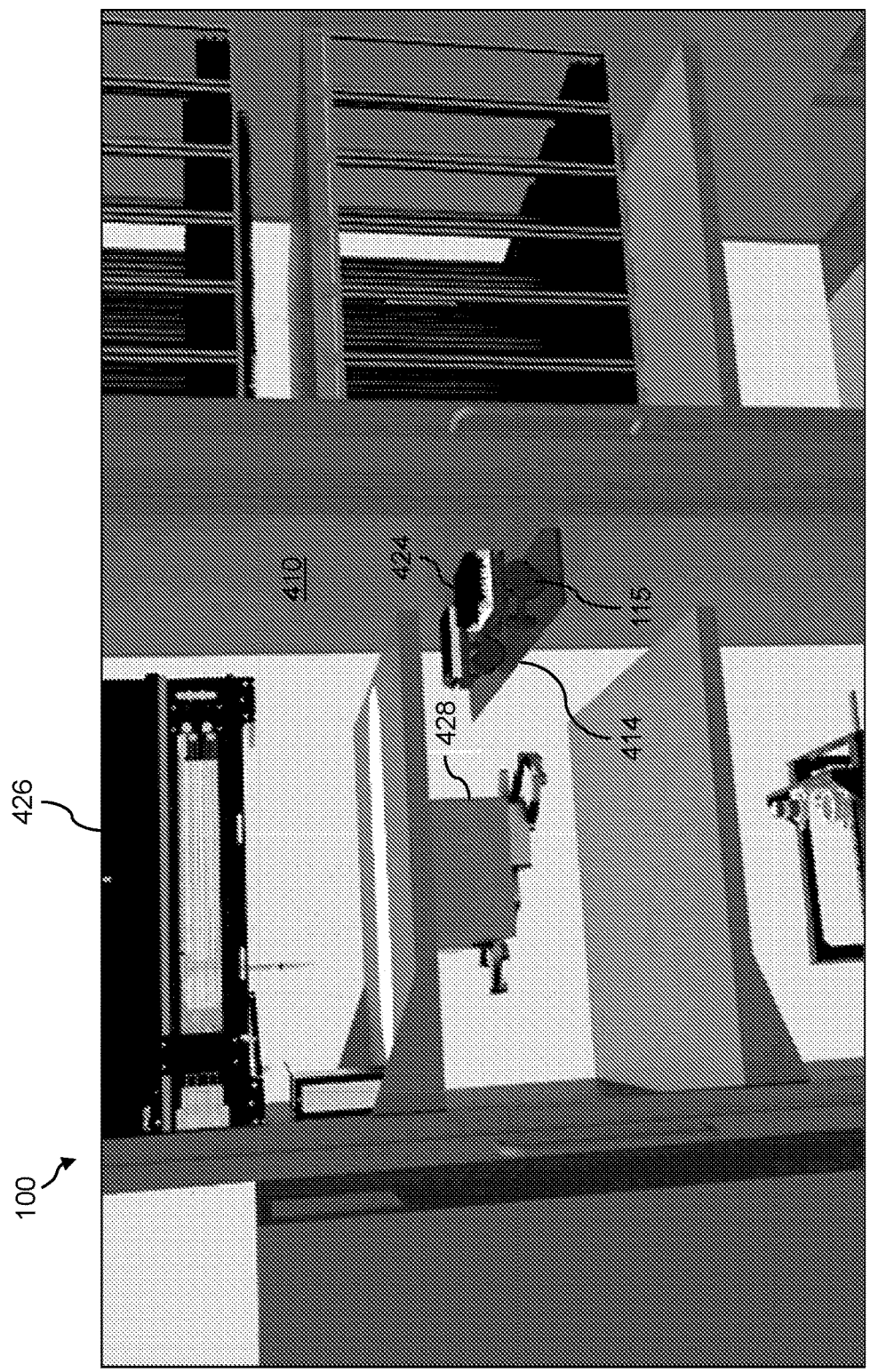
Figure 93:
Figure 94:
Figure 95:
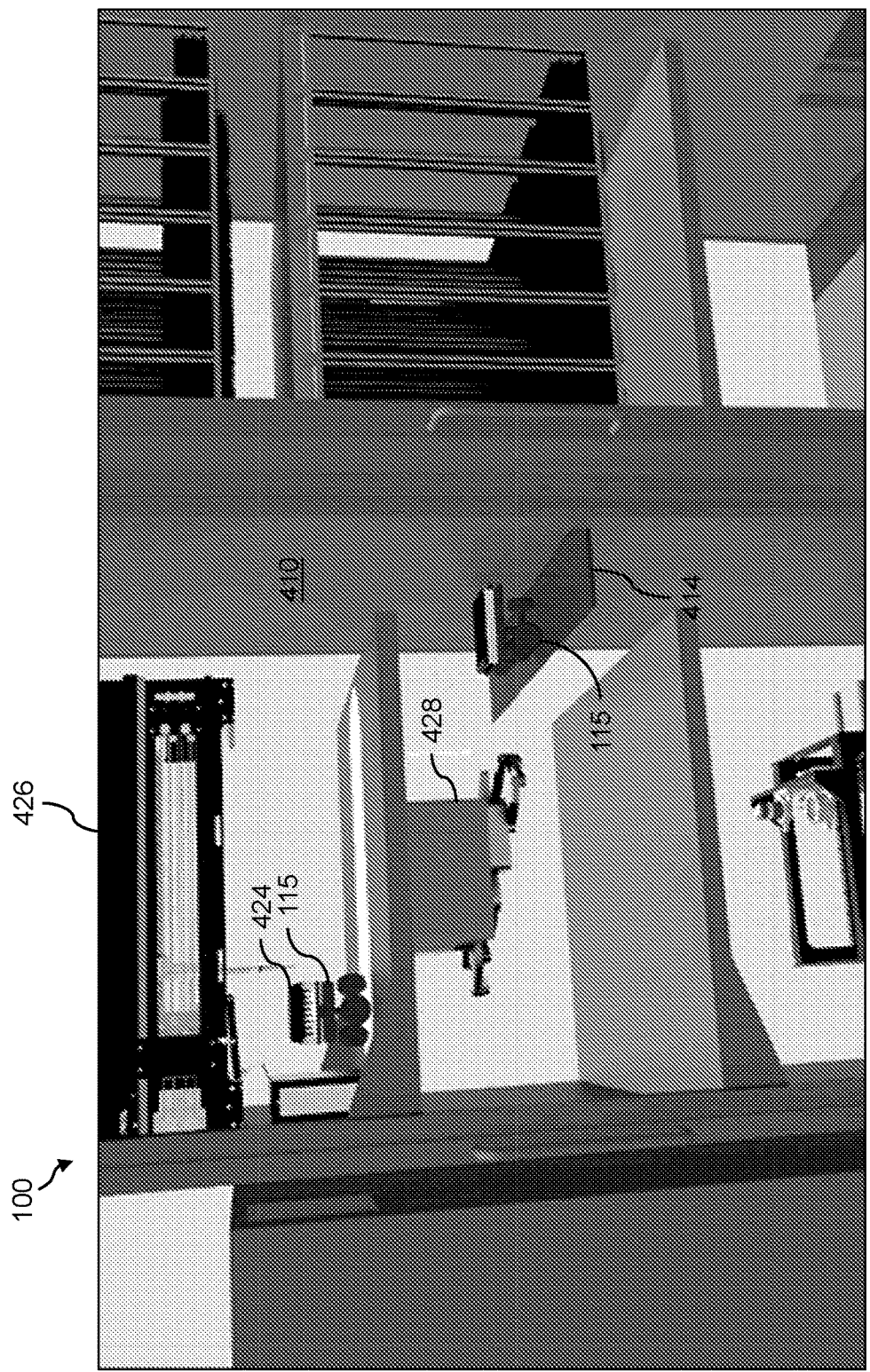
Figure 96:
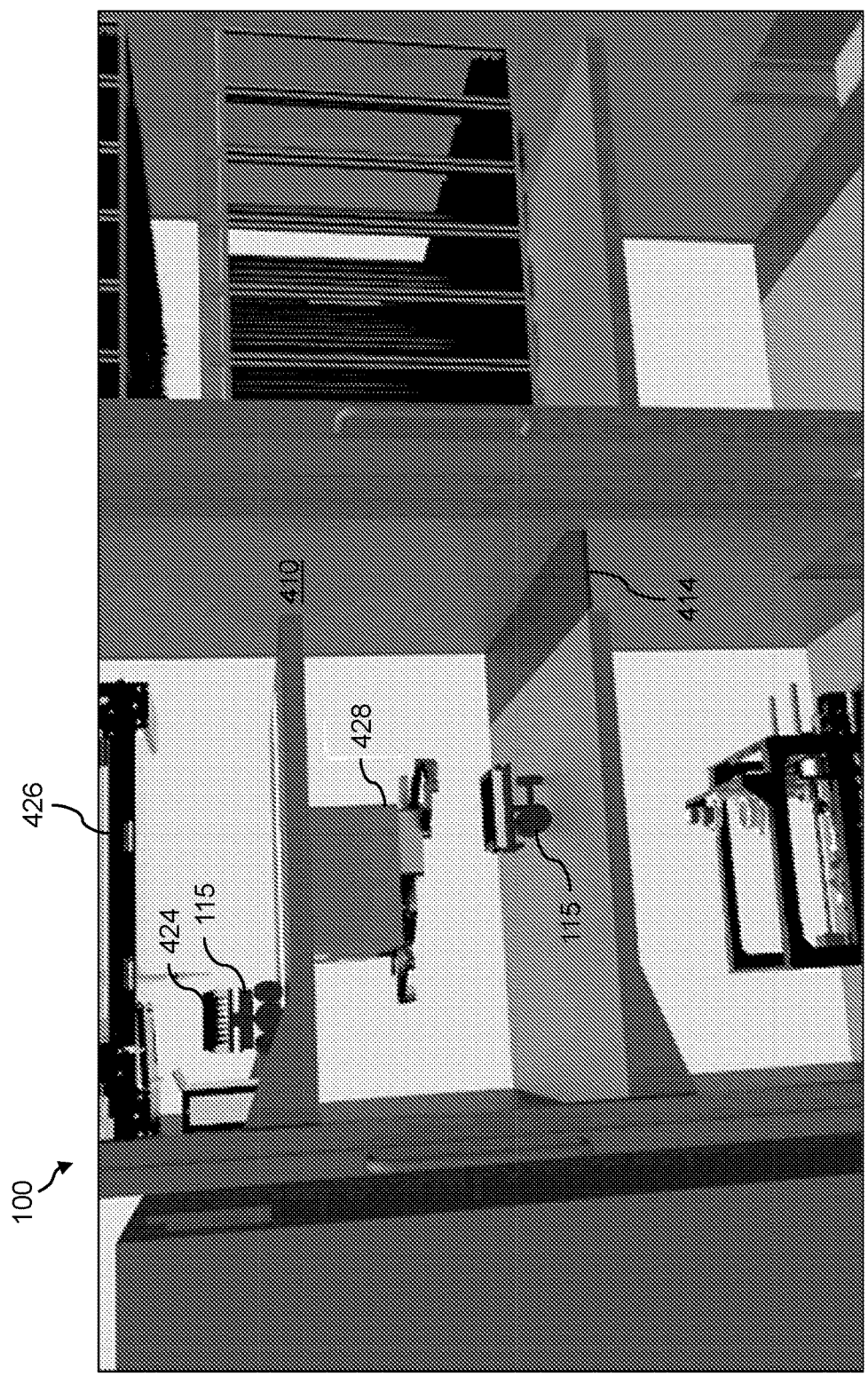
Figure 97:
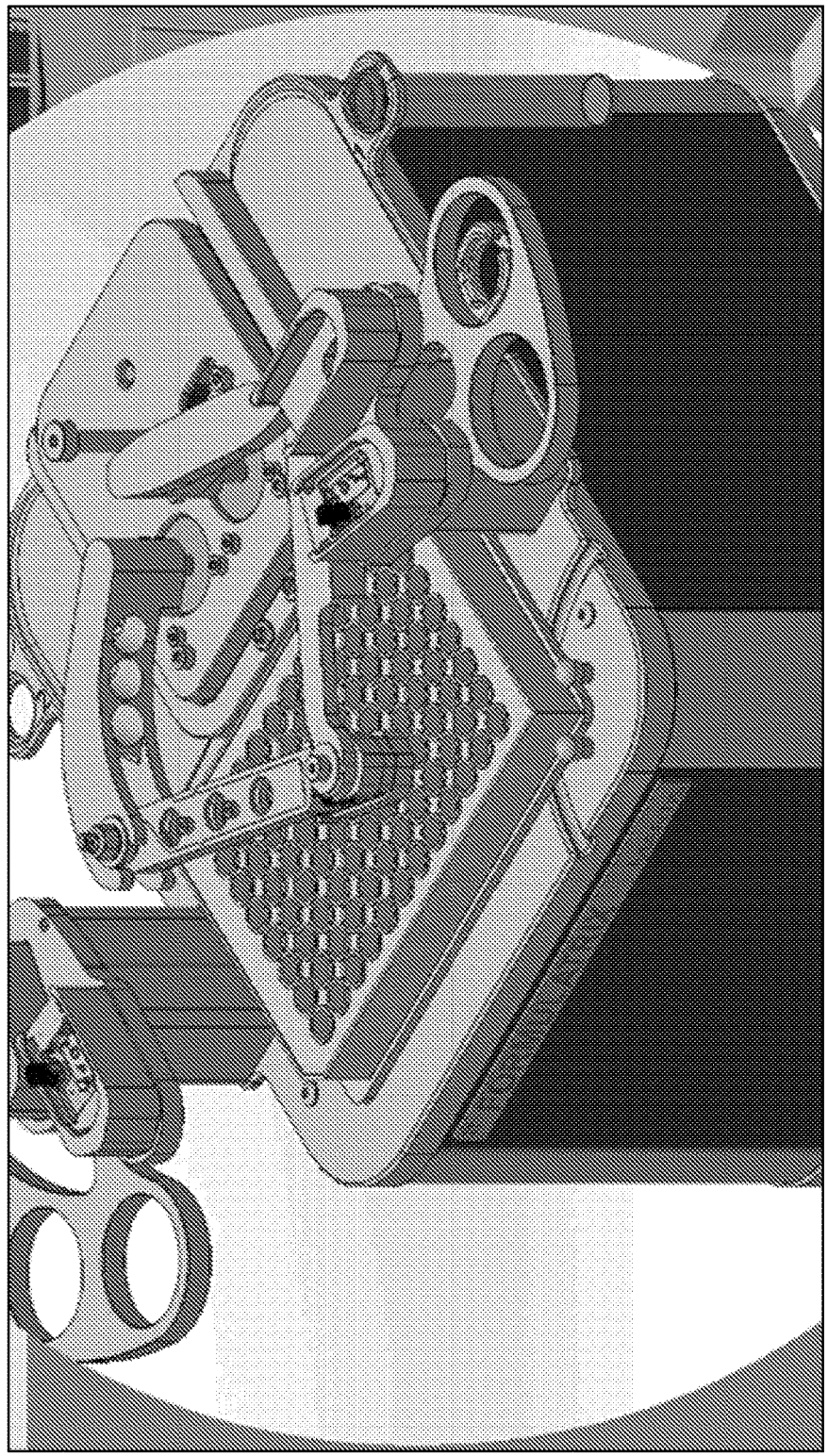
Figure 98:
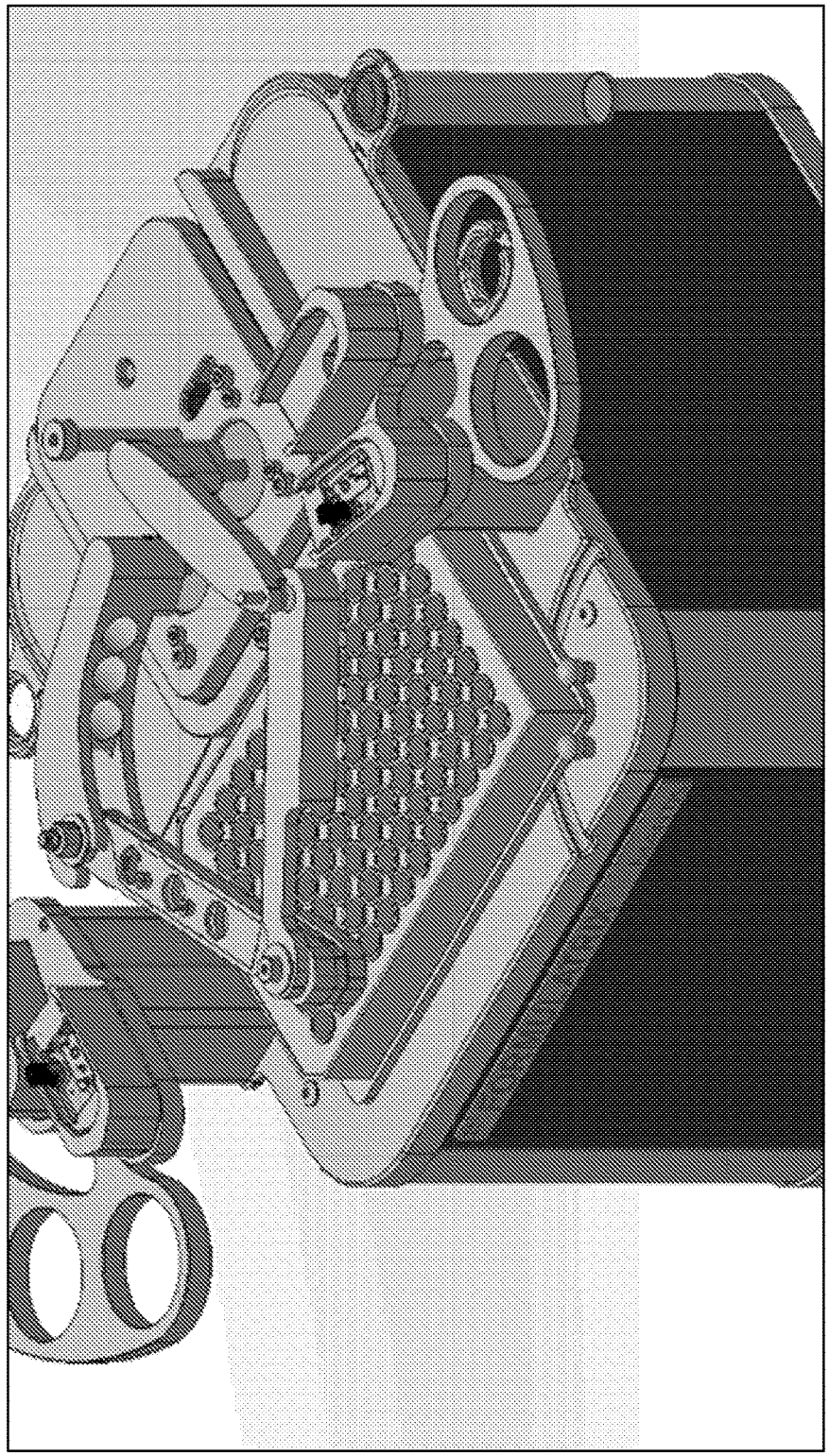
Figure 99:
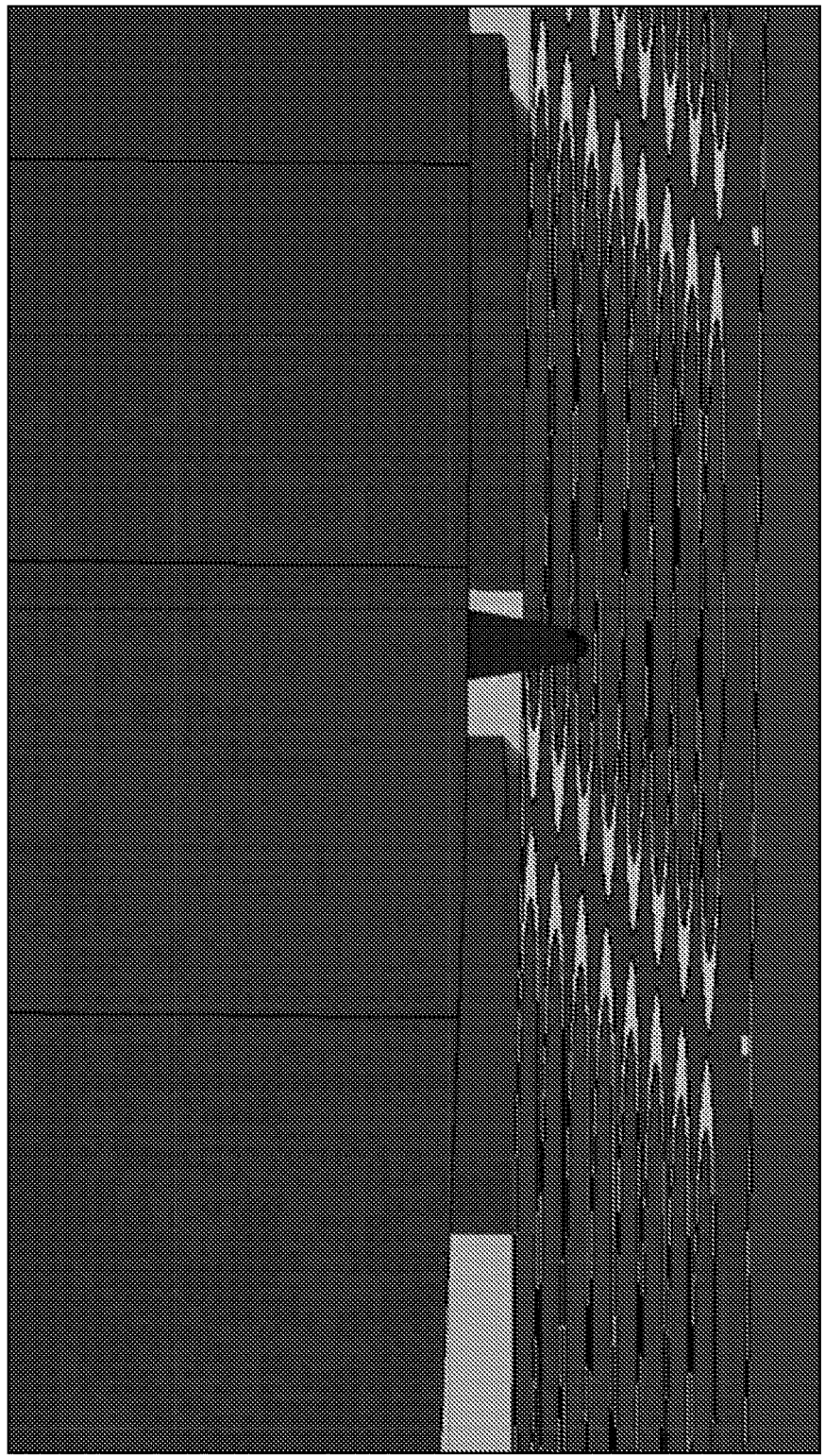
Figure 100:
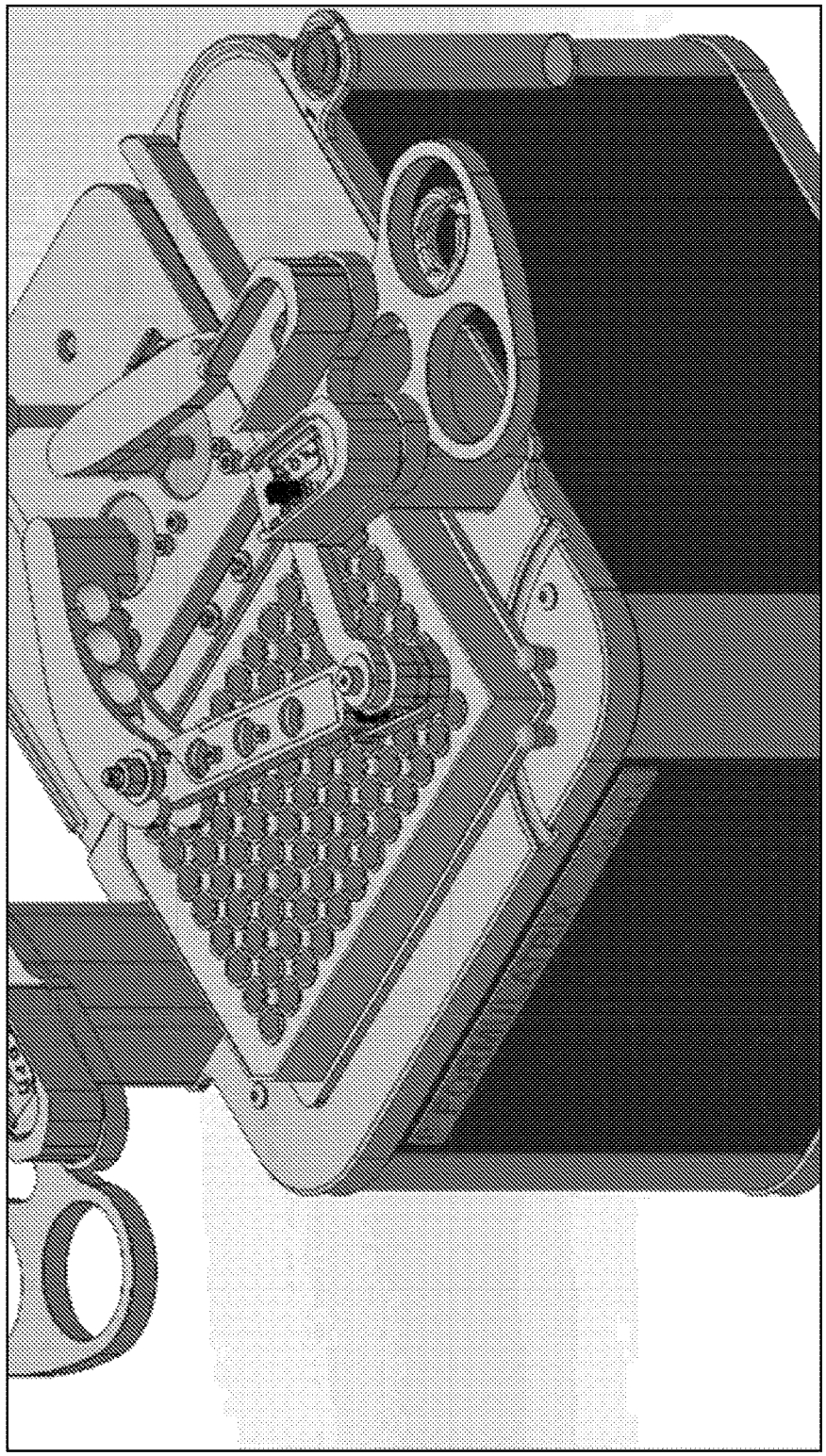
Figure 101:
Figure 102:
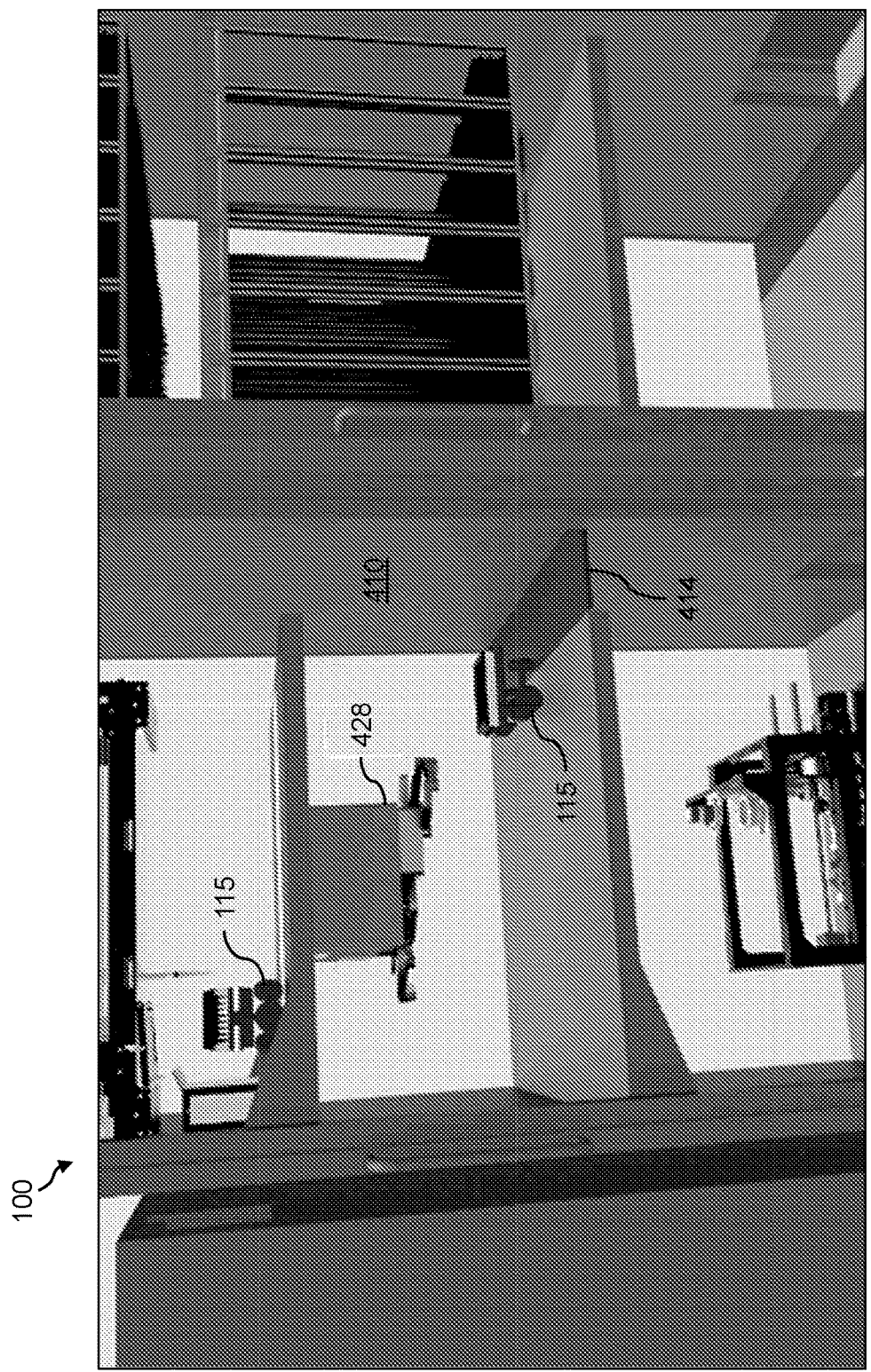

Having thus described the subject matter of this application in general terms, reference will now be made to the accompanying Drawings, which are not necessarily drawn to scale, and wherein:

FIG. 1 illustrates a block diagram of an example of a rover-based integrated laboratory system comprising a liquid handler device in combination with one or more mobile rover devices;

FIG. 2 illustrates an example of one instantiation of a rover-based integrated laboratory system comprising a liquid handler device in combination with one or more mobile rover devices;

FIG. 3 and FIG. 4 illustrate a perspective view of an example of a mobile rover device and without an enclosure, respectively;

FIG. 5 and FIG. 6 illustrate a side view of the mobile rover device shown in FIG. 3 and FIG. 4 with and without the enclosure, respectively;

FIG. 7 illustrates a perspective view of the underside of the mobile rover device shown in FIG. 3 and FIG. 4;

FIG. 8 illustrates an example of encoded markings that can provide visual position feedback information to a mobile rover device in a workspace;

FIG. 9 illustrates an example of a mobile rover device in a workspace encoded with a grid of encoded markings as shown in FIG. 8;

FIG. 10, FIG. 11, FIG. 12, and FIG. 13 illustrate side views of the spatula mechanism behavior sequence of the mobile rover device shown in FIG. 3 through FIG. 7;

FIG. 14 illustrates a top view of the mobile rover device shown in FIG. 3 through FIG. 7 and shows a labware carrier and capacitive sensing regions thereof;

FIG. 15 illustrates a top view of the mobile rover device shown in FIG. 3 through FIG. 7 and shows labware to be sensed in relation to the capacitive sensing regions of the labware carrier;

FIG. 16 illustrates a top view showing a concept of capacitive sensing integrated into a labware carrier of a mobile rover device;

FIG. 17 illustrates a cross-sectional view of an example of an arrangement of capacitive sensing regions in a rover device labware carrier;

FIG. 18A and FIG. 18B illustrate examples of typical motion profile curves of a body both with and without "jerk," respectively;

FIG. 19 illustrates a block diagram of an example of control electronics of a mobile rover device;

FIG. 20, FIG. 21, FIG. 22, and FIG. 23 illustrate perspective views of the spatula mechanism behavior sequence of the mobile rover device shown in FIG. 3 through FIG. 7;

FIG. 24, FIG. 25, FIG. 26, FIG. 27, and FIG. 28 illustrate perspective views of a spatula labware hand-off behavior sequence of the mobile rover device shown in FIG. 3 through FIG. 7 integrated with a storage shelf;

FIG. 29 illustrates a perspective view of a mobile rover device shown in animated fashion for illustration purposes only in the following sequence of operations;

FIG. 30 through FIG. 66 show a series of screenshots showing a sequence of operations of a simple liquid handler device in combination with one or more mobile rover devices;

FIG. 67 illustrates a perspective view of a mobile rover device shown in animated fashion for illustration purposes only in the following sequence of operations; and FIG. 68 through FIG. 113 show a series of screenshots showing a sequence of operations of a simplified modular cell culture automation system in combination with one or more mobile rover devices.

DETAILED DESCRIPTION

The subject matter of this application now will be described more fully hereinafter with reference to the accompanying Drawings, in which some, but not all embodiments of the disclosed subject matter are shown. Like numbers refer to like elements throughout. The disclosed subject matter can be embodied in many different forms and should not be construed as limited to the embodiments set forth herein; rather, these embodiments are provided so that this disclosure will satisfy applicable legal requirements. Indeed, many modifications and other embodiments of the disclosed subject matter set forth herein will come to mind to one skilled in the art to which the disclosed subject matter pertains having the benefit of the teachings presented in the foregoing descriptions and the associated Drawings. Therefore, it is to be understood that the disclosed subject matter is not to be limited to the specific embodiments disclosed and that modifications and other embodiments are intended to be included within the scope of the appended claims.

In some embodiments, a mobile-robot-based integrated laboratory system is described herein, and includes autonomous mobile robots that transport materials within the system. The mobile robots can be adapted to perform a variety of tasks within the laboratory, such as, but not limited to, the retrieval, transport, and positioning of materials. For purposes herein, the mobile robots may also be referred to as mobile rover devices or rover devices or rovers.

In some embodiments, a rover-based integrated laboratory system described herein can provide autonomous mobile robots adapted to transport labware, especially microplates, between components (e.g., automated laboratory instruments) of an integrated laboratory automation system. For example, in some embodiments, each mobile rover device is adapted to carry a single piece of labware having Society for Biomolecular Screening (SBS)-format standard footprint (length of 127.76 mm and width of 85.48 mm) or a labware rack adapted to have that footprint.

In some embodiments, a mobile rover device of a rover-based integrated laboratory system described herein can navigate within a workspace without predefined tracks or paths. The rover-navigable workspace can include features that allow the rover to use sensors to track its current position within the workspace. For example, the rover-navigable surface of the workspace can include an array of fiducial markers that define a coordinate system of the workspace. Accordingly, the rover can be equipped with a downward-facing camera that is adapted to observe the array of fiducial markers and continuously determine the current position of the rover within the workspace.

In some embodiments, a rover-based integrated laboratory system can support autonomous tuning of instrument positions within the workspace layout, wherein instruments can be placed freely within the rover-navigable workspace. Each instrument can include at least one receptacle for loading labware into the instrument. For example, this receptacle can be a labware carrier hand, which is adapted to carry labware for the function of the instrument as well as to provide a location for the rover to drop-off or retrieve the labware from an instrument. A rover can include sensors, such as outward-facing cameras, that enable a rover to identify an instrument and align at a precise position of the instrument labware receptacle for delivery of labware loaded on the rover. In one example, a rover includes a forward-facing camera which is adapted to identify fiducial markers at each labware receptacle of each instrument, and a rover is able to learn and adapt to the precise position of each labware receptacle. If an instrument were removed from the workspace and replaced at roughly the same position, a rover of the above described embodiment could adapt to the shifted instrument position as part of its normal workflow, removing the need for a complex recalibration process that can require manual intervention. If the instrument were shifted significantly from its originally trained position in the system, the autonomous tuning capability of the rover device enables a streamlined recalibration process.

Figure 103:
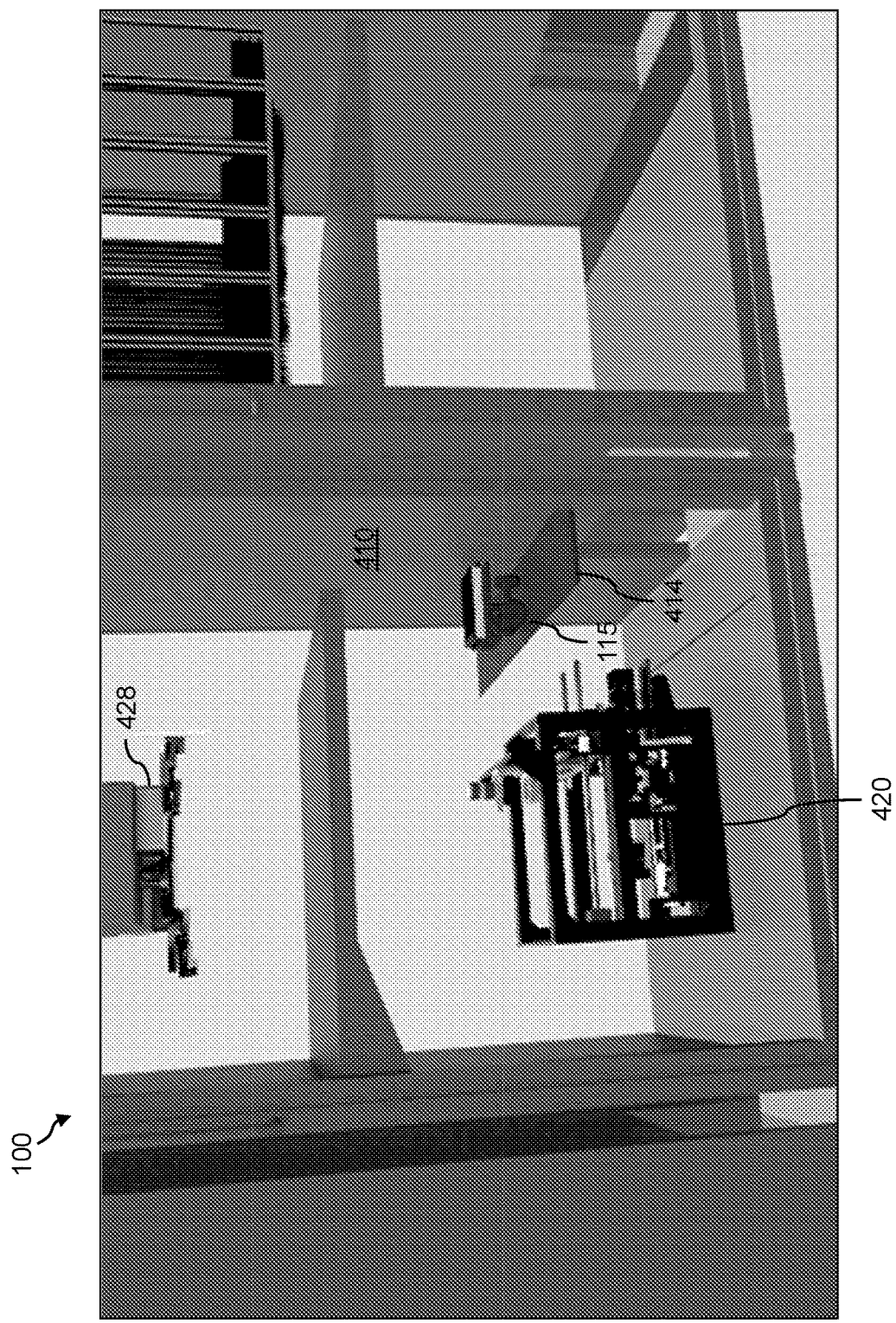
Figure 104:
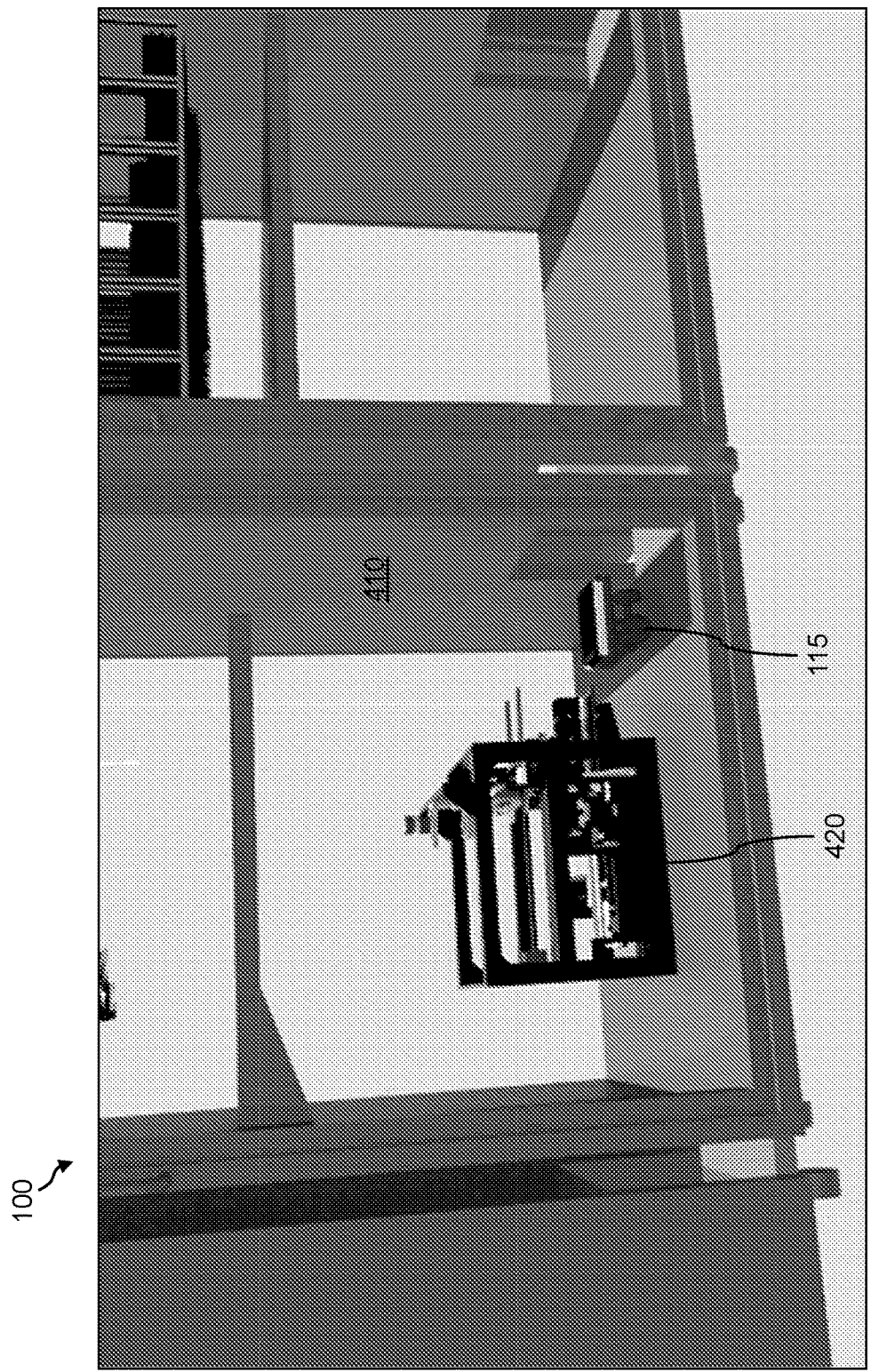
Figure 105:
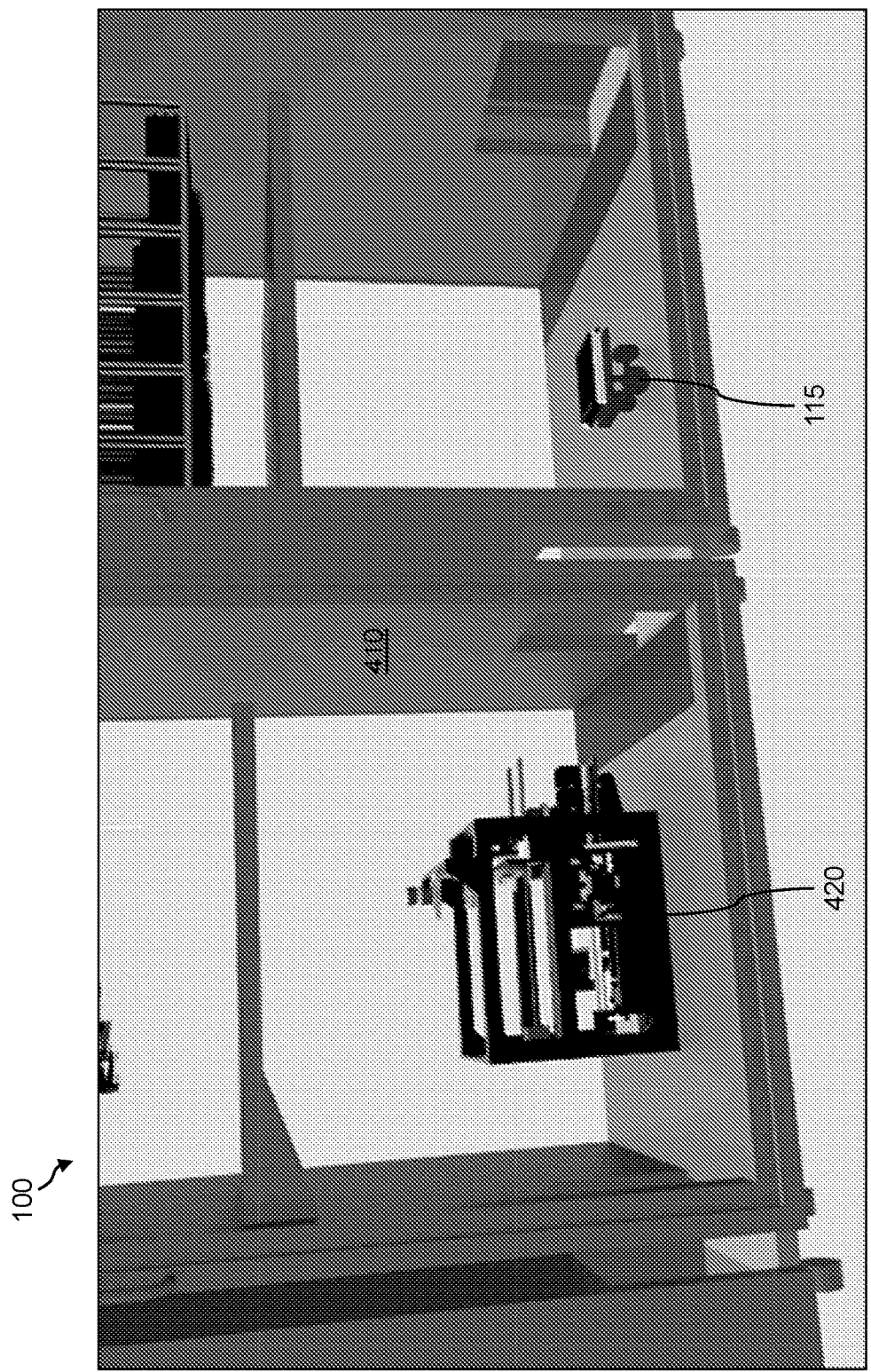
Figure 106:
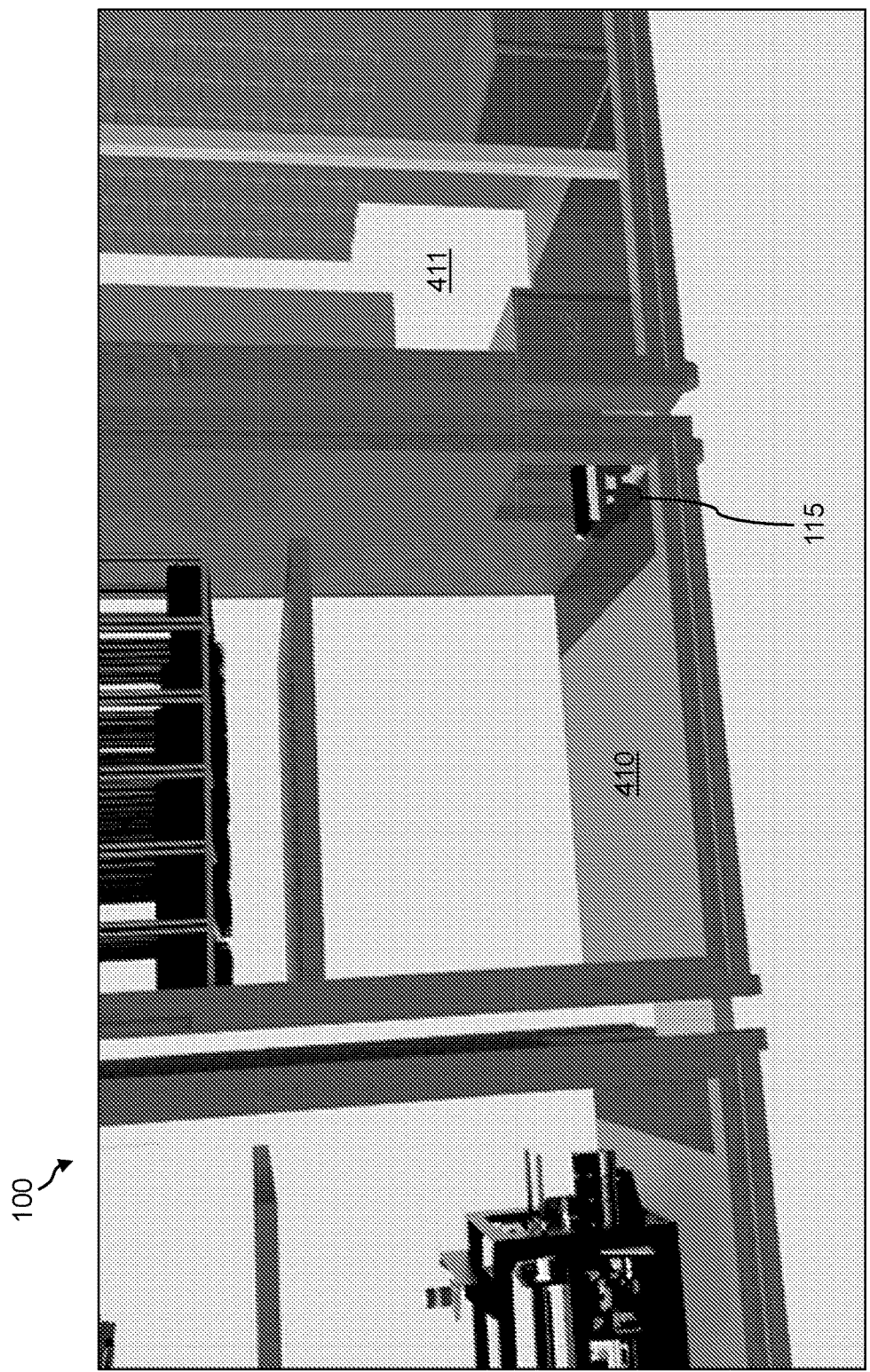
Figure 107:
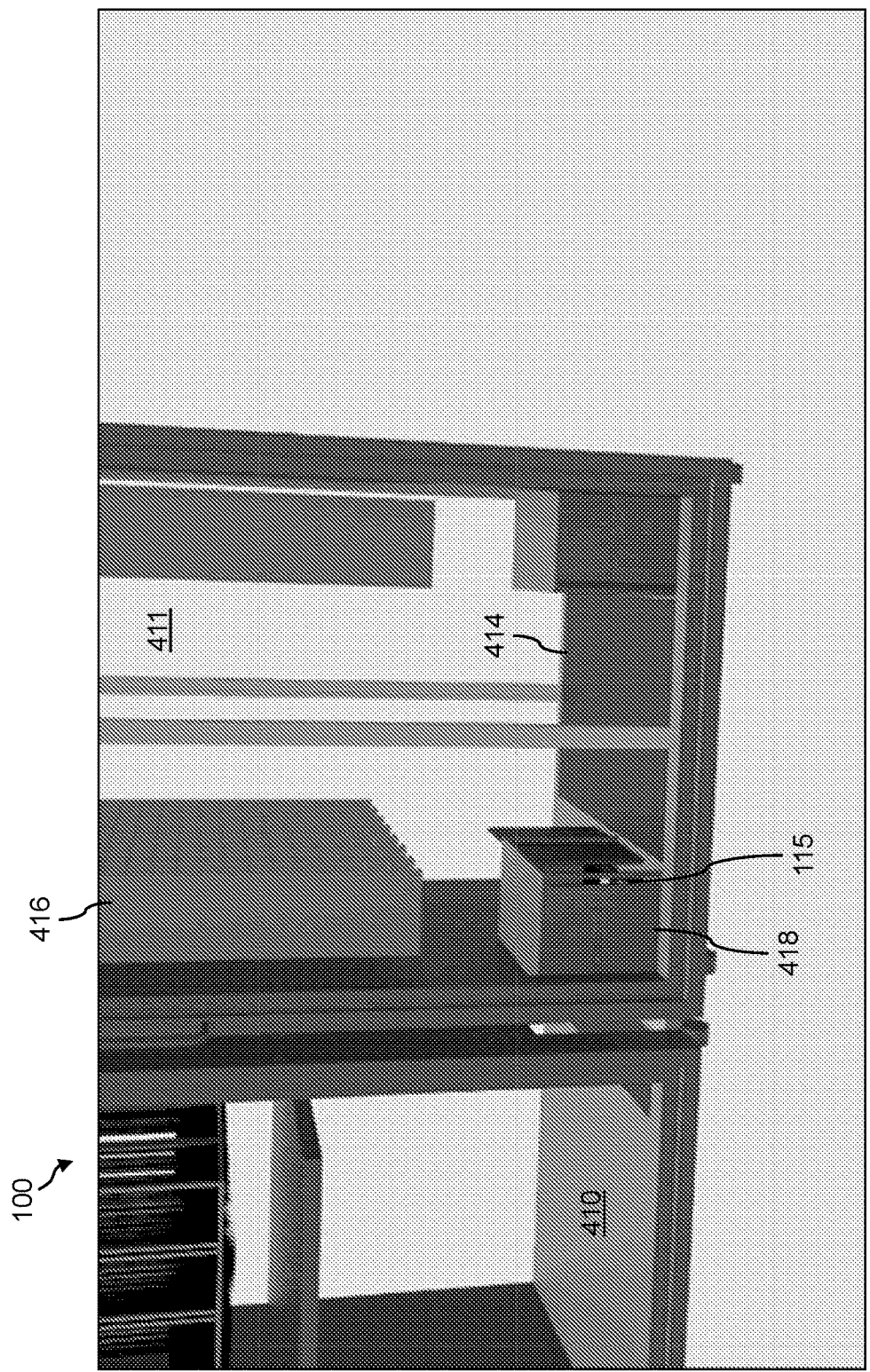
Figure 108:
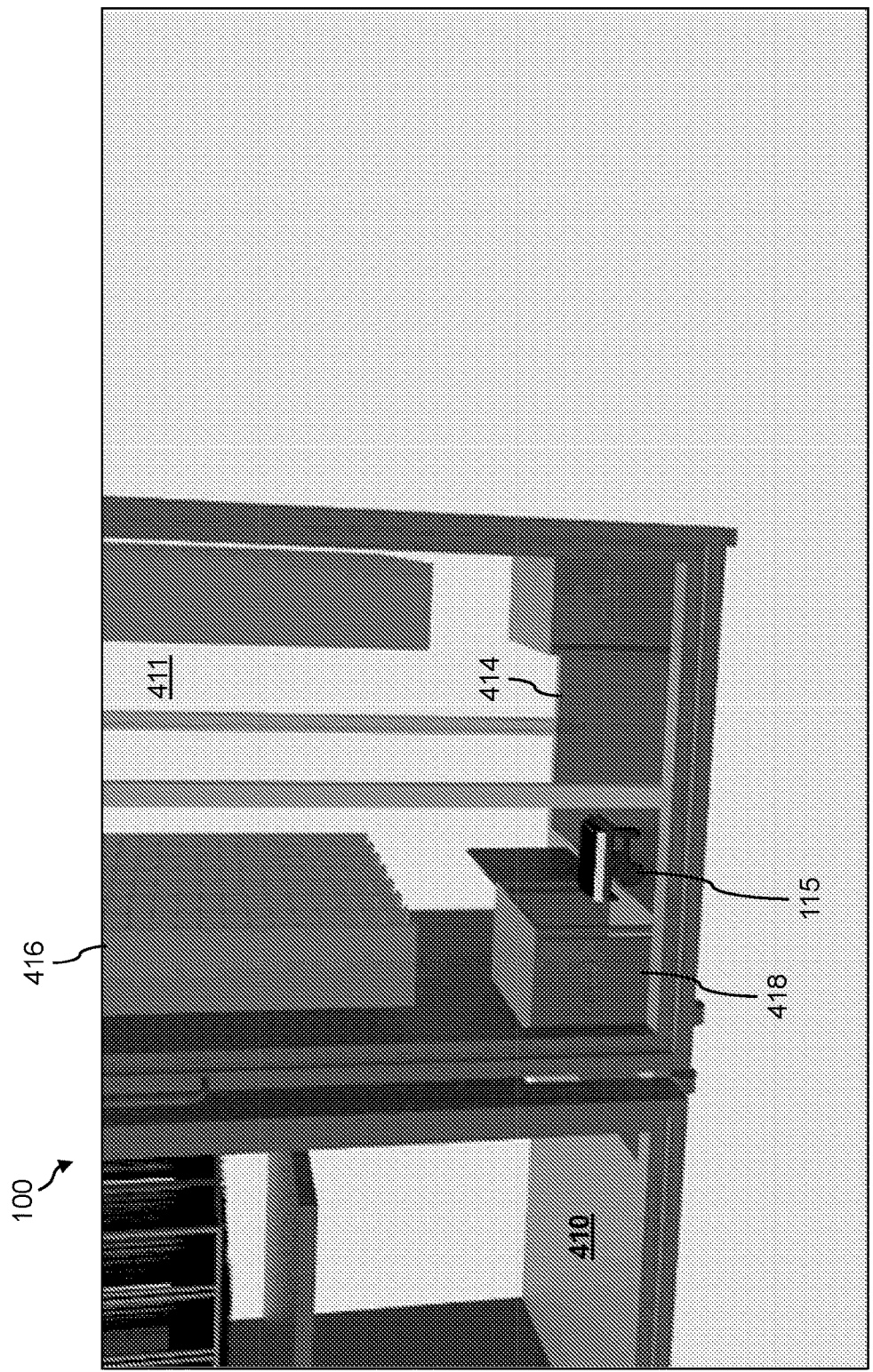
Figure 109:
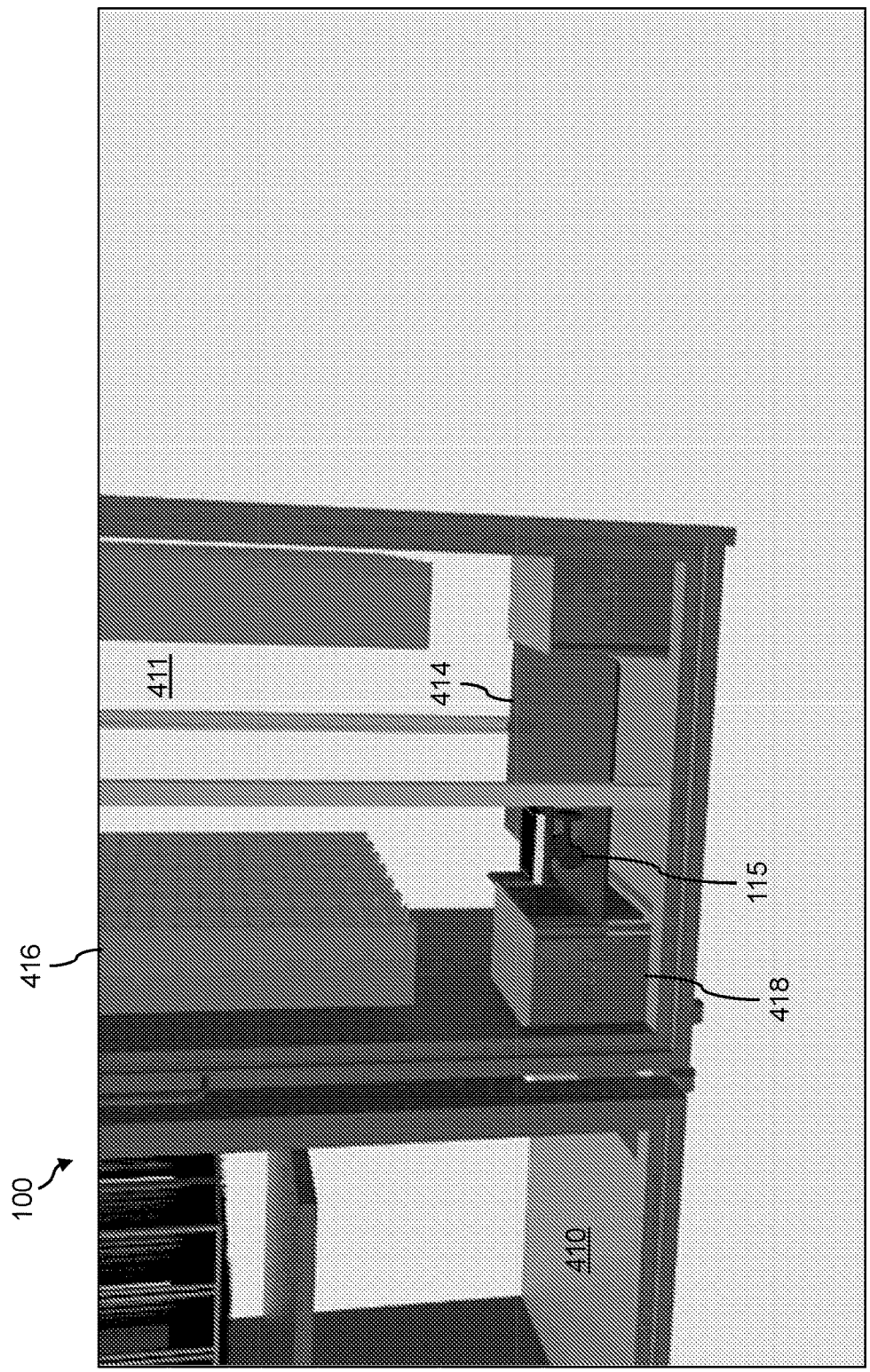
Figure 110:
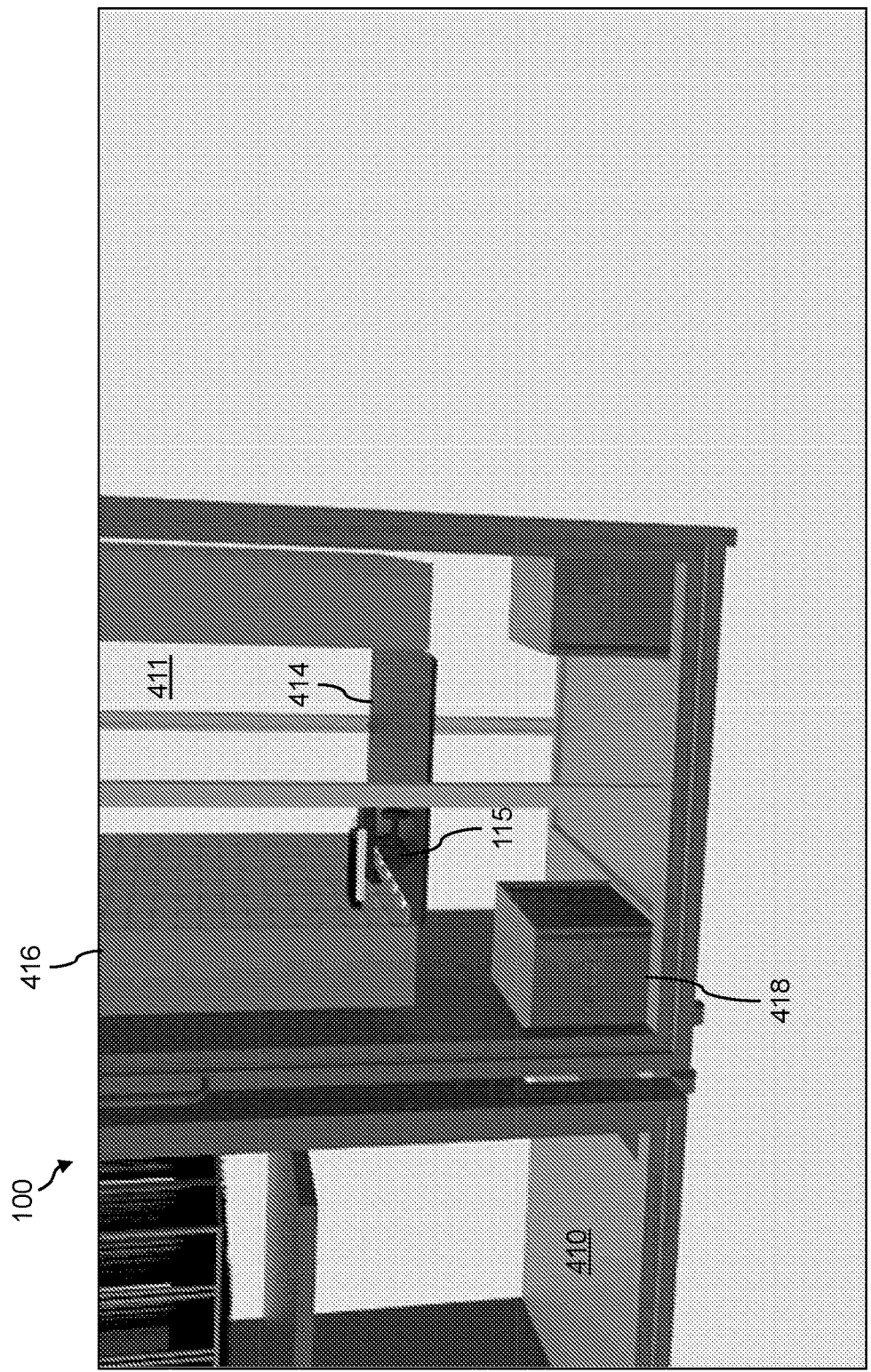
Figure 111:
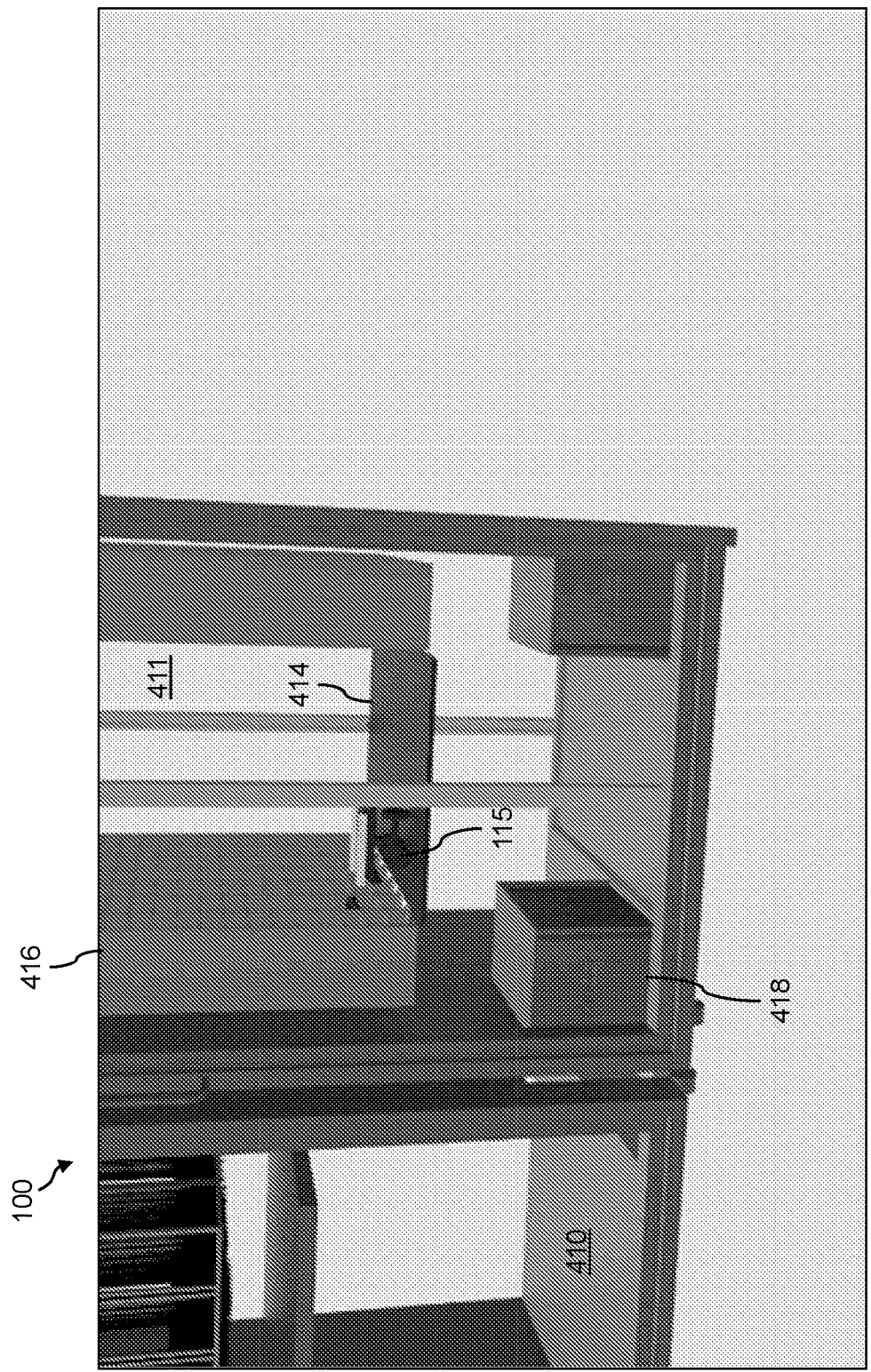
Figure 112:
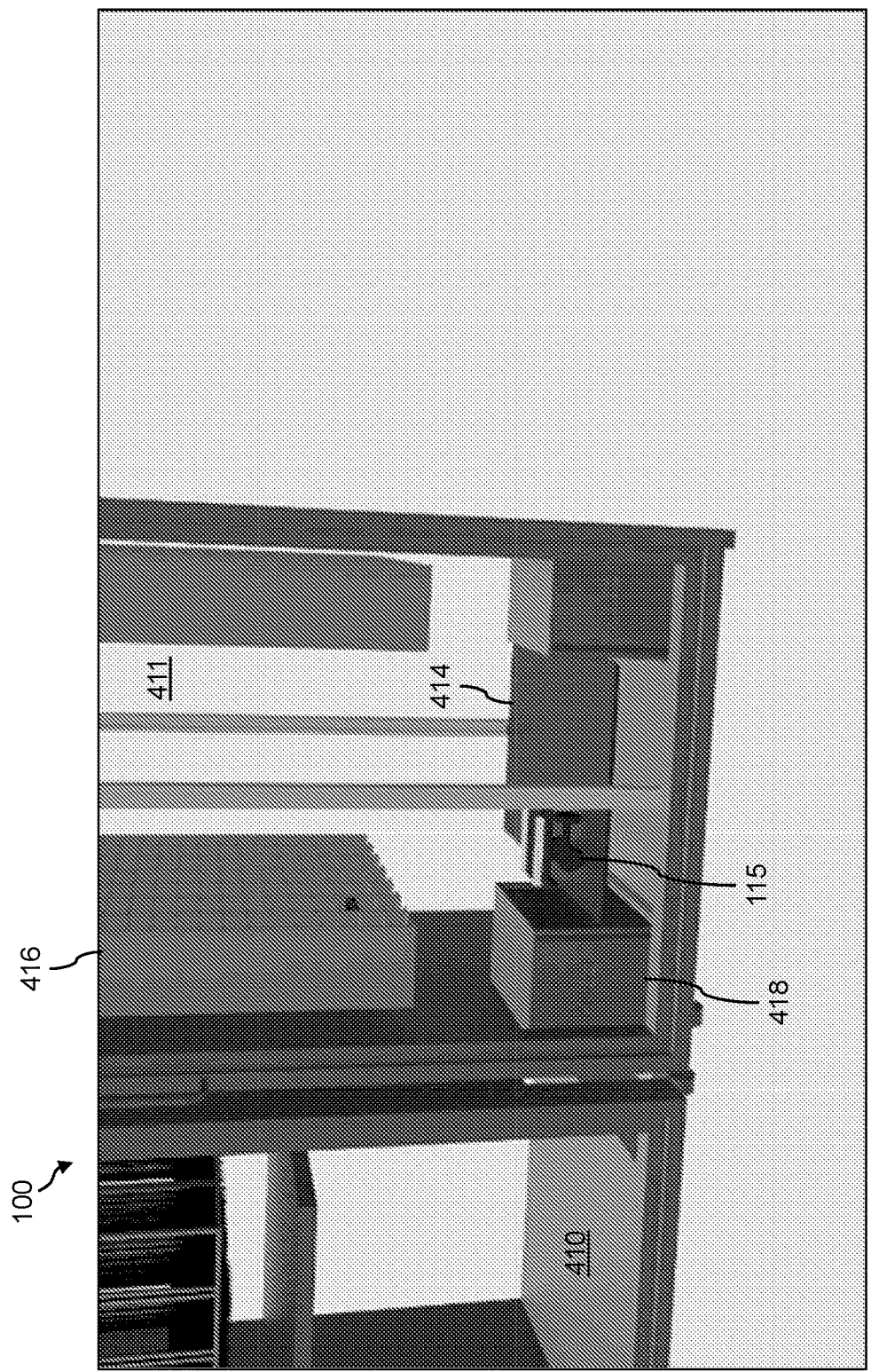
Figure 113:
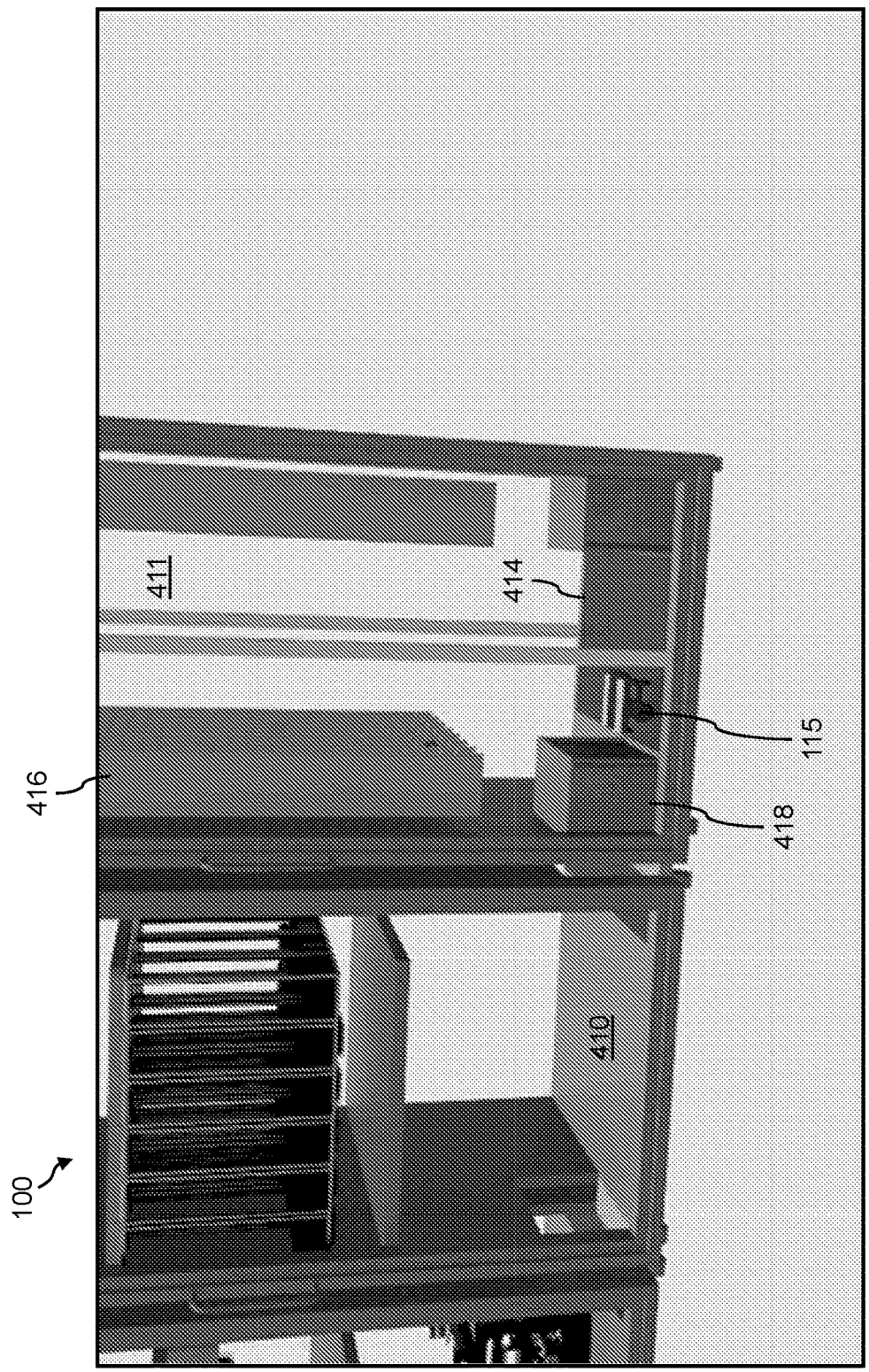

In some embodiments, in a rover-based integrated laboratory system described herein, a workspace can be divided into vertically arranged levels and the workspace can include at least one elevator that is adapted to move a rover from one level to another, such as the elevator 414 shown in FIG. 103. For example, an instrument or storage shelf can be arranged vertically between vertically arranged levels of the workspace, which the rover can access from the elevator platform.

As compared with conventional integrated laboratory systems, a rover-based integrated laboratory system described herein centers on improving convenience and flexibility of laboratory automation system integration. In particular, the rover-based integrated laboratory system can provide enhancements to:
  a. Modularity in design and assembly of integrated laboratory systems.
    1. Expandability of integrated laboratory systems to add functionality or increase throughput.
    2. Simplify modifications to integrated laboratory systems.
  b. Reducing the cost of designing and assembling integrated laboratory systems by reducing the number of complex components.
  c. Reducing the footprint of integrated laboratory systems of comparable functionality.
  d. Simplifying serviceability of such integrated systems (swapping out mobile robots remotely, address problems on individual modules).

More specifically and referring now to FIG. 1, a block diagram is provided as an example of a closed rover-based integrated laboratory system 100 comprising a fleet controller or manager 105 and a liquid handler device 110 in combination with one or more mobile rover devices 115. For purposes herein, the fleet controller or manager 105 will be referred to as "fleet controller 105". Notably, while this embodiment describes a liquid handler device 110, the system 100 is not limited to this particular instrument, and in other embodiments can comprise any laboratory instrument not inconsistent with the objectives of this disclosure, such as an air handler device and the like. Air handler devices are understood to be devices that deliver reactive gas or gasses to reactants in solution within labware, such as labware 120 previously described. Consequently, rover-based integrated laboratory systems described herein can be used in biological-based procedures and methods, and/or in synthetic procedures such as synthetic protein synthesis or small molecule synthesis involving liquid and/or gaseous reagents. Thus, embodiments of the rover-based integrated laboratory system 100 can improve upon existing laboratory automation integration systems with respect to customization, ease of use, and serviceability. These improvements can be achieved with the use of autonomous mobile robots (e.g., rover devices 115) to increase the modularity of an integrated system. The various instruments and devices in an integrated laboratory system constitute system modules. The mobile robots constitute the integration system used to interface modules with one another. The autonomous mobile robots (e.g., rover devices 115) can be used to position labware (e.g., labware 120) within the liquid handler device 110.

In some preferred embodiments, the rover-based integrated laboratory system 100 uses autonomous mobile robots (e.g., rover devices 115) in a laboratory environment. The autonomous mobile robot, or rover, is capable of executing commands to carry out tasks in an integrated system workflow. A typical task can include transporting materials between instruments in an integrated system.

In a rover-based integrated laboratory system 100, system modules are placed into a workspace, and rovers are able to maneuver within this workspace to access the various modules. In some embodiments, the rovers and/or system are able to generate and maintain a map of a workspace including the modules and their positions within the limits of rover-navigable area of a workspace. In addition, the rover possesses localization and odometry technologies that allow the rover, system modules, and a fleet controller to be aware of the rover's location in a workspace at all times. Thus, in some embodiments, the rover is able to navigate itself freely within designated bounds of a workspace.

In some instances, a workspace within a rover-based integrated laboratory system 100 can be expanded without increasing the footprint of the system by incorporating one or more vertically positioned platforms. Such a system can include elevators to allow rovers to access the platforms of different heights. Some instruments can be arranged vertically between, above, or below platforms such that the rover can interface those instruments while positioned on the elevator. As such the footprint of an integrated laboratory system can be significantly reduced by implementing a rover-based integrated laboratory system. An example of a rover-based laboratory integrated system 100 that includes workspace that incorporates a number of vertically-arranged platforms is shown with reference to FIG. 68 through FIG. 113.

In some embodiments, a rover described herein is configured to wirelessly communicate, and is not bound to the system 100 with cables. For instance, a rover can be configured to communicate wirelessly with instruments and with other rovers in the system 100 via a fleet controller, such as fleet controller 105. A rover can be battery powered and capable of maneuvering itself to a battery charging station arranged in the workspace if the battery levels fall below a threshold or during idle periods.

A rover described herein (e.g., a rover device 115) can execute commands generated by fleet controller 105 (see FIG. 1) that oversees the execution of a workflow by an integrated system. In some embodiments, fleet controller 105 can run a scheduling program which allows it to coordinate tasks for the entire workflow in a centralized way. Fleet controller 105 can comprise control software that schedules tasks for a variety of workflows occurring within a workspace, such as several different cell culture experiments taking place within one cell culture system. For example, the scheduling software on fleet controller 105 can dictate certain tasks to be performed at specific times, and fleet controller 105 can assign a rover to carry out the task. In another embodiment, commands can also be generated in a distributed manner, with each module in an integrated system developing its own sequence of actions to achieve a particular workflow. Additionally, rovers in the system can be selected for a task based on availability and location in the system.

In some embodiments, a rover device can carry labware which contain liquid samples or reagents. A rover device must execute its motion in a manner that prevents disturbance and spillage of any liquid in the labware it carries. For example, this spill-free motion is achieved by limiting the 'jerk' of the executed motion. In the field of physics, jerk is a term known to represent the rate of change of acceleration. In other words, the rate of change of acceleration must be appropriately minimized for any movement executed by the rover device in order to minimize the disturbance to materials carried by the rover device. This principle is described in more detail below with reference to FIGS. 18A and 18B.

In some embodiments, a rover device described herein is holonomic, meaning the degrees of freedom that can be controlled by the device are equal to the total degrees of freedom of the device. A rover mobile robot device on a workspace surface plane has a total of three degrees of freedom, including the position of the device on the two coordinate axes of the plane and the orientation of the device on the plane. A rover device is holonomic if it can be controlled to move through any of these degrees of freedom simultaneously. For example, the rover device can be adapted to be holonomic by providing three omnidirectional wheels on the rover device. The omnidirectional wheels can be arranged in a way that enables the rover device to move through three degrees of freedom based on the relative velocities and direction of rotation of each wheel.

In addition to the primary role of transporting materials within an integrated system, a rover (e.g., rover device 115) can be adapted for a variety of specialized functions. In one embodiment, the rover device can be provided a kinematic labware carrier. A kinematic labware carrier would ensure that labware can be placed in repeatable position on the rover device. The position of a kinematic labware carrier can be calibrated relative to a rover positioning sensor and driving mechanisms. With such a calibrated kinematic labware carrier, a rover can precisely position the labware within an instrument without transferring the labware to the instrument. For example, in a rover-based integrated system including an automated liquid handling system and a storage module, a rover can retrieve a piece of labware containing samples from the labware storage module, transport the labware to the liquid handling device, and position itself and the labware within the liquid handling device to enable the liquid handling device to directly perform liquid handling operations on the samples contained by the labware on the rover device.

In some embodiments, a rover can have a mechanism for transferring materials on and off the rover without external aid. For example, such a mechanism can be a labware carrier that can extend forward off the front of the rover as well as raise and lower the height of the labware carrier. Such an embodiment provides the rover device 115 a self-contained mechanism for retrieving labware from one instrument labware receptacle and dropping it off at another, such as is shown in the embodiment illustrated in FIGS. 20-28.

In some instances, a weigh scale can be provided in the labware carrier of a rover device described herein. Such a weigh scale would allow the rover device to sense changes in the mass of the labware on the labware carrier. For example, a rover device with such a weigh scale in the labware carrier can allow the rover to measure liquids dispensed into labware on the labware carrier. The rover device can be commanded to carry an empty reagent reservoir from a liquid handling device to a reagent dispensing device in order to refill the empty reservoir. At the reagent dispensing device, the rover would position itself such that the reagent dispensing device can dispense new reagent into the reagent reservoir. The rover device can use the weigh scale to measure changes in mass of the reagent reservoir as it is filled by the reagent dispenser in order to judge the amount of fluid dispensed by the reagent dispenser. In future operations at the liquid handling device, the rover device can use the weigh scale to measure changes in mass of the reagent reservoir in order to determine when the reagent reservoir is empty and must be refilled.

In some embodiments, a rover device can comprise an outward facing vision sensor which is capable of reading barcodes printed on a piece of labware. Such a barcode-reading sensor can allow the rover to verify the identity of a piece of labware prior to retrieval of said piece of labware. Such a barcode reading sensor can also allow the rover device to take inventory of the materials stored in a labware storage module.

In some cases, a rover device can detect the presence of labware on the rover device's labware carrier. A number of mechanisms for achieving this feature exist in the art. For example, a rover device can be provided with capacitive sensing features in its labware carrier, which enable detection of the presence of typical labware. Capacitive sensing features can also be provided that enable detection of whether the labware is properly seated on the labware carrier.

The specific technologies required to provide the rover with the above-described capabilities can fall outside the scope of this disclosure, which describes aspects of an overall rover-based laboratory integrated system and methods relating to the same.

A rover-based integrated laboratory system 100 described herein can provide one or more advantages and/or improvements over conventional integration systems. For example, being able to navigate freely within the workspace, a rover described herein can switch between tasks depending on current demand. For example, in a typical integration platform, a conveyor and robot arm pair can only be capable of transferring labware between two specific modules, while a rover in a rover-based integration platform described herein can perform the same transfer and then go on to execute a different function. Thus, systems 100 described herein are dynamic and versatile, where a current task is dictated by the demand of the system rather than being limited to the fixed configurations modules in conventional systems.

The use of rovers (e.g., rover devices 115) to position labware and materials within a device can reduce a footprint of the device. For example, a liquid handling device with a deck of positions to place labware and materials has a fixed area and a fixed labware capacity associated with that area. The greater the capacity of the deck, the greater the footprint of the device. Floor and counter space in a laboratory is limited and extremely valuable, and smaller instrument footprints are thus desired. A device designed to make use of rovers for positioning labware and materials within it does not require as many motorized axes or fixed deck positions as a comparable system not compatible with rovers. Rovers can maneuver into the instrument when required and transfer materials to and from storage modules, which can make use of vertical space for storage, when those materials are required. The footprint of an integrated system can be further reduced by arranging modules vertically such that a rover device can access them via an elevator platform.

A rover-based integrated laboratory system 100 described herein enables flexibility in the layout of integrated systems and simplifies expansion or modification of such systems. Because the rover-based integrated laboratory system 100 does not require a rigid layout of conveyors and manipulators, rover-compatible modules can be arranged freely within rover-navigable space. If additional modules are needed or existing modules require rearrangement, the system enables streamlined generation of a new map for the updated workspace. The complexities of rearranging the workflows in a typical integrated system can be automated by the rover-based integrated laboratory system 100 to improve the user experience and ease the deployment of new products.

The modularity of a rover-based integrated laboratory system 100 described herein can enhance the serviceability of the system. In the case of a malfunction in the field, a rover can simply be removed from the system by a user. The malfunctioning rover can be repaired remotely, reducing the need for a service visit to the system site which can be an expensive undertaking for the service provider. Additionally, the integrated system can continue to function normally without the malfunctioning rover, as the remaining rovers can take on tasks that would have been assigned to the malfunctioning rover. Such an issue can halt all productivity in a conventional laboratory integration system, whereas the rover-based integration system is able to continue working, although perhaps at a lower throughput.

Generally, in some embodiments, a rover-based laboratory integrated system described herein can comprise the following components: at least one laboratory component that is adapted to perform a laboratory technique; at least one labware component that is adapted to be used in the laboratory technique; and at least one rover component that is operatively connected to said laboratory and said labware components, wherein the rover component is an autonomous mobile robot.

Referring now again to FIG. 1, a rover-based integrated laboratory system 100 can comprise a fleet controller 105 and a liquid handler device 110 in combination with one or more rover devices 115. The controller 105 can be any computing device (e.g., server, desktop computer, laptop computer, tablet device, smart phone, cloud computing device, and the like) that is capable of controlling the overall operations of the rover-based integrated laboratory system 100. Additionally, the fleet controller 105 can be built into the liquid handler device 110 in some cases, or be separate from the liquid handler device 110 in other cases, both of which are shown in FIG. 2.

FIG. 2 shows a simplified example of one instantiation of a rover-based integrated laboratory system 100 that includes a fleet controller 105 and a liquid handler device 110 in combination with one or more rover devices 115. Each of the rover devices 115 can be an autonomous mobile robot. The exemplary liquid handler device 110 can be a multi-channel liquid handler, such as an 8-channel liquid handler, and the liquid handler device 110 can have independent spanning and independent Z actuation on each channel. The 8-channel liquid handler is merely exemplary, and is not limited to 8-channels. In some embodiments, a liquid handler device can have 1, 2, 3, 4, 5, 6, 7, 9, 10, or more than 10 channels. The liquid handler can have a fixed span or be independent spanning with independent Z actuation on each channel, as a particular method or procedure requires. Using an 8-channel liquid handler device 110 as an example, an 8-channel liquid handler device 110 can further have capacity for one or multiple rover devices 115. For instance, in some embodiments, a liquid handler device 110 described herein can have a capacity of one, two, three, four, five, six, seven, eight, nine, ten, or more than ten rover devices 115. The rover devices 115 can be used to position labware (e.g., labware 120) within the liquid handler device 110 for the channels to perform pipetting operations. More details of a rover device 115 are shown and described with reference to FIG. 3 through FIG. 28. Additionally, more details of examples of the presently disclosed rover-based laboratory integrated system 100 are shown and described with reference to FIG. 30 through FIG. 66 and with reference to FIG. 68 through FIG. 113.

Referring now to FIG. 3 through FIG. 7, various views of an example of one instantiation of a mobile rover device 115 are shown, which is one example of an autonomous mobile robot in the rover-based integrated laboratory system 100. Namely, FIG. 3 and FIG. 4 show a perspective view of the rover device 115 with and without an enclosure, respectively. FIG. 5 and FIG. 6 show a side view of the rover device 115 with and without the enclosure, respectively. FIG. 7 shows a perspective view of the underside of the rover device 115.

In some examples, the rover device 115 can include a baseplate/chassis assembly 130 to which other components can be directly or indirectly coupled. For example, a set of four omni-wheels 132 are coupled to the underside of the baseplate/chassis assembly 130. In one example, three of the omni-wheels 132 are powered omni-wheels 132 while one of the omni-wheels 132 is a passive omni-wheel 132. Each of the three powered omni-wheels 132 is driven by a wheel motor 134 (e.g., DC motor). In some instances, each omni-wheel 132 can rotate 360° about an axis, although in other cases, each omni-wheel 132 can rotate less than 360° about an axis. In some embodiments, one or two passive omni-wheels 132 can be assembled in fixed fashion to the baseplate/chassis assembly 130. The purpose of the passive omni-wheel 132 is to provide suspension and/or stability.

Accordingly, a rover device 115 described herein can be holonomic, meaning the degrees of freedom that can be controlled by the device are equal to the total degrees of freedom of the device. The rover device 115 on a workspace surface plane has a total of three degrees of freedom, including the position of the device on the two coordinate axes of the plane and the orientation of the device on the plane. The rover device 115 is holonomic if it can be controlled to move through any of these degrees of freedom simultaneously. In this example, the rover device 115 is holonomic because of the three powered omni-wheels 132. The three powered omni-wheels 132 can be arranged in a way that enables the rover device 115 to move through three degrees of freedom based on the relative velocities and direction of rotation of each wheel.

The rover device 115 includes a forward-facing camera 136, a downward-facing camera 138, and a pair of downward-facing infrared light emitting diodes (IR LED) illumination devices 140 (one on the left and one on the right), as shown for example in FIG. 7. In some instances, the rover device 115 can comprise one or more forward-facing IR LEDs, and can also in some instances comprise one or more rearward-facing IR LEDs. The forward-facing camera 136 and the downward-facing camera 138 are, for example, digital cameras, such as a CCD or CMOS-based camera. The rover device 115 can also optionally comprise a rear-facing camera (not labeled). The IR LEDs can illuminate a scene in which the IR LEDs face, and this IR illumination can be detected by one or more of the cameras (e.g. cameras 136 and/or 138) facing in the direction of the scene. In some embodiments, the IR LEDs are a component of one or more barcode scanning devices, and corresponding IR-receiving barcode scanning sensors are positioned on the rover device, such as at the locations shown for the cameras 136,138. Mounted atop the baseplate/chassis assembly 130 is a labware carrier 142. The labware carrier 142 further includes an integrated labware transfer mechanism 144. The integrated labware transfer mechanism 144 provides vertical movement and has a spatula mechanism 146, which is a slideable spatula mechanism. In the rover device 115, the spatula mechanism 146 can be used to drop off and pick up a microplate from a lab instrument, wherein the spatula mechanism 146 of the integrated labware transfer mechanism 144 can be extended off the mobile robot as well as raised and lowered, as shown for instance in FIGS. 10-13. Namely, as needed the labware transfer mechanism 144 can be extended upward a certain amount and then returned to the lowered position. In one example, the labware transfer mechanism 144 has a vertical range of motion of up to about 8 mm. In one example, the spatula mechanism 146 has a horizontal range of motion of up to about 130 mm.

Further, the labware carrier 142 can comprise motors or any other mechanisms (not shown) for driving any motions of the labware transfer mechanism 144. The labware 120 can sit atop the spatula mechanism 146 and be transported about a workspace via the rover device 115 and manipulated via the labware transfer mechanism 144 and the spatula mechanism 146 of the labware carrier 142.

The various components of a rover device 115 described herein can be enclosed in a body or housing 150. A camera window 152 can be provided in the body or housing 150 at the forward-facing camera 136. A rover device 115 can have any dimensions not inconsistent with the objectives of this disclosure. In some cases, rover device 115 can have a length of 120 mm to 250 mm, 150 mm to 225 mm, 175 mm to 200 mm, 120 mm to 225 mm, 120 mm to 200 mm, 120 mm to 185 mm, 120 mm to 150 mm, 135 mm to 250 mm, 150 mm to 250 mm, 175 mm to 250 mm, or 200 mm to 250 mm; a width of 75 mm to 125 mm, 75 mm to 115 mm, 75 mm to 105 mm, 75 mm to 90 mm, 85 mm to 125 mm, 95 mm to 125 mm, or 105 mm to 125 mm; a height when the labware transfer mechanism 144 is not extended of 75 mm to 125 mm, 75 mm to 115 mm, 75 mm to 100 mm, 75 mm to 90 mm, 85 mm to 125 mm, 100 mm to 125 mm or 110 mm to 125 mm; and when the labware transfer mechanism 144 is extended a height of the unextended mechanism 144 plus 1 mm, plus 2 mm, plus 3 mm, plus 4 mm, plus 5 mm, plus 6 mm, plus 7 mm, plus 8 mm, plus 9 mm, plus 10 mm, or plus more than 10 mm (e.g. if an unextended height is 100 mm and the extended height is plus 8 mm, then the total extended height is 100 mm+8 mm=108 mm total extended height). In a particular example, a rover device 115 described herein can have a length of about 186 mm, a width of about 105 mm, a height of about 100 mm when the labware transfer mechanism 144 is not extended, and a height of about 108 mm when the labware transfer mechanism 144 is extended.

Referring now to FIG. 8, exemplary fiducial markers 200 that include encoded markings can provide visual position feedback information to a mobile rover device disclosed herein in a workspace. Namely, each of the fiducial markers 200 includes encoded markings that can be associated with a position in the workspace. For example and referring now to FIG. 9, a workspace 205 includes a path or track 210 that includes an arrangement or grid of fiducial markers 200, wherein each of the fiducial markers 200 is uniquely encoded to correspond to its physical position within the path or track 210. In one example, each of the fiducial markers 200 is about 15 mm square. In one example, each of the fiducial markers 200 is uniquely encoded using an array of dots, such as a 6×6 array of dots, such as is shown in FIG. 8. In another example, each fiducial marker 200 can include a barcode, which can be identified by one of the cameras 136, 138, or in instances where the rover device 115 comprises one or more barcode scanning devices, each barcode can be identified by the barcode scanning device. In yet another example, each fiducial marker 200 can be a uniquely encoded RFID tag and the rover device 115 includes a downward-facing RFID reader (not shown) in addition to or in place of the downward-facing camera 138. FIG. 9 shows an example of a rover device 115 operating in the workspace 205 using the fiducial markers 200, wherein the information in the fiducial markers 200 can be captured and/or detected using the downward-facing camera 138.

Referring still to FIG. 8 and FIG. 9, using the fiducial markers 200 that provides a 2D coordinate system, the rover device 115 can navigate within a workspace without predefined tracks or paths. For example, the rover-navigable workspace 205 includes features (e.g., fiducial markers 200) that allow the rover device 115 to use sensors to track its current position within the workspace 205. For example, the rover-navigable surface of the workspace 205 can include an array of fiducial markers 200 that define a coordinate system of the workspace 205. Accordingly, the downward-facing camera 138 of the rover device 115 can be used to observe the array of fiducial markers 200 and continuously determine the current position of the rover device 115 within the workspace 205.

Figure 10:
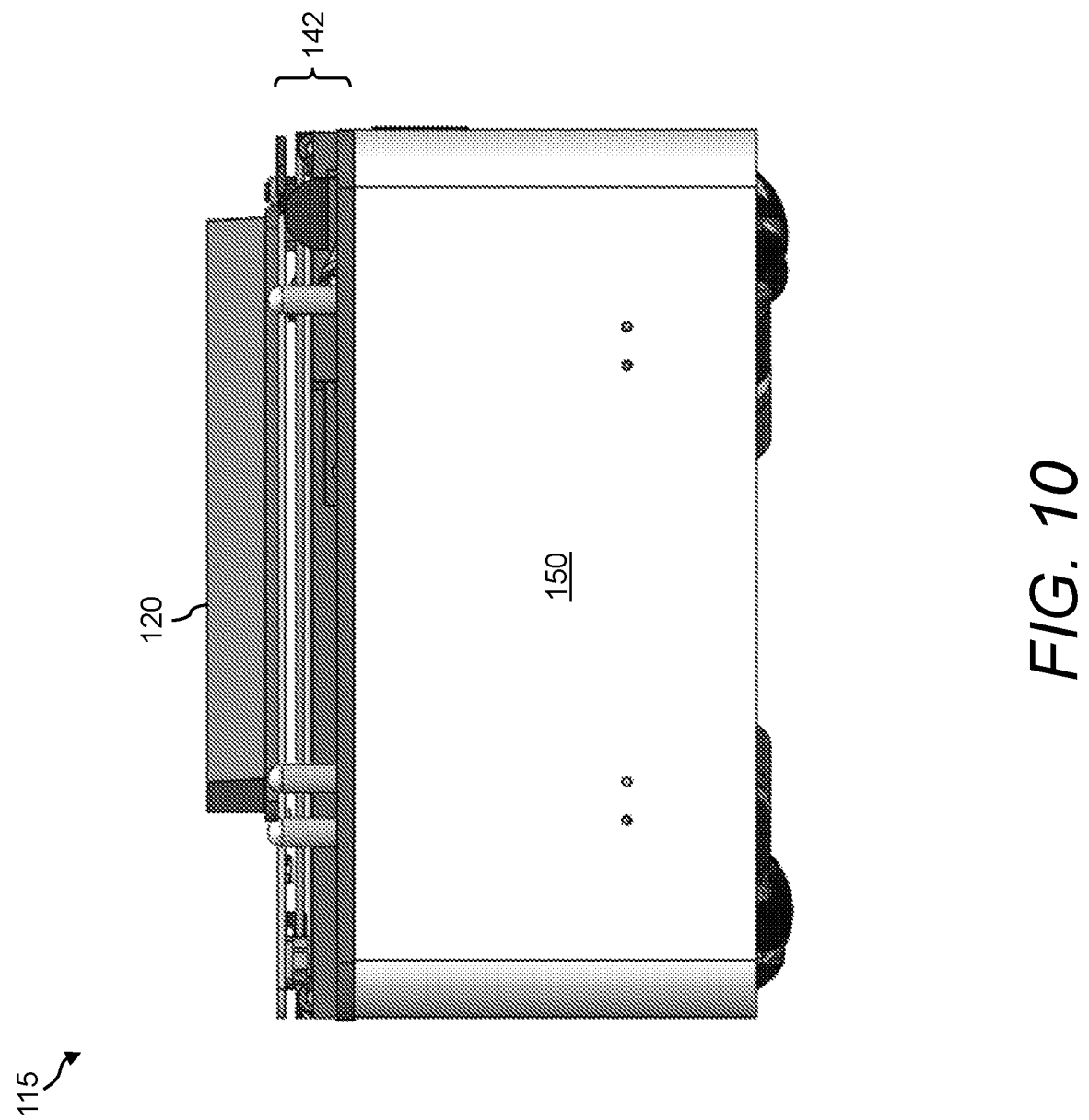
Figure 11:
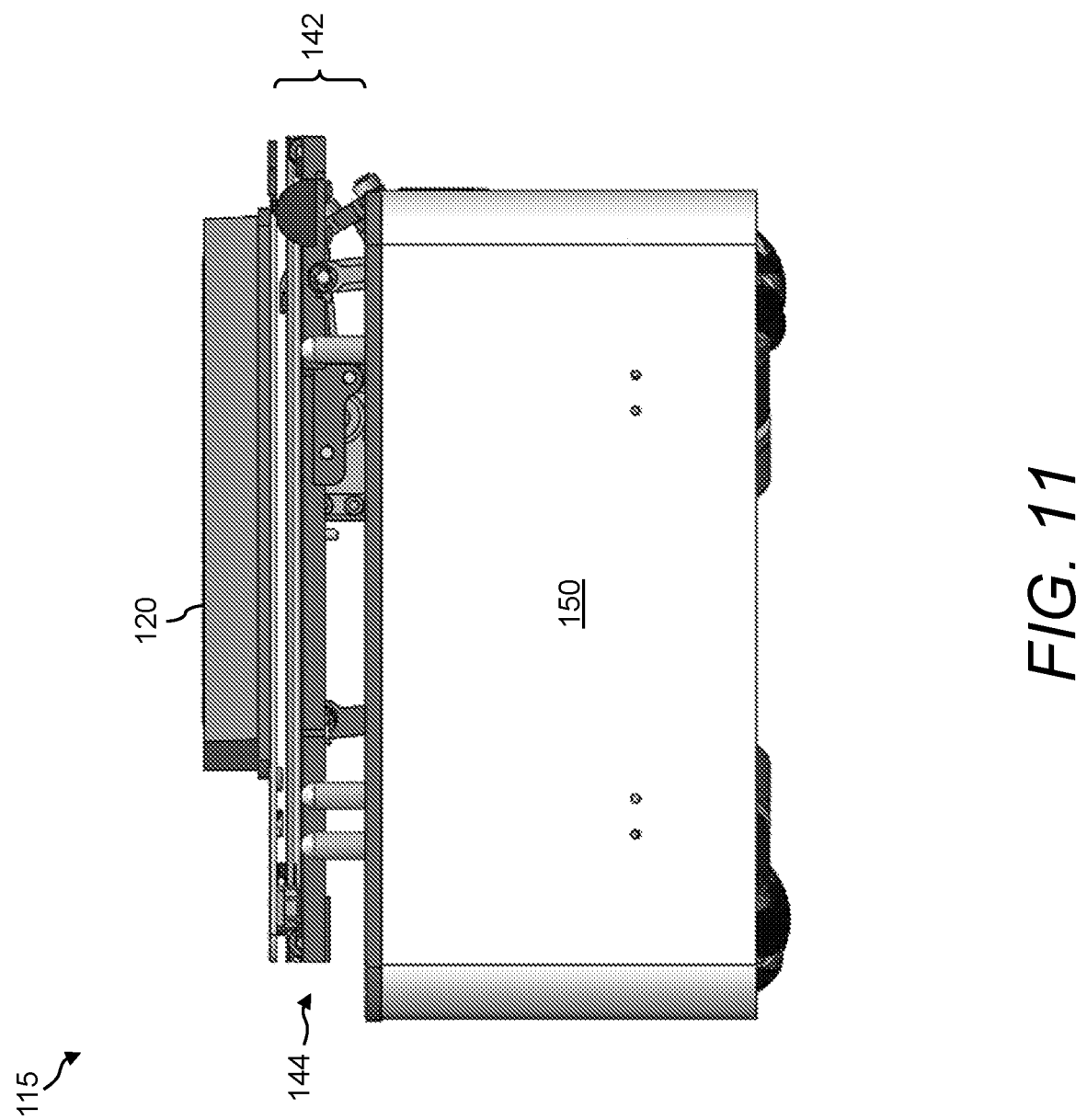
Figure 12:
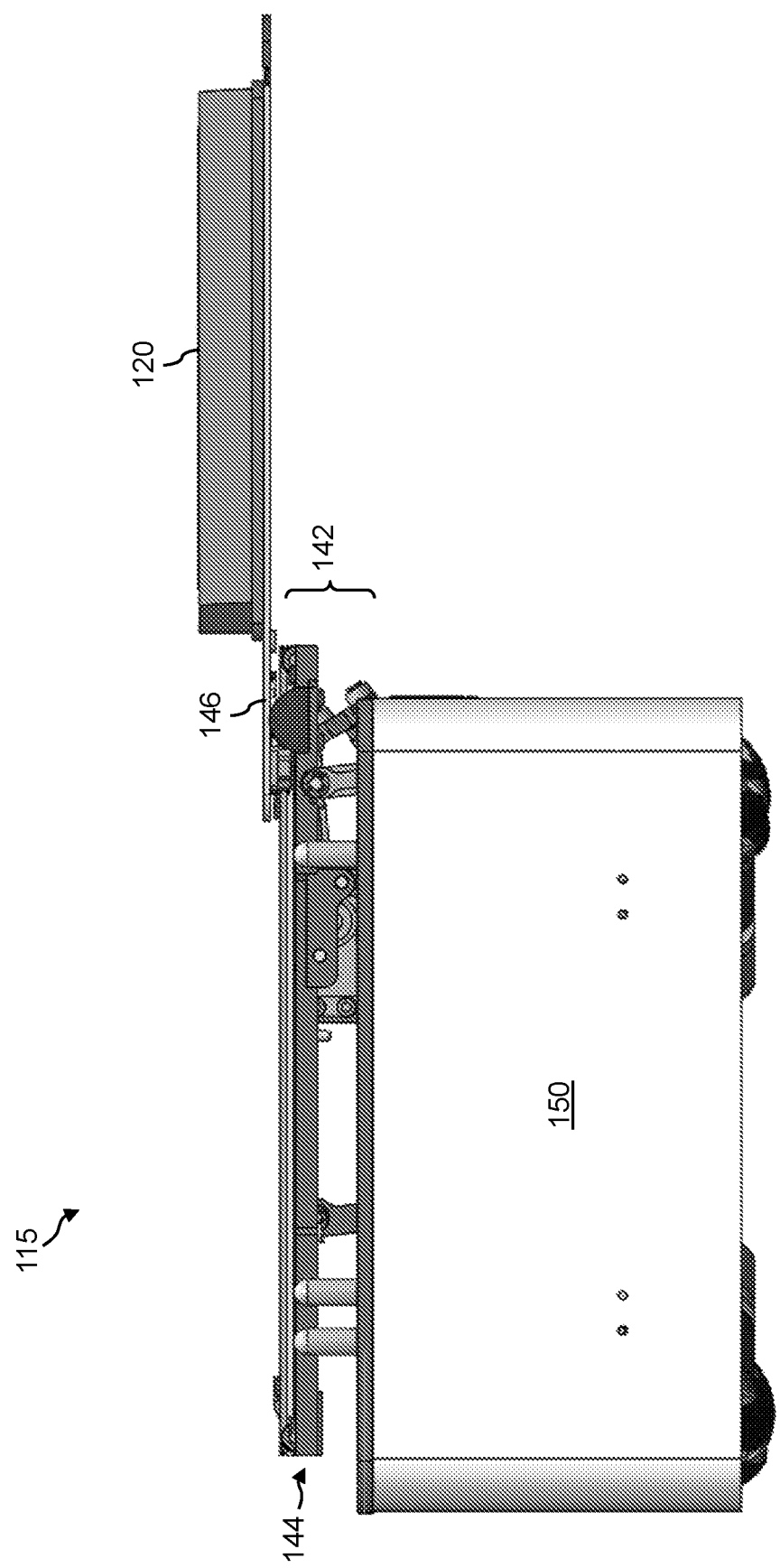
Figure 13:
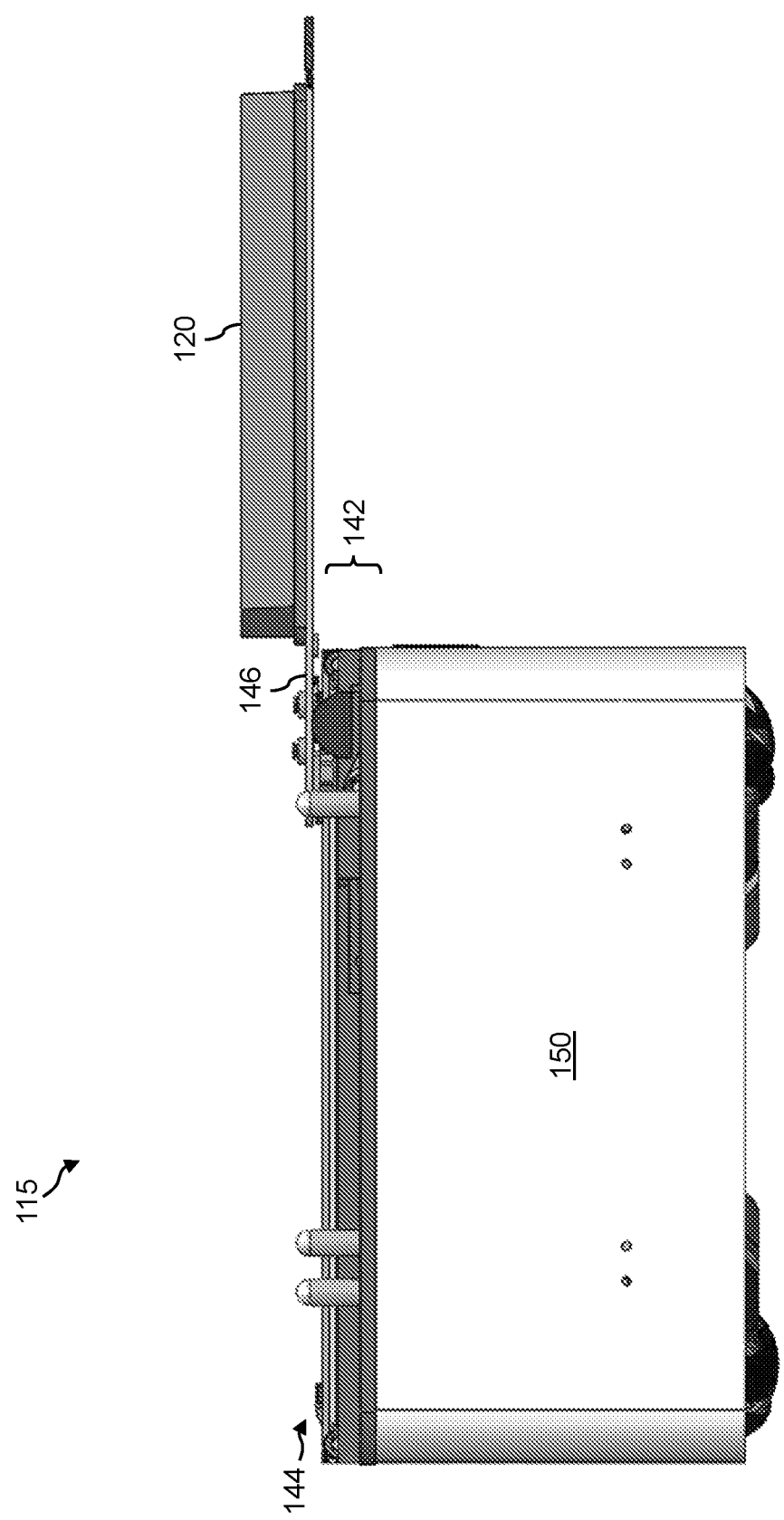

Referring now to FIG. 10, FIG. 11, FIG. 12, and FIG. 13 is side views showing the spatula mechanism behavior sequence of the mobile rover device 115 shown in FIG. 3 through FIG. 7. Namely, the labware transfer mechanism 144 and the spatula mechanism 146 of the labware carrier 142 is the spatula mechanism in the mobile rover device 115. In the behavior sequence, the labware transfer mechanism 144 can be extended upward from the top of the body or housing 150 (see FIG. 11) or not extended upward (see FIG. 10). Similarly, the spatula mechanism 146 can be extended sideways from the end of the body or housing 150 (see FIG. 13) or not extended sideways (FIG. 10). Further, both the labware transfer mechanism 144 and the spatula mechanism 146 can be extended (see FIG. 12).

Referring now to FIG. 14 is a top view of the mobile rover device 115 shown in FIG. 3 through FIG. 7, and shows a labware carrier 142 and capacitive sensing regions. Namely, the sensing regions sense the presence and absence of the labware 120 and/or sensing obstacles. Capacitive sensing (sometimes capacitance sensing) is a technology based on capacitive coupling that can detect and measure anything that is conductive or has a dielectric different from air. In the mobile rover device 115, capacitive sensing can be used, for example, to detect and measure proximity, position, and/or displacement of the labware 120 and/or of any obstacles in the path of the rover device 115.

In some examples, the spatula mechanism 146 can be formed fully or in part of a printed circuit board (PCB) that includes certain sensing electrodes. For example, one electrode can form a ground reference zone 160, another electrode can form a labware presence detection zone 162, another electrode can form a front labware edge detection zone 164F, and another electrode can form a rear labware edge detection zone 164R. Additionally, another electrode can form a left-side front-edge collision detection zone 166L and another electrode can form a right-side front-edge collision detection zone 166R. In some embodiments, a spatula mechanism 146 can have all of these sensing electrodes, although in other embodiments the spatula mechanism 146 can have less than all of these sensing electrodes. Further, a ground reference zone 160 can be provided in relation to each of the labware presence detection zone 162, the front labware edge detection zone 164F, the rear labware edge detection zone 164R, the left-side front-edge collision detection zone 166L, and the right-side front-edge collision detection zone 166R.

Referring now to FIG. 15, a mobile rover device 115 shown in FIG. 3 through FIG. 7 can have labware 120 that is sensed in relation to the capacitive sensing regions of the labware carrier 142. In this example, the labware presence detection zone 162 can be used to detect generally the presence of the labware 120. Then, the front labware edge detection zone 164F and the rear labware edge detection zone 164R can be used to detect more precisely the position of the labware 120 atop the spatula mechanism 146 of the labware carrier 142.

Further to the example, FIG. 16 shows a top view illustrating the concept of the capacitive sensing integrated into the labware carrier 142 of the mobile rover device 115. Additionally, FIG. 17 shows a cross-sectional view taken along line A-A of FIG. 16, which shows an example of the arrangement of capacitive sensing regions in the labware carrier 142. FIG. 16 and FIG. 17 show the labware 120 in relation to certain capacitive sensing regions, such as the labware presence detection zone 162, the front labware edge detection zone 164F, and the rear labware edge detection zone 164R. Further, FIG. 17 shows electrical field lines 168 between the electrodes, which are the field lines that can be disrupted and/or altered by the absence and/or presence of the labware 120.

In the rover-based integrated laboratory system 100, the rover device 115 is adapted to carry labware which contains liquid samples or reagents. Accordingly, the rover device 115 must execute its motion in a manner that prevents disturbance and spillage of any liquid in the labware it carries. This spill-free motion is achieved by limiting the 'jerk' of the executed motion. In the field of physics, jerk is a term known to represent the rate of change of acceleration. In other words, the rate of change of acceleration must be appropriately minimized for any movement executed by the rover device in order to minimize the disturbance to materials carried by the rover device.

Referring now to FIG. 18A and FIG. 18B, typical motion profile curves of a body both with and without "jerk," respectively are shown. For example, plot 170 shows the typical motion profile curve of a body with jerk. By contrast, plot 172 shows the typical motion profile curve of a body without jerk. In a rover-based integrated laboratory system 100 described herein, the "body" can be, for example, the mobile rover device 115 shown in FIG. 3 through FIG. 7. Because the rover device 115 must move in a way that prevents "sloshing" of liquids in the labware, its motion must appropriately minimize 'jerk', or the rate of change of acceleration. In other words, the rover device 15 must move with an "S-curve" motion profile, wherein the velocity profile is not a trapezoid.

Each of the mobile rover device 115, such as the rover device 115 shown in FIG. 3 through FIG. 7, includes certain control electronics. For example, FIG. 19 show a block diagram of an example of rover control electronics 125 of the mobile rover device 115. In this example, the rover control electronics 125 includes a processor 180, a motor driver 182, an image processing algorithm 184, a localization algorithm 186, a capacitance detection algorithm 188, a communications interface 190, and a weigh scale 192. All control electronics can be powered by battery power 194, which can be any rechargeable or non-rechargeable battery sources.

The processor 180 is the master controller that is used to manage the overall operations of the mobile rover device 115. The processor 180 can be any standard controller or microprocessor device that is capable of executing program instructions. A certain amount of data storage (not shown) can be associated with the processor 180, such as a memory storage device.

The rover device 115 can execute commands generated by the processor 180, which oversees the execution of a workflow of the rover-based integrated laboratory system 100. In one example, the processor 180 can run a scheduling program that allows it to coordinate tasks for the entire workflow in a centralized way. In another example, commands can also be generated in a distributed manner, with each module in an integrated system developing its own sequence of actions to achieve a particular workflow. The rover devices 115 in the system can be selected for a task based on availability and location in the workspace.

The motor driver 182 can be any motor driver circuitry or module for controlling any motors (e.g., servo motors) within the rover device 115. Example of motors driven by the motor driver 182 can include the wheel motors 134 and any motors (not shown) in the labware carrier 142.

The image processing algorithm 184 is an algorithm for controlling and/or processing the digital image information from any cameras in the rover device 115, such as the forward-facing camera 136 and the downward-facing camera 138. In one example, the processor 180 and/or image processing algorithm 184 processes image information of the fiducial markers 200 captured by the forward-facing camera 136 and/or downward-facing camera 138 to continuously determine the current position of the rover device 115 within a workspace. In another example, the processor 180 and/or image processing algorithm 184 processes image information from the forward-facing camera 136 wherein the rover device 115 can learn and adapt to the precise position of instruments in the workspace. If an instrument were removed from the workspace and replaced at roughly the same position, the rover device 115 can adapt to the shifted instrument position as part of its normal workflow, removing the need for a complex recalibration process that can require manual intervention. If the instrument were shifted significantly from its originally trained position in the workspace, the autonomous tuning capability of the rover device 115 enables a streamlined recalibration process. Accordingly, in a rover-based integrated laboratory system 100 described herein, lab instruments can be place freely in the rover-navigable workspace.

The localization algorithm 186 is an algorithm for controlling and/or processing locational information collected by the various sensors on the rover. For example, the locational information can include information generated by the image processing algorithm 184 from images captured by one or more of the cameras 136,138 positioned on the rover device 115. The localization algorithm 186 can identify particular features or patterns in the information that correspond to particular features or patterns in the workspace having known locations and/or coordinates (e.g. the fiducial markers 200), and from those features and patterns determine a location of the rover device 115 at that moment.

The capacitance detection algorithm 188 is an algorithm for processing the information from any capacitance sensing electrodes in the rover device 115, such as the labware presence detection zone 162, the front labware edge detection zone 164F, the rear labware edge detection zone 164R, the left-side front-edge collision detection zone 166L, and the right-side front-edge collision detection zone 166R.

The communications interface 190 can be any wired and/or wireless communication interface for connecting to a network (not shown) and by which information can be exchanged with other devices connected to the network. For example, using communications interface 190, any rover device 115 can communicate wirelessly with any other rover device 115 and/or with the fleet controller 105 of the rover-based integrated laboratory system 100. Examples of wired communication interfaces can include, but are not limited to, USB ports, RS232 connectors, RJ45 connectors, Ethernet, and any combinations thereof. Examples of wireless communication interfaces can include, but are not limited to, an Intranet connection, Internet, ISM, Bluetooth® technology, Wi-Fi, Wi-Max, IEEE 402.11 technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols.

Accordingly, the rover device 115 is not bound to the system with cables. Namely, the rover device 115 can communicate wirelessly with instruments and with other rover devices 115 in the system via the processor 180 and the communications interface 190. Further, the rover device 115 can be battery powered (e.g., battery power 194) and capable of maneuvering itself to a battery charging station (not shown) arranged in the workspace when the battery levels fall below a threshold or during idle periods.

The weigh scale 192 can be installed in the spatula mechanism 146 or in any other location of the labware carrier 142. The weigh scale 192 can be used to measure changes in the mass of the materials carried by the rover device 115. For example, the weigh scale 192 can be used to measure the amount of liquids added to or removed from a piece of labware atop the spatula mechanism 146.

In an example of using the weigh scale 192, the rover device 115 can be commanded to carry an empty reagent reservoir from a liquid handling device to a reagent dispensing device in order to refill the empty reservoir. At the reagent dispensing device, the rover device 115 would position itself such that the reagent dispensing device can dispense new reagent into the reagent reservoir. Then, the rover device 115 can use the weigh scale 192 to measure changes in mass of the reagent reservoir as it is filled by the reagent dispenser in order to judge the amount of fluid dispensed by the reagent dispenser. Additionally, the rover device 115 can use the weigh scale 192 to measure changes in mass of the reagent reservoir in order to determine when the reagent reservoir is empty and must be refilled.

In some embodiments, the rover-based integrated laboratory system 100 can include RFID technology. For example, the liquid handler device 110 and/or the rover devices 115 can be equipped with RFID technology. In this example, the processor 180 has capability to process RFID data from one or more RFID readers (not shown) in the liquid handler device 110 and/or the rover devices 115.

Referring now to FIG. 20, FIG. 21, FIG. 22, and FIG. 23, a spatula mechanism behavior sequence is disclosed for the mobile rover device 115 shown in FIG. 3 through FIG. 7. In the rover device 115, the spatula mechanism is, for example, the labware transfer mechanism 144 and the spatula mechanism 146 of the labware carrier 142. Additionally, FIG. 24, FIG. 25, FIG. 26, FIG. 26, and FIG. 28 shows the spatula labware hand-off behavior sequence of the mobile rover device 115 shown in FIG. 3 through FIG. 7 integrated with a labware storage shelf or rack 198.

Referring now to FIG. 29 is a perspective view of the mobile rover device 115 shown in animated fashion for illustration purposes only in the following sequence of operations shown in in FIG. 35 through FIG. 66. Namely, FIG. 35 through FIG. 66 show a series of screenshots displaying a sequence of operations of a simple liquid handler device 310 in combination with one or more rover devices 115. The simple liquid handler device 310 is an example of the liquid handler device 110 of the rover-based integrated laboratory system 100 shown in FIG. 1.

In the sequence shown in FIG. 35 through FIG. 66, a basic liquid handling protocol is programmed on a pipetting instrument 314 designed to interface with rovers (e.g., rover devices 115) that are carrying labware (e.g., labware 120). In operation, first labware 120 is loaded onto the rover devices 115, wherein the labware 120 can include, for example, pipette tips, a 96-well deep well source block, and a 96-well destination plate. Using capacitance sensing as described hereinabove with reference to FIG. 14, FIG. 15, FIG. 16, and FIG. 17, the rover devices 115 can detect the presence of labware 120 placed onto them. The user then programs a liquid handling protocol using a software graphical user interface (GUI) (e.g., GUI 312). When the user is ready to initiate the process, the pipetting instrument 314 is commanded to execute the protocol. The rover devices 115 can maneuver themselves into the pipetting instrument 314, and position the labware 120 such that the pipetting instrument 314 can interact with the labware 120. The pipetting instrument 314 executes a series of liquid transfer operations including, for example, first picking up pipette tips, then aspirating liquid from the deep well block, and then dispensing liquid into the 96-well plate. Finally, the results of the liquid handling operation are carried out of the pipetting instrument 314 and delivered to the user.

Referring now to FIG. 67, a mobile rover device 115 is shown in another animated fashion for illustration purposes only in the following sequence of operations shown in FIG. 68 through FIG. 113. Namely, FIG. 68 through FIG. 113 show a series of screenshots displaying a sequence of operations of a simplified modular cell culture automation system 410 in combination with one or more rover devices 115. The simplified modular cell culture automation system 410 is an example of the liquid handler device 110 of the rover-based integrated laboratory system 100 shown in FIG. 1.

In the sequence shown in FIG. 68 through FIG. 113, the rover (e.g., rover device 115) can be fitted with an omniwheel based drivetrain and can be capable of moving in any direction without turning around. The rover device 115 can also be fitted with a gripper tool to pull labware from passive storage devices.

Further, a simplified modular cell culture automation system 410 shown in shown in FIG. 68 through FIG. 113 is an example of the rover-based integrated laboratory system 100 that includes workspace that is divided into vertically arranged levels. For example, the workspace can include one or more elevator platforms 414 for moving the rover devices 115 from one level to another as described hereinbelow.

As illustrated in the sequence, the rover device 115 can begin by entering a cell incubation chamber 411, which stores cell culture samples in SBS-format labware in a passive hotel system. The rover (e.g., rover device 115) will then retrieve a sample plate 412. The rover device 115 can then maneuver onto the elevator platform 414 (FIG. 70 through FIG. 75), which lifts the rover device 115 to the level of the desired sample plate 412. The rover device 115 can then maneuver itself to the desired storage location to retrieve the sample plate 412 from a storage shelf 416. The elevator can then return the rover device 115 to the ground plane (FIG. 70 through FIG. 75), and the rover device 115 can exit the incubation chamber through an air lock 418. The rover device 115 can then navigate itself to an imager module 420. Another elevator platform 414 can raise the rover device 115 to the appropriate height to interface with the imager module 420, and the rover delivers the sample plate 412 to the imager module 420. The imager module 420 can then proceed to analyze the cell culture sample.

In parallel, a second rover device 115 can be outfitted with a pipette tip caddy holder 422 and navigates itself to a consumable storage module through yet another elevator platform 414. This second rover device 115 can retrieve a pipette tip caddy 424 from the storage, and then can navigate itself to a pipetting instrument 426. In parallel, the first rover 115 can retrieve the sample plate 412 from the imager module 420 and then can navigate itself to the pipetting instrument 426. At the pipetting instrument 426, a number of rover devices 115 can maneuver labware and consumables within the pipetting instrument 426 in order to enable transfer of reagents and samples between labware (FIG. 77 through FIG. 96). After the samples have been received by the pipetting instrument 426, the rover device 115 can navigate the sample plate 412 to a reagent dispenser 428 (FIG. 97 through FIG. 100). The reagent dispenser 428 can then deliver the desired volume of reagent to the sample plate 412. Finally, the sample plate 412 can be returned to the cell incubation chamber 411 (FIG. 101 through FIG. 113).

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" cannot expressly appear with the value, amount or range. Accordingly, unless indicated to the contrary, the numerical parameters set forth in the following specification and attached claims are not and need not be exact, but can be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments±100%, in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A rover-based laboratory integrated system for labware component handling, comprising:
a workspace comprising a fleet controller, a communications interface, an elevator platform and an elevator;
a laboratory component within the workspace, the laboratory component being adapted to perform a laboratory technique;
a labware component within the workspace that is adapted to be used in the laboratory technique; and
a plurality of rover components in communication with the fleet controller through the communications interface within the workspace that is operatively connected to the laboratory and the labware components, wherein the workspace is adapted with the elevator platform and the elevator to lift and lower each of the rover components within the workspace, and each of the rover components being an autonomous mobile robot comprising a labware component carrier platform with capacitive sensing regions, wherein the capacitive sensing regions use a capacitance detection algorithm and capacitive sensing electrodes located in the labware component and the labware carrier platform to sense a presence or absence of a labware component positioned on the labware component carrier platform.

2. The laboratory integrated system as in claim 1, wherein the laboratory component comprises a liquid handler device, and wherein the laboratory technique includes a pipetting operation.

3. The laboratory integrated system as in claim 2, wherein the liquid handler device is a multi-channel liquid handler with independent spanning and independent Z-actuation on each of the channels.

4. The laboratory integrated system as in claim 3, wherein the liquid handler device is an 8-channel liquid handler with independent spanning and independent Z-actuation on each of the 8 channels.

5. The laboratory integrated system as in claim 1, wherein the capacitance detection algorithm comprises input from the capacitive sensing electrodes located within a labware presence detection zone, a front labware edge detection zone, a rear labware edge detection zone, a left side front-edge collision detection zone, and a right side front-edge collision detection zone.

6. The laboratory integrated system as in claim 1, wherein the autonomous mobile robot is holonomic.

7. The laboratory integrated system as in claim 6, wherein the autonomous mobile robot comprises an omni-wheel based drivetrain and capable of moving in any direction without turning around.

8. The laboratory integrated system as in claim 1, wherein the autonomous mobile robot comprises one or more navigational cameras.

9. The laboratory integrated system as in claim 8, wherein the workspace comprises a plurality of fiducial markers forming a 2D coordinate system, and wherein the navigational cameras are adapted to identify a location of the autonomous mobile robot within the workspace through recognition of one or more of the fiducial markers.

10. The laboratory integrated system as in claim 1, wherein the autonomous mobile robot comprises a labware component transfer mechanism.

11. The laboratory integrated system as in claim 10, wherein the labware component transfer mechanism comprises a spatula mechanism that is adapted to transfer the labware component from the autonomous mobile robot to a location within the workspace.

12. The laboratory integrated system as in claim 1, wherein the autonomous mobile robot is adapted to move within the workspace using an S-curve velocity motion profile.

13. The laboratory integrated system as in claim 1, wherein the workspace, the laboratory component, the labware component, or any combination thereof comprise an RFID tag, and wherein the autonomous mobile robot comprises an RFID reader.

14. The laboratory integrated system as in claim 1, wherein the fleet controller is adapted to command each of the plurality of rover components to engage the labware component for the laboratory technique.

15. The laboratory integrated system as in claim 1, wherein the workspace comprises two or more system modules and the fleet controller, wherein each of the plurality of rover components is adapted to generate a map of the workspace, and wherein each of the rover components navigates freely within the workspace using the map and the fleet controller.

16. The laboratory integrated system as in claim 15, wherein each of the plurality of rover components is in wireless communication with the fleet controller, and wherein the fleet controller commands each of the plurality of rover component to execute tasks of a workflow.

17. The laboratory integrated system as in claim 1, wherein each of the plurality of rover components is adapted to transport and position the labware component or materials contained by the labware component.

18. The laboratory integrated system as in claim 1, wherein each of the plurality of rover components comprises a labware component carrier platform with a weigh scale.

19. The laboratory integrated system as in claim 1, wherein the autonomous mobile robot comprises a gripper tool.

20. The laboratory integrated system as in claim 1, wherein the laboratory technique is cell culturing, and wherein the autonomous mobile robot comprises an omni-wheel based drive train and a gripping tool.

21. A method for integrating a laboratory system comprising the steps of:
providing a laboratory integrated system described in claim 1;
programming a protocol for the laboratory technique using the fleet controller; and
commanding each of the plurality of rover components with the fleet controller to execute the protocol.

22. The method as in claim 21, further comprising the step of generating a map of the workspace using the autonomous mobile robot.

23. The method as in claim 22, further comprising navigating the autonomous mobile robot freely within the workspace using the map.

24. The method as in claim 23, wherein the autonomous mobile robot navigates within the workspace using an S-curve velocity motion profile.

25. The method as in claim 21, further comprising the step of communicating wirelessly with the communications interface between each of the plurality of rover components and the laboratory component during execution of the protocol by the autonomous mobile robot.

26. The method as in claim 21, wherein the commanding step includes commanding a pipetting technique.

27. The method as in claim 21, wherein the commanding step includes commanding a cell culture technique.

28. The method as in claim 21, wherein the workspace comprises an autonomous mobile robot-navigable surface having an array of fiducial marks that define a coordinate system of the workspace.

29. The method as in claim 28, further comprises tracking a current position of the autonomous mobile robot within the workspace using a downward-facing camera positioned on the autonomous mobile robot, the current position of the autonomous mobile robot being determined by identifying one or more of the fiducial marks under the autonomous mobile robot using images captured by the downward-facing camera.

30. The method as in claim 21, wherein the protocol comprises transporting and positioning of the labware component or materials contained by the labware component in the workspace.

* * * * *